(12) United States Patent
Ryu et al.

(10) Patent No.: US 8,080,377 B2
(45) Date of Patent: Dec. 20, 2011

(54) METHOD FOR CONFIRMING THE EXPOSURE ON CHRYSENE

(75) Inventors: Jae-Chun Ryu, Seoul (KR); Youn-Jung Kim, Seoul (KR); Mi-Kyung Song, Ulsan (KR); Hee-Kyung Jeon, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 111 days.

(21) Appl. No.: 12/253,052

(22) Filed: Oct. 16, 2008

(65) Prior Publication Data
US 2009/0291855 A1 Nov. 26, 2009

(30) Foreign Application Priority Data
May 23, 2008 (KR) .................. 10-2008-0047946

(51) Int. Cl.
*C12Q 1/68* (2006.01)
*C12P 19/34* (2006.01)
*C07H 21/02* (2006.01)

(52) U.S. Cl. ....... 435/6.1; 435/91.2; 536/23.1; 536/24.3

(58) Field of Classification Search .................. None
See application file for complete search history.

(56) References Cited

FOREIGN PATENT DOCUMENTS
KR 10-2005-0075134 A 7/2005

OTHER PUBLICATIONS

Castorena-Torres, F. et al., Toxicology in Vitro, vol. 22, pp. 411-421 (2008).*
Courter, L. A. et al., Cancer Lett., vol. 265, pp. 135-147 (2008).*
Genbank Accession No. NM_000499, revision history, downlaoded May 6, 2011.*
Elovaara et al. (2006). "Polycyclic Aromatic Hydrocarbon (PAH) Metabolizing Enzyme Activities in Human Lung, and Their Inducibility by Exposure to Naphthalene, Phenanthrene, Pyrene, Chrysene, and Benzo(a)Pyrene as Shown in the Rat Lung and Liver." Arch. Toxicol., 81:169-182.
Bultelle et al. (2002). "Identification of Differentially Expressed Genes in *Dreissena polymorpha* Exposed to Contaminants." Marine Environmental Research, 54:385-389.

* cited by examiner

*Primary Examiner* — Teresa E Strzelecka
(74) *Attorney, Agent, or Firm* — Greenlee Sullivan P.C.

(57) ABSTRACT

The present invention relates to a method for confirming the exposure on chrysene using a DNA fragment whose expression is increased or decreased specifically when it is exposed to chrysene. The method of the present invention is effective in determination of risk by chrysene and monitoring the chrysene exposure, so that it can be effectively used as a tool for examining the mechanism of chrysene induced toxicity.

9 Claims, 2 Drawing Sheets
(1 of 2 Drawing Sheet(s) Filed in Color)

```
                    SEQUENCE LISTING

<160> NUMBER OF SEQ ID NOS: 105

<210> SEQ ID NO 1
<211> LENGTH: 18
<212> TYPE: DNA
<213> ORGANISM: Artificial Sequence
<220> FEATURE:
<223> OTHER INFORMATION: NM_000499 sense primer

<400> SEQUENCE: 1
caccatcccc cacagcac                                             18

<210> SEQ ID NO 2
<211> LENGTH: 20
<212> TYPE: DNA
<213> ORGANISM: Artificial Sequence
<220> FEATURE:
<223> OTHER INFORMATION: NM_000499 antisense primer

<400> SEQUENCE: 2
```

```
acaaagacac aacgcccctt                                              20

<210> SEQ ID NO 3
<211> LENGTH: 20
<212> TYPE: DNA
<213> ORGANISM: Artificial Sequence
<220> FEATURE:
<223> OTHER INFORMATION: BX649164 sense primer

<400> SEQUENCE: 3
cagaccaaga gcctctccac                                              20

<210> SEQ ID NO 4
<211> LENGTH: 20
<212> TYPE: DNA
<213> ORGANISM: Artificial Sequence
<220> FEATURE:
<223> OTHER INFORMATION: BX649164 antisense primer

<400> SEQUENCE: 4
atcacttggc ccatgaaaag                                              20

<210> SEQ ID NO 5
<211> LENGTH: 22
<212> TYPE: DNA
<213> ORGANISM: Artificial Sequence
<220> FEATURE:
<223> OTHER INFORMATION: NM_004881 sense primer

<400> SEQUENCE: 5
agggtgaagt cctcctgaag gt                                           22

<210> SEQ ID NO 6
<211> LENGTH: 22
<212> TYPE: DNA
<213> ORGANISM: Artificial Sequence
<220> FEATURE:
<223> OTHER INFORMATION: NM_004881 antisense primer

<400> SEQUENCE: 6
gtgggtcata ctggccttgt ct                                           22

<210> SEQ ID NO 7
<211> LENGTH: 23
<212> TYPE: DNA
<213> ORGANISM: Artificial Sequence
<220> FEATURE:
<223> OTHER INFORMATION: BM913048 sense primer

<400> SEQUENCE: 7
gatacttcca caggtcccac aac                                          23

<210> SEQ ID NO 8
<211> LENGTH: 21
<212> TYPE: DNA
<213> ORGANISM: Artificial Sequence
<220> FEATURE:
<223> OTHER INFORMATION: BM913048 antisense primer

<400> SEQUENCE: 8
gcaagagtcc atcctgcagt t                                            21

<210> SEQ ID NO 9
<211> LENGTH: 26
<212> TYPE: DNA
<213> ORGANISM: Artificial Sequence
```

```
<220> FEATURE:
<223> OTHER INFORMATION: NM_006426 sense primer

<400> SEQUENCE: 9
tgggaagatg gacgagaatg agttcg                                          26

<210> SEQ ID NO 10
<211> LENGTH: 24
<212> TYPE: DNA
<213> ORGANISM: Artificial Sequence
<220> FEATURE:
<223> OTHER INFORMATION: NM_006426 antisense primer

<400> SEQUENCE: 10
actccactcc ctcgaagatg ttgt                                            24

<210> SEQ ID NO 11
<211> LENGTH: 24
<212> TYPE: DNA
<213> ORGANISM: Artificial Sequence
<220> FEATURE:
<223> OTHER INFORMATION: NM_133493 sense primer

<400> SEQUENCE: 11
gccaagattt accacgtttg ccca                                            24

<210> SEQ ID NO 12
<211> LENGTH: 24
<212> TYPE: DNA
<213> ORGANISM: Artificial Sequence
<220> FEATURE:
<223> OTHER INFORMATION: NM_133493 antisense primer

<400> SEQUENCE: 12
tgaaggacca gaactgagcc acat                                            24

<210> SEQ ID NO 13
<211> LENGTH: 24
<212> TYPE: DNA
<213> ORGANISM: Artificial Sequence
<220> FEATURE:
<223> OTHER INFORMATION: AB03307 sense primer

<400> SEQUENCE: 13
tgcggatatg gacgggaaat ccat                                            24

<210> SEQ ID NO 14
<211> LENGTH: 24
<212> TYPE: DNA
<213> ORGANISM: Artificial Sequence
<220> FEATURE:
<223> OTHER INFORMATION: AB03307 antisense primer

<400> SEQUENCE: 14
tctcttgtgt agcagcttgc ctct                                            24

<210> SEQ ID NO 15
<211> LENGTH: 24
<212> TYPE: DNA
<213> ORGANISM: Artificial Sequence
<220> FEATURE:
<223> OTHER INFORMATION: NM_021603 sense primer

<400> SEQUENCE: 15
ggcaataaga agcgcaggca aatc                                            24
```

<210> SEQ ID NO 16
<211> LENGTH: 24
<212> TYPE: DNA
<213> ORGANISM: Artificial Sequence
<220> FEATURE:
<223> OTHER INFORMATION: NM_021603 antisense primer

<400> SEQUENCE: 16
aaggtctaaa gcccagggaa gaag                                          24

<210> SEQ ID NO 17
<211> LENGTH: 21
<212> TYPE: DNA
<213> ORGANISM: Artificial Sequence
<220> FEATURE:
<223> OTHER INFORMATION: BC035124 sense primer

<400> SEQUENCE: 17
ttcgccgtcc tttacatcta c                                             21

<210> SEQ ID NO 18
<211> LENGTH: 19
<212> TYPE: DNA
<213> ORGANISM: Artificial Sequence
<220> FEATURE:
<223> OTHER INFORMATION: BC035124 antisense primer

<400> SEQUENCE: 18
agagcctggg gactcacat                                                19

<210> SEQ ID NO 19
<211> LENGTH: 25
<212> TYPE: DNA
<213> ORGANISM: Artificial Sequence
<220> FEATURE:
<223> OTHER INFORMATION: Y11307 sense primer

<400> SEQUENCE: 19
attgtagaaa ggaagccttg ctcat                                         25

<210> SEQ ID NO 20
<211> LENGTH: 20
<212> TYPE: DNA
<213> ORGANISM: Artificial Sequence
<220> FEATURE:
<223> OTHER INFORMATION: Y11307 antisense primer

<400> SEQUENCE: 20
tccaatcgtg gctgcattag                                               20

<210> SEQ ID NO 21
<211> LENGTH: 24
<212> TYPE: DNA
<213> ORGANISM: Artificial Sequence
<220> FEATURE:
<223> OTHER INFORMATION: AK095363 sense primer

<400> SEQUENCE: 21
ttcacgatcc accctttcag gcta                                          24

<210> SEQ ID NO 22
<211> LENGTH: 23
<212> TYPE: DNA
<213> ORGANISM: Artificial Sequence
<220> FEATURE:
<223> OTHER INFORMATION: AK095363 antisense primer

<400> SEQUENCE: 22

```
acacatacct gctgcccatt ctc                                          23

<210> SEQ ID NO 23
<211> LENGTH: 24
<212> TYPE: DNA
<213> ORGANISM: Artificial Sequence
<220> FEATURE:
<223> OTHER INFORMATION: AK097009 sense primer

<400> SEQUENCE: 23
tgccacagag aagacgggat ttga                                         24

<210> SEQ ID NO 24
<211> LENGTH: 24
<212> TYPE: DNA
<213> ORGANISM: Artificial Sequence
<220> FEATURE:
<223> OTHER INFORMATION: AK097009 antisense primer

<400> SEQUENCE: 24
aggtggtgga cggactgtaa ttga                                         24

<210> SEQ ID NO 25
<211> LENGTH: 19
<212> TYPE: DNA
<213> ORGANISM: Artificial Sequence
<220> FEATURE:
<223> OTHER INFORMATION: NM_004864 sense primer

<400> SEQUENCE: 25
cctgagacac ccgattcct                                               19

<210> SEQ ID NO 26
<211> LENGTH: 20
<212> TYPE: DNA
<213> ORGANISM: Artificial Sequence
<220> FEATURE:
<223> OTHER INFORMATION: NM_004864 antisense primer

<400> SEQUENCE: 26
acagttccat cagaccagcc                                              20

<210> SEQ ID NO 27
<211> LENGTH: 24
<212> TYPE: DNA
<213> ORGANISM: Artificial Sequence
<220> FEATURE:
<223> OTHER INFORMATION: BU587578 sense primer

<400> SEQUENCE: 27
ccgtgccggg tttatcattg cttt                                         24

<210> SEQ ID NO 28
<211> LENGTH: 24
<212> TYPE: DNA
<213> ORGANISM: Artificial Sequence
<220> FEATURE:
<223> OTHER INFORMATION: BU587578 antisense primer

<400> SEQUENCE: 28
tcgacgtgtc cagtgttgaa ggaa                                         24

<210> SEQ ID NO 29
<211> LENGTH: 24
<212> TYPE: DNA
<213> ORGANISM: Artificial Sequence
```

```
<220> FEATURE:
<223> OTHER INFORMATION: BQ683841 sense primer

<400> SEQUENCE: 29
agtccctgat tgctgtcttc caga                                          24

<210> SEQ ID NO 30
<211> LENGTH: 24
<212> TYPE: DNA
<213> ORGANISM: Artificial Sequence
<220> FEATURE:
<223> OTHER INFORMATION: BQ683841 antisense primer

<400> SEQUENCE: 30
accagggtcc ttctggttct ttgt                                          24

<210> SEQ ID NO 31
<211> LENGTH: 25
<212> TYPE: DNA
<213> ORGANISM: Artificial Sequence
<220> FEATURE:
<223> OTHER INFORMATION: NM_001013632 sense primer

<400> SEQUENCE: 31
gactactcca ataagttcgg ctttg                                         25

<210> SEQ ID NO 32
<211> LENGTH: 23
<212> TYPE: DNA
<213> ORGANISM: Artificial Sequence
<220> FEATURE:
<223> OTHER INFORMATION: NM_001013632 antisense primer

<400> SEQUENCE: 32
catatgtgtg ccatcgttga aga                                           23

<210> SEQ ID NO 33
<211> LENGTH: 24
<212> TYPE: DNA
<213> ORGANISM: Artificial Sequence
<220> FEATURE:
<223> OTHER INFORMATION: NM_032872 sense primer

<400> SEQUENCE: 33
ggcggtgaag aaacggaatc tgaa                                          24

<210> SEQ ID NO 34
<211> LENGTH: 24
<212> TYPE: DNA
<213> ORGANISM: Artificial Sequence
<220> FEATURE:
<223> OTHER INFORMATION: NM_032872 antisense primer

<400> SEQUENCE: 34
gaaagatgtt gcgacccagg cttt                                          24

<210> SEQ ID NO 35
<211> LENGTH: 21
<212> TYPE: DNA
<213> ORGANISM: Artificial Sequence
<220> FEATURE:
<223> OTHER INFORMATION: BC042390 sense primer

<400> SEQUENCE: 35
gggggactaa cctatcgaga a                                             21
```

```
<210> SEQ ID NO 36
<211> LENGTH: 21
<212> TYPE: DNA
<213> ORGANISM: Artificial Sequence
<220> FEATURE:
<223> OTHER INFORMATION: BC042390 antisense primer

<400> SEQUENCE: 36
gatccagtgc tgatagcaac c                                              21

<210> SEQ ID NO 37
<211> LENGTH: 24
<212> TYPE: DNA
<213> ORGANISM: Artificial Sequence
<220> FEATURE:
<223> OTHER INFORMATION: NM_000596 sense primer

<400> SEQUENCE: 37
atcattccat cctttgggac gcca                                           24

<210> SEQ ID NO 38
<211> LENGTH: 24
<212> TYPE: DNA
<213> ORGANISM: Artificial Sequence
<220> FEATURE:
<223> OTHER INFORMATION: NM_000596 antisense primer

<400> SEQUENCE: 38
tgtctcctgt gccttggcta aact                                           24

<210> SEQ ID NO 39
<211> LENGTH: 22
<212> TYPE: DNA
<213> ORGANISM: Artificial Sequence
<220> FEATURE:
<223> OTHER INFORMATION: NM_005319 sense primer

<400> SEQUENCE: 39
accaaaccta agaagccagt tg                                             22

<210> SEQ ID NO 40
<211> LENGTH: 20
<212> TYPE: DNA
<213> ORGANISM: Artificial Sequence
<220> FEATURE:
<223> OTHER INFORMATION: NM_005319 antisense primer

<400> SEQUENCE: 40
tagcgctctt cttcggagtt                                                20

<210> SEQ ID NO 41
<211> LENGTH: 21
<212> TYPE: DNA
<213> ORGANISM: Artificial Sequence
<220> FEATURE:
<223> OTHER INFORMATION: AK094474 sense primer

<400> SEQUENCE: 41
acctgcctcc tcatcgtctt c                                              21

<210> SEQ ID NO 42
<211> LENGTH: 18
<212> TYPE: DNA
<213> ORGANISM: Artificial Sequence
<220> FEATURE:
<223> OTHER INFORMATION: AK094474 antisense primer

<400> SEQUENCE: 42
```

```
cacctgcttg ccgtccac                                              18
```

<210> SEQ ID NO 43
<211> LENGTH: 24
<212> TYPE: DNA
<213> ORGANISM: Artificial Sequence
<220> FEATURE:
<223> OTHER INFORMATION: NM_001769 sense primer

<400> SEQUENCE: 43

```
gcaccaagtg catcaaatac ctgc                                       24
```

<210> SEQ ID NO 44
<211> LENGTH: 24
<212> TYPE: DNA
<213> ORGANISM: Artificial Sequence
<220> FEATURE:
<223> OTHER INFORMATION: NM_001769 antisense primer

<400> SEQUENCE: 44

```
agccatagtc caatggcaag gaca                                       24
```

<210> SEQ ID NO 45
<211> LENGTH: 24
<212> TYPE: DNA
<213> ORGANISM: Artificial Sequence
<220> FEATURE:
<223> OTHER INFORMATION: NM_001553 sense primer

<400> SEQUENCE: 45

```
acttgagctg tgaggtcatc ggaa                                       24
```

<210> SEQ ID NO 46
<211> LENGTH: 24
<212> TYPE: DNA
<213> ORGANISM: Artificial Sequence
<220> FEATURE:
<223> OTHER INFORMATION: NM_001553 antisense primer

<400> SEQUENCE: 46

```
ataccagcac ccagccagtt actt                                       24
```

<210> SEQ ID NO 47
<211> LENGTH: 24
<212> TYPE: DNA
<213> ORGANISM: Artificial Sequence
<220> FEATURE:
<223> OTHER INFORMATION: NM_003897 sense primer

<400> SEQUENCE: 47

```
agccctttaa tctgacttcg gagc                                       24
```

<210> SEQ ID NO 48
<211> LENGTH: 24
<212> TYPE: DNA
<213> ORGANISM: Artificial Sequence
<220> FEATURE:
<223> OTHER INFORMATION: NM_003897 antisense primer

<400> SEQUENCE: 48

```
caggtacgcc tggtgtttct ttgt                                       24
```

<210> SEQ ID NO 49
<211> LENGTH: 24
<212> TYPE: DNA
<213> ORGANISM: Artificial Sequence

```
<220> FEATURE:
<223> OTHER INFORMATION: NM_003516 sense primer

<400> SEQUENCE: 49
gaactgaaca agctgctggg caaa                                              24

<210> SEQ ID NO 50
<211> LENGTH: 24
<212> TYPE: DNA
<213> ORGANISM: Artificial Sequence
<220> FEATURE:
<223> OTHER INFORMATION: NM_003516 antisense primer

<400> SEQUENCE: 50
tctccgtctt cttagggagc agta                                              24

<210> SEQ ID NO 51
<211> LENGTH: 18
<212> TYPE: DNA
<213> ORGANISM: Artificial Sequence
<220> FEATURE:
<223> OTHER INFORMATION: AK074377 sense primer

<400> SEQUENCE: 51
ctggtacgac gcggagat                                                     18

<210> SEQ ID NO 52
<211> LENGTH: 21
<212> TYPE: DNA
<213> ORGANISM: Artificial Sequence
<220> FEATURE:
<223> OTHER INFORMATION: AK074377 antisense primer

<400> SEQUENCE: 52
cgacagtcgt tcagagaatc a                                                 21

<210> SEQ ID NO 53
<211> LENGTH: 20
<212> TYPE: DNA
<213> ORGANISM: Artificial Sequence
<220> FEATURE:
<223> OTHER INFORMATION: BX640965 sense primer

<400> SEQUENCE: 53
gccctgttcc agcaataaga                                                   20

<210> SEQ ID NO 54
<211> LENGTH: 20
<212> TYPE: DNA
<213> ORGANISM: Artificial Sequence
<220> FEATURE:
<223> OTHER INFORMATION: BX640965 antisense primer

<400> SEQUENCE: 54
gagagccaaa aatgtcccaa                                                   20

<210> SEQ ID NO 55
<211> LENGTH: 24
<212> TYPE: DNA
<213> ORGANISM: Artificial Sequence
<220> FEATURE:
<223> OTHER INFORMATION: NM_018492 sense primer

<400> SEQUENCE: 55
tctggactga gagtggcttt caca                                              24
```

```
<210> SEQ ID NO 56
<211> LENGTH: 24
<212> TYPE: DNA
<213> ORGANISM: Artificial Sequence
<220> FEATURE:
<223> OTHER INFORMATION: NM_018492 antisense primer

<400> SEQUENCE: 56
agccaagctt ctgcataaac ggag                                          24

<210> SEQ ID NO 57
<211> LENGTH: 20
<212> TYPE: DNA
<213> ORGANISM: Artificial Sequence
<220> FEATURE:
<223> OTHER INFORMATION: CR600021 sense primer

<400> SEQUENCE: 57
cttggcacga tatgcagcaa                                               20

<210> SEQ ID NO 58
<211> LENGTH: 25
<212> TYPE: DNA
<213> ORGANISM: Artificial Sequence
<220> FEATURE:
<223> OTHER INFORMATION: CR600021 antisense primer

<400> SEQUENCE: 58
cagccaaaga taaacaacca tatga                                         25

<210> SEQ ID NO 59
<211> LENGTH: 22
<212> TYPE: DNA
<213> ORGANISM: Artificial Sequence
<220> FEATURE:
<223> OTHER INFORMATION: NM_006101 sense primer

<400> SEQUENCE: 59
tgctacacat gttgggtctg ta                                            22

<210> SEQ ID NO 60
<211> LENGTH: 21
<212> TYPE: DNA
<213> ORGANISM: Artificial Sequence
<220> FEATURE:
<223> OTHER INFORMATION: NM_006101 antisense primer

<400> SEQUENCE: 60
ccgagagatc ttctgacatg c                                             21

<210> SEQ ID NO 61
<211> LENGTH: 24
<212> TYPE: DNA
<213> ORGANISM: Artificial Sequence
<220> FEATURE:
<223> OTHER INFORMATION: NM_003318 sense primer

<400> SEQUENCE: 61
tcatgcccat ttggaagagt ccca                                          24

<210> SEQ ID NO 62
<211> LENGTH: 24
<212> TYPE: DNA
<213> ORGANISM: Artificial Sequence
<220> FEATURE:
<223> OTHER INFORMATION: NM_003318 antisense primer

<400> SEQUENCE: 62
```

```
aggcacaacc aaatctcggc attc                                          24

<210> SEQ ID NO 63
<211> LENGTH: 32
<212> TYPE: DNA
<213> ORGANISM: Artificial Sequence
<220> FEATURE:
<223> OTHER INFORMATION: U65410 sense primer

<400> SEQUENCE: 63
acttaaatat ctccctacct atactgagtc aa                                 32

<210> SEQ ID NO 64
<211> LENGTH: 30
<212> TYPE: DNA
<213> ORGANISM: Artificial Sequence
<220> FEATURE:
<223> OTHER INFORMATION: U65410 antisense primer

<400> SEQUENCE: 64
tagtaactgt agatggaaaa acttgtgcta                                    30

<210> SEQ ID NO 65
<211> LENGTH: 22
<212> TYPE: DNA
<213> ORGANISM: Artificial Sequence
<220> FEATURE:
<223> OTHER INFORMATION: NM_001067 sense primer

<400> SEQUENCE: 65
ctagttaatg ctgcggacaa ca                                            22

<210> SEQ ID NO 66
<211> LENGTH: 21
<212> TYPE: DNA
<213> ORGANISM: Artificial Sequence
<220> FEATURE:
<223> OTHER INFORMATION: NM_001067 antisense primer

<400> SEQUENCE: 66
catttcgacc acctgtcact t                                             21

<210> SEQ ID NO 67
<211> LENGTH: 24
<212> TYPE: DNA
<213> ORGANISM: Artificial Sequence
<220> FEATURE:
<223> OTHER INFORMATION: AB091343 sense primer

<400> SEQUENCE: 67
gctgtgcatt tctcttggca gtga                                          24

<210> SEQ ID NO 68
<211> LENGTH: 24
<212> TYPE: DNA
<213> ORGANISM: Artificial Sequence
<220> FEATURE:
<223> OTHER INFORMATION: AB091343 antisense primer

<400> SEQUENCE: 68
tagacgctgc tcaccacatt ctgt                                          24

<210> SEQ ID NO 69
<211> LENGTH: 22
<212> TYPE: DNA
<213> ORGANISM: Artificial Sequence
```

```
<220> FEATURE:
<223> OTHER INFORMATION: BC022255 sense primer

<400> SEQUENCE: 69
gaatggttga gatgtttctg ga                                          22

<210> SEQ ID NO 70
<211> LENGTH: 27
<212> TYPE: DNA
<213> ORGANISM: Artificial Sequence
<220> FEATURE:
<223> OTHER INFORMATION: BC022255 antisense primer

<400> SEQUENCE: 70
gcaatcaatt ttaacaagtt atccttt                                     27

<210> SEQ ID NO 71
<211> LENGTH: 2608
<212> TYPE: DNA
<213> ORGANISM: Homo sapiens

<400> SEQUENCE: 71
ctcaccctga aggtgacagt tccttggaac cttccctgat ccttgtgatc ccaggctcca    60
agagtccacc cttcccagct cagctcagta cctcagccac ctccaagatc cctacactga   120
tcatgctttt cccaatctcc atgtcggcca cggagtttct tctggcctct gtcatcttct   180
gtctggtatt ctgggtaatc agggcctcaa gacctcaggt ccccaaaggc ctgaagaatc   240
caccagggcc atgggctggc ctctgattg ggcacatgct gaccctggga aagaacccgc    300
acctggcact gtcaaggatg agccagcagt atggggacgt gctgcagatc cgaattggct   360
ccacacccgt ggtggtgctg agcggcctgg acaccatccg gcaggccctg gtgcggcagg   420
gcgatgattt caagggccgg cccgacctct acaccttcac cctcatcagt aatggtcaga   480
gcatgtcctt cagcccagac tctggaccag tgtgggctgc ccgccggcgc ctggcccaga   540
atggcctgaa aagtttctcc attgcctctg acccagcctc ctcaacctcc tgctacctgg   600
aagagcatgt gagcaaggag gctgaggtcc tgataagcac gttgcaggag ctgatggcag   660
ggcctgggca ctttaacccc tacaggtatg tggtggtatc agtgaccaat gtcatctgtg   720
ccatttgctt tggccggcgc tatgaccaca accaccaaga actgcttagc ctagtcaacc   780
tgaataataa tttcggggag gtggttggct ctggaaaccc agctgacttc atccctattc   840
ttcgctacct acccaacccct tccctgaatg ccttcaagga cctgaatgag aagttctaca   900
gcttcatgca gaagatggtc aaggagcact acaaaaacctt tgagaagggc cacatccggg   960
acatcacaga cagcctgatt gagcactgtc aggagaagca gctggatgag aacgccaatg  1020
tccagctgtc agatgagaag atcattaaca tcgtcttgga cctctttgga gctgggtttg  1080
acacagtcac aactgctatc tcctggagcc tcatgtattt ggtgatgaac cccagggtac  1140
agagaaagat ccaagaggag ctagacacag tgattggcag gtcacggcgg cccggctct   1200 ctgacagatc ccatctgccc tatatggagg ccttcatcct ggagaccttc gacactctt   1260 ccttcgtccc cttcaccatc ccccacagca caacaagaga cacaagtttg aaaggctttt  1320
acatccccaa ggggcgttgt gtctttgtaa accagtggca gatcaaccat gaccagaagc  1380
tatgggtcaa cccatctgag ttcctacctg aacggtttct caccctgat ggtgctatcg   1440 acaaggtgtt aagtgagaag gtgattatct ttggcatggg caagcggaag tgtatcggtg  1500
agaccattgc ccgctgggag gtcttttctct tcctggctat cctgctgcaa cgggtggaat  1560
tcagcgtgcc actgggcgtg aaggtggaca tgaccccat ctatgggcta accatgaagc   1620
```

-continued

| | |
|---|---|
| atgcctgctg tgagcacttc caaatgcagc tgcgctctta ggtgcttgag agccctgagg | 1680 |
| cctagactct gtctacctgg tctggttggg cagccagacc agcaggctgg cctatgtggt | 1740 |
| ctaaggttca gcctgaaact catagacact gatctggctg cagttttgct atctgggctg | 1800 |
| tgggcaagcc taagggatcc tgcctgcccc taccctggac ttgcctctgc acaccctcca | 1860 |
| gagacaacag gtaaaacagg gccacataga tgctgatgga gccttcccaa gttgtgcttg | 1920 |
| agccaggagg cctgctaggg ttaggaggtc cttaggcctc tgagaagctc tgaagaactc | 1980 |
| tctggaagcc cctgggccca gtacctagct ggctctgtga gggtgctgac tggcttcagc | 2040 |
| aagttagaac tagccaaacc aggaccctgt ccaatctttg acaattggga gctgccaaga | 2100 |
| gtgaagggaa gagacagccc aggatactgg cacagaggta gtctcactgc ttgaactagg | 2160 |
| ctgagcaatc tgaccctatg ggtctaggac acagttcctg gaacatcac attcctctgc | 2220 |
| ccttcctgca ggcaggaaca aacagggctg ccttctggcc ttgtaagacc cttattgctg | 2280 |
| tcctggaggg gctggggact tgtgtctgcg gggatcagag cgcacaggga gtgcacatat | 2340 |
| ccaggcacca ggactagggc tggagtgagg ggggggtatt tcaattaccct tctattggtc | 2400 |
| tcccttctct acactcttgt aataaaatgt ctatttttaa tgtttgtaca caacaatcct | 2460 |
| tctattctag cctgcattga gcttgcatgc ttgcataaga gcttaagaac cattgattta | 2520 |
| atgtaatagg gaaaattcta acccaggtat ccaaaaatgt gtaagaacaa ctacctgagc | 2580 |
| taaataaaga tattgttcag aaatccta | 2608 |

<210> SEQ ID NO 72
<211> LENGTH: 9360
<212> TYPE: DNA
<213> ORGANISM: Homo sapiens

<400> SEQUENCE: 72

| | |
|---|---|
| attctgggat gcataccaat cagccggcga ctagaaccag gacttttaca gagaggaggg | 60 |
| cactctgggg ccaggctctc aaggagaaag aggggttcca aaactcagaa atgccacctc | 120 |
| atcttgggcc caacatgcca acatgggctg gcaccatcac aaaccacctg cactgccctg | 180 |
| gactggggat gtatctgcaa gaaggtggtg ttggggcctg gtctgagacc atcctctcaa | 240 |
| ccaacaggcc agtgggaaga tgaaccctat ggcagggagc tcagtgctgg ctctaaccaa | 300 |
| gaggtgggca gaccctgggc ctgtggccaa gtggtcaatt atccttcccc attttccata | 360 |
| gcatatgggc actgctgcta ggggctgtca aaggcacagc cgggccaggc cctgggaggg | 420 |
| ttggcgctgc tcaaggaaag acacaagagt ggagaggcag gactccgggg cgagcagaat | 480 |
| gtggtgcttc taactcttgg ttgctcaacc ctgggcaagt tcaatggagg caaaacagag | 540 |
| ataatgatgc accccacctc ttggagtagc tgagaactga gaaagctccc acgagccatg | 600 |
| cactaccaag gtgcctgcca ctctgcaatt atgagccatt agtattagct ctttcctgac | 660 |
| accaggccta gggagcccgt gtgggtacca gaattctatt ctcatccttg ccctgagcc | 720 |
| acaaggtaac aaacccagct atgaccgac tgggccttgc caacactgaa ttaaaaaaac | 780 |
| atacattaac tccgaactaa gaaaggcaag gtgtgctgag attccaggca tgtgatgaat | 840 |
| ctctccctcc cctcctcaaa gggaaaagga aaaccgcata aggagggga gcacgggact | 900 |
| gcagaaagat ctcagggcct gccgggttca atcctgccca cttacaaaca cagtgccctt | 960 |
| ggataagtct ctgagactca atttcctcat cgataagatc ggaaaatagg acgtacttgc | 1020 |
| aggatcggca tggaaattaa atgaattgat gcgtgaaaaa tatctggcac ctataggcat | 1080 |
| aaagtcaaaa tcagttgcct ttaagcaaac aagttctcaa ttatctgcct aaatgaagga | 1140 |

```
cagaagcagc ttttctggta tcaattagca atggggggag aacaggagac ccctcttccc    1200
aattaagttt tgtgcttgat attaacatgg atttttttg agaatccacc agccacagat      1260 gcagggctg gaagaccagc aagcttcagg gacagcagga aactaccaag aaacctcaaa      1320
gatttttagg gaagcagggt gatccacaca gcacaaggcc cctgacaggt gaggtttgtc    1380
agatttcctt tgctggcacc cagatgatgc tgtgcctcct gacttgagga aggttcaatg    1440
cttcccctac tctgtttcaa gccctgcaga cttttgattc acctgacacc agagccagac    1500
tgaactctca ataattcatg cctctgagcc tttgcacatg ccattccttc tgggtggaga    1560
aaacacacat taactcccct gggtagaagg agcagcatgt gcaaaggttc agaggcaaga    1620
attgttcccc tctccctacc ccattcccct gctacactcc gcacatccct ccactgtatg    1680
taacatgtgc acatgtccat cttccaacca gagatcacag gatgtacaag agcaaccgtc    1740
tgcctctact ctctcatgca ggtcctgaat ccatatggac aggtcatgcc cactgttgcc    1800
tatgtcagct ctagccaccc atgtcctgga catcacaact ccacaagccc caagctactt    1860
aatttgtcca cggtctgtcc tcagacacca ctgctgcttt cctcccaga tgcctgagtc      1920 atcctgaata gggttactca atggcaaagt cagctctcaa ttaactgaat ttcctccttg    1980
tcccatttcc tctcttcctg gtgcatggta acaactcact tgctggaatg gagagctcct    2040
gtgatttgag ggcaatttac aacctctatc accaaagcag gccctgccca gcagctgccc    2100
ctcagcaatg aggacactaa gatcagtcct ggagcgccat cacaccaaaa tgtaagttca    2160
aagggaggga ctgagttgct cattgctgga ttcccagtgg tgtgctggta acaggctct      2220 tcagggaaa agattctgat ttgcagtgtt tgccaatttc tgtgatataa atactctcac      2280
tctggccaat ttcaagctgc caatgtgaca tcactgaatg gagttgagat atgcagtagc    2340
acaccactac gtacattaca cacacaccca cacccacact cacacccctt gatatggttt    2400
ggctgcgtcc ccacccaaat ctcatcttga attgtagctc ccataatccc tgcatgtcat    2460
gggagggacg tggtgggagg taattgaatc acaggggcag gttttcccca tgctgttctc    2520
atgatagtga ataagtctcc caagacctga aggttttata aaggacagtt cccttacaca    2580
ggctctcttg cctgccacca tgtaagatgt gcctttgctc ctccttcgcc ttctaccatg    2640
attgtgagac ctccccagcc atgtggaact gtgagtccat taaatctctt tttctttaca    2700
aattacctag tctcaggtat ttcttcatag cagtatgaaa atagcagtat gaaaaagaac    2760
taatacactc cccaacgcac acacacacaa agcagcaaat aaccacaaaa gcacaggtaa    2820
taatagaata aaataattag gaaaaaaatt gagtatttat tactttataa aatataatt      2880 acaggctggg catggtggct cacgcctgta atcccagcac tttgggaggc cggggtgggc    2940
agatcacctg aggtcaggag ttcgagacca gcctggccca catggtgaaa ccctgtctcc    3000
actaaaaata caaaaattag ccgggagtag tggtgcacgc ctgtagtccc agctactcgg    3060
gaggctgagg catgagaatc gcttgaacgt gcgtgggagg cagaggttgt agtgagccga    3120
gatcatgcca ttgcactcca gcctgagcaa caagagccaa aactccatct caaaaaaaaa    3180
attattatat atatatatac acacatatat atgtataaaa tttatggcca gtcacagtgg    3240
ctcataattg taattccagc actttgagag gctgaggcag gtggaccacc tgaggtcagc    3300
agttcaagac cagcctggcc aacatagtga acccccatct ctactaaaaa tacaaaaatt    3360
agccaggcat ggtggcaggc gcctgtaatc ccagctattc gggaggctga ggcaggagaa    3420
ttgcttgaac cccggagaca gaggttgcag cgagccgaga tcgcgccact gcactccagc    3480
ctggcaatag agtgagactc catctcaaaa caacaacaac aacaacaaca acaaaatcgt    3540
```

```
ctaacttcct gatcttcctg atcattgatt ttcccatagg tatgatcagc aacttgcttg    3600
ggaaaggagc cgtggaccag ctgacacggc tggtgctggt gaatgccctc tacttcaacg    3660
gccagtggaa gactcccttc ccgactcca gcacccaccg ccgcctcttc cacaaatcag     3720
acggcagcac tgtctctgtg cccatgatgg ctcagaccaa caagttcaac tatactgagt    3780
tcaccacgcc cgatggccat tactacgaca tcctggaact gccctaccac ggggacaccc    3840
tcagcatgtt cattgctgcc ccttatgaaa aagaggtgcc tctctctgcc ctcaccaaca    3900
ttctgagtgc ccagctcatc agccactgga aggcaacat gaccaggctg ccccgcctcc     3960
tggttctgcc caagtaagcc accccgctat ctccccgacc taccaacccc tctctcctgg    4020
ctccctaaag tcaccgcccc caggttgaat ttcccagatc tgtgacgctt gcaggacatg    4080
catgtgtggg aggctgatgg gaaactgtgg cctgggtttg attatgagtc ttgcaatcat    4140
ccctccccct gtttctgctg gagggcaggg acagctctt cctgaccaca ccccacatt      4200 gactatcccc agaatacccca gcaaaagccc ccaaaaggag agtcagagaa atgagggagg   4260
tgggggccca atcagtccac atctacttag ggtcgcccca tcagcacttc catccccaac    4320
cctttcaagt caacatccaa acaaaagaaa tcacttccaa ggacggagca gctcaaagcg    4380
cagcttctag ctgggggttcc aagaaagcag attttttcgaa atccttctgc agaaggaagc  4440
aaagagattt tttgaaatct ttctgcagaa ggagaaggct ggagctgggg aactccagaa    4500
ttatagggaa gcctcccacc acgctcatcc caaatttccg gatgctataa tgccaggctt    4560
ggggaaagag gagaatttag ttggttagct ggtgcgtgct ctcacttgca tcctctctct    4620
tcctcttttt ttttttctc ctctctctct ggctcataaa aatggaggta attagttgtg     4680
ccctggtgag aagcagagag tgcacaaagg cccctgctt gagtcctctt cagggttagc     4740
tctcagaaac acaatctgca gaacagattt ttgttccaac atccttgcag gagaatttgc    4800
ccttagcttc ccccacccca gccaggctga ataaaattat gctgaaacta ctgtcttatt    4860
tgaggaaagt aattagtcat aggtgggagg gggtggggag attgcagaag aatgttcatg    4920
aatattagga ttttcagctc taaggggga ctttgtaaac agctttagaa gaagaaccag     4980
gccggctggg tgtggtggct catgcctgta atctcagcat ttggggaggc caaggcgggc    5040
ggatcacttg aggtcaggag tttgagacca gcctggccaa catggtgaaa ccctgtctct    5100
attaaaaata caaaaattag ccggctgtgg tagcgagcgc ctatgatccc agctactccg    5160
gaggctgagg ccagagaatc acatgaacct gggaggtgga ggctgcagtg agccgagatc    5220
acgccactgc actccagcct gggggacaga gcaagaatct gtttcaaaaa aaaaaaaaa     5280 gaaaatagg aaggaaggaa ggaaaggaaa ggaaagaaga gagagagaaa gaaagagaga     5340 gaaagaaga aagaaagaaa gaaagaaaga aagaaagaaa gaaagaaaga aagaaagaaa     5400
gaaagaaaaa gaaaggaaag aaagaacgaa cgaaccaggc ctccctctcc aaccttcacc    5460
tccgtcccta ttctggccac ttgattcggg ggacacctgg taggggatgg ggaaaggtgg    5520
gagctgccag ccagagggga ccccggcttg agcagcctct tgctgctatc tgcaggttct    5580
ccctggagac tgaagtcgac ctcaggaagc ccctagagaa cctgggaatg actgacatgt    5640
tcagacagtt tcaggctgac ttcacgagtc tttcaggtaa gaagactttc ctttgcattt    5700
tctcacccca gtggactgcg ggggcccta agaggaaaaa ggaacctctc cttgagagcg     5760
gcagctgatc taatcctgta tccacatctg tttcagacca agagcctctc acgtcgcgc     5820 aggcgctgca gaaagtgaag atcgaggtga acgagagtgg cacggtggcc tcctcatcca    5880
caggtgagtc tggctcaggt gaggctccac gggtgtcgcc tccatcgccc ttcaggataa    5940
```

```
ctggtcccca gacccggaaa ggaccccgca gccctctcgg cacagagcag ctctgtctgt    6000
gctcagccat cacccactcc ccacctgttt ctcagcctgg aaaacgggct tgggaccatg    6060
gaaccctgtt tcctcgcctg atggctccta agttccctga ctgtgaaaag gcctcctaaa    6120
gaaaaaccca agttgttccc acagtgggaa gtaaacttaa gaaacatgct tatcaggctg    6180
ggcatggtgg ctcccacctg taatcccagc gctttggggg accaaggcag gtggatcact    6240
tgaggtcagg aattcgagac cagcctgggc aacatggcaa aaccctatct ctactaaaaa    6300
tacaaaaatt aggcaggcgt ggtggcatgt gcctgtagtc ccagctactt gggaggctga    6360
ggcaggagaa tcacttgaat ccaggaggca gaggttgcag tgagccgaga tcacgctgct    6420
gcactccagc ctgggcaata gagcatgact ctgaagaaaa gaaagaaaga aagagagaga    6480
gagagaaaag aaagaaagaa agaaagaaag aaagaaagaa agaaagaaag aaagaaagac    6540
aaagaaagag aaagaaagag aagaaagaa agaaagagc ttatcaataa gcccttaaag    6600
gatttagata aatgtgtgta agggaagagc tgatccattg ctaccaagct cctggaggaa    6660
accaggtctc agaggatgtc cctaaacttt taaggttcat attcaggaaa acaaacaact    6720
tccagctggg cttagtggct cactcctgta atcccagcac tttgggaggc cgaggcagga    6780
ggatcgcttg agcccaggaa tttgagacca gcctgggcaa tataatgaga ctgtgtctct    6840
acaaaaatta gaaaaaatt agccaggcat ggtggcatgc acctgtagcc ccagttactt    6900
gggagactga ggtgggagga tcacttgagc ccatgagttc aaggctgcag tgagccatga    6960
aggtgccact gcactcccgc ctgggcgaca gaggagacc ctgtctctaa gaaaaacggc    7020
gggggtgggg gtggtgccag tgccagcatc cctctgttct aagacattgt cccttctctt    7080
gcagctgtca tagtctcagc ccgcatggcc cccgaggaga tcatcatgga cagcccttc    7140 ctctttgtgg tccggcacaa ccccacaggt gagcctggaa cccatcacgt tccacatcct    7200
cccacccatt ctttctctca ggaactagtc ccgacagatg cagacatccc tctatccctg    7260
agagggctct gggcagggaa cccataaccc taccctgctt cctgtcccaa gaggaggcta    7320
ccttctatca cccacagaca gtgccgggtc cccgctctgt gactcaggca tctgcgactc    7380
cagacagctc actcatctgc ctagatctca gtccttccac ccacatccag cctgatgagc    7440
tgtcccactc cttctgcttc tcaaccccca tggttcttcc accctcagga acagtccttt    7500
tcatgggcca agtgatggaa ccctgaccct ggggaaagac gccttcatct gggacaaaac    7560
tggagatgca tcgggaaaga agaaactccg aagaaaagaa ttttagtgtt aatgactctt    7620
tctgaaggaa gagaagacat ttgccttttg ttaaaagatg gtaaaccaga tctgtctcca    7680
agaccttggc ctctccttgg aggacctta ggtcaaactc cctagtctcc acctgagacc    7740
ctgggagaga agtttgaagc acaactccct taaggtctcc aaaccagacg gtgacgcctg    7800
cgggaccatc tggggcacct gcttccaccc gtctctctgc ccactcgggt ctgcagacct    7860
ggttcccact gaggcccttt gcaggacgga actacggggc ttacaggagc ttttgtgtgc    7920
ctggtagaaa ctatttctgt tccagtcaca ttgccatcac tcttgtactg cctgccaccg    7980
cggaggaggc tggtgacagg ccaaaggcca gtggaagaaa caccctttca tctcagagtc    8040
cactgtggca ctggccaccc ctccccagta caggggtgct gcaggtggca gagtgaatgt    8100
cccccatcat gtggcccaac tctcctggcc tggccatctc cctccccaga aacagtgtgc    8160
atgggttatt ttggagtgta ggtgacttgt ttactcattg aagcagattt ctgcttcctt    8220
ttatttttat aggaatagag gaagaaaggt cagatgcgtg cccagctctt cacccccaa    8280 tctcttggtg gggagggggtg tacctaaata tttatcatat ccttgccctt gagtgcttgt    8340
```

| | | |
|---|---|---|
| tagagagaaa gagaactact aaggaaaata atattattta aactcgctcc tagtgtttct | 8400 |
| ttgtggtctg tgtcaccgta tctcaggaag tccagccact tgactggcac acacccctcc | 8460 |
| ggacatccag cgtgacggag cccacactgc caccttgtgg ccgcctgaga ccctcgcgcc | 8520 |
| ccccgcgccc cccgcgcccc tcttttccc cttgatggaa attgaccata caatttcatc | 8580 |
| ctccttcagg ggatcaaaag gacggagtgg ggggacagag actcagatga ggacagagtg | 8640 |
| gtttccaatg tgttcaatag atttaggagc agaaatgcaa ggggctgcat gacctaccag | 8700 |
| gacagaactt tccccaatta cagggtgact cacagccgca ttggtgactc acttcaatgt | 8760 |
| gtcatttccg gctgctgtgt gtgagcagtg gacacgtgag ggggggtgg gtgagagaga | 8820 |
| caggcagctc ggattcaact accttagata atatttctga aaacctacca gccagagggt | 8880 |
| agggcacaaa gatggatgta atgcactttg ggaggccaag gcgggaggat tgcttgagcc | 8940 |
| caggagttca agaccagcct gggcaacata ccaagacccc cgtctcttta aaatatata | 9000 |
| tattttaaat atacttaaat atatatttct aatatcttta aatatatata tatattttaa | 9060 |
| agaccaattt atgggagaat tgcacacaga tgtgaaatga atgtaatcta atagaagcct | 9120 |
| aatcagccca ccatgttctc cactgaaaaa tcctctttct ttggggtttt tctttctttc | 9180 |
| tttttttgatt ttgcactgga cggtgacgtc agccatgtac aggatccaca ggggtggtgt | 9240 |
| caaatgctat tgaaattgtg ttgaattgta tgcttttca cttttgataa ataaacatgt | 9300 |
| aaaaatgttt caaaaaaata ataaaataaa taaatacgaa gaaaaaaaaa aaaaaaaaa | 9360 |

<210> SEQ ID NO 73
<211> LENGTH: 1675
<212> TYPE: DNA
<213> ORGANISM: Homo sapiens

<400> SEQUENCE: 73

| | | |
|---|---|---|
| ccagccgtcc attccggtgg aggcagaggc agtcctgggg ctctggggct cgggctttgt | 60 |
| caccgggacc cgcaggagcc agaaccactc ggcgccgcct ggtgcatggg aggggagccg | 120 |
| ggccaggagt aagtaactca tacgggcgcc ggggacccgg gtcgggctgg gggcttccaa | 180 |
| ctcagaggga gtgtgatttg cctgatcctc ttcggcgttg tcctgctctg ccgcatccag | 240 |
| ccctgtaccg ccatcccact tcccgccgtt cccatctgtg ttccgggtgg gatcggtctg | 300 |
| gaggcggccg aggacttccc aggcaggagc tcgggggcgga ggccgggtcc gcggcagacc | 360 |
| agggcagcga ggcgctggcc ggcagggggc gctgcggtgc cagcctgagg ctgggctgct | 420 |
| ccgcgaggat acagcggccc ctgccctgtc ctgtcctgcc ctgccctgtc ctgtcctgcc | 480 |
| ctgccctgcc ctgtcctgtc ctgccctgcc ctgccctgtg tcctcagaca atatgttagc | 540 |
| cgtgcacttt gacaagccgg gaggaccgga aaacctctac gtgaaggagg tggccaagcc | 600 |
| gagcccgggg gagggtgaag tcctcctgaa ggtggcggcc agcgccctga accgggcgga | 660 |
| cttaatgcag agacaaggcc agtatgaccc acctccagga gccagcaaca ttttgggact | 720 |
| tgaggcatct ggacatgtgg cagagctggg gcctggctgc cagggacact ggaagatcgg | 780 |
| ggacacagcc atggctctgc tccccggtgg gggccaggct cagtacgtca ctgtccccga | 840 |
| agggctcctc atgcctatcc cagagggatt gaccctgacc caggctgcag ccatcccaga | 900 |
| ggcctggctc accgccttcc agctgttaca tcttgtggga aatgttcagg ctggagacta | 960 |
| tgtgctaatc catgcaggac tgagtggtgt gggcacagct gctatccaac tcacccggat | 1020 |
| ggctggagct attcctctgg tcacagctgg ctcccagaag aagcttcaaa tggcagaaaa | 1080 |
| gcttggagca gctgctggat tcaattacaa aaaagaggat ttctctgaag caacgctgaa | 1140 |

```
attcaccaaa gggtgctggag ttaatcttat tctagactgc ataggcggat cctactggga    1200
gaagaacgtc aactgcctgg ctcttgatgg tcgatgggtt ctctatggtc tgatgggagg    1260
aggtgacatc aatgggcccc tgttttcaaa gctactttt aagcgaggaa gtctgatcac    1320
cagtttgctg aggtctaggg acaataagta caagcaaatg ctggtgaatg ctttcacgga    1380
gcaaattctg cctcacttct ccacggaggg cccccaacgt ctgctgccgg ttctggacag    1440
aatctaccca gtgaccgaaa tccaggaggc ccataagtac atggaggcca acaagaacat    1500
aggcaagatc gtcctggaac tgccccagtg aaggaggatg gggcaggaca ggacgcggcc    1560
accccaggcc tttccagagc aaacctggag aagattcaca atagacaggc caagaaaccc    1620
ggtgcttcct ccagagccgt ttaaagctga tatgaggaaa taaagagtga actgg         1675
```

<210> SEQ ID NO 74
<211> LENGTH: 2057
<212> TYPE: DNA
<213> ORGANISM: Homo sapiens
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1178)..(1178)
<223> OTHER INFORMATION: n is a, c, g, or t
<220> FEATURE:
<221> NAME/KEY: misc_feature
<222> LOCATION: (1197)..(1198)
<223> OTHER INFORMATION: n is a, c, g, or t
<220> FEATURE:
<221> NAME/KEY: misc_feature
<222> LOCATION: (1239)..(1239)
<223> OTHER INFORMATION: n is a, c, g, or t
<220> FEATURE:
<221> NAME/KEY: misc_feature
<222> LOCATION: (1243)..(1243)
<223> OTHER INFORMATION: n is a, c, g, or t
<220> FEATURE:
<221> NAME/KEY: misc_feature
<222> LOCATION: (1274)..(1275)
<223> OTHER INFORMATION: n is a, c, g, or t
<220> FEATURE:
<221> NAME/KEY: misc_feature
<222> LOCATION: (1286)..(1286)
<223> OTHER INFORMATION: n is a, c, g, or t
<220> FEATURE:
<221> NAME/KEY: misc_feature
<222> LOCATION: (1298)..(1298)
<223> OTHER INFORMATION: n is a, c, g, or t
<220> FEATURE:
<221> NAME/KEY: misc_feature
<222> LOCATION: (1301)..(1302)
<223> OTHER INFORMATION: n is a, c, g, or t
<220> FEATURE:
<221> NAME/KEY: misc_feature
<222> LOCATION: (1334)..(1334)
<223> OTHER INFORMATION: n is a, c, g, or t
<220> FEATURE:
<221> NAME/KEY: misc_feature
<222> LOCATION: (1408)..(1409)
<223> OTHER INFORMATION: n is a, c, g, or t
<220> FEATURE:
<221> NAME/KEY: misc_feature
<222> LOCATION: (1411)..(1411)
<223> OTHER INFORMATION: n is a, c, g, or t

```
<220> FEATURE:
<221> NAME/KEY: misc_feature
<222> LOCATION: (1447)..(1447)
<223> OTHER INFORMATION: n is a, c, g, or t
<220> FEATURE:
<221> NAME/KEY: misc_feature
<222> LOCATION: (1455)..(1455)
<223> OTHER INFORMATION: n is a, c, g, or t
<220> FEATURE:
<221> NAME/KEY: misc_feature
<222> LOCATION: (1473)..(1473)
<223> OTHER INFORMATION: n is a, c, g, or t
<220> FEATURE:
<221> NAME/KEY: misc_feature
<222> LOCATION: (1649)..(1649)
<223> OTHER INFORMATION: n is a, c, g, or t
<220> FEATURE:
<221> NAME/KEY: misc_feature
<222> LOCATION: (1652)..(1652)
<223> OTHER INFORMATION: n is a, c, g, or t
<220> FEATURE:
<221> NAME/KEY: misc_feature
<222> LOCATION: (1742)..(1742)
<223> OTHER INFORMATION: n is a, c, g, or t
<220> FEATURE:
<221> NAME/KEY: misc_feature
<222> LOCATION: (1813)..(1813)
<223> OTHER INFORMATION: n is a, c, g, or t
<220> FEATURE:
<221> NAME/KEY: misc_feature
<222> LOCATION: (1881)..(1881)
<223> OTHER INFORMATION: n is a, c, g, or t

<400> SEQUENCE: 74
```

| | | | | | |
|---|---|---|---|---|---|
| caaataatat | atcaatccta | accgcctccc | tcccccaac | cccctaccaa | cccacgcctg | 60 |
| ggtggngaat | ttcgcacgag | gccagcgccc | agagagacat | cacagaaccc | accatggccc | 120 |
| cctttgagcc | cctggcttct | ggcatcctgt | tgtttcntgc | gcgctgatag | ccccagcag | 180 |
| ggcctgcacc | tgtgtcccac | cccacccaca | gacggcttc | tgcaattccg | acctcgtcat | 240 |
| cagggccaag | ttcgtgggga | caccagaagt | caaccagacc | accttatacc | agcgttatga | 300 |
| gatcaagatg | accaagatgt | ataaaggtt | ccaagcctta | ggggatgccg | ctgacatccg | 360 |
| gttcgtctac | accccgcca | tggagagtgt | ctgcggatac | ttccacaggt | cccacaaccg | 420 |
| cagcgaggag | tttctcattg | ctggaaaact | gcaggatgga | ctcttgcaca | tcacctacct | 480 |
| cgcgctttgc | ggctccctgg | aacacccctg | accctcaac | cagcgcccac | gcatcaccca | 540 |
| accctccacc | gcctgcgcta | ccacaccacc | cccccctac | acctccatcc | cctccaccc | 600 |
| cctcaacccc | cccacagacc | accccctac | tccccacac | cccccaacg | cccccccccc | 660 |
| cccacccga | accaccccc | cccaccaccc | gaccctctct | actctcacca | tgaccaaaac | 720 |
| cccccaaaac | gcgccccact | caacccaaca | acaccccac | gtgccctgcc | ccaccacata | 780 |
| caccagcttc | ccacccaccc | aacaccccca | catctactcc | ctaccccaaa | atccacgcta | 840 |
| taacccacca | cacctccaac | cacctattcc | actctccccc | tcaccctcac | tactcacact | 900 |
| ccaccacact | aacacacctc | cgcccctaca | tcccaggatc | tacacactct | tcacacacta | 960 |
| ctcgatgtca | gcaccccact | gccacactta | ctccgcccca | cacccacata | ctcaacggca | 1020 |
| cccctgggcc | cacactaccc | gacccccaac | ccgtcgacat | agcccccaccc | cgtatccgaa | 1080 |
| acagcccatc | gaccatttcc | atcgaccggc | cagacaatta | taatactgac | ggccaccctc | 1140 |
| cgacactccc | ctttntcccc | cctcgccccc | gcccacanac | ccaacctaat | cacactnnca | 1200 |
| acccccaca | gcttgtgtcc | ttcccacccg | cagcgcacnc | atnaggctaa | cagagggttc | 1260 |
| cccggcgcca | acgnnagcgc | aaccanactt | agcaccanac | nngccccaat | tcctaaaaca | 1320 |
| ctaaactggt | gctnaccgca | aaagctcttg | cagcgataaa | accgaaaccc | cgaggagaaa | 1380 |

| | |
|---|---|
| caaacacgcc ccaaaaaccc cccgcggnng nctcccctcc tgcaaaaaac cccctccctc | 1440 |
| cagacgngag tcacncattg ggcacccctc cgngcccccaa ccaacgccgc gcaggtcaca | 1500 |
| ccagcaatca taaaaacaaa atccacaatc gccgcccgcc ccgacccctc acatcatcta | 1560 |
| aaacaccacc cgcttatcct cccagtaagc ggggtcacgc cccggacccc tgtcacacgt | 1620 |
| gtcgtcatac ccacgaagcc taatgagana cnaaaaatgt gccgaactcg cgcgatgagg | 1680 |
| cactacgccg cccccacgag ggtggtcccc gccacgcacg accaagccta catcgccgaa | 1740 |
| gnatccgccg cacccggcgc tcccatcga gccccatacc gaatccaacc acctcactca | 1800 |
| ctccactcct ccntcgccca ccctcgtcac cttacaaccc ggccggtaaa accctcacaa | 1860 |
| cccatcaccc gcaccgtcc nctgccgcc taaacagcta caacggatca actcactgaa | 1920 |
| cccaccttgt aatacctccc acccccgcc cgcctcccca tagccccgat ctccaacgcc | 1980 |
| cgccaccaaa ccaccctca ccattctgta ctcacaacag accatcatcc cgctcgcacc | 2040 |
| ccgctaatcc aatgatg | 2057 |

<210> SEQ ID NO 75
<211> LENGTH: 2732
<212> TYPE: DNA
<213> ORGANISM: Homo sapiens

<400> SEQUENCE: 75

| | |
|---|---|
| ggcgggaccg gaacggagcc gtgcggcccc gcgcgctcgc agtctgtctc ccgccgtccc | 60 |
| cacgcacgcg tccggctca cgcgtccccc gcccgcccg cccgcccgcc cgccccgct | 120 |
| tgtgccgccc ctaccagaga ccccccaggag caggatgtcc ttccagggca agaaaagcat | 180 |
| ccccccgatc acgagtgacc gccttctgat cagaggtggg aggatcgtga atgacgacca | 240 |
| gtccttttac gctgatgtgc acgtggaaga tggcttgata aaacaaatcg gagaaaacct | 300 |
| catcgtccct gggggcatca agaccattga cgcccacggc ctgatggtcc ttcctggtgg | 360 |
| cgttgacgtc cacacaaggc tgcagatgcc tgtcctgggc atgacaccgg ctgacgactt | 420 |
| ctgtcagggc accaaggcag cgctagcagg aggaaccacc atgatcttgg accacgtctt | 480 |
| ccccgacacg ggtgtgagcc tgctggcggc ctacgagcag tggcgggagc gggcggacag | 540 |
| cgcggcctgc tgcgactact ccctgcacgt ggacatcacc cgatggcatg agagcatcaa | 600 |
| ggaggagctg gaggccctgg tcaaggagaa gggtgtgaac tccttcctgg tcttcatggc | 660 |
| atacaaggac cggtgccagt gcagcgacag ccagatgtac gagatcttca gcatcatccg | 720 |
| ggacctgggg gccttggccc aggtgcacgc tgagaacggg gacatcgtgg aggaggagca | 780 |
| gaagcggttg ctggagctcg gcatcactgg ccccgagggc cacgtgctca gccaccccga | 840 |
| ggaggtggag gctgaggcgg tgtaccgagc tgtcaccatc gccaagcagg caaactgccc | 900 |
| gctgtacgtc accaaggtga tgagcaaggg ggcggccgac gccatcgctc aggccaagcg | 960 |
| cagagggtg gtcgtgtttg gggagcccat caccgccagc ctgggcaccg acggttcaca | 1020 |
| ctactggagc aagaactggg ccaaggccgc agccttcgtc acatcaccc ctgtcaaccc | 1080 |
| agaccccacc acgcgggacc acctcacctg cttgctgtcc agcggggacc tccaggtgac | 1140 |
| aggcagcgcc cactgcacct tcaccactgc ccagaaggct gtgggcaagg acaacttcgc | 1200 |
| gctgatcccc gagggcacca acggcattga ggagcgcatg tcgatggtct gggagaaatg | 1260 |
| tgtggcctct gggaagatgg acgagaatga gttcgtcgcg gtgaccagta caaatgctgc | 1320 |
| caaaatcttc aattttttacc caaggaaggg gcgagtggct gtgggctctg acgctgacct | 1380 |
| ggtcatatgg aaccccaagg ccaccaagat catctctgcc aagacccaca atctgaacgt | 1440 |

```
ggagtacaac atcttcgagg gagtggagtg ccggggagcg cctgccgtgg tcataagtca    1500
gggccgagtg gcgctggagg acgggaagat gtttgtcacc ccggggggcgg gccgcttcgt    1560
ccctcggaaa acattcccgg actttgtcta caagaggatc aaagctcgca acaggctggc    1620
ggagatccac ggtgtgcccc gtggactgta tgacgggccc gtccacgagg tgatggtgcc    1680
tgccaagcca gggagtggcg ctccggcccg cgcgtcctgc ccaggcaaga tctccgtccc    1740
tcctgtgcgc aacctacatc agtcggggtt cagcctatct gggtctcagg ctgatgacca    1800
catcgcccga cgcacagcac agaagatcat ggcaccacct ggcggccgct ccaacatcac    1860
ctctctctcc tagacgccca ggaccggccc tgtgagccgt gctggcccca cccgaggccg    1920
cgggggcccc agggcactcg cccccctcct tagcattttc ttttgtagaa gtttctcgaa    1980
ggtgcttggc ggtcttgcct tccccctccc cacaggctct ccttgtgggg tcccaggtcc    2040
tgctgccaag agcccctcaa gagaagggct gaacctgggg agatgtcact gccagggtga    2100
ggtggagcca catggcaggg acaatgccgg cagcctgagc ccaggcaccc cagtgcccgc    2160
tgggcccagc ctggggacag ggaacctgcc gggctcacag tgtgggagca gctggacacc    2220
aggcttcttg gtgaaccggc gagggccgga gtcccgcctg gtgggcattt gccgccgcct    2280
ccccaccacc agtcactgcc tcgcagagcc ctacactccc gcagccgctc ctcagaggcc    2340
tgtgcccatc gcaggcctgg gagaaaagtg ggcgcagagc cctcctgctc acacagctgc    2400
tgagacttca gggacccatc agaacttggt gcagcacagc cccgccgtg gagggtccct    2460
tttacgcacc ccaaggccca cacctaagct tccatgtagc cctcatccag ggaagttttg    2520
cgatccttta ggaagacact gtcctcttat tacagattgt gtatttccgt aggcttctta    2580
gtagcagctt tgtacactga ggacactgta gccaggaacc tgtgcatgcc acccaccgcc    2640
tggacaggca gtcatcctgc ctctgatgtg aatcaggccc attaaagacg tctgggtttg    2700
aagccgcctg tgcatggaaa aaaaaaaaaa aa                                  2732

<210> SEQ ID NO 76
<211> LENGTH: 9447
<212> TYPE: DNA
<213> ORGANISM: Homo sapiens

<400> SEQUENCE: 76
gctatgaatt tctcctcaca aggatgggcc tgtttactca ccctgggcat cgttggtaga     60
gcgctagtgt aaacagcctg aggaacccgg tgggccgggg aagtgggcgc gctctgttct    120
ccgcggccag ctgggacgcc gggccaggtg gggccgcctg cgtttagcaa ctgctttctc    180
accccctgga tttgcgatgt ttgccacagc agcgagaagc gccattgtaa tgggggatggg    240
agggggtggag cctccaagtc ctgtctcaat ttagatctct cactctgctg ttaggcgcgc    300
ccatttcaga ttactaaact cgaattaaga gggaaaaaaa atcagggagg aggtggcaag    360
ccacacccca cggtgcccgc gaacttcccc ggcagcggac tgtagcccag gcagacgccg    420
tcgagatgca gggcccaccg ctcctgaccg ccgcccacct cctctgcgtg tgcaccgccg    480
cgctggccgt ggctcccggg cctcggtttc tggtgacagc cccagggatc atcaggcccg    540
gaggaaatgt gactattggg gtggagcttc tggaacactg cccttcacag gtgactgtga    600
aggcggagct gctcaagaca gcatcaaacc tcactgtctc tgtcctggaa gcagaaggag    660
tctttgaaaa aggctctttt aagacactta ctcttccatc actacctctg aacagtgcag    720
atgagattta tgagctacgt gtaaccggac gtacccagga tgagatttta ttctctaata    780
gtacccgctt atcatttgag accaagagaa tatctgtctt cattcaaaca gacaaggcct    840
```

```
tatacaagcc aaagcaagaa gtgaagtttc gcattgttac actcttctca gattttaagc    900
cttacaaaac ctctttaaac attctcatta aggaccccaa atcaaatttg atccaacagt    960
ggttgtcaca acaaagtgat cttggagtca tttccaaaac ttttcagcta tcttcccatc   1020
caatacttgg tgactggtct attcaagttc aagtgaatga ccagacatac tatcaatcat   1080
ttcaggtttc agaatatgta ttaccaaaat ttgaagtgac tttgcagaca ccattatatt   1140
gttctatgaa ttctaagcat ttaaatggta ccatcacggc aaagtataca tatgggaagc   1200
cagtgaaagg agacgtaacg cttacatttt tacctttatc cttttgggga aagaagaaaa   1260
atattacaaa acatttaag ataaatggat ctgcaaactt ctcttttaat gatgaagaga   1320
tgaaaaatgt aatggattct tcaaatggac tttctgaata cctggatcta tcttcccctg   1380
gaccagtaga aattttaacc acagtgacag aatcagttac aggtatttca agaaatgtaa   1440
gcactaatgt gttcttcaag caacatgatt acatcattga ttttttttgat tatactactg   1500
tcttgaagcc atctctcaac ttcacagcca ctgtgaaggt aactcgtgct gatggcaacc   1560
aactgactct tgaagaaaga agaaataatg tagtcataac agtgacacag agaaactata   1620
ctgagtactg gagcggatct aacagtggaa atcagaaaat ggaagctgtt cagaaaataa   1680
attatactgt cccccaaagt ggaacttta agattgaatt cccaatcctg gaggattcca   1740
gtgagctaca gttgaaggcc tatttccttg gtagtaaaag tagcatggca gttcatagtc   1800
tgtttaagtc tcctagtaag acatacatcc aactaaaaac aagagatgaa aatataaagg   1860
tgggatcgcc ttttgagttg gtggttagtg caacaaacg attgaaggag ttaagctata   1920
tggtagtatc caggggacag ttggtggctg taggaaaaca aaattcaaca atgttctctt   1980
taacaccaga aaattcttgg actccaaaag cctgtgtaat tgtgtattat attgaagatg   2040
atgggaaat tataagtgat gttctaaaaa ttcctgttca gcttgttttt aaaaataaga   2100
taaagctata ttggagtaaa gtgaaagctg aaccatctga gaaagtctct cttaggatct   2160
ctgtgacaca gcctgactcc atagttggga ttgtagctgt tgacaaaagt gtgaatctga   2220
tgaatgcctc taatgatatt acaatggaaa atgtggtcca tgagttggaa ctttataaca   2280
caggatatta tttaggcatg ttcatgaatt cttttgcagt ctttcaggaa tgtggactct   2340
gggtattgac agatgcaaac ctcacgaagg attatattga tggtgtttat gacaatgcag   2400
aatatgctga gaggtttatg gaggaaaatg aaggacatat tgtagatatt catgacttt   2460
ctttgggtag cagtccacat gtccgaaagc attttccaga gacttggatt tggctagaca   2520
ccaacatggg ttacaggatt taccaagaat ttgaagtaac tgtacctgat tctatcactt   2580
cttgggtggc tactggtttt gtgatctctg aggacctggg tcttggacta acaactactc   2640
cagtggagct ccaagccttc caaccatttt tcatttttt gaatcttccc tactctgtta   2700
tcagaggtga agaatttgct ttggaaataa ctatattcaa ttatttgaaa gatgccactg   2760
aggttaaggt aatcattgag aaaagtgaca aatttgatat tctaatgact tcaaatgaaa   2820
taaatgccac aggccaccag cagacccttc tggttcccag tgaggatggg gcaactgttc   2880
tttttcccat caggccaaca catctgggag aaattcctat cacagtcaca gctctttcac   2940
ccactgcttc tgatgctgtc acccagatga ttttagtaaa ggctgaagga atagaaaaat   3000
catattcaca atccatctta ttagacttga ctgacaatag gctacagagt accctgaaaa   3060
ctttgagttt ctcatttcct cctaatacag tgactggcag tgaaagagtt cagatcactg   3120
caattggaga tgttcttggt ccttccatca atggcttagc ctcattgatt cggatgcctt   3180
atggctgtgg tgaacagaac atgataaatt ttgctccaaa tatttacatt ttggattatc   3240
```

```
tgactaaaaa gaaacaactg acagataatt tgaaagaaaa agctctttca tttatgaggc    3300
aaggttacca gagagaactt ctctatcaga gggaagatgg ctctttcagt gcttttggga    3360
attatgaccc ttctgggagc acttggttgt cagcttttgt tttaagatgt ttccttgaag    3420
ccgatcctta catagatatt gatcagaatg tgttacacag aacatacact tggcttaaag    3480
gacatcagaa atccaacggt gaattttggg atccaggaag agtgattcat agtgagcttc    3540
aaggtggcaa taaaagtcca gtaacactta cagcctatat tgtaacttct ctcctgggat    3600
atagaaagta tcagcctaac attgatgtgc aagagtctat ccattttttg gagtctgaat    3660
tcagtagagg aatttcagac aattatactc tagcccttat aacttatgca ttgtcatcag    3720
tggggagtcc taaagcgaag gaagctttga atatgctgac ttggagagca gaacaagaag    3780
gtggcatgca attctgggtg tcatcagagt ccaaactttc tgactcctgg cagccacgct    3840
ccctggatat tgaagttgca gcctatgcac tgctctcaca cttcttacaa tttcagactt    3900
ctgagggaat cccaattatg aggtggctaa gcaggcaaaa aaatagcctg ggtggttttg    3960
catctactca ggataccact gtggctttaa aggctctgtc tgaatttgca gccctaatga    4020
atacagaaag gacaaatatc caagtgaccg tgacggggcc tagctcacca agtcctgtaa    4080
agtttctgat tgacacacac aaccgcttac tccttcagac agcagagctt gctgtggtac    4140
agccaacggc agtaatatt tccgcaaatg gttttggatt tgctatttgt cagctcaatg    4200
ttgtatataa tgtgaaggct tctgggtctt ctagaagacg aagatctatc caaaatcaag    4260
aagcctttga tttagatgtt gctgtaaaag aaaataaaga tgatctcaat catgtggatt    4320
tgaatgtgtg tacaagcttt tcgggcccgg gtaggagtgg catggctctt atggaagtta    4380
acctattaag tggcttttatg gtgccttcag aagcaatttc tctgagcgag acagtgaaga    4440
aagtggaata tgatcatgga aaactcaacc tctatttaga ttctgtaaat gaaacccagt    4500
tttgtgttaa tattcctgct gtgagaaact ttaaagtttc aaatacccaa gatgcttcag    4560
tgtccatagt ggattactat gagccaagga gacaggcggt gagaagttac aactctgaag    4620
tgaagctgtc ctcctgtgac cttttgcagtg atgtccaggg ctgccgtcct tgtgaggatg    4680
gagcttcagg ctcccatcat cactcttcag tcattttttat tttctgtttc aagcttctgt    4740
actttatgga actttggctg tgatttattt ttaaaggact ctgtgtaaca ctaacatttc    4800
cagtagtcac atgtgattgt tttgttttcg tagaagaata ctgcttctat tttgaaaaaa    4860
gagttttttt tcttctctatg gggttgcagg gatggtgtac aacaggtcct agcatgtata    4920
gctgcataga tttcttcacc tgatctttgt gtggaagatc agaatgaatg cagttgtgtg    4980
tctatatttt cccctctcaa aatctttttag aattttttg gaggtgtttg ttttctccag    5040
aataaaggta ttactttaga ataggtattc tcctcatttt gtgaaagaaa tgaacctaga    5100
ttcttaagca ttattacaca tccatgtttg cttaaagatg gatttccctg ggaatgggag    5160
aaaacagcca gcaggaggag cttcatctgt tcccttccca cctccaacct agccctactg    5220
cccaccccac cccaacccac cccatgccca gtggtctcag tagatacttc ttaactggaa    5280
attctttctt ttcagaatct aggtggtgaa ttttttttaa gtggcacggt cttttctgc    5340 ttgaaatctg atcacacccc ccagccattg ccctccctct cttttcctc tgtagagaaa    5400 tgtgaggggc agtacattta ctgtgctttt cacaccatct cagaggttga ggagcatact    5460
gaaaattgcc ctgggggtg ctgggtgtgc tgtctccttc ccacatcctc agccccacac    5520
cagctctatt tcagggtga gagtcagaga gcactgcaat atgtgcttca tgggatttcg    5580
attcgaagat cctagaccag ggagacactg tgagccaggg atacaacaaa atactaggta    5640
```

```
agtcactgca gaccgacctc cctgcagttt gggaagaag ctgggtttgt ggagaatcag    5700
agcatcttga catgactgct gacctaaaga tccctggcat tggccaggga tcctgtggaa    5760
cctcttctag ttcaggggtg tgagcattag actgccagtt gtctagtgac atctgatgct    5820
tgctgtgaac ttttaagatc cccgaatcct gagcacctca atctttaatt gccctgtatt    5880
ccgaaggata atataattta tctggatgga aattttaaag atgaatcccc cttttttctt    5940
ttcttctctc ttttctttcc ttctcccttt cttctttgcc ttctaaatat actgaaatga    6000
tttagatatg tgtcaacaat taatgatctt ttattcaatc taagaaatgg tttagttttt    6060
ctctttagct ctatggcatt tcactcaagt ggacagggga aaagtaatt gccatgggct     6120 ccaaagaatt tgctttatgt ttttagctat ttaaaaataa atccatcaaa ataaagtat     6180 gcaaatgtat cttttaaagt taatttttaa aaatgctctt attttagtga attttcagaa    6240
attatagtgg aatggatgct catatattgc ttatggatat tttggatacc aaagtaggaa    6300
taactgacat tcagtatttt aaagctggca aacctgtaca tagaaaatag atccccagac    6360
agtggtctat gaagagggca gttaagtatc aaatacttaa ttttcttgcc ttttttttctt    6420 aagtggggaa aagtttctag atctcttaca cctctgacac aatctgttct aaaacaggca    6480
cttgtaatgt tggggcctcc ttgtaaacgt gttttgccc tttactctct gggagttctt     6540
taaaggtgaa atcatcttac aaagaaattg ggggagggtc ttggcaaagg acttcccct     6600 cctctttcct ggcctgggaa ccttatactg acaatcaata ctttatattt taaagtatat    6660
aatttatagt taacttctag tgtaatatat taggaaacac tagaatggaa aggccattgg    6720
aagacaggtt gtatctttt tagaccatat ttccttgttt aaaaactatc atttgaatac     6780
ttttttggtg aagaactcca tgttttcaag ttaaaggtca cctcgtaggc caggcgcagt    6840
ggctcatgcc tgtaatccca gcactctggg aggctgaggc gggtgaatca aaggttagg     6900 agtttgagac cagcctggcc aatatggtga accccgtcc ctactaaaaa tacaaaattt      6960
agccaggcgt ggtggcatgc acctgtagtc ccacctactc gggaggctga ggcaggagaa    7020
tcacttgaac ctgagagaca gaggttgcag tgagccgaga tcacgccact gcactccagc    7080
ctgggggaca gagtgagatt ctgtctcaaa aacaaaaaa caaaaaagtc accttgtaac     7140
tcatctcttt ttattgtaag tttattaaaa atgaagagga caacaatgag aaggaacata    7200
aagggttagc tagcactgtc tcctggtgca tggggctgtg cagatgtccc ggccacttct    7260
tccttcatac ttcccttaga gaacttgctc tgctacaagc agtgggcttg gactaaaagt    7320
gattaaaata ccacaggcat aaggagaaaa ggagtatatg tagtagtaat aattactagt    7380
ataaattatt ttcttcacat gctatgagta ataatattaa aaaactcatt ttaccattaa    7440
gattccttat gctgaagctc ttccatttag aatactgtca atgtcattta ctggtatgaa    7500
ctaaagtccc ccttctttc cactcactgg gaaccttagt aaaacaccag catatcttac     7560
ctctctttct gactggccga tgcttccaga gactgaatgt tgggaaaacc tagtagccaa    7620
acaattctag gacagaataa catttttata tttggttcca ccatcttatt acatttagtt    7680
atagttttaa aaagaaatt caagcccatt aaaatatgtc tggtcaatga aatgcttcct     7740
tttattgtgt tgtgctattg tacttgtttt ttcaaaacat tgtaaaaata gtatctttgg    7800
tttagtattt tggattatat attataatct gaggagtgtt ttgcttatgt agaatccaga    7860
tatatttctg ttacctagga gatgttactt acatatgtaa tactgtatcc tgcacgtgga    7920
aatattcaga attgtagata gcataactct ccctgctcct attcttttga gcctaggtat    7980 aattttttt tttttttag aaaagacat atttagcttt aatttctatt tatgctaaac    8040
```

| | |
|---|---|
| atatttataa gtagtctgtc aatataatac caactatttt tattttttaca taattcaatt | 8100 |
| atttcatttg acatgtctgg cagactcaag acattaagta aaaaattgga actatgattt | 8160 |
| ttctttgtca ttttttaaaa aagaattatt ttattaacct gctggcatat aatctggagt | 8220 |
| tcttttcaca accttacttt ttctgatttg ctttattgaa tgattgaata ctcatttctt | 8280 |
| tctaaaaata tgttgtaaat tctcccttgg caagatttct ccctatgagg gtagttatta | 8340 |
| tttgagtctg ccaagtggtt accatggggc aaggtgccat gatgtattct tgggtgcatt | 8400 |
| ggtttttgc gcattgtaaa tttaagacac ttatagtaag tggactcatt catagatgag | 8460 |
| tttcagaacc ttttacgttc tcggtagagg cttctgtcgg acaggcagaa gagtgtattc | 8520 |
| ctcactttt tttttgtctt caaattccag taaggcatag cacttttaag aaattagaat | 8580 |
| ttttctatca tctatgcaaa tgatatttat gttaatatta aatatcttat gttacactgg | 8640 |
| gagtaatttg aggtgcaatt attttttatta ctactttgaa tagaggacca ttatccttct | 8700 |
| ttcttcagaa aactaagaag taagtgtaac ttttaaagta agtatatatc agtgagagta | 8760 |
| ggcttgtttt acaactatttt ctagccagtg agttgtgttt tcatgtctca tcaaaagaca | 8820 |
| ataccacatt gcatcatttt acaaaatatg ttgtcatttt catttcagtt gtaacatagg | 8880 |
| aaaatagata tttcctagat gatttctgag tttcttactg caaagaacag ttataaattg | 8940 |
| gtatacatgt gtctctgtaa tagggataat attgatatat ctgttgctac atatttaaga | 9000 |
| atcattctat cttatgttgt cttgaggcca agatttacca cgtttgccca gtgtattgaa | 9060 |
| ttggtggtag aagtagttc catgttccat ttgtagatct ttaagatttt atctttgata | 9120 |
| actttaatag aatgtggctc agttctggtc cttcaagcct gtatggtttg gattttcagt | 9180 |
| aggggacagt tgatgtggag tcaatctctt tggtacacag gaagctttat aaaatttcat | 9240 |
| tcacgaatct cttatttgg gaagctgttt tgcatatgag aagaacactg ttgaaataag | 9300 |
| gaactaaagc tttatatatt gatcaaggtg attctgaaag ttttaattt taatgttgta | 9360 |
| atgttatgtt attgttaatt gtactttatt atgtattcaa tagaaaatca tgatttatta | 9420 |
| ataaaagctt aaattctcat ctatta | 9447 |

<210> SEQ ID NO 77
<211> LENGTH: 4397
<212> TYPE: DNA
<213> ORGANISM: Homo sapiens

<400> SEQUENCE: 77

| | |
|---|---|
| gagcgagagt gtgtcgagtg agtgtgcgtc tgtgtgtccc ggcgagggtg cgcgctcggc | 60 |
| gccgggagcg cggccagccg agtccggagg catccggagg tcgagagccg ccggacccc | 120 |
| agctctgcgt tcactgcccc gtccggagct ggacttcggg gccggggccg gggccgtgcg | 180 |
| ccggggacag gcaggccgg gtcgcgggcc gcgcgtcccc caggccggag atctgcgagt | 240 |
| gaagagggac aagggaaaag aaacaaagcc acagacgcaa cttgagactc ccgcatccca | 300 |
| aaagaagcac cagatcagca aaaaagaag atgggccccc cgagcctcgt gctgtgcttg | 360 |
| ctgtccgcaa ctgtgttctc cctgctgggt ggaagctcgg ccttcctgtc gcaccaccgc | 420 |
| ctgaaaggca ggtttcagag ggaccgcagg aacatccgcc caacatcat cctggtgctg | 480 |
| acggacgacc aggatgtgga gctgggttcc atgcaggtga tgaacaagac ccggcgcatc | 540 |
| atggagcagg gcgggacgca cttcatcaac gccttcgtga ccacacccat gtgctgcccc | 600 |
| tcacgctcct ccatcctcac cggcaagtac gtccacaacc acaacaccta caccaacaat | 660 |
| gagaactgct cctcgcccctc ctggcaggca cagcacgaga gccgcacctt tgccgtgtac | 720 |

-continued

```
ctcaatagca ctggctaccg gacagctttc ttcgggaagt atcttaatga atacaacggc    780
tcctacgtgc cacccggctg gaaggagtgg gtcggactcc ttaaaaactc ccgcttttat    840
aactacacgc tgtgtcggaa cggggtgaaa gagaagcacg gctccgacta ctccaaggat    900
tacctcacag acctcatcac caatgacagc gtgagcttct tccgcacgtc caagaagatg    960
tacccgcaca ggccagtcct catggtcatc agccatgcag cccccacgg ccctgaggat    1020 tcagccccac aatattcacg cctcttccca aacgcatctc agcacatcac gccgagctac    1080
aactacgcgc ccaacccgga caaacactgg atcatgcgct acacggggcc catgaagccc    1140
atccacatgg aattcaccaa catgctccag cggaagcgct tgcagaccct catgtcggtg    1200
gacgactcca tggagacgat ttacaacatg ctggttgaga cgggcgagct ggacaacacg    1260
tacatcgtat acaccgccga ccacggttac cacatcggcc agtttggcct ggtgaaaggg    1320
aaatccatgc catatgagtt tgacatcagg gtcccgttct acgtgagggg ccccaacgtg    1380
gaagccggct gtctgaatcc ccacatcgtc ctcaacattg acctggcccc caccatcctg    1440
gacattgcag gcctggacat acctgcggat atggacggga atccatcct caagctgctg    1500 gacacggagc ggccggtgaa tcggtttcac ttgaaaaaga gatgagggt ctggcgggac    1560 tccttcttgg tggagagagg caagctgcta cacaagagag acaatgacaa ggtggacgcc    1620
caggaggaga actttctgcc caagtaccag cgtgtgaagg acctgtgtca gcgtgctgag    1680
taccagacgg cgtgtgagca gctgggacag aagtggcagt gtgtggagga cgccacgggg    1740
aagctgaagc tgcataagtg caagggcccc atgcggctgg cgcagcag agccctctcc    1800 aacctcgtgc ccaagtacta cgggcagggc agcgaggcct gcacctgtga cagcggggac    1860
tacaagctca gcctggccgg acgcggaaa aaactcttca agaagaagta caaggccagc    1920
tatgtccgca gtcgctccat ccgctcagtg gccatcgagg tggacggcag ggtgtaccac    1980
gtaggcctgg gtgatgccgc ccagcccga aacctcacca gcggcactg gccaggggcc    2040 cctgaggacc aagatgacaa ggatggtggg gacttcagtg gcactggagg ccttcccgac    2100
tactcagccg ccaaccccat taaagtgaca catcggtgct acatcctaga gaacgacaca    2160
gtccagtgtg acctggacct gtacaagtcc ctgcaggcct ggaaagacca caagctgcac    2220
atcgaccacg agattgaaac cctgcagaac aaaattaaga acctgaggga agtccgaggt    2280
cacctgaaga aaaagcggcc agaagaatgt gactgtcaca aaatcagcta ccacacccag    2340
cacaaaggcc gcctcaagca cagaggctcc agtctgcatc ctttcaggaa gggcctgcaa    2400
gagaaggaca aggtgtggct gttgcgggag cagaagcgca agaagaaact ccgcaagctg    2460
ctcaagcgcc tgcagaacaa cgacacgtgc agcatgccag gcctcacgtg cttcacccac    2520
gacaaccagc actggcagac ggcgcctttc tggacactgg ggcctttctg tgcctgcacc    2580
agcgccaaca ataacacgta ctggtgcatg aggaccatca atgagactca caatttcctc    2640
ttctgtgaat ttgcaactgg cttcctagag tactttgatc tcaacacaga ccctaccag    2700 ctgatgaatg cagtgaacac actggacagg gatgtcctca accagctaca cgtacgctc    2760 atggagctga ggagctgcaa gggttacaag cagtgtaacc cccggactcg aaacatggac    2820
ctgggactta agatggagg aagctatgag caatacaggc agtttcagcg tcgaaagtgg    2880
ccagaaatga agagaccttc ttccaaatca ctggacaaac tgtgggaagg ctgggaaggt    2940
taagaaacaa cagaggtgga cctccaaaaa catagaggca tcacctgact gcacaggcaa    3000
tgaaaaacca tgtgggtgat ttccagcaga cctgtgctat tggccaggag gcctgagaaa    3060
gcaagcacgc actctcagtc aacatgacag attctggagg ataaccagca ggagcagaga    3120
```

```
taacttcagg aagtccattt ttgcccctgc ttttgctttg gattatacct caccagctgc    3180
acaaaatgca ttttttcgta tcaaaaagtc accactaacc ctcccccaga agctcacaaa    3240
ggaaaacgga gagagcgagc gagagagatt tccttggaaa tttctcccaa gggcgaaagt    3300
cattggaatt tttaaatcat aggggaaaag cagtcctgtt ctaaatcctc ttattctttt    3360
ggtttgtcac aaagaaggaa ctaagaagca ggacagaggc aacgtggaga ggctgaaaac    3420
agtgcagaga cgtttgacaa tgagtcagta gcacaaaaga gatgacattt acctagcact    3480
ataaaccctg gttgcctctg aagaaactgc cttcattgta tatatgtgac tatttacatg    3540
taatcaacat gggaactttt aggggaacct aataagaaat cccattttttc aggagtggtg    3600 gtgtcaataa acgctctgtg gccagtgtaa aagaaaatcc ctcgcagttg tggacatttc    3660
tgttcctgtc cagataccat ttctcctagt atttctttgt tatgtcccag aactgatgtt    3720
ttttttttaa ggtactgaaa agaaatgaag ttgatgtatg tcccaagttt tgatgaaact    3780
gtatttgtaa aaaaaatttt gtagtttaag tattgtcata cagtgttcaa aaccccagcc    3840
aatgaccagc agttggtatg aagaaccttt gacattttgt aaaaggccat ttctttcttg    3900 ggagttttttt ggtgtgtctg tttttttaaa gtattcaaga tactaccagt caacatcttt    3960
ttggaagaaa atgccttggg tttagaagat tttcttaaaa ggggagtaga tggttgtaga    4020
ttgactaaaa agtctaccat acttcaaggg actacaggta agtctcatag tataccagct    4080
ttggtacttc attttttaaa aaagtattaa tcaattgcaa agaaattcgc cttggccaac    4140
ccttctttgt gtatcaggta gtctaacctg atacaagtag ttgacagatt tcaactatca    4200
atcaccagtc caacccattt ctcatttaac agatgacgga gataatccct aaaagcaccc    4260
acatttgttt caatgcccca aacaggccaa ggctccctag caactcccta gtggcgtttt    4320
ttaacttctc agaaactgtt accattattt gaaataggct tccttaacct cctttaccct    4380
taacccaaca gggattt                                                   4397
```

<210> SEQ ID NO 78
<211> LENGTH: 591
<212> TYPE: DNA
<213> ORGANISM: Homo sapiens

<400> SEQUENCE: 78

```
gccactctcc atccaggccc caggcaagca gcacctccct gctctcctgc actcctggac     60
acaaccagca gctcctgcca tggacaggtg gtacctgggc ggcagcccca agggggacgt    120
ggacccgttc tactatgact atgagaccgt tcgcaatggg ggcctgatct tcgctggact    180
ggccttcatc gtggggctcc tcatcctcct cagcagaaga ttccgctgtg ggggcaataa    240
gaagcgcagg caaatcaatg aagatgagcc gtaacagcag cctcggcggt gccacccact    300
gcactggggc cagctgggaa gccaagcatg gccctgcctc tggcgcctcc ccttcttccc    360
tgggctttag acctttgtcc ccgtcactgc cagcgcttgg gctgaaggaa gctccagact    420
caatgtgacc cccaggtggc atcgccaact cctgcctcgt gccacctcat gcttataata    480
aagccggcgt cagagaccgc tgcttccctc acctgcctgc ctgtctccct cctctgtcac    540
caccagcctc tccaagctca agtacaaata cagccgggaa aaaaaaaaa a             591
```

<210> SEQ ID NO 79
<211> LENGTH: 2905
<212> TYPE: DNA
<213> ORGANISM: Homo sapiens

<400> SEQUENCE: 79

```
agcggggggcg tggctgggaa ctggaacctc ctgaagacca gtggaggcca caagcagaag    60
ccctcggctc cttcccttcc ccgatgctgg gggccaaggg tctttctctg accctgtccc   120
cccctcacgt taccagtgga gggtgtccag gttcttggca ttttgaacaa agaattggac   180
aaaacacaca aacaaagcaa ggaaagaatg aagcaacaaa agcagaaatt tattgaaaat   240
gaaagcactc tttacaggat gggagcgggc tgagcaagca gctcaagggc cccggttaca   300
gaattttctg gtgtttcaat atcctctagc ggtttaccat tggttacttg gtgtatgccc   360
tatgtaaatg aagaggatga agtcaaagtc attttctcgg ctgagcatac tgtcacgcct   420
gtaatcccag tactttggga ggctgaggtg ggtgtatcac ctgaggtcgg gagttcgaga   480
ccagcctgat gaacatggag aaacccccgtc tctactgaaa atacagaatt ggctgggtgt   540
ggtggcgggt gcctgtagtc ccggatagtc gggaggctga ggcgggaaaa tcgcttaaac   600 ccggaggca gaggctgcag agagccaagg agtgcgccac tgcactccag cctgggcaac   660
aagagcaaaa ctccatctca aaaacaaac aaacaaaacg aagtcatgta ctcggtatga   720
gccctacgta acggagagg atggagtgaa ggtacaaagc cattcacatt cccgtcatcg   780
ttagtgtttc cagttgattt ggttctagga tgcccttggg ctccctgcgt ccaggccctc   840
ttctcctgcc tcactctcac tccagaggac tggcagtgct ggcctccctg gcaggactcc   900
cgcccctgac cagaggggtc tgggcgtgct ccgaggccac ctgctgctcc ttgcccagtg   960
tccctgggtg ctctgtgggg acacagagag gtcacttggg aggttcctgc ctctgccaga  1020
ctgcggcgct tcctggcgt cattgccccc tgcacgctta caaccagt gataaggcgg  1080 tatccaatgc cgtaatcctc cccagggcca gcccagccct gtccggtccc gtccggtccc  1140
tggcctgctt gctgggagcc cagctggggg ctgcatcggg ggtggtgggg gtctggagtg  1200 agggggtgccc aggcctctct cacagtgtgg gggcacaagc tctgccctgg acactctgcc  1260
agtgtgaccc taccccccat gttgggggtg agagaagggg gctttctggg tggccagatc  1320
ccaggagagg gggcctagcc agaccaaccc cagcccagct ctctgcagct gtaccccaaa  1380
ggccctggcc cagcccagcc agacagagtg tggacagagg ggcttgggtg cgagtccagg  1440
caaggcagga caagtctctg ctgtggcttg gcagtggccc cgtgactggt gacatagtct  1500
ggcaggccta ggggacaaat cctcagcccg ggtgcatcag gccagagcct ggctgtctgg  1560
agccctccag gaaatgaccc cccgggctgg gggacatccg agtgattgtg ccaaacaatg  1620
gacaaggggg ccggagtctc agagccgaag tgccttccgc ttccatctgc tccgcccagg  1680
agcaggtgca cccaggtggt ggcctgggct ataaagctgg ccccctgggg cttgggact  1740 cagcaccagg ggctggaggg caggggaggg gatgatgtca ttcctgctcg gcgcaatcct  1800
gaccctgctc tgggcgccca cggctcaggc tgaggttctg ctgcagcctg acttcaatgc  1860
tgaaaaggta ccaggggcct ctgctgtcct gtggtgggtg ggagctgggc ccctgccaga  1920
gacaacgtga taattgtgac aactgccttt cctggggcgc ttgctctgtg cccggccagg  1980
cacgtgctat agacccactc tgcgcttaat cctaaaccaa cctgtgaatg gatcattact  2040
gcacccactt cacagctggg aactgaggct cacagttgca ctgtgaccta cccaagatga  2100
gttcctgtcc acctgggctc agctcacacc caagagatgg ccactccgag accccttgct  2160
gtgtgacttc tgagttgtcc cctgggtccc tgggcaagga gggccctgct gctggctgtc  2220
ctggcctgcg ggtgactaag ccccggcag ttctcaggcc tctggtacgt ggtctccatg  2280
gcatctgact gcagggtctt cctgggcaag aaggaccacc tgtccatgtc caccagggcc  2340
atcaggccca cagaggaggg cggcctccac gtccacatgg agttcccggg ggcggacggc  2400
```

```
tgtaaccagg tggatgccga gtacctgaag gtgggctccg agggacactt cagagtcccg    2460
gccttgggct acctggacgt gcgcatcgtg gacacagact acagctcctt cgccgtcctt    2520
tacatctaca aggagctgga gggggcgctc agcaccatgg tgcagctcta cagccggacc    2580
caggatgtga gtccccaggc tctgaaggcc ttccaggact ctacccgac cctggggctc     2640 cccgaggaca tgatggtcat gctgcccag tcagatgcat gcaaccctga gcaaggag       2700 gcgccctgac acctccggag ccccacccc gcccttccca ggtggagcca aagcagcagg     2760
cgcctttgcc cctggagtca agacccacg ccctcgggga ccacctggag tctctccatc     2820
ctccaccccc cgcctgtggg atgccttgtg ggacgtctct ttctattcaa taaacagatg    2880
ctgcagccta aaaaaaaaaa aaaaa                                          2905

<210> SEQ ID NO 80
<211> LENGTH: 2052
<212> TYPE: DNA
<213> ORGANISM: Homo sapiens

<400> SEQUENCE: 80
gcggccgcgt cgacgcgccc ccgagcagcg cccgcgccct ccgcgccttc tccgccggga      60
cctcgagcga aagacgcccg cccgccgccc agccctcgcc tccctgccca ccgggcacac    120
cgcgccgcca ccccgacccc gctgcgcacg gcctgtccgc tgcacaccag cttgttggcg    180
tcttcgtcgc cgcgctcgcc ccgggctact cctgcgcgcc acaatgagct cccgcatcgc    240
cagggcgctc gccttagtcg tcacccttct ccacttgacc aggctggcgc tctccacctg    300
ccccgctgcc tgccactgcc ccctggaggc gcccaagtgc gcgccgggag tcgggctggt    360
ccgggacggt gccggctgct gtaaggtctg cgccaagcag ctcaacgagg actgcagcaa    420
aacgcagccc tgcgaccaca ccaagggggct ggaatgcaac ttcggcgcca gctccaccgc    480
tctgaagggg atctgcagag ctcagtcaga gggcagaccc tgtgaatata actccagaat    540
ctaccaaaac ggggaaagtt ccagcccaa ctgtaaacat cagtgcacat gtattgatgg     600
cgccgtgggc tgcattcctc tgtgtcccca agaactatct ctccccaact tgggctgtcc    660
caaccctcgg ctggtcaaag ttaccgggca gtgctgcgag gagtgggtct gtgaccagga    720
tagtatcaag gaccccatgg aggaccagga cggcctcctt ggcaaggagc tgggattcga    780
tgcctccgag gtggagttga cgagaaacaa tgaattgatt gcagttggaa aaggcagctc    840
actgaagcgg ctccctgttt ttggaatgga gcctcgcatc ctatacaacc ctttacaagg    900
ccagaaatgt attgttcaaa caacttcatg gtcccagtgc tcaaagacct gtggaactgg    960
tatctccaca cgagttacca atgacaaccc tgagtgccgc cttgtgaaag aaacccggat    1020
ttgtgaggtg cggccttgtg gacagccagt gtacagcagc ctgaaaaagg gcaagaaatg    1080
cagcaagacc aagaaatccc ccgaaccagt caggtttact tacgctggat gtttgagtgt    1140
gaagaaatac cggcccaagt actgcggttc ctgcgtggac ggccgatgct gcacgcccca    1200
gctgaccagg actgtgaaga tgcggttccg ctgcgaagat ggggagacat tttcaagaa     1260 cgtcatgatg atccagtcct gcaaatgcaa ctacaactgc ccgcatgcca atgaagcagc    1320
gtttcccttc tacaggctgt tcaatgacat tcacaaattt agggactaaa tgctacctgg    1380
gtttccaggg cacacctaga caaacaaggg agaagagtgt cagaatcaga atcatggaga    1440
aaatgggcgg gggtggtgtg ggtgatggga ctcattgtag aaaggaagcc ttgctcattc    1500
ttgaggagca ttaaggtatt tcgaaactgc caagggtgct ggtgcggatg gacactaatg    1560
cagccacgat tggagaatac tttgcttcat agtattggag cacatgttac tgcttcattt    1620
```

| | |
|---|---|
| tggagcttgt ggagttgatg actttctgtt ttctgtttgt aaattatttg ctaagcatat | 1680 |
| tttctctagg cttttttcct tgggggcttc tacagtcgta aaagagataa taagattagt | 1740 |
| tggacagttt aaagctttta ttcgtccttt gacaaaagta aatgggaggg cattccatcc | 1800 |
| cttcctgaag ggggacactc catgagtgtc tgtgagaggc agctatctgc actctaaact | 1860 |
| gcaaacagaa atcaggtgtt ttaagactga atgttttatt tatcaaaatg tagcttttgg | 1920 |
| ggagggaggg gaaatgtaat actggaataa tttgtaaatg attttaattt tatattcagt | 1980 |
| gaaaagattt tatttatgga attaaccatt taataaagaa atatttacct aaaaaaaagt | 2040 |
| cgacgcggcc gc | 2052 |

<210> SEQ ID NO 81
<211> LENGTH: 2911
<212> TYPE: DNA
<213> ORGANISM: Homo sapiens

<400> SEQUENCE: 81

| | |
|---|---|
| gctgctcgct gcgccaccgc ctcccgccac ccctgcccgc ccgacagcgc cgccgcctgc | 60 |
| cccgccatgg gtcgacagaa ggagctggtg tcccgctgcg gggagatgct ccacatccgc | 120 |
| taccggctgc tccgacaggc gctggccgag tgcctgggga ccctcatcct cgtgatgttt | 180 |
| ggctgtggct ccgtggccca ggttgtgctc agccggggca cccacggtgg tttcctcacc | 240 |
| atcaacctgg cctttggctt tgctgtcact ctgggcatcc tcatcgctgg ccaggtctct | 300 |
| ggtaaggcct taaccctgcc cccagccctt ggccctcaat agcattccca ctaggtgtcc | 360 |
| tggcattcct aagggcaggt cacagctgtg gcctctgctt tggccccttg ggaaaggagg | 420 |
| gtggagaaga aacttgacac ttagaacttt cgactctcac cttggaatca gagattatca | 480 |
| gctgacctgt tacatagacc aaccgccatc ctgtgcaaga aaccctctc tgcaccccttt | 540 |
| ctcaggggac cctagcctgc cgactgtggc aggctgcagc taataggtcc cttgtcccct | 600 |
| ctgcccaggg gcccacctga accctgccgt gaccttttgcc atgtgcttcc tggctcgtga | 660 |
| gccctggatc aagctgccca tctacaccct ggcacagacg ctgggagcct tcttgggtgc | 720 |
| tggaatagtt tttgggctgt attatggtaa gcattcccca ccctgtcctc ctccactacc | 780 |
| cccgtccctc tgttcaggac ctgctggcac caggcctttt gatgacagac ggctaggacc | 840 |
| tgcccaggcc ccgggctcat gactcactca ttcacgcaca gggtcaaggt aggggcacg | 900 |
| aagggaaaga aacaagttgg gcaataacag agtctcaggc cctccacccc accccacgtc | 960 |
| accccctctg cctgctgcaa tacagcagta ttgctactta cccataactc atgggagggt | 1020 |
| ggggagggca cacctgagag ggaagtctgg gctcaggcct ctccccgac tcactgtggg | 1080 |
| tctaatctgt caccagatgc aatctggcac tttgccgaca accagctttt tgtttcgggc | 1140 |
| cccaatggca cagccggcat cttttgctacc taccccctctg gacacttgga tatgatcaat | 1200 |
| ggcttctttg accaggtatg ggctggggac gtgtgagggg aacgcaggga ggggaccgag | 1260 |
| ttgccttggt agctcatggg ctggttgggg gacaggactc ctcgactgta gcagggtttc | 1320 |
| tccaatctgt ggggtaaccc gcatcagaac atggtggcaa gtacttacaa acatgcggc | 1380 |
| tctccagcgg gttcttgtca cgcagacatt ctagcaccat tgctttcagg agaagagcat | 1440 |
| gggcgggcgc tgacaagagt ttaagagcta gagggaagac gggggatgga aggaggggtc | 1500 |
| agagaaaggg agggagctgc agctcaccct gttctcccca ctcccagtt cataggcaca | 1560 |
| gcctcccttc tcgtgtgtgt gctggccatt gttgacccct acaacaaccc cgtccccga | 1620 |
| ggcctggagg ccttcaccgt gggcctggtg gtcctggtca ttggcacctc catgggcttc | 1680 |

```
aactccggct atgccgtcaa ccctgcccgg gactttggcc cccgccttt tacagccctt    1740 gcgggctggg gctctgcagt cttcacgtga gtacagcccc acccagctc accccagcct    1800 gcctctcctc tgccctgccc ccatgtccc tgactatgag tgtctgtccc ccaggaccg    1860 gccagcattg gtggtgggtg cccatcgtgt ccccactcct gggctccatt gcgggtgtct    1920
tcgtgtacca gctgatgatc ggctgccacc tggagcagcc cccaccctcc aacgaggaag    1980
agaatgtgaa gctggcccat gtgaagcaca aggagcagat ctgagtgggc aggggccatc    2040
tccccactcc gctgccctgg ccttgagcat ccactgactg tccaagggcc actcccaaga    2100 agccccttc acgatccacc ctttcaggct aaggagctcc ctatctaccc tcaccccacg    2160
agacagcccc ttcaggattt ccactggacc ttgcccaaat agcaccttag gccactgccc    2220
ctaagctggg gtggaaccgg aatttgggtc aatacatcct tttgtctccc aagggaagag    2280
aatgggcagc aggtatgtgt gtgtgtgcat gtgtgtgcat gtgtgtgcat gtgtgtgcag    2340
gggtgtgtgt gtgtgggggg ggttcccaga tattcagggc aagggaccag tcggaaggga    2400
ttctggctat tgggggagcc cagagacagg ggaaggcagc ctgtccatct gtgcataagg    2460
agaggaaagt tccagggtgt gtatgtttca ggggcttcac atggaggagc tgcagataga    2520
tatgtgtttc tgtgtatgtg tatgtctgcc ttttttccta agtgggggct tctacaggct    2580
tttgggaagt agggtggatg tgggtagggc tgggaggagg gggccacagc ttaggtttgg    2640
agctctggat gtacatacat aagtaggagc agtgggacgt gtttctgtca taatgcaggc    2700
atgaagggtg gagtgaagtc aggtcataag tttcatgttt gcttttgttt tgttttgttt    2760
ttaatgtatg tagcagatgt tacagtctta gggatccggg atgggagacc ccactttaga    2820
aagggtcgtc actcctttaa tcctctactc aacaatgtac tcttttactt ttatattaaa    2880
aaaaataaaa taaatatgtg cctaaaacct c                                 2911
```

<210> SEQ ID NO 82
<211> LENGTH: 2255
<212> TYPE: DNA
<213> ORGANISM: Homo sapiens

<400> SEQUENCE: 82

```
agtccctcgc cgagccgcgt ggtgcactga agccggcgtg gggaggagag ccgatgaagg     60
agaacgctaa catgggggct ccaggcagaa tctctaatgg gagagattta ggacctgagg    120
gagccgggag accegggage ccacggtctg gtcggccacc tcctctcctc cccgggcgcg    180
aggcctagga gaccgcaagc caccctccaa gaatgcgcgt gcagtcgttg ccgtggcaac    240
gtgcaagcct gcatgggccc accgctaaag gaaaggggag gttgttgggg gtgtgggggc    300
tggtcccctg gaggtccaaa ctcatcacgc ggcggtagca cgagggaact gggaacgtcc    360
cctcccccgt gtcccaaatc ctctgggagc cagaacgcaa gtcgcatcgc ctctctgagc    420
ctcagtttcc acatctgcca tatggaggca agattattgg ttccaagttc cccgaagagt    480
tatctggagg gtaacgatcc aggctagtcc ccacttatgg ttggacgtcc aaggaatggg    540
tttaagcggc tcagataact cctgcgaccc cacccaccc ccaggcccgc tcgccatggc    600
cctcttcggg gccctcttcc tagcgctgct ggcaggcgca catgcagagt tcccaggctg    660
caagatccgc gtcacctcca aggcgctgga gctggtgaag caggaggggc tgcgcttct    720 ggagcaagag ctggagacta tcaccattcc ggacctgcgg ggcaaagaag gccacttcta    780
ctacaacatc tctgaggtga aggtcacaga gctgcaactg acatcttccg agctcgattt    840
ccagccacag caggagctga tgcttcaaat caccaatgcc tccttgggc tgcgcttccg    900
```

| | |
|---|---|
| gagacagctg ctctactggt tcttctatga tgggggctac atcaacgcct cagctgaggg | 960 |
| tgtgtccatc cgcactggtc tggagctctc ccgggatccc gctggacgga tgaaagtgtc | 1020 |
| caatgtctcc tgccaggcct ctgtctccag aatgcacgcg gccttcgggg gaaccttcaa | 1080 |
| gaaggtgtat gattttctct ccacgttcat cacctcaggg atgcgcttcc tcctcaacca | 1140 |
| gcagatctgc cctgtcctct accacgcagg gacggtcctg ctcaactccc tcctggacac | 1200 |
| cgtgcctgtg cgcagttctg tggacgagct tgttggcatt gactattccc tcatgaagga | 1260 |
| tcctgtggct tccaccagca acctggacat ggacttccgg ggggccttct tcccctgac | 1320 |
| tgagaggaac tggagcctcc ccaaccgggc agtggagccc cagctgcagg aggaagagcg | 1380 |
| gatggtgtat gtggccttct ctgagttctt cttcgactct gccatggaga gctacttccg | 1440 |
| ggcgggggcc ctgcagctgt tgctggtggg ggacaaggtg ccccacgacc tggacatgct | 1500 |
| gctgagggcc acctactttg ggagcattgt cctgctgagc ccagcagtga ttgactcccc | 1560 |
| attgaagctg gagctgcggg tcctggcccc accgcgctgc accatcaagc cctctggcac | 1620 |
| caccatctct gtcactgcta gcgtcaccat tgccctggtc ccaccagacc agcctgaggt | 1680 |
| ccagctgtcc agcatgacta tggacgcccg tctcagcgcc aagatggctc tccggggaa | 1740 |
| ggccctgcgc acgcagctgg acctgcgcag gttccgaatc tattccaacc attctgcact | 1800 |
| ggagtcgctg gctctgatcc cattacaggc ccctctgaag accatgctgc agattggggt | 1860 |
| gatgcccatg ctcaatgagc ggacctggcg tggggtgcag atcccactac ctgagggcat | 1920 |
| caactttgtg catgaggtgg tgacgaacca tgcgggattc ctcaccatcg gggctgatct | 1980 |
| ccactttgcc aaagggctgc gagaggtgat tgagaagaac cggcctgctg atgtcagggc | 2040 |
| gtccactgcc cccacaccgt ccacagcagc tgtctgagcc ctcaatcccc aagctggcag | 2100 |
| ctgtcattca ggaccccaac ccctctcagc ccctcttttc ccacattcat agcctgtagt | 2160 |
| gccccctcta acccccagtg ccacagagaa gacgggattt gaagctgtac ccaatttaat | 2220 |
| tccataatca atctatcaat tacagtccgt ccacc | 2255 |

<210> SEQ ID NO 83
<211> LENGTH: 1220
<212> TYPE: DNA
<213> ORGANISM: Homo sapiens

<400> SEQUENCE: 83

| | |
|---|---|
| agtcccagct cagagccgca acctgcacag ccatgcccgg caagaactc aggacggtga | 60 |
| atggctctca gatgctcctg gtgttgctgg tgctctcgtg gctgccgcat gggggcgccc | 120 |
| tgtctctggc cgaggcgagc cgcgcaagtt tcccggacc ctcagagttg cactccgaag | 180 |
| actccagatt ccgagagttg cggaaacgct acgaggacct gctaaccagg ctgcgggcca | 240 |
| accagagctg ggaagattcg aacaccgacc tcgtcccggc ccctgcagtc cggatactca | 300 |
| cgccagaagt gcggctggga tccggcgcc acctgcacct gcgtatctct cgggccgccc | 360 |
| ttcccgaggg gctccccgag gcctcccgcc ttcaccgggc tctgttccgg ctgtccccga | 420 |
| cggcgtcaag gtcgtgggac gtgacacgac cgctgcggcc tcagctcagc cttgcaagac | 480 |
| cccaggcgcc cgcgctgcac ctgcgactgt cgccgccgcc gtcgcagtcg gaccaactgc | 540 |
| tggcagaatc ttcgtccgca cggccccagc tggagttgca cttgcggccg caagccgcca | 600 |
| gggggcgccg cagagcgcgt gcgcgcaacg gggaccactg tccgctcggg cccgggcgtt | 660 |
| gctgccgtct gcacacggtc cgcgcgtcgc tggaagacct gggctgggcc gattgggtgc | 720 |
| tgtcgccacg ggaggtgcaa gtgaccatgt gcatcggcgc gtgcccgagc cagttccggg | 780 |

```
cggcaaacat gcacgcgcag atcaagacga gcctgcaccg cctgaagccc gacacggtgc      840
cagcgccctg ctgcgtgccc gccagctaca atcccatggt gctcattcaa aagaccgaca      900
ccggggtgtc gctccagacc tatgatgact tgttagccaa agactgccac tgcatatgag      960
cagtcctggt ccttccactg tgcacctgcg cggaggacgc gacctcagtt gtcctgccct     1020
gtggaatggg ctcaaggttc ctgagacacc cgattcctgc ccaaacagct gtatttatat     1080
aagtctgtta tttattatta atttattggg gtgaccttct tggggactcg ggggctggtc     1140
tgatggaact gtgtatttat ttaaaactct ggtgataaaa ataaagctgt ctgaactgtt     1200
aaaaaaaaaa aaaaaaaaaa                                                 1220
```

<210> SEQ ID NO 84
<211> LENGTH: 1314
<212> TYPE: DNA
<213> ORGANISM: Homo sapiens
<220> FEATURE:
<221> NAME/KEY: misc_feature
<222> LOCATION: (611)..(611)
<223> OTHER INFORMATION: n is a, c, g, or t
<220> FEATURE:
<221> NAME/KEY: misc_feature
<222> LOCATION: (1004)..(1004)
<223> OTHER INFORMATION: n is a, c, g, or t
<220> FEATURE:
<221> NAME/KEY: misc_feature
<222> LOCATION: (1028)..(1028)
<223> OTHER INFORMATION: n is a, c, g, or t
<220> FEATURE:
<221> NAME/KEY: misc_feature
<222> LOCATION: (1128)..(1128)
<223> OTHER INFORMATION: n is a, c, g, or t
<220> FEATURE:
<221> NAME/KEY: misc_feature
<222> LOCATION: (1150)..(1150)
<223> OTHER INFORMATION: n is a, c, g, or t
<220> FEATURE:
<221> NAME/KEY: misc_feature
<222> LOCATION: (1153)..(1153)
<223> OTHER INFORMATION: n is a, c, g, or t
<220> FEATURE:
<221> NAME/KEY: misc_feature
<222> LOCATION: (1181)..(1181)
<223> OTHER INFORMATION: n is a, c, g, or t

```
<400> SEQUENCE: 84
gggaaccgag gaagaggaag aagatttgcc tgatgctcaa actgcagcta aaagagcttc       60
cagaatttat aacacatgag cccccaaaaa gccgggactg gcagctttaa gaagcaaagg      120
aatttcctct caggaccgtg ccgggtttat cattgctttg ttatttgtaa ggactgaaat      180
gtacaaaacc cttcaatggg atgtgtgttt tatcaactgc ttcaccagta aattttgcat      240
gatggctaag ctaacatacc ccaagaataa taataacttg gaaaaacgac aaaccgcgcg      300
cgtaaacgcc gggtcgcgcc attgggcgct tctataccac ccccaccgcc gtttattttg      360
ggatccccgg ggacgtgcgc agaaaccccc cacccgacgc cgcgaggcct gccgcgtgg      420 ggtgggcccc tcccccgaga ttattccctg gtccgtagaa gcgggcaccc ctcacccct      480 tagtggcccg cgccgtgtcg cgcggtgggc ggccgctgtc tcccgcctct gcgcgccgca      540
cccaaaagtc aattgtgctc cgtgtgagcg cgcgggcatg gccccccgcg cccttcgtat      600
atagagcagg nataggctcg cggctcatac aagagccgcc gcctccagat ggtgactact      660
acggcacccg gcggggtggt gcgcgctatc gctcgctgtg ttgccccgcg cgctggcccg      720
cgcaccgact tagacgtgat cggggggtgca gaacagtcac gagtgcacca gctaagttga      780
ggtaggcctc gccgtccagg accggagcca gtagatcccg gcaccggggc gcgacgccga      840
```

```
caagataagt cgctctcgtg cgacttctgg cgatcaggga atatatgacg cacgaacgcg    900
gcggcgtgcg aaggacgtag tggggtaaca ctacactatg gtttttggtt gcggcccact    960
ctcttcgtcc ttggagaggt agtatcagcg tacctgatgc gcgncgagct gccgggcgcg   1020
tatcctanga acaggagcct cacgggtctt aaatgacccg cggggagga ggatacaccc   1080 actactcccc ccggcccgaa cgtgcagaga gggacctgca acgttggnca caagttgtcc   1140
cgcttgtgtn gcnaggtcgt cggctgcaca cacgcagtgc ncgatgcgac acggtggtcg   1200
ggtcgtcgcg gccccggcag aggatgggac acgagaagca tgagcgcgga gccacgacga   1260
cctaagtgcc tatcatgtac cgcgacctct gatagcgtag ggcggaggcg cgtg         1314
```

<210> SEQ ID NO 85
<211> LENGTH: 1482
<212> TYPE: DNA
<213> ORGANISM: Homo sapiens
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (733)..(733)
<223> OTHER INFORMATION: n is a, c, g, or t
<220> FEATURE:
<221> NAME/KEY: misc_feature
<222> LOCATION: (877)..(877)
<223> OTHER INFORMATION: n is a, c, g, or t
<220> FEATURE:
<221> NAME/KEY: misc_feature
<222> LOCATION: (965)..(965)
<223> OTHER INFORMATION: n is a, c, g, or t
<220> FEATURE:
<221> NAME/KEY: misc_feature
<222> LOCATION: (971)..(971)
<223> OTHER INFORMATION: n is a, c, g, or t
<220> FEATURE:
<221> NAME/KEY: misc_feature
<222> LOCATION: (976)..(976)
<223> OTHER INFORMATION: n is a, c, g, or t
<220> FEATURE:
<221> NAME/KEY: misc_feature
<222> LOCATION: (1072)..(1072)
<223> OTHER INFORMATION: n is a, c, g, or t
<220> FEATURE:
<221> NAME/KEY: misc_feature
<222> LOCATION: (1101)..(1101)
<223> OTHER INFORMATION: n is a, c, g, or t
<220> FEATURE:
<221> NAME/KEY: misc_feature
<222> LOCATION: (1149)..(1149)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1200)..(1200)
<223> OTHER INFORMATION: n is a, c, g, or t
<220> FEATURE:
<221> NAME/KEY: misc_feature
<222> LOCATION: (1246)..(1246)
<223> OTHER INFORMATION: n is a, c, g, or t
<220> FEATURE:
<221> NAME/KEY: misc_feature
<222> LOCATION: (1331)..(1331)
<223> OTHER INFORMATION: n is a, c, g, or t
<220> FEATURE:
<221> NAME/KEY: misc_feature
<222> LOCATION: (1344)..(1344)
<223> OTHER INFORMATION: n is a, c, g, or t
<220> FEATURE:
<221> NAME/KEY: misc_feature
<222> LOCATION: (1353)..(1353)
<223> OTHER INFORMATION: n is a, c, g, or t
<220> FEATURE:
<221> NAME/KEY: misc_feature
<222> LOCATION: (1440)..(1440)
<223> OTHER INFORMATION: n is a, c, g, or t
<220> FEATURE:
<221> NAME/KEY: misc_feature
<222> LOCATION: (1482)..(1482)
<223> OTHER INFORMATION: n is a, c, g, or t

<400> SEQUENCE: 85

| | | | | | |
|---|---|---|---|---|---|
| ccgctcccag | ccacagcctc | ccgcgcctcg | ctcagctcca | acatgggaaa | aatctccagc | 60 |
| cctacagaga | ctgagcggtg | catcgagtcc | ctgattgctg | tcttccagaa | gtatgctgga | 120 |
| aaggatggtt | ataactacac | tctctccaag | acagagttcc | taagcttcat | gaatacagaa | 180 |
| ctagctgcct | tcacaaagaa | ccanaaggac | cctggtgtcc | ttgaccgcat | gatgaagaaa | 240 |
| ctggacacca | acagtgatgg | gcagctaaat | ttctcagaat | ttcttaatct | gattgggggg | 300 |
| ctagctatgg | cttggcatga | ctccttcctc | aaaggtgtcc | cttcccagaa | gcggacctga | 360 |
| ggaccccttg | gccctggggc | ttcgaacccc | cccgctttc | cttccaccct | ttctgggatc | 420 |
| gtctccgagg | cgcagccatg | ccctggggca | cactaaccac | cctcatggga | gggccccacg | 480 |
| ctgcccaata | gctaataaaa | gcggatgggg | cacgttttgt | tgagagcgct | ggggaagaac | 540 |
| aaaagaaggg | gaagaagttc | ggaggggatt | ccgtagggtc | cggggtggcg | cgggcaaaaa | 600 |
| agggaggggg | aatggggaga | gtggcggccc | gggtgggctc | ctgtaggcgt | tggggtctcc | 660 |
| gttcgaggcc | gcgcgcttgt | ttctttgggt | gcagcccgag | cggggggtga | atagagcctt | 720 |
| gggcgcccag | agncgccgcg | ccttatataa | ccgctgagac | gccgcgctga | cattgtacga | 780 |
| ctgtggtgcg | cgcggggagag | acaggccgga | cggggccgcg | gaaaaagcgc | tgttgccggc | 840 |
| ggttgaagga | gccgcgcgcg | cggcggcatc | ttgtctncgt | ccgccgctca | gccgccagta | 900 |
| tccaggccgc | taggcggcgc | agaatagctc | gtggcgtcgc | ccgcgcccgc | ggccgctgtc | 960 |
| gaganaaccg | ngggganaagg | cccgggcgcg | ccatctcgga | tagtatttcc | gcgcgcgggg | 1020 |
| ggggagaggg | acgtgagccc | ggacagtagg | gggggcggg | cgggacctga | tncggcgccg | 1080 |
| ccgcataagg | acgagaggcc | ncccgtcacg | cgctcgagcc | gcggccccca | gcgcggtacg | 1140 |
| gccccggana | gaacncacan | tgcccccgc | gtcgatgctc | gtggtcgtcg | tcctgccgtn | 1200 |
| gacggaactc | catgcgcgag | gacgcatatg | gagcgagacg | cagccntacc | gggcggggcg | 1260 |
| tcgggcggca | gctcgagggg | cgcgaagtat | ggggttgtgt | gcccaatgtg | ccagctactt | 1320 |
| gtccgcccgc | nctccgtgct | tatnctacac | ganacacagg | ctggcaccgg | ggtcctccgt | 1380 |
| gcattcccgt | cgcctggttc | tgcgacgcgg | gaccgaggat | gggggctgac | cccggggagn | 1440 |
| tgggcttcgc | ccccgcggct | cgagagtacg | cgggcgcgca | cn | | 1482 |

<210> SEQ ID NO 86
<211> LENGTH: 1278
<212> TYPE: DNA
<213> ORGANISM: Homo sapiens

<400> SEQUENCE: 86

| | | | | | |
|---|---|---|---|---|---|
| agaactgatt | ctggaggaag | tgggatcaga | ggccaaaggc | agaaggtgga | aggggggcttc | 60 |
| atgagtcatc | tgccctcagc | ctgggccagg | tgtaggggag | atctttgtgc | cagccaccct | 120 |
| agagtagatc | tgggtggaag | atgactggat | tcaacacccc | cagggctgga | aggatctgtg | 180 |

```
gggttgaagg agctgagtct gtcagtcctt cctggttagg ggttggaggc tctgcctcca      240
cagtccaggc tgaggcagag gcctgcctct ccttccagag aagtcgggtg aagggagaa       300 atggcagtct ctaagactcc gagcgtacct ggctaacttc catagtgccc agagaaggag      360
ctcagtcggc aaggactagc cgaggatccc agtcctagca gcctcctgtc ccctgctcat      420
gtgtctaaca gcctttaacc ttctcagcac ctaggaaccc aggcagcctg ggactatctg      480
atccacttgt tctaaaacac agcaggtcca tggccagcag gcctctgccc ccgggacgcc      540
aggaggagga gaatgccaaa gactccgggc ggaaaccctc accggtgcgg ccccgaggct      600
gcctgcccag cattgatgag gcccgaccgg caggtccagg tccagccccg gcctcgcgcc      660
ggggctccat gctgggcctg gccgcgtcct ctccccgccg caactcgctg gtcgggccag      720
gcgcgggtcc tggggggtcag cggccatccc tgggcccggt gccccctctg ggctcaaggg     780
tcagcttctc agggttgccc ctggcgcccg cccgttgggt ggcgccctcc taccgcacgg      840
agccagtgcc cggggagcgc tgggaggctg cgcgtgcaca gcgtgccctg gaggcggcgc      900
tggccgcagg gctgcacgac gcgtgctact ccagcgacga ggccgcgcgg ctggtgcggg      960
agctctgcga gcaggtgcac gttcgcctgc gcgagctcag cccgccacgc tacaagctgg     1020
tatgcagtgt ggtgctgggg ccgcgcgcgg gccagggcgt tcacgtggtc agccgtgcgc     1080
tctgggacgt ggcgcgcgat gggctggcct cggtctccta caccaacacc tcgctcttcg     1140
cggtggccac ggtccacggg ctctactgcg agtgaggggg agtccaattc tgcaaaattg     1200
tttattatcc taggaggagg ccccctggg gctcacatcc aataaataa gtgtctgaca      1260 gtaaaaaaaa aaaaaaaa                                                   1278

<210> SEQ ID NO 87
<211> LENGTH: 1898
<212> TYPE: DNA
<213> ORGANISM: Homo sapiens

<400> SEQUENCE: 87
agctgctggc tgggctgcct gttgagtcag ccttcttccc tcacggctct tctcccggtc       60
cctgaaactc ggctgccagg ggagctggag ccacctgcga aggtgtcctc ccatactgga      120
cccctacagg aagctccgtg tgcccagctg gggcacagcc ccagctgatg ccccagaggg      180
gccacccatc gcaagagggg ctttgggctc tgccctccct cccatggcg catgggccaa       240 agcctgagac tgaaggactg ttggacctca gcttcctgac agaggaggag caggaggcca      300
ttgctggcgt cctccaacga gatgcccgcc tgcgccagct ggaggagggg cgggtcagca      360
agctccgggc tcagtggca gaccctgggc agctgaagat cctgacaggg gactggttcc       420
aggaagcacg ctcccagcgg caccacaatg cccacttcgg ctctgacctt gtccgagcgt      480
ctatgcgcag gaagaagagc accagggag accaggctcc aggccacgac agggaggctg       540
aggctgctgt gaaagagaag gaagaggggc cagagcccag gctcaccatt gatgaggccc      600
ctcaggagag gctcagggag actgaggctt cagatcctga ggaggcgtcc caggcccagg      660
aagatcctgg ccaaggagac caacaggtct gtgccgagga ggctgacccg gagctggagc      720
ccgcgtcggg gggagagcag gagccgcggc cccagcaagc ccagaccaag gccgcgtccc      780
agatcctgga gaatggggag gaggcccgg ggccgacccc ctctctcgac cgcatgctca       840
gcagcagctc ctcggtgtcc agccttaact cctccacgct gagcggcagc cagatgagcc      900
tgtcaggcga cgcggaggcg gtgcaggtcc gcggctccgt gcacttcgcg ctgcactacg      960
agccgggcgc cgccgagctg cgcgtgcacg tgatccagtg ccagggcctg gccgccgccc     1020
```

| | |
|---|---|
| ggcgccgccg ctcggacccc tacgtcaaaa gctacctcct cccggataag cagagcaagc | 1080 |
| gcaagacggc ggtgaagaaa cggaatctga atccggtttt caacgagact ctccggtact | 1140 |
| ccgtcccgca ggccgagctt cagggccgcg tgctgagcct gtctgtgtgg caccgcgaaa | 1200 |
| gcctgggtcg caacatcttt ctgggcgaag ttgaagtgcc cctggacacg tgggactggg | 1260 |
| gctctgagcc cacctggctc cccctgcagc cccgggtccc accctctccc gacgaccttc | 1320 |
| cgagccgcgg gttactcgcc ctgtccctca agtacgtccc cgccggctcc gagggcgcag | 1380 |
| gactgccccc gagcggggag ctgcacttct gggtgaagga ggctcgggac ctcctgccgc | 1440 |
| tgcgggcagg atccctggac acttacgtac aatgcttcgt gctgcctgat gacagccagg | 1500 |
| ccagccgcca gcgtacaagg gttgtgcgac gcagcctcag ccctgtgttc aatcacacca | 1560 |
| tggtgtacga tggctttggg cctgctgacc tgcgccaggc ttgtgccgag ctctccctct | 1620 |
| gggaccatgg ggccctggcc aaccgccagc tgggggcac acgcctcagc ctgggcaccg | 1680 |
| gcagcagcta tgggctgcag gtgccctgga tggattccac acctgaggag aagcagctgt | 1740 |
| ggcaagccct cctggagcag ccgtgcgaat gggtggatgg ccttctaccc ctcagaacca | 1800 |
| acctggcccc caggacgtag ccccaccaag cctctctctc tggaccccca tctcagggcc | 1860 |
| tgcccttggc taaagtcaat aaagtctatt ctaagagc | 1898 |

<210> SEQ ID NO 88
<211> LENGTH: 4781
<212> TYPE: DNA
<213> ORGANISM: Homo sapiens

<400> SEQUENCE: 88

| | |
|---|---|
| cgaaactacc ggaaggacct tgctaaactc catcgggagg tgagaagcac acctttgaca | 60 |
| gccacacctg gaggccgagg agacatgaaa tatggcatat atgctgtaga gaatgagcat | 120 |
| atgaatcggc tacagtctca aagggcaatg cttctgcagg gcactgaaag cctgaaccgg | 180 |
| gccacccaaa gtattgaacg ttctcatcgg attgccacag agactgacca gattggctca | 240 |
| gaaatcatag aagagctggg ggaacaacga gaccagttag aacgtaccaa gagtagactg | 300 |
| gtaaacacaa gtgaaaactt gagcaaaagt cggaagattc tccgttcaat gtccagaaaa | 360 |
| gtgacaacca caagctgct gctttccatt atcatcttac tggagctcgc catcctggga | 420 |
| ggcctggttt actacaaatt cttccgcagc cattgaactt ctatagggaa gggtttgtgg | 480 |
| accagaactt tgaccttgtg aatgcatgat gttagggatg tggatagaat aagcatattg | 540 |
| ctgctgtggg ctgacagttc aaggatgcac tgtatagcca ggctgtggga ggagggagga | 600 |
| aagatgaaaa accacttaaa tgtgaaggaa caacagcaac aagaccagta tgatatacca | 660 |
| aggtaataaa tgctgtttat gacttctta aatttacata gtactgtagc atattaatac | 720 |
| cctgtgaact gcaaaaaacc aaatacattt acagtagtat tggtcaccaa aatagagggg | 780 |
| aaactttaca attgtgagaa tgtgtaaatg ttctcattaa ggcagtattg acccagacaa | 840 |
| ccatttagta ttcatctatc ccctcaatgc ctcataattc tggaatgcct gttgtgaaac | 900 |
| atgtcagtgc acagtgtctc ctaaattctc acacgtgctt gattttctga ttcatctggt | 960 |
| gaactgggag taggaagttg gtcatagaca atatgccctc cttctcttgt ctgaccaaag | 1020 |
| cttgaagcaa tcacatctac tgccaggtta gctgtagtct tcgcctcttc ctctgaggtg | 1080 |
| gccaactgag gattgacttc aacaagatcc agtgctgata gcaaccctgg aagaacaaag | 1140 |
| tgtgacaaaa cctcaggttc ccttgctgct actctcagtg agggtcatcc cactgggaca | 1200 |
| gggagaacaa gccaaagtaa aaacaagagt ccatttata gtagaaaata cctatttta | 1260 |

```
ggaagcccct tgcacctcat cctcttggcc atgaatttaa gttaaaacac tgttgtgcta      1320
tagtagatta aaagaaacct tttaagataa tgaaataaac catccctgtt caactaacat      1380
aacaggcata attgtcaggc gttctggaaa aggaaaaggc ttggtgttgg gtggggagg       1440 ttttcatcct gcttgttggc aaaatgtatg ccacctccag tatgactagg aaccttccag     1500
atgcctgcct ggaaatgaat caagtatgaa ggcagaggaa atctgccact tgcactagcc     1560
aaactgcatt cccactttg  aactctaatg tgttatctgt atctgttaga gcaccacacc     1620
atatgccctg aaatgtagtt attactgcaa acttcattct caccctgca  ggcctgagct     1680 ctggaggcag gttccacatc taacaacatc tttttgtctc ccagcagact gacccagtgt     1740
cttgtacttg atcaagagaa aattcagcca tatgttaatt atttatctg  gacttcagtt     1800 accttctgtt aaggtttgag aacttgtgtc aaagttctcg gtagtgttcc tttggcctgg     1860
agcaagtgga agggaagctt aaaccagaag aacctatcca gacctgctac tatgctcacc     1920
cctctaaatg cctcacttct ctatagaatt taacttttta gttggttatt ctggatgaag     1980
ggtgatctga acaagctagt attcaggaat acaagtatct aagaatattt agggtggcca     2040
taaagtctgg aaacacaggc aaatgtacct aatggtttat tgatattaca ctatagtaca     2100
tgatgtgctg aatgccatca tgtccgttca gcatcttccc ttattagcaa tgcatagttg     2160
agtgtacagt gccaaactgc aaccaacagg tgtattactg tagcatttcc atcatttcct    2220
gcacatggac ctgtgttcct gatttgtctc tgatttccac tgactaaacc tgcaccttta    2280
gcatatccca gaagtggtca tcaaagtttg cactattaga aatatataca tgacttatgt    2340
ttccagacta ttgccaccct ataaattaag caaactgctt tatgtatcta gttgacagca    2400
ttataacagt gcagtggcac aatcatggct cactgcagcc tcaacctccc aagtagttgg    2460
gacacctggc taattatttt ttgtagaaac ggggtcacac tatgttgccc acgctggtct    2520 tgaaccctg  gggtcaagta atcctcttgc cttggcctcc cagagtactg ggattatagg    2580
tatgaaccac tgtgcctagc cccatgagtg tcttttggag taaaatattg tagcatagga    2640
acaaagagac aagccatgcc atatataagt gctagaggtt attaacccct gctctaagtg    2700 gtgttttag  gaagcaaagc agagaattga acccccaagt tctctggcca ataacctaag    2760
gaccactggc aacatctaag attgcagatc tgagaattag accagtactg cctgcctttt    2820
tgtactgcct aaggttctgg caggctgtgg cgctaaggag accatttctc aatgtgagtt    2880
tctatcccag ctagtcaagg gttctctata gccctgaacc tttcaatctg ggtctctat    2940 ctatacccta gttccatcag atggttactg aagcagtatg atttggtagt tctttaaatt    3000
ttggaatgaa aggtcatttg aagtagcttt aaaaccagaa gctttctgac agaaatggaa    3060
actgtttgca aacaagtatg agttttggaa aagtagccag tcttgataac gtagaattca    3120
tcttagtact ctttccatca gccattctca tctaactgta tccccttat  tagaaatcct    3180 ttcaggctct agtacaagac ctaccctaca taaaggaccc aagatattgt ccagtttgca    3240
gatttcttca agagatcagc tttagctcca aattcacaac tcccaatgaa ccaatctctt    3300
agagtgcaaa ttacagcctt gcactcttat cttatcttgc cttcttatct taatctgcct    3360
ttagataact caaagaactg catcagtttg acaatttatt cttgtattta attgtttaaa    3420
tatacaattt tttactcatt attaccttag tgtaatttgg taagagccat gtccaagcat    3480
gactctaaag gactatatcc ttttattag  catggccata taattttag  ctacaaaagt    3540 ttaagcaaaa acaaactctg caatgatgtg gaatagcaga aaagatcctt tgcaggcaag    3600
agactctagc atatttacct atgtagttaa caggctgcag acctggttgc tacataccctg   3660
```

```
tattgtgtat ttcctcagca atatacatgc cttctcgata ggttagtccc ccgacaacag    3720
gagttcctgt ggctggagcc agtgtagggt caaatgcatc aatatcaaaa ctcaaatgga    3780
ttggtctttg tctcctaaaa aggaagagga taaataataa cttaaaataa tacttaactg    3840
gttgtccttg acactcatcc cttcttatgg ttgcaactcc ttgattttgt tgctattagt    3900
cctagtactt tgttaataaa gctgttaata catttccagg cttcctattc ttggaagtta    3960
ctgagattgg caatattaac ttcctacata ccacttcatg atactgccat ttgttctgca    4020
tacctcagac agactaactc caatgtatat ttctgcctta cactgggtat tagaacctct    4080
tatactaata actgtcaata gagagatttc ttcacttcta gatgagattg ggctctcatc    4140
tagagacaat ttaattagac aatttaaatt agtctaattt aaattggctt gatgtaagtt    4200
atggttgctc ttattctctg aacgtaacag cagctgaagt gaactctaat tttaggtctg    4260
cagttttaac atcttccatt tctaacttca ttatagcccc agtgtccaaa ggctgaagct    4320
aacaactaag tttcttaaca gcttatgaaa tgacatacta ccagataaca attctgacat    4380
taatcaccca gaagtaaaga cttggtattg ggaaaatgct cttaaaatta ccatttgatt    4440
agtattcatc tgccatcttt ctacactgcc aagatttgct taatataaaa ctcagatgaa    4500
acaatcgtga ggctgggaag aatgggacag ttgaaacaat aaatgcttgt catctcagaa    4560
gataagcatt aaagatggag ataagaaaaa attcatgaga cagaagatct aggcaatgat    4620
ttagaggaaa cctcctccca aaaacccccag aggaagaata tgacctgtgt ttcaaatttt    4680
gcctttctga actatttaaa attatgtgta tgttttgct ttgtatttta aaagtaaagc    4740
tgctgtcctc aagaaacagg ctaaaaaaaa aaaaaaaaa a    4781

<210> SEQ ID NO 89
<211> LENGTH: 1660
<212> TYPE: DNA
<213> ORGANISM: Homo sapiens

<400> SEQUENCE: 89
ggtgcactag caaaacaaac ttattttgaa cactcagctc ctagcgtgcg gcgctgccaa      60
tcattaacct cctggtgcaa gtggcgcggc ctgtgccctt tataaggtgc gcgctgtgtc     120
cagcgagcat cggccaccgc catcccatcc agcgagcatc tgccgccgcg ccgccgccac     180
cctcccagag agcactggcc accgctccac catcacttgc ccagagtttg gccaccgcc     240 cgccgccacc agcccagaga gcatcggccc ctgtctgctg ctcgcgcctg gagatgtcag     300
aggtccccgt tgctcgcgtc tggctggtac tgctcctgct gactgtccag gtcggcgtga     360
cagccggcgc tccgtggcag tgcgcgccct gctccgccga gaagctcgcg ctctgcccgc     420
cggtgtccgc ctcgtgctcg gaggtcaccc ggtccgccgg ctgcggctgt tgcccgatgt     480
gcgccctgcc tctgggcgcc gcgtgcggcg tggcgactgc acgctgcgcc cggggactca     540
gttgccgcgc gctgccgggg gagcagcaac ctctgcacgc cctcacccgc ggccaaggcg     600
cctgcgtgca ggagtctgac gcctccgctc cccatgctgc agaggcaggg agccctgaaa     660
gcccagagag cacggagata actgaggagg agctcctgga taatttccat ctgatggccc     720
cttctgaaga ggatcattcc atcctttggg acgccatcag tacctatgat ggctcgaagg     780
ctctccatgt caccaacatc aaaaaatgga aggagccctg ccgaatagaa ctctacagag     840
tcgtagagag tttagccaag gcacaggaga catcaggaga agaaatttcc aaattttacc     900
tgccaaactg caacaagaat ggattttatc acagcagaca gtgtgagaca tccatggatg     960
gagaggcggg actctgctgg tgcgtctacc cttggaatgg gaagaggatc cctgggtctc    1020
```

| | |
|---|---|
| cagagatcag gggagacccc aactgccaga tatattttaa tgtacaaaac tgaaaccaga | 1080 |
| tgaaataatg ttctgtcacg tgaaatattt aagtatatag tatatttata ctctagaaca | 1140 |
| tgcacattta tatatatatg tatatgtata tatatatagt aactacttttt tatactccat | 1200 |
| acataacttg atatagaaag ctgtttattt attcactgta agtttatttt ttctacacag | 1260 |
| taaaaacttg tactatgtta ataacttgtc ctatgtcaat ttgtatatca tgaaacactt | 1320 |
| ctcatcatat tgtatgtaag taattgcatt tctgctcttc caaagctcct gcgtctgttt | 1380 |
| ttaaagagca tggaaaaata ctgcctagaa aatgcaaaat gaaataagag agagtagttt | 1440 |
| ttcagctagt ttgaaggagg acggttaact tgtatattcc accattcaca tttgatgtac | 1500 |
| atgtgtaggg aaagttaaaa gtgttgatta cataatcaaa gctacctgtg gtgatgttgc | 1560 |
| cacctgttaa aatgtacact ggatatgttg ttaaacacgt gtctataatg gaaacattta | 1620 |
| caataaatat tctgcatgga aatactgtta aaaaaaaaaa | 1660 |

<210> SEQ ID NO 90
<211> LENGTH: 732
<212> TYPE: DNA
<213> ORGANISM: Homo sapiens

<400> SEQUENCE: 90

| | |
|---|---|
| catcggcgct ttgccacttg tacccgagtt tttgattctc aacatgtccg agactgctcc | 60 |
| tgccgctccc gctgccgcgc ctcctgcgga gaaggcccct gtaaagaaga aggcggccaa | 120 |
| aaaggctggg ggtacgcctc gtaaggcgtc tggtcccccg gtgtcagagc tcatcaccaa | 180 |
| ggctgtggcc gcctctaaag agcgtagcgg agtttctctg gctgctctga aaaaagcgtt | 240 |
| ggctgccgcc ggctatgatg tggagaaaaa caacagccgt atcaaacttg gtctcaagag | 300 |
| cctggtgagc aagggcactc tggtgcaaac gaaaggcacc ggtgcttctg gctccttaa | 360 |
| actcaacaag aaggcagcct ccggggaagc caagcccaag gttaaaaagg cgggcggaac | 420 |
| caaacctaag aagccagttg ggcagccaa gaagcccaag aaggcggctg cggcgcaac | 480 |
| tccgaagaag agcgctaaga aaacaccgaa gaaagcgaag aagccggccg cggccactgt | 540 |
| aaccaagaaa gtggctaaga gcccaaagaa ggccaaggtt gcgaagccca gaaagctgc | 600 |
| caaaagtgct gctaaggctg tgaagcccaa ggccgctaag cccaaggttg tcaagcctaa | 660 |
| gaaggcggcg cccaagaaga aataggcgaa cgcctacttc taaaacccaa aaggctcttt | 720 |
| tcagagccac ca | 732 |

<210> SEQ ID NO 91
<211> LENGTH: 2199
<212> TYPE: DNA
<213> ORGANISM: Homo sapiens

<400> SEQUENCE: 91

| | |
|---|---|
| agtctgagcc tccggcaccg gccgcgcagc tggaggcggc ggagcggaag gtgtagggtg | 60 |
| ggccggcaaa gtcaaccggc cgctctggat catctgggaa ttcaagagag cgattggaga | 120 |
| gaggtctgat gtatccacac tgtcttgtct tggggaaggc cccagaagtt ccaggctcca | 180 |
| ttccaggccc tgtgtgggc tcagttgccc ctcttaaggg gtcagtggga cagtccctct | 240 |
| ggggctgcct ctcacaggga gttgtccatg ccatcttggc cttgggccta gtgtcctggc | 300 |
| ctgggctgcc tgctgttctg gcccaatcat agcctggagg gaaagtcttc taattgggct | 360 |
| ggaggctcca ggtcccttaa cgcatgcctc aaccccgggt ttctgtcctc tgcctcccac | 420 |
| cactctggtg ccgtctgaat taccctgctg gggggacagc agtggcatac tcatgcctaa | 480 |

```
gtgactggct ttcaccccag tagtgattgc cctccatcaa cactgcccac cccaggttgg      540
ggctacccca gcccatcttt acaaaacagg gcaaggtgaa ctaatggagt gggtggagga      600
gttggaagaa atcccagcgt cagtcaccgg gatagaattc caaggaacc ctcttttttgg     660 aggatggttt ccatttctgg aggcgatctg ccgacagggt gaatgccttc ttgcttgtct     720
tctggggaat cagagagagt ccgttttgtg gtgggaagag tgtggctgtg tactttgaac     780
tcctgtaaat tctctgactc atgtccacaa aaccaacagt tttgtgaatg tgtctggagg     840
caagggaagg gccactcagg atctatgttg aagggaagag gcctggggct ggagtattcg     900
cttcctaaag ggcagtgtga ggtggtggtg gggtgtgggg agtagaggcg ttcagtcagc     960
ccagtttgac aggatgtggg actgagagaa aaagctaggt ttgaggctga gatcaggtta     1020
ccgtcgcttt cttaactgct ccctgcctgg ttggtgctgg gactgcccct catttgtctc     1080
ttcttttggg gctcctccca gcccagactc tagccccctc cccttccca acagccttga      1140 cttcatctca gctccagagc ccgccctctc ttcctgcagc ctgggaactt cagccggctg     1200
gagccccacc atggctgcaa tccgaaagaa gctggtgatc gttggggatg gtgcctgtgg    1260
gaagacctgc ctcctcatcg tcttcagcaa ggatcagttt ccggaggtct acgtccctac    1320
tgtctttgag aactatattg cggacattga ggtggacggc aagcaggtgg agctggctct    1380
gtgggacaca gcagggcagg aagactatga tcgactgcgg cctctctcct acccggacac    1440
tgatgtcatc ctcatgtgct tctccatcga cagccctgac agcctggaaa acattcctga    1500
gaagtggacc ccagaggtga agcacttctg ccccaacgtg cccatcatcc tggtggggaa    1560
taagaaggac ctgaggcaag acgagcacac caggagagag ctggccaaga tgaagcagga    1620
gcccgttcgg tctgaggaag gccgggacat ggcgaaccgg atcagtgcct ttggctacct    1680
tgagtgctca gccaagacca aggagggagt gcgggaggtg tttgagatgg ccactcgggc    1740
tggcctccag gtccgcaaga caagcgtcg gagggctgt cccattctct gagatcccca     1800
aggcctttcc tacatgcccc ctcccttcac aggggtacag aaattatccc cctacaaccc    1860
cagcctcctg agggctccat gctgaaggct cccattttca gttccctcct gcccaggact    1920
gcattgtttt ctagccccga ggtggtggca cgggccctcc ctcccagcgc tctgggagcc    1980
acgcctatgc cctgcccttc ctcagggccc ctggggatct tgccccctttt gaccttcccc    2040 aaaggatggt cacacaccag cactttatac acttctggct cacaggaaag tgtctgcagt    2100
aggggaccca gagtcccagg cccctggagt tgttttcggc aggggccttg tctctcactg    2160
catttggtca gggggcatg aataaaggct acaggctcc                            2199
```

<210> SEQ ID NO 92
<211> LENGTH: 1246
<212> TYPE: DNA
<213> ORGANISM: Homo sapiens

<400> SEQUENCE: 92

```
gaccagccta cagccgcctg catctgtatc cagcgccagg tcccgccagt cccagctgcg      60
cgcgcccccc agtcccgcac ccgttcggcc caggctaagt tagcccctcac catgccggtc    120 aaaggaggca ccaagtgcat caaatacctg ctgttcggat ttaacttcat cttctggctt    180
gccgggattg ctgtccttgc cattggacta tggctccgat tcgactctca gaccaagagc    240
atcttcgagc aagaaactaa taataataat tccagcttct acacaggagt ctatattctg    300
atcgagccgc gcgccctcat gatgctggtg ggcttcctgg gctgctgcgg ggctgtgcag    360
gagtcccagt gcatgctggg actgttcttc ggcttcctct tggtgatatt cgccattgaa    420
```

```
atagctgcgg ccatctgggg atattcccac aaggatgagg tgattaagga agtccaggag    480
ttttacaagg acacctacaa caagctgaaa accaaggatg agcccagcg ggaaacgctg     540 aaagccatcc actatgcgtt gaactgctgt ggtttggctg ggggcgtgga acagtttatc    600
tcagacatct gccccaagaa ggacgtactc gaaaccttca ccgtgaagtc ctgtcctgat    660
gccatcaaag aggtcttcga caataaattc cacatcatcg gcgcagtggg catcggcatt    720
gccgtggtca tgatatttgg catgatcttc agtatgatct tgtgctgtgc tatccgcagg    780
aaccgcgaga tggtctagag tcagcttaca ccctgagca ggaaagttta cccatgaaga     840
ttggtgggat ttttgtttg tttgttttgt tttgtttgtt gtttgttgtt tgttttttg      900 ccactaattt tagtattcat tctgcattgc tagataaaag ctgaagttac tttatgtttg    960
tcttttaatg cttcattcaa tattgacatt tgtagttgag cgggggtttt ggtttgcttt   1020
ggtttatatt tttcagttg tttgttttg cttgttatat taagcagaaa tcctgcaatg    1080
aaaggtacta tatttgctag actctagaca agatattgta cataaaagaa tttttttgtc   1140
tttaaataga tacaaatgtc tatcaacttt aatcaagttg taacttatat tgaagacaat   1200
ttgatacata ataaaaaatt atgacaatgt caaaaaaaaa aaaaaa                  1246

<210> SEQ ID NO 93
<211> LENGTH: 1124
<212> TYPE: DNA
<213> ORGANISM: Homo sapiens

<400> SEQUENCE: 93
gccgctgcca ccgcaccccg ccatggagcg gccgtcgctg cgcgccctgc tcctcggcgc     60
cgctgggctg ctgctcctgc tcctgccccct ctcctcttcc tcctcttcgg acacctgcgg   120
cccctgcgag ccggcctcct gccgcccct gccccgctg ggctgcctgc tgggcgagac      180
ccgcgacgcg tgcggctgct gccctatgtg cgcccgcggc gagggcgagc cgtgcgggg    240 tggcggcgcc ggcagggggt actgcgcgcc gggcatggag tgcgtgaaga gccgcaagag    300
gcggaagggt aaagccgggg cagcagccgg cggtccgggt gtaagcggcg tgtgcgtgtg    360
caagagccgc tacccggtgt gcggcagcga cggcaccacc tacccgagcg gctgccagct    420
gcgcgccgcc agccagaggg ccgagagccg cggggagaag gccatcaccc aggtcagcaa    480
gggcacctgc gagcaaggtc cttccatagt gacgccccc aaggacatct ggaatgtcac     540
tggtgcccag gtgtacttga gctgtgaggt catcggaatc ccgacacctg tcctcatctg    600
gaacaaggta aaagggggtc actatggagt tcaaggaca gaactcctgc ctggtgaccg     660
ggacaacctg gccattcaga cccggggtgg cccagaaaag catgaagtaa ctggctgggt    720
gctggtatct cctctaagta aggaagatgc tggagaatat gagtgccatg catccaattc    780
ccaaggacag gcttcagcat cagcaaaaat tacagtggtt gatgccttac atgaaatacc    840
agtgaaaaaa ggtgaaggtg ccgagctata aacctccaga atattattag tctgcatggt    900
taaaagtagt catggataac tacattacct gttcttgcct aataagtttc ttttaatcca    960
atccactaac actttagtta tattcactgg ttttacacag agaaatacaa aataaagatc   1020
acacatcaag actatctaca aaaatttatt atatatttac agaagaaaag catgcatatc   1080
attaaacaaa taaatacttt tttatcacaa aaaaaaaaaa aaaa                   1124

<210> SEQ ID NO 94
<211> LENGTH: 1254
<212> TYPE: DNA
<213> ORGANISM: Homo sapiens
```

<400> SEQUENCE: 94

```
ctcacttggc cttacactcc gctcggctca ccatgtgtca ctctcgcagc tgccacccga      60
ccatgaccat cctgcaggcc ccgaccccgg cccctccac catcccggga ccccggcggg      120
gctccggtcc tgagatcttc accttcgacc ctctcccgga gcccgcagcg gccctgccg      180
ggcgccccag cgcctctcgc gggcaccgaa agcgcagccg cagggttctc taccctcgag      240
tggtccggcg ccagctgcca gtcgaggaac cgaacccagc caaaaggctt ctctttctgc      300
tgctcaccat cgtcttctgc cagatcctga tggctgaaga gggtgtgccg cgcccctgc      360
ctccagagga cgcccctaac gccgcatccc tggcgcccac ccctgtgtcc gccgtcctcg      420
agcccttaa tctgacttcg gagccctcgg actacgctct ggacctcagc actttcctcc      480
agcaacaccc ggccgccttc taactgtgac tccccgcact cccccaaaaag aatccgaaaa      540
accacaaaga acaccaggc gtacctggtg cgcgagagcg tatccccaac tgggacttcc      600
gaggcaactt gaactcagaa cactacagcg gagacgccac ccggtgcttg aggcgggacc      660
gaggcgcaca gagaccgagg cgcatagaga ccgaggcaca gcccagctgg gctaggccc      720
ggtgggaagg agagcgtcgt taatttattt cttattgctc ctaattaata tttatatgta      780
tttatgtacg tcctcctagg tgatggagat gtgtacgtaa tatttatttt aacttatgca      840
agggtgtgag atgttccccc tgctgtaaat gcaggtctct tggtatttat tgagctttgt      900
gggactggtg gaagcaggac acctggaact gcggcaaagt aggagaagaa atggggagga      960
ctcgggtggg ggaggacgtc ccggctggga tgaagtctgg tggtgggtcg taagtttagg      1020
aggtgactgc atcctccagc atctcaactc cgtctgtcta ctgtgtgaga cttcggcgga      1080
ccattaggaa tgagatccgt gagatccttc catcttcttg aagtcgcctt tagggtggct      1140
gcgaggtaga gggttggggg ttggtgggct gtcacggagc gactgtcgag atcgcctagt      1200
atgttctgtg aacacaaata aaattgattt actgtctgca aaaaaaaaaa aaaa            1254
```

<210> SEQ ID NO 95
<211> LENGTH: 534
<212> TYPE: DNA
<213> ORGANISM: Homo sapiens

<400> SEQUENCE: 95

```
cgactttccc gatcgccagg caggagtttc tctcggtgac tactatcgct gtcatgtctg      60
gtcgtggcaa gcaaggaggc aaggcccgcg ccaaggccaa gtcgcgctcg tcccgcgctg      120
gccttcagtt cccggtaggg cgagtgcatc gcttgctgcg caaaggcaac tacgcggagc      180
gagtgggggc cggcgcgccc gtctacatgg ctgcggtcct cgagtatctg accgccgaga      240
tcctggagct ggcgggcaac gcggctcggg acaacaagaa gacgcgcatc atccctcgtc      300
acctccagct ggccatccgc aacgacgagg aactgaacaa gctgctgggc aaagtcacca      360
tcgcccaggg cggcgtcttg cctaacatcc aggccgtact gctccctaag aagacggaga      420
gtcaccacaa gcaaagggc aagtgaggct gacgtccggc ccaagtgggc ccagcccggc      480
ccgcgtctcg aaggggcacc tgtgaactca aaaggctctt ttcagagcca ccca            534
```

<210> SEQ ID NO 96
<211> LENGTH: 3919
<212> TYPE: DNA
<213> ORGANISM: Homo sapiens

<400> SEQUENCE: 96

```
agagcagctg gcagcgcggc gggcagcgtt tgccgagcgg gcgctccggg tcgcacgcaa      60
```

```
gtccgcgcgg ggtccgggcc acgcacgcgg tttcatcgcc atccccagcc gggccaggcg    120
cgcaggcaga caagctgttc gcggcgaccg gagagctccg acaccatgtg gatccaggtt    180
cggaccatgg atgggaggca gacccacacg gtggactcgc tgtccaggct gaccaaggtg    240
gaggagctga ggcggaagat ccaggagctg ttccacgtgg agccaggcct gcagaggctg    300
ttctacaggg gcaaacagat ggaggacggc catacccctct tcgactacga ggtccgcctg    360
aatgacacca tccagctcct ggtccgccag agcctcgtgc tcccccacag caccaaggag    420
cgggactccg agctctccga caccgactcc ggctgctgcc tgggccagag tgagtcagac    480
aagtcctcca cccacggcga ggcggccgcc gagactgaca gcaggccagc cgatgaggac    540
atgtgggatg agacggagtt ggggctgtac aaggtcaatg agtacgtcga tgctcgggac    600
acgaacatgg gggcgtggtt tgaggcgcag gtggtcaggt tgacgcggaa ggcccccctcc    660 cgggacgagc cctgcagctc cacgtccagg ccggcgctgg aggaggacgt catttaccac    720
gtgaaatacg acgactaccc ggagaacggc gtggtccaga tgaactccag ggacgtccga    780
gcgcgcgccc gcaccatcat caagtggcag gacctggagg tgggccaggt ggtcatgctc    840
aactacaacc ccgacaaccc caaggagcgg ggcttctggt acgacgcgga gatctccagg    900
aagcgcgaga ccaggacggc gcgggaactc tacgccaacg tggtgctggg ggatgattct    960
ctgaacgact gtcggatcat cttcgtggac gaagtcttca agattgagcg gccgggtgaa   1020
gggagcccca tggttgacaa ccccatgaga cggaagagcg ggccgtcctg caagcactgc   1080
aaggacgacg tgaacagact ctgccgggtc tgcgcctgcc acctgtgcgg gggccggcag   1140
gaccccgaca agcagctcat gtgcgatgag tgcgacatgg ccttccacat ctactgcctg   1200
gacccgcccc tcagcagtgt tcccagcgag acgagtggg actgccctga gtgccggaat   1260
gatgccagcg aggtggtact ggcgggagag cggctgagag agagcaagaa gaaggcgaag   1320
atggcctcgg ccacatcgtc ctcacagcgg gactggggca agggcatggc ctgtgtgggc   1380
cgcaccaagg aatgtaccat cgtcccgtcc aaccactacg gacccatccc ggggatcccc   1440
gtgggcacca tgtggcggtt ccgagtccag gtcagcgagt cgggtgtcca tcggccccac   1500
gtggctggca tccatggccg gagcaacgac ggagcgtact ccctagtcct ggcgggggc   1560 tatgaggatg atgtggacca tgggaattttt tcacataca cgggtagtgg tggtcgagat   1620
cttcccggca caagaggac cgcggaacag tcttgtgatc agaaactcac caacaccaac   1680
agggcgctgg ctctcaactg ctttgctccc atcaatgacc aagaagggc cgaggccaag   1740 gactggcggt cggggaagcc ggtcagggtg gtgcgcaatg tcaagggtgg caagaatagc   1800
aagtacgccc ccgctgaggg caaccgctac gatggcatct acaaggttgt gaaatactgg   1860
cccgagaagg ggaagtccgg gtttctcgtg tggcgctacc ttctgcggag ggacgatgat   1920
gagcctggcc cttggacgaa ggaggggaag gaccggatca agaagctggg gctgaccatg   1980
cagtatccag aaggctacct ggaagccctg gccaaccgag agcgagagaa ggagaacagc   2040
aagagggagg aggaggagca gcaggagggg ggcttcgcgt cccccaggac gggcaagggc   2100
aagtggaagc ggaagtcggc aggaggtggc ccgagcaggg ccgggtcccc gcgccggaca   2160
tccaagaaaa ccaaggtgga gccctacagt ctcacggccc agcagagcag cctcatcaga   2220
gaggacaaga gcaacgccaa gctgtggaat gaggtcctgg cgtcactcaa ggaccggccg   2280
gcgagcggca gcccgttcca gttgttcctg agtaaagtgg aggagacgtt ccagtgtatc   2340 tgctgtcagag agctggtgtt ccggcccatc acgaccgtgt ccagcacaa cgtgtgcaag   2400 gactgcctgg acagatcctt tcgggcacag gtgttcagct gccctgcctg ccgctacgac   2460
```

```
ctggccgcag ctatgccatg caggtgaacc agcctctgca gaccgtcctc aaccagctct   2520
tccccggcta cggcaatggc cggtgatctc caagcacttc tcgacaggcg ttttgctgaa   2580
aacgtgtcgg agggctcgtt catcggcact gattttgttc ttagtgggct taacttaaac   2640
aggtagtgtt tcctccgttc cctaaaaagg tttgtcttcc ttttttttt  atttatattt   2700 ttcaaatcta tacattttca ggaatttatg tattctggct aaaagttgga cttctcagta   2760
ttgtgtttag ttctttgaaa acataaaagc ctgcaatttc tcgacaaaac aacacaagat   2820
tttttaaaga tggaatcaga aactacgtgg tgtggaggct gttgatgttt ctggtgtcaa   2880
gttctcagaa gttgctgcca ccaactcttt aagaaggcga caggatcagt ccttctctcg   2940
ggttctggcc cccaaggtca gagcaagcat cttcctgaca gcattttgtc atctaaagtc   3000
cagtgacatg gttcccgtg  gtggcccgtg gcagcccgtg gcatggcgtg gctcagctgt   3060
ctgttgaagt tgttgcaagg aaaagaggaa acatctcggg cctagttcaa acctttgcct   3120
caaagccatc ccccaccaga ctgcttagcg tctgagatcc gcgtgaaaag tcctctgccc   3180
acgagagcag ggagttgggg ccacgcagaa atggcctcaa ggggactctg ctccacgtgg   3240
ggccaggcgt gtgactgacg ctgtccgacg aaggcggcca cggacggacg ccagcacacg   3300
aagtcacgtg caagtgcctt tgattcgttc cttctttcta aagacgacag tctttgttgt   3360
tagcactgaa ttattgaaaa tgtcaaccag attctagaaa ctgcggtcat ccagttcttc   3420
ctgacaccgg atgggtgctt gggaaccgtt tgagccttat agatcattta cattcaattt   3480
ttttaactca gcaagtgaga acttacaaga gggtttttt  ttaagttttt ttttctctta   3540
atgaacacat tttctaaatg aattttttt  gtagttactg tatatgtacc aagaaagata   3600
taacgttagg gttgggtgg  tttggttttt gtattttttt tcttttgaaa gggttttgtta  3660 attttctaa  ttttaccaaa gtttgcagcc tatacctcaa taaaacaggg atattttaaa   3720
tcacatacct gcagacaaac tggagcaatg ttattttaa  agggttttt  tcacctcctt   3780 attcttagat tattaatgta ttagggaaga atgagacaat tttgtgtagg cttttctaa   3840 agtccagtac tttgtccaga tttagattc  tcagaataaa tgttttcgc  agaaaaaaaa   3900 aaaaaaaaaa aaaaaaaa                                                 3919
```

<210> SEQ ID NO 97
<211> LENGTH: 5959
<212> TYPE: DNA
<213> ORGANISM: Homo sapiens

<400> SEQUENCE: 97

```
gggattacaa ttcgagatga gatttgggtg gatagacaga gccaaaccat atcagctaca     60
ttttcaagaa ttttgtaagc cagtcatcaa gcacagatat catcaaaaag taagaatat     120 gaaatatatg agaaatagag gcaataaatg cccaacactc atcagtccct aattcagcta    180
ctacaccttc agtattacct gtgctcctga gattgtgtct gctgcatctt tatggtggaa    240
gccccattga tggggctcct catcacttcc cagtggccca gcagggatg  ttgtgtcagt    300 agcctgaagg gcccacagtg ggagcattta accatgcac  attggcagat gctgccaatc    360
agggcttgat tgcccaaaga gggttgttgg gcatttacca gcacaccact aggctacaaa    420
gaagtggaga aaatagggga gggtggcttt tcaagaagtt tggctctaaa gagcagaaaa    480
agaaaggatg gtaatggaag gatgaggtga gattgagaga aggctggtca aacaggaaag    540
gtctgaatgt gtttgaaagc ttctcccaat aggttgaaga tactggagga agggttgatc    600
cctacagtga ggagcccaaa gagacaggcc taggagaagg ctggtcccgg agtagacacc    660
```

```
gggacaagct ttccactgta aggtaacagg aggaatcgga gggagagggg caggtaagtg    720
agagtgtcag tgagcgggcg cagaggggac tcccctccag cacttctgtt tccctgtgat    780
gcaggagagg aggccttggg tgttggaccc taagaaggaa ctcagtcaat cactgtgaga    840
tgtgtgagtg aacacatggc tgccaggtat acagggccg tggtgctact cagggtttga    900
ggaagggaga gaacctttga agctgtggta agggagagct ggggcattga tctgggatgc    960
agaggttgct gtggttgaga gctactccag tgagcaacat gatggcttca gagtgagcag   1020
gccccatggg agagagccca gctgtgtctt cctggagcgg taacacctttt ccctattcc   1080 ataggtatcc tggcatccat ctgtggtggc cttgtgatgc ttttgcctga aaccaagggt   1140
attgccttgc cagagacagt ggatgatgta gaaaaacttg gcaggtactg tacaaaattc   1200
aatgcaccct aaataaaagc aatatttaaa accacggggg aaagaatgac attgagaaaa   1260
ttgaatatcc acagggaaaa aaataagaat aaatcctcat ctcatattgt aagcaaaaaa   1320
ttcaaagtag atacaaaagg ttaacataaa aaaaccctc cagagctaga taagagtatg   1380
cattgttttt tttaatgtgg ttgtgaagag agaagcattt tcacgtaagg tgctaagact   1440
cagaagtgat ctaaaggcag gaactgctga tgtgggaaag tggaaattgc tgggacatac   1500
agcagcaggg gattaacagt gtggcttact ctacagagtg aggatgcgtc aggtctgtct   1560
agatggaatg gcataggcag gttttcaaga ctgactacaa agtgaaatgt cactgaacaa   1620
catgttatag tatttataaa aaactaaaac caaaggtgtt ttctctctgc agctggatag   1680
gaagacagat gacacacaga tgatagataa taggtagatg atagataata ggtagatgga   1740
tgatagatag atataataga tgataatcat agatagataa gtgatagtag ataaatgata   1800
aataatagat gatagatgat agatagatac agatagataa atagacaggt agatgatagg   1860
taatgtctgg atagataggt ggatagataa atagataata gatgatagat aataaacatt   1920
agtaggaaga tagagagatt gagttttgga gggggtgtt taaatagggt ataagtaaaa    1980 ctaatacccca gccaatatat taacatgagg agtaatgtca agaaaaattc acattacaca   2040
aattctttct aattgtttga aatttttca ttaaaacata gagatatgaa tatgagaatg    2100
tatagtacaa gatgtaaaat attaatatgt gccctctgtg gacacaaatg ggctgggaag   2160
aggggtaggg aagggaggac catcactttc ttgccagaga cttccatact gtttgatttt   2220 cttttaaaaat tagaacacgt agtcttgtgt tgcttgtgta gttttaaaaa atgatgtaac   2280
agctaattta acaactaaaa agcaatctta ataatgactt aggaattaag aacatggagc   2340
tctaaatatt tttaatatat aaaaaatcct gaggaacagc tttcttccct ttgattctat   2400
tccactgact gccttctgtt tacacaatga gagtgatgct ttcattcttt atccccaaac   2460
caatcaggat cagatttgca aactcatcag gaaaaaatgg aagaaaaggg agtcctctga   2520
aatcaagact tttctactgc ttcagtaaca ttaaaaataa acagctagga gaggttttt    2580 tgttttttgtt tttgtttgtt tttggcttgg ggagtgtggg tggaaggggg ttgtctaaat   2640
ggtgtgcaag gaaaatcaat acccaactaa catataaaca tgaaggatta taccagcaaa   2700
aatttaaggt acccagattc tttctaattt ttttctgttt ataatttttc ataatgaaaa   2760
gttgggtaca ttaattaatt atacctagtc tctatacatg aaaaaaaatc tagtagaagt   2820
atggtttaca gtgctacaat ttaagcacat taattgtgat ccatggttat ttactctaca   2880
aaaattactt agtgctaaat tactaaaact tgctagcatt tcccttttaa aaatcacact   2940
ggattatttt atcgtttctg ctggttttg ttcatgttaa cagctcattt ccaaatatat   3000
gttaattcag tagaagttca taaagaactt aaatgctata atgctaacaa accccctgtat  3060
```

```
cagaggaacc agcccccaat atttcagcat aggttctatt ttccataagt gttggccagc   3120
tgagaaataa aaagagtaca aagagaggaa ttttacagct gggccgctgg gggtgacatc   3180
acatatcggt aggactgtga tgcccacctg agccttaaag ccagcaagtt tttattaagg   3240
gtttcaaaag gggaggggt gtaagaacag ggagtaggta caaagatcac atgcttcaaa    3300
gggcaaaaag gagaacaaag atcacaaggc aaagggcaaa acaaacatc acaagacaaa    3360 gagcaaaagc agaatgactg aaaagggtct atgttcagcg gtgcatgtat tgtcttgata   3420
aacatcttaa acaacagaaa acagggttct agagcagaga actggtctga cctcaaattt   3480
accagggcgg ggtttcccaa tcctagtaag cctgagggta ctgcaggagg ccagggtgta   3540
tttcagtcct tatctcaact gcataaggca gactctccca gtgcgactgt ttatagacct   3600 cccctagga acgcattcct ttcccagggt cttaattatt aatattcctt gctaggaaaa     3660
gacttcagca atatcttccc tacttgcaca tccatttata ggctctctgc aagaagaaaa   3720
atatggctgt attctgcccg atcccacaag cagtcagacc ttatggttgt cttctcttgt   3780
tccctgaaaa tcgctgttac tctgttctat ttcaaggtgc actgatttca tattgttcaa   3840
acacacatgt tttataatca atttgtacag ttaacacagt agtggcctg agtgacatac    3900 atcctcagct tacaaagata acaggattaa gagattaagg taagagatgc ataagaaatt   3960
ataaaagtat taattttggg aactgataaa tgtccatatt aaaatgaaat attcacaatt   4020
tatgttcaga gattgaagta agacaggca taagaaatta taaaagtatt aatctgggga    4080
actgataaat gtccatatca aaatgaaatc ttcacaattt atattcctct gctgtggctc   4140
cagctggtcc ctccattcag ggtccttgac ttcctgcaac accctgtct aaggtctgaa    4200 cacagacaaa aaatgatcct ggagacagat attgttgtta ccttagagtt gggttttcat   4260
gaatgtattt gatcaaaacc agctatacta ttaaataata acagaacacc ctcttctaac   4320
tagttacata atctttccta aagactttct cctttgtttt ttcagtccac attcctgtaa   4380
atgtggcagg aataagaaaa ccccagtttc ccgctctcac ctttgaggcc cccgacaaag   4440
acagaaagaa ggagctatcc aggagctgat cctccttgca aagctgtgcc ttgcagagat   4500
gcacgtgtgc atttcagcta catcatgccg cgctgttgta atactgtata aagacctcaa   4560
tctatccaga gtattttat ataatgttgg atgagttagg atttgtaatg ctgttgaagt     4620
ttctgggaac acataatatg tagccagttt aacaaagaag ctgtcaggtg cacagcccctt  4680 cctgggtttt ttttcttgtg ttccctgtgg tctctgaccc attaggctaa agagagacaa   4740
gagaagcccc caacctgatt ctcatgacag ctccatcaag aatgtgggat gtgccgacca   4800
aggatttgag aaagttgtac agaaatgtgt tcatcaaatc tggtcaaggg actaagctcc   4860
tagctgacca tccattctga agattgcatg gaggatgaac atctgggaat cctgttaatg   4920
agaaggctga atcacaggca actgggccaa agggtgtgag cattcatgtt ctctgctcac   4980
cttggtttcc gcacaccttc gcaatgtgaa caggtcagga gtccctcccg tccacctcct   5040
ctgtaacagc tggggttcca ggcatggttt aggccctgtt ccagcaataa gaaccaatct   5100
gctgtacaat ctgaggactt ggctgtgtta tttacaaaat gatgctgtgg ttctgagatt   5160
atttgggaca tttttggctc tccttagtg gacacctaga gccacagatt cccttcttta    5220
ctaaacaaat cccatggatt ctgatttctg gtcttatga ttttaaaagt gaaggatat     5280 ttttcttata tttgtgagtt cagttccgat ggtgcccgtg gtcaaagcg aaaaacatgg    5340 acaattccta ttcattctta gcactttgac atgtcttggg gaaaagctta catttttaatt  5400 taaaagaaag atcaattata tccatgctta acaggatcag caggagcttt ataaatgact   5460
```

| | |
|---|---|
| ttacagagac taataaggga tttgatctttt cttttttttgt tatcgaggct tttgaaatgt | 5520 |
| ggaacttgtg tgttctgctt tatatgttat attcaatatc ttttcagatg cagtctatat | 5580 |
| tttatgctga gttttaaaaa tgaaatactt tatgcaaaca ggcaaaattg gtaccaaagg | 5640 |
| gaaacattaa ccatgaggaa gagcattttt ctaaggagaa caggtgacaa tatacacatg | 5700 |
| tgcgctaatc gtaaaatgag catcttagtc tttaaaacac atcagaattg aatacgaata | 5760 |
| atctatttgt cgatgaaata aacacaactc tttgaggatt tgagactaca ttcacccttt | 5820 |
| attcacagtc acttgcagtt ttgcttttct ctgcatttct ctgctgtaag atgactgttg | 5880 |
| cattgttgaa ttgtattttg agtggatatt tttgtttggt aacaattaaa attttaaatc | 5940 |
| gtaaaaaaaa aaaaaaaaa | 5959 |

<210> SEQ ID NO 98
<211> LENGTH: 1899
<212> TYPE: DNA
<213> ORGANISM: Homo sapiens

<400> SEQUENCE: 98

| | |
|---|---|
| agcgcgcgac ttttgaaag ccaggagggt tcgaattgca acggcagctg ccgggcgtat | 60 |
| gtgttggtgc tagaggcagc tgcagggtct cgctgggggc cgctcgggac caattttgaa | 120 |
| gaggtacttg gccacgactt attttcacct ccgacctttc cttccaggcg gtgagactct | 180 |
| ggactgagag tggctttcac aatggaaggg atcagtaatt tcaagacacc aagcaaatta | 240 |
| tcagaaaaaa agaaatctgt attatgttca actccaacta taaatatccc ggcctctccg | 300 |
| tttatgcaga agcttggctt tggtactggg gtaaatgtgt acctaatgaa aagatctcca | 360 |
| agaggtttgt ctcattctcc ttgggctgta aaaaagatta tcctatatg taatgatcat | 420 |
| tatcgaagtg tgtatcaaaa gagactaatg gatgaagcta agattttgaa aagccttcat | 480 |
| catccaaaca ttgttggtta tcgtgctttt actgaagcca atgatggcag tctgtgtctt | 540 |
| gctatggaat atggaggtga aaagtctcta aatgacttaa tagaagaacg atataaagcc | 600 |
| agccaagatc cttttccagc agccataatt ttaaagttg ctttgaatat ggcaagaggg | 660 |
| ttaaagtatc tgcaccaaga aaagaaactg cttcatggag acataaagtc ttcaaatgtt | 720 |
| gtaattaaag gcgattttga acaattaaa atctgtgatg taggagtctc tctaccactg | 780 |
| gatgaaaata tgactgtgac tgaccctgag gcttgttaca ttggcacaga gccatggaaa | 840 |
| cccaaagaag ctgtggagga gaatggtgtt attactgaca aggcagacat atttgccttt | 900 |
| ggccttactt tgtgggaaat gatgacttta tcgattccac acattaatct ttcaaatgat | 960 |
| gatgatgatg aagataaaac ttttgatgaa agtgattttg atgatgaagc atactatgca | 1020 |
| gcgttgggaa ctaggccacc tattaatatg gaagaactgg atgaatcata ccagaaagta | 1080 |
| attgaactct tctctgtatg cactaatgaa gaccctaaag atcgtccttc tgctgcacac | 1140 |
| attgttgaag ctctggaaac agatgtctag tgatcatctc agctgaagtg tggcttgcgt | 1200 |
| aaataactgt ttattccaaa atatttacat agttactatc agtagttatt agactctaaa | 1260 |
| attggcatat ttgaggacca tagtttcttg ttaacatatg gataactatt tctaatatga | 1320 |
| aatatgctta tattggctat aagcacttgg aattgtactg gttttctgt aaagttttag | 1380 |
| aaactagcta cataagtact ttgatactgc tcatgctgac ttaaaacact agcagtaaaa | 1440 |
| cgctgtaaac tgtaacatta aattgaatga ccattacttt tattaatgat ctttcttaaa | 1500 |
| tattctatat tttaatggat ctactgacat tagcactttg tacagtacaa aataaagtct | 1560 |
| acatttgttt aaaacactga acctttttgct gatgtgttta tcaaatgata actggaagct | 1620 |

| | |
|---|---:|
| gaggagaata tgcctcaaaa agagtagctc cttggatact tcagactctg gttacagatt | 1680 |
| gtcttgatct cttggatctc ctcagatctt tggttttttgc tttaatttat taaatgtatt | 1740 |
| ttccatactg agtttaaaat ttattaattt gtaccttaag catttcccag ctgtgtaaaa | 1800 |
| acaataaaac tcaaatagga tgataaagaa taaaggacac tttgggtacc agaaaaaaaa | 1860 |
| aaaaaaaaaa aaaaaaaaaa aaaaaaaaaa aaaaaaaaa | 1899 |

<210> SEQ ID NO 99
<211> LENGTH: 1876
<212> TYPE: DNA
<213> ORGANISM: Homo sapiens

<400> SEQUENCE: 99

| | |
|---|---:|
| cgggacgcgg gaacggttcc ctcccggccc cccgcgccct ttccgaggtt ccctgccttg | 60 |
| acttccccga gttctacgac aacctcagcg acagcgggag gagctgggca atcggttttg | 120 |
| cagggcaaac tccaggctct cctcatttat tattctctgg gcggcgcacg ggagaccctg | 180 |
| cagggcaaca gagcagagcg actacagctc ccaggagcca acgctgcagg gctgagccga | 240 |
| cgcgggggac agacaggacc taaatggtgg tcggaggaag ggcaaggcag acctcttctg | 300 |
| ttaccttagc gccagcaaac cgagccgccg ccgtcgccaa gccaggagac caaccccccag | 360 |
| tctcccgact aagtattttt aaatctggcg gggcttccct tcccgagcca accactccca | 420 |
| ccgtttacag ccccaaccag tcagcgtgag gcccgccatt tttcaaaccc tcttcccgcc | 480 |
| gccaatcagg atcgagcagt acattcctct cctgaccggt tctaacgggt ctgggagtta | 540 |
| acgacctggg cgacccaccg aacctgctag gctggggcgt ggagggcggg tctggtaaga | 600 |
| cactgaccaa tcgttagcct ccgtggcaag ggggcgggga ctatctgggt ttgaataatc | 660 |
| gtcagaacca atcagattag tggggatgtg gcccgtggcc tagctcgtca agttgccgtg | 720 |
| gcgcggagaa ctctgcaaaa caagaggctg aggattgcgt tagagataaa ccagttcacg | 780 |
| ccggagcccc gtgagggaag cgtctccgtt gggtccggcc gctctgcggg actctgagga | 840 |
| aaagctcgca ccaggtggac gcggatctgt caacatgggg aaaggagacc ccaacaagcc | 900 |
| gcggggcaaa atgtcctcgt acgccttctt cgtgcagacc tgccgggaag agcacaagaa | 960 |
| gaaacacccg gactcttccg tcaatttcgc ggaattctcc aagaagtgtt cggagagatg | 1020 |
| gaagaccatg tctgcaaagg agaagtcgaa gtttgaagat atggcaaaaa gtgacaaagc | 1080 |
| tcgctatgac agggagatga aaattacgt tcctcccaaa ggtgataaga aggggaagaa | 1140 |
| aaaggacccc aatgctccta aaaggccacc atctgccttc ttcctgtttt gctctgaaca | 1200 |
| tcgcccaaag atcaaaagtg aacaccctgg cctatccatt ggggatactg caaagaaatt | 1260 |
| gggtgaaatg tggtctgagc agtcagccaa agataaacaa ccatatgaac agaaagcagc | 1320 |
| taagctaaag gagaaatatg aaaaggatat tgctgccatat cgtgccaagg gcaaaagtga | 1380 |
| agcaggaaag aagggccctg gcaggccaac aggctcaaag aagaagaacg aaccagaaga | 1440 |
| tgaggaggag gaggaggaag aagaagatga agatgaggag gaagaggatg aagatgaaga | 1500 |
| ataaatggct atcctttaat gatgcgtgtg gaatgtgtgt gtgtgctcag gcaattattt | 1560 |
| tgctaagaat gtgaattcaa gtgcagctca atactagctt cagtatataaa actgtacaga | 1620 |
| tttttgtata gctgataaga ttctctgtag agaaaatact tttaaaaaat gcaggttgta | 1680 |
| gcttttttgat gggctactca tacagttaga ttttacagct tctgatgttg aatgttccta | 1740 |
| aatatttaat ggttttttta atttcttgtg tatggtagca cagcaaactt gtaggaatta | 1800 |
| gtatcaatag taaattttgg gttttttagg atgttgcatt tcgttttttt aaaaaaaatt | 1860 |

```
ttgtaataaa attatg                                                    1876

<210> SEQ ID NO 100
<211> LENGTH: 2150
<212> TYPE: DNA
<213> ORGANISM: Homo sapiens

<400> SEQUENCE: 100
ctcgagccac gaaggccccg ctgtcctgtc tagcagatac ttgcacggtt tacagaaatt      60
cggtccctgg gtcgtgtcag gaaactggaa aaaaggtcat aagcatgaag cgcagttcag     120
tttccagcgg tggtgctggc cgcctctcca tgcaggagtt aagatcccag gatgtaaata     180
aacaaggcct ctatacccct caaaccaaag agaaaccaac ctttggaaag ttgagtataa     240
acaaaccgac atctgaaaga aagtctcgc tatttggcaa aagaactagt ggacatggat      300
cccggaatag tcaacttggt atattttcca gttctgagaa aatcaaggac ccgagaccac     360
ttaatgacaa agcattcatt cagcagtgta ttcgacaact ctgtgagttt cttacagaaa     420
atggttatgc acataatgtg tccatgaaat ctctacaagc tccctctgtt aaagacttcc     480
tgaagatctt cacatttctt tatggcttcc tgtgcccctc atacgaactt cctgacacaa     540
agtttgaaga agaggttcca agaatcttta agaccttggg tatccttttt gcactatcca     600
aaagctccat gtacacagtg ggggctcctc atacatggcc tcacattgtg gcagccttag     660
tttggctaat agactgcatc aagatacata ctgccatgaa agaaagctca cctttatttg     720
atgatgggca gccttgggga gaagaaactg aagatggaat tatgcataat aagttgtttt     780
tggactacac cataaaatgc tatgagagtt ttatgagtgg tgccgacagc tttgatgaga     840
tgaatgcaga gctgcagtca aaactgaagg atttatttaa tgtggatgct tttaagctgg     900
aatcattaga agcaaaaaac agagcattga tgaacagat tgcaagattg gaacaagaaa      960
gagaaaaaga accgaatcgt ctagagtcgt tgagaaaact gaaggcttcc ttacaaggag    1020
atgttcaaaa gtatcaggca tacatgagca atttggagtc tcattcagcc attcttgacc    1080
agaaattaaa tggtctcaat gaggaaattg ctagagtaga actagaatgt gaaacaataa    1140
aacaggagaa cactcgacta cagaatatca ttgacaacca gaagtactca gttgcagaca    1200
ttgagcgaat aaatcatgaa agaaatgaat tgcagcagac tattaataaa ttaaccaagg    1260
acctggaagc tgaacaacag aagttgtgga atgaggagtt aaaatatgcc agaggcaaag    1320
aagcgattga acacaatta gcagagtatc acaaattggc tagaaaatta aaacttattc     1380
ctaaaggtgc tgagaattcc aaaggttatg actttgaaat taagtttaat cccgaggctg    1440
gtgccaactg ccttgtcaaa tacagggctc aagtttatgt acctcttaag gaactcctga    1500
atgaaactga agaagaaatt aataaagccc taaataaaaa aatgggtttg gaggatactt    1560
tagaacaatt gaatgcaatg ataacagaaa gcaagagaag tgtgagaact ctgaaagaag    1620
aagttcaaaa gctggatgat cttttaccaa caaaaattaa ggaagcagag gaagaggatg    1680
aaaaatgtgc cagtgagctt gagtccttgg agaaacacaa gcacctgcta gaaagtactg    1740
ttaaccaggg gctcagtgaa gctatgaatg aattagatgc tgttcagcgg gaataccaac    1800
tagttgtgca aaccacgact gaagaaagac gaaagtggg aaataacttg caacgtctgt    1860
tagagatggt tgctacacat gttgggtctg tagagaaaca tcttgaggag cagattgcta    1920
aagttgatag agaatatgaa gaatgcatgt cagaagatct ctcggaaaat attaaagaga    1980
ttagagataa gtatgagaag aaagctctac taattaagtc ttctgaagaa tgaagataaa    2040
atgttgatca tgtatatata tccatagtga ataaaattgt ctcagtaaaa aaaaaaaaaa    2100
```

```
aaaaaaaaaa aaaaaaaaaa aaaaaaaaaa aaaaaaaaaa aaaaaaaaaa              2150

<210> SEQ ID NO 101
<211> LENGTH: 2984
<212> TYPE: DNA
<213> ORGANISM: Homo sapiens

<400> SEQUENCE: 101
ggaaattcaa acgtgtttgc ggaaaggagt ttgggttcca tcttttcatt tccccagcgc      60
agctttctgt agaaatggaa tccgaggatt taagtggcag agaattgaca attgattcca     120
taatgaacaa agtgagagac attaaaaata agtttaaaaa tgaagacctt actgatgaac     180
taagcttgaa taaaatttct gctgatacta cagataactc gggaactgtt aaccaaatta     240
tgatgatggc aaacaaccca gaggactggt tgagtttgtt gctcaaacta gagaaaaaca     300
gtgttccgct aagtgatgct cttttaaata aattgattgg tcgttacagt caagcaattg     360
aagcgcttcc cccagataaa tatggccaaa atgagagttt tgctagaatt caagtgagat     420
ttgctgaatt aaaagctatt caagagccag atgatgcacg tgactacttt caaatggcca     480
gagcaaactg caagaaattt gcttttgttc atatatcttt tgcacaattt gaactgtcac     540
aaggtaatgt caaaaaaagt aaacaacttc ttcaaaaagc tgtagaacgt ggagcagtac     600
cactagaaat gctggaaatt gccctgcgga atttaaaccct ccaaaaaaag cagctgcttt     660
cagaggagga aagaagaat ttatcagcat ctacggtatt aactgcccaa gaatcatttt     720
ccggttcact tgggcattta cagaatagga caacagttg tgattccaga ggacagacta     780
ctaaagccag gtttttatat ggagagaaca tgccaccaca agatgcagaa ataggttacc     840
ggaattcatt gagacaaact aacaaaaacta aacagtcatg cccatttgga agagtcccag     900
ttaaccttct aaatagccca gattgtgatg tgaagacaga tgattcagtt gtaccttgtt     960
ttatgaaaag acaaacctct agatcagaat gccgagattt ggttgtgcct ggatctaaac    1020
caagtggaaa tgattcctgt gaattaagaa atttaaagtc tgttcaaaat agtcatttca    1080
aggaacctct ggtgtcagat gaaaagagtt ctgaacttat tattactgat tcaataaccc    1140
tgaagaataa aacggaatca agtcttctag ctaaattaga agaaactaaa gagtatcaag    1200
aaccagaggt tccagagagt aaccagaaac agtggcaatc taagagaaag tcagagtgta    1260
ttaaccagaa tcctgctgca tcttcaaatc actggcagat tccggagtta gcccgaaaag    1320
ttaatacaga gcagaaacat accacttttg agcaacctgt cttttcagtt tcaaaacagt    1380
caccaccaat atcaacatct aaatggtttg acccaaaatc tatttgtaag acaccaagca    1440
gcaatacctt ggatgattac atgagctgtt ttagaactcc agttgtaaag aatgactttc    1500
cacctgcttg tcagttgtca acaccttatg gccaacctgc ctgtttccag cagcaacagc    1560
atcaaatact tgccactcca cttcaaaatt tacaggtttt agcatcttct tcagcaaatg    1620
aatgcatttc ggttaaagga agaatttatt ccatttttaa gcagatagga agtggaggtt    1680
caagcaaggt atttcaggtg ttaaatgaaa agaaacagat atatgctata aaatatgtga    1740
acttagaaga agcagataac caaactcttg atagttaccg gaacgaaata gcttatttga    1800
ataaactaca caacacagt gataagatca tccgacttta tgattatgaa atcacggacc    1860
agtacatcta catggtaatg gagtgtggaa atattgatct aatagttgg cttaaaagga    1920 aaaaatccat tgatccatgg gaacgcaaga gttactggaa aaatatgtta gaggcagttc    1980
acacaatcca tcaacatggc attgttcaca gtgatcttaa accagctaac tttctgatag    2040
ttgatggaat gctaaagcta attgattttg ggattgcaaa ccaaatgcaa ccagatacaa    2100
```

```
caagtgttgt taaagattct caggttggca cagttaatta tatgccacca gaagcaatca    2160
aagatatgtc ttcctccaga gagaatggga aatctaagtc aaagataagc cccaaaagtg    2220
atgtttggtc cttaggatgt attttgtact atatgactta cgggaaaaca ccatttcagc    2280
agataattaa tcagatttct aaattacatg ccataattga tcctaatcat gaaattgaat    2340
ttcccgatat tccagagaaa gatcttcaag atgtgttaaa gtgttgttta aaaagggacc    2400
caaaacagag gatatccatt cctgagctcc tggctcatcc ctatgttcaa attcaaactc    2460
atccagttaa ccaaatggcc aagggaacca ctgaagaaat gaaatatgtt ctgggccaac    2520
ttgttggtct gaattctcct aactccattt tgaaagctgc taaaacttta tatgaacact    2580
atagtggtgg tgaaagtcat aattcttcat cctccaagac ttttgaaaaa aaaggggaa    2640 aaaaatgatt tgcagttatt cgtaatgtca ataccacct ataaaatata ttggactgtt    2700
atactcttga atccctgtgg aaatctacat ttgaagacaa catcactctg aagtgttatc    2760
agcaaaaaaa attcagtaga ttatctttaa aagaaaactg taaaaatagc aaccacttat    2820
ggtactgtat atattgtaga cttgttttct ctgttttatg ctcttgtgta atctacttga    2880
catcatttta ctcttggaat agtgggtgga tagcaagtat attctaaaaa actttgtaaa    2940
taaagttttg tggctaaaat gacactaaaa aaaaaaaaa aaaa                      2984
```

<210> SEQ ID NO 102
<211> LENGTH: 1484
<212> TYPE: DNA
<213> ORGANISM: Homo sapiens

<400> SEQUENCE: 102

```
tggaagcgcg tgcttttgtt tgtgtccctg gccatggcgc tgcagctctc ccgggagcag      60
ggaatcaccc tgcgcgggag cgccgaaatc gtggccgagt tcttctcatt cggcatcaac     120 agcatttat atcagcgtgg catatatcca tctgaaacct ttactcgagt gcagaaatac     180
ggactcacct tgcttgtaac tactgatctt gagctcataa aatacctaaa taatgtggtg     240
gaacaactga aagattggtt atacaagtgt tcagttcaga aactggttgt agttatctca     300
aatattgaaa gtggtgaggt cctggaaaga tggcagtttg atattgagtg tgacaagact     360
gcaaaagatg acagtgcacc cagagaaaag tctcagaaag ctatccagga tgaaatccgt     420
tcagtgatca gacagatcac agctacggtg acatttctgc cactgttgga agtttcttgt     480
tcatttgatc tgctgattta tacagacaaa gatttggttg tacctgaaaa atgggaagag     540
tcgggaccac agtttattac caattctgag gaagtgcgcc ttcgttcatt tactactaca     600
atccacaaag taaatagcat ggtggcctac aaaattcctg tcaatgactg aggatgacat     660
gaggaaaata atgtaattgt aattttgaaa tgtggttttc ctgaaatcag gtcatctata     720
gttgatatgt tttatttcat tggttaatt ttacatggag aaaaccaaaa tgatacttac     780
tgaactgtgt gtaattgttc cttttatttt tttggtacct atttgactta ccatggagtt     840
aacatcatga atttattgca cattgttcaa aaggaaccag gaggttttt tgtcaacatt     900 gtgatgtata ttcctttgaa gatagtaact gtagatggaa aaacttgtgc tataaagcta     960
gatgctttcc taaatcagat gttttggtca gtagtttga ctcagtatag gtagggagat    1020
atttaagtat aaaatacaac aaaggaagtc taaatattca gaatctttgt taaggtcctg    1080
aaagtaactc ataatctata aacaatgaaa tattgctgta tagctccttt tgaccttcat    1140
ttcatgtata gttttcccta ttgaatcagt ttccaattat ttgactttaa tttatgtaac    1200
ttgaacctat gaagcaatgg atatttgtac tgtttaatgt tctgtgatac agaacagatt    1260
```

| | |
|---|---:|
| aatactccct ttttatcatt acagttagct aaaaaattgc caggcagtcc acaaaacaga | 1320 |
| atttgcttta agaccaaccc acagagtcag ctggagacta acggcgctgg ggcctgctgg | 1380 |
| gccgggatat agtcgtgttt agctaagtgt cgagagcatt aagaagaaag tcctggttgg | 1440 |
| aggcgcaagg cctgcagcac cagctgtgga atccccaata atgt | 1484 |

<210> SEQ ID NO 103
<211> LENGTH: 5698
<212> TYPE: DNA
<213> ORGANISM: Homo sapiens

<400> SEQUENCE: 103

| | |
|---|---:|
| aggttcaagt ggagctctcc taaccgacgc gcgtctgtgg agaagcggct tggtcggggg | 60 |
| tggtctcgtg gggtcctgcc tgtttagtcg ctttcagggt tcttgagccc cttcacgacc | 120 |
| gtcaccatgg aagtgtcacc attgcagcct gtaaatgaaa atatgcaagt caacaaaata | 180 |
| aagaaaaatg aagatgctaa gaaaagactg tctgttgaaa gaatctatca aaagaaaaca | 240 |
| caattggaac atattttgct ccgcccagac acctacattg gttctgtgga attagtgacc | 300 |
| cagcaaatgt gggtttacga tgaagatgtt ggcattaact atagggaagt cacttttgtt | 360 |
| cctggttttgt acaaaatctt tgatgagatt ctagttaatg ctgcggacaa caaacaaagg | 420 |
| gacccaaaaa tgtcttgtat tagagtcaca attgatccgg aaaacaattt aattagtata | 480 |
| tggaataatg aaaaggtat tcctgttgtt gaacacaaag ttgaaaagat gtatgtccca | 540 |
| gctctcatat ttggacagct cctaacttct agtaactatg atgatgatga aaagaaagtg | 600 |
| acaggtggtc gaaatggcta tgagccaaaa ttgtgtaaca tattcagtac caaatttact | 660 |
| gtggaaacag ccagtagaga atacaagaaa atgttcaaac agacatggat ggataatatg | 720 |
| ggaagagctg gtgagatgga actcaagccc ttcaatggag aagattatac atgtatcacc | 780 |
| tttcagcctg atttgtctaa gtttaaaatg caaagcctgg acaaagatat tgttgcacta | 840 |
| atggtcagaa gagcatatga tattgctgga tccaccaaag atgtcaaagt ctttcttaat | 900 |
| ggaaataaac tgccagtaaa aggatttcgt agttatgtgg acatgtattt gaaggacaag | 960 |
| ttggatgaaa ctggtaactc cttgaaagta atacatgaac aagtaaacca caggtgggaa | 1020 |
| gtgtgtttaa ctatgagtga aaaaggcttt cagcaaatta gctttgtcaa cagcattgct | 1080 |
| acatccaagg gtggcagaca tgttgattat gtagctgatc agattgtgac taaacttgtt | 1140 |
| gatgttgtga agaagaagaa caagggtggt gttgcagtaa aagcacatca ggtgaaaaat | 1200 |
| cacatgtgga ttttttgtaaa tgccttaatt gaaaacccaa cctttgactc tcagacaaaa | 1260 |
| gaaaacatga ctttacaacc caagagcttt ggatcaacat gccaattgag tgaaaaattt | 1320 |
| atcaaagctg ccattggctg tggtattgta gaaagcatac taaactgggt gaagtttaag | 1380 |
| gcccaagtcc agtaaacaa gaagtgttca gctgtaaaac ataatagaat caagggaatt | 1440 |
| cccaaactcg atgatgccaa tgatgcaggg ggccgaaact ccactgagtg tacgcttatc | 1500 |
| ctgactgagg gagattcagc caaaactttg gctgtttcag gccttggtgt ggttgggaga | 1560 |
| gacaaatatg gggttttccc tcttagagga aaaatactca atgttcgaga agcttctcat | 1620 |
| aagcagatca tggaaaatgc tgagattaac aatatcatca agattgtggg tcttcagtac | 1680 |
| aagaaaaact atgaagatga agattcattg aagacgcttc gttatgggaa gataatgatt | 1740 |
| atgacagatc aggaccaaga tggttcccac atcaaaggct tgctgattaa ttttatccat | 1800 |
| cacaactggc cctctcttct gcgacatcgt tttctggagg aatttatcac tcccattgta | 1860 |
| aaggtatcta aaacaagca agaaatggca ttttacagcc ttcctgaatt tgaagagtgg | 1920 |

```
aagagttcta ctccaaatca taaaaaatgg aaagtcaaat attacaaagg tttgggcacc    1980
agcacatcaa aggaagctaa agaatacttt gcagatatga aaagacatcg tatccagttc    2040
aaatattctg gtcctgaaga tgatgctgct atcagcctgg cctttagcaa aaaacagata    2100
gatgatcgaa aggaatggtt aactaatttc atggaggata gaagacaacg aaagttactt    2160
gggcttcctg aggattactt gtatggacaa actaccacat atctgacata taatgacttc    2220
atcaacaagg aacttatctt gttctcaaat tctgataacg agagatctat cccttctatg    2280
gtggatggtt tgaaaccagg tcagagaaag gttttgttta cttgcttcaa acggaatgac    2340
aagcgagaag taaaggttgc ccaattagct ggatcagtgg ctgaaatgtc ttcttatcat    2400
catggtgaga tgtcactaat gatgaccatt atcaatttgg ctcagaattt tgtgggtagc    2460
aataatctaa acctcttgca gcccattggt cagtttggta ccaggctaca tggtggcaag    2520
gattctgcta gtccacgata catctttaca atgctcagct cttggctcg attgttattt     2580 ccaccaaaag atgatcacac gttgaagttt ttatatgatg acaaccagcg tgttgagcct    2640
gaatggtaca ttcctattat tcccatggtg ctgataaatg gtgctgaagg aatcggtact    2700
gggtggtcct gcaaaatccc caactttgat gtgcgtgaaa ttgtaaataa catcaggcgt    2760
ttgatggatg gagaagaacc tttgccaatg cttccaagtt acaagaactt caagggtact    2820
attgaagaac tggctccaaa tcaatatgtg attagtggtg aagtagctat tcttaattct    2880
acaaccattg aaatctcaga gcttcccgtc agaacatgga cccagacata caagaacaa    2940 gttctagaac ccatgttgaa tggcaccgag aagacacctc ctctcataac agactatagg    3000
gaataccata cagataccac tgtgaaattt gttgtgaaga tgactgaaga aaaactggca    3060
gaggcagaga gagttggact acacaaagtc ttcaaactcc aaactagtct cacatgcaac    3120
tctatggtgc ttttttgacca cgtaggctgt ttaaagaaat atgacacggt gttggatatt    3180
ctaagagact ttttttgaact cagacttaaa tattatggat taagaaaaga atggctccta    3240
ggaatgcttg gtgctgaatc tgctaaactg aataatcagg ctcgctttat cttagagaaa    3300
atagatggca aaataatcat tgaaaataag cctaagaaag aattaattaa agttctgatt    3360
cagaggggat atgattcgga tcctgtgaag gcctggaaag aagcccagca aaaggttcca    3420
gatgaagaag aaaatgaaga gagtgacaac gaaaaggaaa ctgaaaagag tgactccgta    3480
acagattctg gaccaaccct taactatctt cttgatatgc ccctttggta tttaaccaag    3540
gaaaagaaag atgaactctg caggctaaga aatgaaaaag aacaagagct ggacacatta    3600
aaaagaaaga gtccatcaga tttgtggaaa gaagacttgg ctacatttat tgaagaattg    3660
gaggctgttg aagccaagga aaacaagat gaacaagtcg gacttcctgg aaagggggg     3720 aaggccaagg ggaaaaaaac acaaatggct gaagttttgc cttctccgcg tggtcaaaga    3780
gtcattccac gaataaccat agaaatgaaa gcagaggcag aaaagaaaaa taaaagaaa    3840 attaagaatg aaaatactga aggaagccct caagaagatg gtgtggaact agaaggccta    3900
aaacaaagat tagaaaagaa acagaaaaga gaaccaggta caagacaaa gaaacaaact    3960 acattggcat ttaagccaat caaaaaagga aagaagagaa atccctggtc tgattcagaa    4020
tcagatagga gcagtgacga aagtaatttt gatgtccctc cacgagaaac agagccacgg    4080
agagcagcaa caaaaacaaa attcacaatg gatttggatt cagatgaaga tttctctcgat   4140 tttgatgaaa aaactgatga tgaagatttt gtcccatcag atgctagtcc acctaagacc    4200
aaaacttccc caaaacttag taacaaagaa ctgaaccac agaaaagtgt cgtgtcagac    4260
cttgaagctg atgatgttaa gggcagtgta ccactgtctt caagccctcc tgctacacat    4320
```

```
ttcccagatg aaactgaaat tacaaaccca gttcctaaaa agaatgtgac agtgaagaag    4380
acagcagcaa aaagtcagtc ttccacctcc actaccggtg ccaaaaaaag ggctgcccca    4440
aaaggaacta aaagggatcc agctttgaat tctggtgtct ctcaaaagcc tgatcctgcc    4500
aaaaccaaga atcgccgcaa aaggaagcca tccacttctg atgattctga ctctaatttt    4560
gagaaaattg tttcgaaagc agtcacaagc aagaaatcca aggggagag tgatgacttc     4620 catatggact ttgactcagc tgtggctcct cgggcaaaat ctgtacgggc aaagaaacct    4680
ataaagtacc tggaagagtc agatgaagat gatctgtttt aaaatgtgag gcgattattt    4740
taagtaatta tcttaccaag cccaagactg gttttaaagt tacctgaagc tcttaacttc    4800
ctcccctctg aatttagttt ggggaaggtg ttttagtac aagacatcaa agtgaagtaa     4860
agcccaagtg ttctttagct ttttataata ctgtctaaat agtgaccatc tcatgggcat    4920
tgttttcttc tctgctttgt ctgtgttttg agtctgcttt cttttgtctt taaaacctga    4980
tttttaagtt cttctgaact gtagaaatag ctatctgatc acttcagcgt aaagcagtgt    5040
gtttattaac catccactaa gctaaaacta gagcagtttg atttaaaagt gtcactcttc    5100 ctcctttct actttcagta gatatgagat agagcataat tatctgtttt atcttagttt     5160
tatacataat ttaccatcag atagaacttt atggttctag tacagatact ctactacact    5220
cagcctctta tgtgccaagt ttttctttaa gcaatgagaa attgctcatg ttcttcatct    5280
tctcaaatca tcagaggcca agaaaaaca ctttggctgt gtctataact tgacacagtc     5340
aatagaatga agaaaattag agtagttatg tgattatttc agctcttgac ctgtcccctc    5400
tggctgcctc tgagtctgaa tctcccaaag agagaaacca atttctaaga ggactggatt    5460
gcagaagact cggggacaac atttgatcca agatcttaaa tgttatattg ataaccatgc    5520
tcagcaatga gctattagat tcattttggg aaatctccat aatttcaatt tgtaaacttt    5580
gttaagacct gtctacattg ttatatgtgt gtgacttgag taatgttatc aacgttttg     5640 taaatattta ctatgttttt ctattagcta aattccaaca attttgtact ttaataaa     5698
```

<210> SEQ ID NO 104
<211> LENGTH: 2639
<212> TYPE: DNA
<213> ORGANISM: Homo sapiens
<400> SEQUENCE: 104

```
ggcacgaggg gccgacgcga gcgccgcgct tcgcttcagc tgctagctgg cccaagggag      60
gcgaccgcgg agggtggcga ggggcggcca ggacccgcag ccccgggcc gggccggtcc      120 ggaccgccag ggagggcagg tcagtgggca gatcgcgtcc gcgggattca atctctgccc     180
gctctgataa cagtcctttt ccctggcgct cacttcgtgc ctggcacccg gctgggcgcc    240
tcaagaccgt tgtctcttcg atcgcttctt tggacttggc gaccatttca gagatgtctt    300
ccagaagtac caaagattta attaaaagta agtggggatc gaagcctagt aactccaaat    360
ccgaaactac attagaaaaa ttaaagggag aaattgcaca cttaaagaca tcagtggatg    420
aaatcacaag tgggaaagga agctgactg ataaagagac acacagactt ttggagaaaa     480
ttcgagtcct tgaggctgag aaggagaaga atgcttatca actcacagag aaggacaaag    540
aaatacagcg actgagagac caactgaagg ccagatatag tactaccgca ttgcttgaac    600
agctggaaga gacaacgaga gaaggagaaa ggagggagca ggtgttgaaa gccttatctg    660
aagagaaaga cgtattgaaa caacagttgt ctgctgcaac ctcacgaatt gctgaacttg    720
aaagcaaaac caatacactc cgtttatcac agactgtggc tccaaactgc ttcaactcat    780
```

| | | |
|---|---|---|
| caataaataa tattcatgaa atggaaatac agctgaaaga tgctctggag aaaaatcagc | 840 |
| agtggctcgt gtatgatcag cagcgggaag tctatgtaaa aggactttta gcaaagatct | 900 |
| ttgagttgga aaagaaaacg gaaacagctg ctcattcact cccacagcag acaaaaaagc | 960 |
| ctgaatcaga aggttatctt caagaagaga agcagaaatg ttacaacgat ctcttggcaa | 1020 |
| gtgcaaaaaa agatcttgag gttgaacgac aaaccataac tcagctgagt tttgaactga | 1080 |
| gtgaatttcg aagaaaatat gaagaaaccc aaaaagaagt tcacaatttta aatcagctgt | 1140 |
| tgtattcaca aagaagggca gatgtgcaac atctggaaga tgataggcat aaaacagaga | 1200 |
| agatacaaaa actcagggaa gagaatgata ttgctagggg aaaacttgaa gaagagaaga | 1260 |
| agagatccga agagctctta tctcaggtcc agtttcttta cacatctctg ctaaagcagc | 1320 |
| aagaagaaca aacaagggta gctctgttgg aacaacagat gcaggcatgt actttagact | 1380 |
| ttgaaaatga aaaactcgac cgtcaacatg tgcagcatca attgcatgta attcttaagg | 1440 |
| agctccgaaa agcaagaaat caaataacac agttggaatc cttgaaacag cttcatgagt | 1500 |
| ttgccatcac agagccatta gtcactttcc aaggagagac tgaaaacaga gaaaagttg | 1560 |
| ccgcctcacc aaaaagtccc actgctgcac tcaatgaaag cctggtggaa tgtcccaagt | 1620 |
| gcaatataca gtatccagcc actgagcatc gcgatctgct tgtccatgtg aatactgtt | 1680 |
| caaagtagca aaataagtat ttgttttgat attaaaagat tcaatactgt attttctgtt | 1740 |
| agcttgtggg cattttgaat tatatatttc acattttgca taaaactgcc tatctacctt | 1800 |
| tgacactcca gcatgctagt gaatcatgta tcttttaggc tgctgtgcat ttctcttggc | 1860 |
| agtgatacct ccctgacatg gttcatcatc aggctgcaat gacagaatgt ggtgagcagc | 1920 |
| gtctactgag actactaaca ttttgcactg tcaaaatact tggtgaggaa agatagctc | 1980 |
| aggttattgc taatgggtta atgcaccagc aagcaaaata ttttatgttt tgggggtttg | 2040 |
| aaaaatcaaa gataattaac caaggatctt aactgtgttc gcatttttta tccaagcact | 2100 |
| tagaaaacct acaatcctaa ttttgatgtc cattgttaag aggtggtgat agatactatt | 2160 |
| tttttttttca tattgtatag cggttattag aaaagttggg gattttcttg atctttattg | 2220 |
| ctgcttacca ttgaaactta acccagctgt gttccccaac tctgttctgc gcacgaaaca | 2280 |
| gtatctgttt gaggcataat cttaagtggc cacacacaat gttttctctt atgttatctg | 2340 |
| gcagtaactg taacttgaat tacattagca cattctgctt agctaaaatt gttaaaataa | 2400 |
| actttaataa acccatgtag ccctctcatt tgattgacag tattttagtt attttttggca | 2460 |
| ttcttaaagc tgggcaatgt aatgatcaga tctttgtttg tctgaacagg tatttttata | 2520 |
| catgcttttt gtaaaccaaa aacttttaaa tttcttcagg ttttctaaca tgcttaccac | 2580 |
| tgggctactg taaatgagaa aagaataaaa ttatttaatg ttttaaaaaa aaaaaaaaa | 2639 |

<210> SEQ ID NO 105
<211> LENGTH: 1376
<212> TYPE: DNA
<213> ORGANISM: Homo sapiens

<400> SEQUENCE: 105

| | | |
|---|---|---|
| gtttgaaatc ggaaagttgg cggggctgcg ggagctgagc ctagagtccg gctgttggct | 60 |
| agagtgggcg cggatctggt gtggggaagg cggcgggact caggcctgcc tgcgaagcat | 120 |
| tgtcctacat aatggtagag gacgaactgg cacttttcga taaaagcata aatgaatttt | 180 |
| ggaataaatt caaagtacg gacacctcct gtcagatggc gggactaaga gatacctaca | 240 |
| aggattccat caaagcattt gcagaaaagc tgtctctgtgaa attaaaggaa gaagaacgaa | 300 |

```
tggttgagat gtttctggaa tatcaaaatc agatcagcag gcaaaataag ctcattcaag      360
aaaaaaagga taacttgtta aaattgattg ctgaagtaaa aggcaaaaag caggaattgg      420
aagtactgac tgcaaatatc caggatctta aggaagaata ttctaggaag aaggaaacta     480
tttctactgc taataaagcg aatgcagaga ggttgaaaag gctgcagaaa tctgcagact     540
tgtataaaga tcgacttgga ctagaaattc gaaaaattta tggtgagaaa ttgcagttta     600
ttttcactaa tattgaccct aagaatcctg agagcccatt tatgttttcc ttacatctca     660
atgaagcaag ggactatgaa gtgtcagata gtgcccctca tcttgagggc ctagcagaat     720
ttcaagagaa tgtaaggaag accaacaatt tttcagcttt tcttgccaat gttcggaaag     780
cttttactgc cacggtttat aattaacata caaatagtgt atataaaaac ggtttatttt     840
tcttctctat tacatatctc tttttttttct tgtttttatt attactatac tttaagtttt    900
agggtacatg tgcacaatgt gcaggtttgt tacatatgta tacatgtgcc atattggtgt     960
gctgcaccca ttaactcgtc atttcattag gtatatctcc taatgctatc cctcccccct   1020
cccccaaccc acaacagtcc ccgttgtgtg atgttcccct tcctgtgtcc atgtgttctc   1080
attgttcaat tcccacctag gagtgagaat atgtggtgtt tggtttttg tcctttcgat    1140 agtttgctga gaatgatggt ttccagcttc atccatgttc ctacaaagga catgaactca   1200
tcctttttta tggctgcata gtattccatg gtgtatatgt gccacatttt cttaatccag   1260
tctatcattg ttggacattt gggttggttc caagtctttg ctattgtgaa tagtgccgaa   1320
ataaacatac gtgtgcatgt gtctccaaaa aaaaaaaaa aaaaaaaaa aaaaaa        1376
```

METHOD FOR CONFIRMING THE EXPOSURE ON CHRYSENE

TECHNICAL FIELD

The present invention relates to a method for confirming the exposure on chrysene by using a marker gene up-regulated or down-regulated by chrysene.

BACKGROUND ART

Chrysene, one of polycyclic aromatic hydrocarbons, is discharged in the environment because of incomplete combustion. It has been used for organic material synthesis or chemical research, but has not been produced as a commercial product. In the environment, the movement of chrysene is hardly detected in soil because it does not have volatility and it is absorbed onto sediment and suspended solids in water, indicating it does not have volatility on the surface of water, either. Decomposition of a microorganism is slower in water than in soil. Absorption in the soil makes the decomposition of a microorganism even slower. Hydrolysis of it does not occur in the environment and the level of its concentration in aquatic living organisms is very low. Chrysene exists as particles in the air and thus it can be eliminated by physical methods.

According to a report by the Ministry of Environment Korea (1997) investigating chrysene concentration in the domestic air and underground shopping centers, the chrysene concentration was 1.80 ng/m$^3$ in Seoul residential area and 1.2 ng/m$^3$ in Taepyeong-dong, Daejeon, Korea. To investigate food contamination by polycyclic aromatic hydrocarbons, the chrysene concentrations in meat processed products sold in 9 cities in Korea were examined. As a result, the concentration of chrysene was 0.176 μg/kg in smoked products, 0.842 μg/kg in poultry, 0.143 μg/kg in meats (Kim M C et al., Korea Food & Drug Administration, 2001 Endocrine Discruptors Research report, 2001, and 0.82 μg/kg in edible oil and fat (Lee J O et al., Korea Food & Drug Administration, Research report 6, 790. 2002).

Chrysene was absorbed via oral pathway in animal tests. It was also absorbed through skin but the absorption rate was very slow and most of the absorbed chrysene was discharged through feces [ASTDR (Agency for Toxic Substance and Disease Registry), 1990). Chrysene is converted into dihydrodiols by an enzyme and further changed into diol-epoxide capable of binding to DNA to produce DNA byproduct. It was reported that diol-epoxide derivatives of chrysene could be potential carcinogens or mutagens. In Ames tests using salmonella TA110 and TA98 strains, chrysene showed mutagenicity in rats even under normal metabolic activity of the liver [HSDB (Hazardous Substance Data bank)].

Reports on the carcinogenicity of the polycyclic aromatic hydrocarbons and changes of gene expression induced by the same have been made intermittently but those reports are mostly limited to benzo[a]pyrene, the most representative polycyclic aromatic hydrocarbon. Despite chrysene has high potential for causing cancer in human, there are not enough data to evaluate risk in human and the screening method is still limited to the conventional GC-MS (Gas Chromatography-Mass Spectrometer) and HPLC (High Performance Liquid Chromatography). GC-MS or HPLC enables quantification but requires high cost equipments and set up for proper conditions for analysis. Therefore, a faster and easier screening method such as real-time PCR (real-time reverse transcript polymerase chain reaction) with primers or DNA microarray chip is required to establish a molecular index to detect toxicity and to evaluate risk in human. It is also important to establish a countermeasure for the exposure on chrysene and a regulation method of the same by using the above method.

Genome sequencing project of various species including 6 species of mammals and 292 species of microorganisms has been completed and reported to NCBI (National Center for Biotechnology Information). Based on this huge data, genome-wide expression study has been undergoing to disclose functions of those genes. DNA microarray is also performed to analyze expressions of thousands of genes at a time (Schena M et al., Proc. Natl. Acad. Sci. USA 93: 10614-10619, 1996).

Microarray is prepared by integrating cDNA (complementary DNA) or 20-25 base pair long oligonucleotide sets on a glass substrate. cDNA microarray has been produced in laboratories and companies such as Agilent and Genomic Solutions, in which cDNAs are fixed by a mechanical method or ink jetting on a chip (Sellheyer K and Belbin T J, J. Am. Acad. Dermatol. 51: 681-692, 2004). Oligonucleotide microarray has been produced in Affymetrix by direct synthesis on a chip via photolithography and in Agilent by fixing synthetic oligonucleotides on a chip (Sellheyer K et al., Am. Acad. Dermatol. 51: 681-692, 2004).

To analyze gene expression, RNAs are extracted from samples such as tissues, which are hybridized with oligonucleotide on DNA microarray. The obtained RNA is labeled with a fluorescent material or an isotope and converted into cDNA. In oligo-microarray, the control and the experimental groups are labeled with two different fluorescent materials (for example, Cy3 and Cy5), followed by hybridization simultaneously on the chip. Images are optically scanned to measure the strength of fluorescence and the results are analyzed. By comparing the strengths of the two different fluorescent materials, gene expression is determined (Somasundaram K et al., Genomics Proteomics I: 1-10, 2002).

The recent DNA microarray based high tech toxicogenomics enables the analysis and quantification of gene expression patterns in specific tissues or cell lines induced by a medicant or novel a drug candidate and other chemicals. That is, by analyzing the expression frequency of a specific gene in a specific cell, it is possible to identify a gene causing side effects of such drugs or harmful action of such environmental pollutant materials. Then, it is further possible to understand the molecular mechanism related to such side effects and functions of drugs and environmental pollutant materials.

The present inventors screened genes up-regulated or down-regulated by chrysene by observing and analyzing gene expression profiles of chrysene in HepG2, a human Hepatoma cell line, using oligo-microarray on which 41,000 human genes are integrated, and further completed this invention by confirming the genes capable of confirming the exposure on chrysene by investigating expressions of target genes by real-time RT-PCR and by establishing a method for confirming the exposure on chrysene.

DISCLOSURE

Technical Problem

It is an objective of the present invention to provide a method for confirming the exposure on chrysene by using a marker gene up-regulated or down-regulated by chrysene.

Technical Solution

To achieve the above objective, the present invention provides a method for confirming the exposure on chrysene comprising the following steps:

1) separating RNAs from human somatic cells of a sample, the experimental group, and from somatic cells of the control group; and, 2) determining the exposure on chrysene by comparing the expression of the gene whose expression is affected by chrysene with that of the control, when the expression of the gene is significantly changed, compared with that of the control, the gene is regarded as being exposed to chrysene.

The present invention also provides a method for confirming the exposure on chrysene comprising the following steps:

1) separating RNAs from human somatic cells of a sample, the experimental group, and from somatic cells of the control group;
2) synthesizing cDNAs with the RNAs separated from the experimental group and the control of step 1) and labeling them with different fluorescent materials;
3) hybridizing the cDNAs of step 2) each labeled with different fluorescent materials with DNA microarray chip comprising oligonucleotide containing the full length or a part of a gene whose expression is changed by chrysene or its complement oligonucleotide;
4) analyzing the DNA microarray chip reacted in step 3); and
5) determining the exposure on chrysene by comparing the expression of the gene whose expression is affected by chrysene with that of the control, when the expression of the gene is significantly changed, compared with that of the control, the gene is regarded as being exposed to chrysene.

In addition, the present invention provides a method for confirming the exposure on chrysene comprising the following steps:

1) separating RNAs from human somatic cells of a sample, the experimental group, and from somatic cells of the control group;
2) performing real-time RT-PCR (reverse transcript polymerase chain reaction) with the RNAs of step 1) using a primer set capable of amplifying the gene whose expression changed by chrysene; and
3) determining the exposure on chrysene by comparing the expression of the gene of step 2) with that of the control, when the expression of the gene is significantly changed, compared with that of the control, the gene is regarded as being exposed to chrysene.

Advantageous Effect

The method of the present invention using a DNA fragment whose expression is increased or decreased specifically when it is exposed to chrysene is effective in determination of risk by chrysene and monitoring the chrysene exposure, so that it can be effectively used as a tool for examining the mechanism of chrysene induced toxicity.

DESCRIPTION OF DRAWINGS

The patent or application file contains at least one drawing executed in color. Copies of this patent or patent application publication with color drawing(s) will be provided by the Office upon request and payment of the necessary fee.

The application of the preferred embodiments of the present invention is best understood with reference to the accompanying drawings, wherein.

MODE FOR INVENTION

Figure 1:
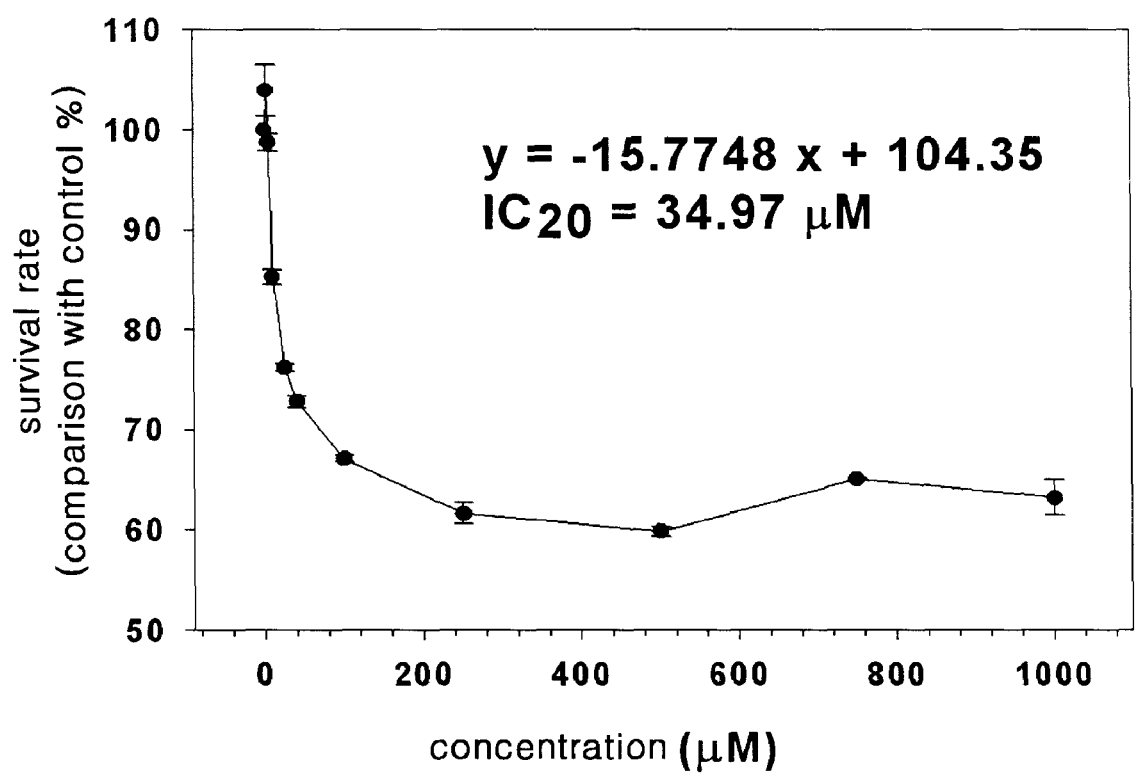
FIG. 1 is a graph illustrating the cytotoxicity of chrysene in a human Hepatoma cell line.

Hereinafter, the present invention is described in detail.

The present invention provides a method for confirming the exposure on chrysene comprising the following steps:

1) separating RNAs from human somatic cells of a sample, the experimental group, and from somatic cells of the control group; and,
2) determining the exposure on chrysene by comparing the expression of the gene whose expression is affected by chrysene with that of the control, when the expression of the gene is significantly changed, compared with that of the control, the gene is regarded as being exposed to chrysene.

The somatic cells of step 1) are the cells originated from human liver or liver cancer cells and tissues and preferably HepG2 cells.

The comparing the expression of a gene in step 2) is performed at the level of mRNA or protein. At this time, the mRNA level comsetson can be performed by oligonucleotide or polynucleotide microarray or RT-PCR. And, the protein level comsetson can be performed by protein microarray or ELISA.

The present invention also provides a method for confirming the exposure on chrysene comprising the following steps:

1) separating RNAs from human somatic cells of a sample, the experimental group, and from somatic cells of the control group;
2) synthesizing cDNAs with the RNAs separated from the experimental group and the control of step 1) and labeling them with different fluorescent materials;
3) hybridizing the cDNAs of step 2) each labeled with different fluorescent materials with DNA microarray chip comprising oligonucleotide containing the full length or a part of a gene whose expression is changed by chrysene or its complement oligonucleotide;
4) analyzing the DNA microarray chip reacted in step 3); and
5) determining the exposure on chrysene by comparing the expression of the gene whose expression is affected by chrysene with that of the control, when the expression of the gene is significantly changed, compared with that of the control, the gene is regarded as being exposed to chrysene.

The somatic cells of step 1) are the cells originated from human liver or liver cancer cells and tissues and preferably HepG2 cells.

In the above method, the DNA microarray of step 4) is the whole human genome oligo microarray (Agilent, USA), but not always limited thereto, and any microarray that is loaded with those genes supposed to be up-regulated or down-regulated (see Table 2 and Table 3), among human genomes, can be used. In a preferred embodiment of the present invention, the DNA microarray chip prepared by the present inventors was used. And for the analysis of step 4), GenePix 4.1 software (Axon Instruments, USA) is preferably used, but not always limited thereto, and any software for analysis known to those in the art can be used.

The above oligonucleotide or its complement oligonucleotide contains 18-30 nucleic acids of the gene whose expression is changed by chrysene and more preferably contains 20-25 nucleic acids.

In this invention, the DNA microarray chip can be prepared by the method well known to those in the art. The method for preparing the microarray chip is as follows. The gene whose expression is affected by chrysene used as a probe DNA molecule is fixed on the substrate of DNA chip. For the fixation, the micropipetting method using piezoelectric way or the method using pin type spotter is used, but not always limited thereto. The substrate of the DNA microarray chip is preferably coated with an active group selected from the group consisting of amino-silane, poly-L-lysine and aldehyde, but not always limited thereto. The substrate can be selected from the group consisting of slide glass, plastic, metal, silicon, nylon membrane and nitrocellulose membrane, but not always limited thereto.

In the above method, the DNA microarray of step 4) is the whole human genome oligo microarray (Agilent, USA), but not always limited thereto, and any microarray that is loaded with those genes supposed to be up-regulated or down-regulated (see Table 2 and Table 3), among human genomes, can be used. And for the analysis of step 4), GenePix 4.1 software (Axon Instruments, USA) is preferably used, but not always limited thereto, and any software for analysis known to those in the art can be used.

In addition, the present invention provides a method for confirming the exposure on chrysene comprising the following steps:

1) separating RNAs from human somatic cells of a sample, the experimental group, and from somatic cells of the control group;
2) performing real-time RT-PCR (reverse transcript polymerase chain reaction) with the RNAs of step 1) using a primer set capable of amplifying the gene whose expression changed by chrysene; and
3) determining the exposure on chrysene by comparing the expression of the gene of step 2) with that of the control, when the expression of the gene is significantly changed, compared with that of the control, the gene is regarded as being exposed to chrysene.

In the method of the present invention, the primer set of step 2) can include any sense or antisense primer set that is capable of amplifying a gene whose expression is changed by chrysene and is designed to produce the amplified product of 100-300 bp in size. The primer of the present invention is preferably selected from the group consisting of the following primer sets 1-35, but not always limited thereto:

primer sets 1—Sense primer represented by SEQ. ID. NO: 1 and anti-sense primer represented by SEQ. ID. NO: 2;
primer sets 2—Sense primer represented by SEQ. ID. NO: 3 and anti-sense primer represented by SEQ. ID. NO: 4;
primer sets 3—Sense primer represented by SEQ. ID. NO: 5 and anti-sense primer represented by SEQ. ID. NO: 6;
primer sets 4—Sense primer represented by SEQ. ID. NO: 7 and anti-sense primer represented by SEQ. ID. NO: 8;
primer sets 5—Sense primer represented by SEQ. ID. NO: 9 and anti-sense primer represented by SEQ. ID. NO: 10;
primer sets 6—Sense primer represented by SEQ. ID. NO: 11 and anti-sense primer represented by SEQ. ID. NO: 12;
primer sets 7—Sense primer represented by SEQ. ID. NO: 13 and anti-sense primer represented by SEQ. ID. NO: 14;
primer sets 8—Sense primer represented by SEQ. ID. NO: 15 and anti-sense primer represented by SEQ. ID. NO: 16;
primer sets 9—Sense primer represented by SEQ. ID. NO: 17 and anti-sense primer represented by SEQ. ID. NO: 18;
primer sets 10—Sense primer represented by SEQ. ID. NO: 19 and anti-sense primer represented by SEQ. ID. NO: 20;
primer sets 11—Sense primer represented by SEQ. ID. NO: 21 and anti-sense primer represented by SEQ. ID. NO: 22;
primer sets 12—Sense primer represented by SEQ. ID. NO: 23 and anti-sense primer represented by SEQ. ID. NO: 24;
primer sets 13—Sense primer represented by SEQ. ID. NO: 25 and anti-sense primer represented by SEQ. ID. NO: 26;
primer sets 14—Sense primer represented by SEQ. ID. NO: 27 and anti-sense primer represented by SEQ. ID. NO: 28;
primer sets 15—Sense primer represented by SEQ. ID. NO: 29 and anti-sense primer represented by SEQ. ID. NO: 30;
primer sets 16—Sense primer represented by SEQ. ID. NO: 31 and anti-sense primer represented by SEQ. ID. NO: 32;
primer sets 17—Sense primer represented by SEQ. ID. NO: 33 and anti-sense primer represented by SEQ. ID. NO: 34;
primer sets 18—Sense primer represented by SEQ. ID. NO: 35 and anti-sense primer represented by SEQ. ID. NO: 36;
primer sets 19—Sense primer represented by SEQ. ID. NO: 37 and anti-sense primer represented by SEQ. ID. NO: 38;
primer sets 20—Sense primer represented by SEQ. ID. NO: 39 and anti-sense primer represented by SEQ. ID. NO: 40;
primer sets 21—Sense primer represented by SEQ. ID. NO: 41 and anti-sense primer represented by SEQ. ID. NO: 42;
primer sets 22—Sense primer represented by SEQ. ID. NO: 43 and anti-sense primer represented by SEQ. ID. NO: 44;
primer sets 23—Sense primer represented by SEQ. ID. NO: 45 and anti-sense primer represented by SEQ. ID. NO: 46;
primer sets 24—Sense primer represented by SEQ. ID. NO: 47 and anti-sense primer represented by SEQ. ID. NO: 48;
primer sets 25—Sense primer represented by SEQ. ID. NO: 49 and anti-sense primer represented by SEQ. ID. NO: 50;
primer sets 26—Sense primer represented by SEQ. ID. NO: 51 and anti-sense primer represented by SEQ. ID. NO: 52;
primer sets 27—Sense primer represented by SEQ. ID. NO: 53 and anti-sense primer represented by SEQ. ID. NO: 54;
primer sets 28—Sense primer represented by SEQ. ID. NO: 55 and anti-sense primer represented by SEQ. ID. NO: 56;
primer sets 29—Sense primer represented by SEQ. ID. NO: 57 and anti-sense primer represented by SEQ. ID. NO: 58;
primer sets 30—Sense primer represented by SEQ. ID. NO: 59 and anti-sense primer represented by SEQ. ID. NO: 60;
primer sets 31—Sense primer represented by SEQ. ID. NO: 61 and anti-sense primer represented by SEQ. ID. NO: 62;
primer sets 32—Sense primer represented by SEQ. ID. NO: 63 and anti-sense primer represented by SEQ. ID. NO: 64;
primer sets 33—Sense primer represented by SEQ. ID. NO: 65 and anti-sense primer represented by SEQ. ID. NO: 66;
primer sets 34—Sense primer represented by SEQ. ID. NO: 67 and anti-sense primer represented by SEQ. ID. NO: 68; and, primer sets 35—Sense primer represented by SEQ. ID. NO: 69 and anti-sense primer represented by SEQ. ID. NO: 70.

In the method to confirm the exposure of chrysene, the somatic cells are preferably the cells originated from the human liver, or liver cancer cells and tissues, and more preferably HepG2 cells, but not always limited thereto. The sample herein is the one who is suspicious to be exposed to chrysene, and the control is a healthy normal human.

The genes exhibiting 2.0 fold higher or less expressions by chrysene exposure were classified according to the functions. The genes are composed of those genes involved in MAPKinase Signaling Pathway, MAPKKK cascade, p53 Signaling Pathway, apoptosis, response to DNA damage stimulus, Response to stress, immune response, cell cycle, Mitotic cell cycle, Cell differentiation, Cell growth, cell proliferation, Alcohol metabolism, DNA metabolism, lipid metabolism, Amino acid metabolism, metal binding, and Transport.

The gene whose expression is changed by chrysene is characteristically selected from the group consisting of the following genes:

Genebank Accession Number: NM_003954 (MAP3K14, Mitogen-activated protein kinase kinase kinase 14), Genebank Accession Number: AB209586 (MAPK13, Mitogen-activated protein kinase 13), Genebank Accession Number: NM_005343 (HRAS, V-Ha-ras Harvey rat sarcoma viral oncogene homolog), Genebank Accession Number: BX647104 (FOS, V-fos FBJ murine osteosarcoma viral oncogene homolog), Genebank Accession Number: NM_007315 (STAT1, Signal transducer and activator of transcription 1, 91 kDa), Genebank Accession Number: BC027933 (MAPK11, Mitogen-activated protein kinase 11), Genebank Accession Number: NM_020529 (NFKBIA, Nuclear factor of kappa light polypeptide gene enhancer in B-cells inhibitor, alpha), Genebank Accession Number: BC014966 (RPS6KA1, Ribosomal protein S6 kinase, 90 kDa, polypeptide 1), Genebank Accession Number: NM_181861 (APAF1, Apoptotic peptidase activating factor), Genebank Accession Number: L41870 [RB1, Retinoblastoma 1 (including osteosarcoma)], Genebank Accession Number: CR612719 (GADD45A, Growth arrest and DNA-damage-inducible, alpha), Genebank Accession Number: BM462208 (PCNA, Proliferating cell nuclear antigen), Genebank Accession Number: M92424 [MDM2, Mdm2, transformed 3T3 cell double minute 2, p53 binding protein (mouse)], Genebank Accession Number: NM_078467 [CDKN1A, Cyclin-dependent kinase inhibitor 1A (p21, Cip1)], Genebank Accession Number: BC089389 (IHPK3, Inositol hexaphosphate kinase 3), Genebank Accession Number: NM_001024807 [APLP1, Amyloid beta (A4) precursor-like protein1], Genebank Accession Number: NM_001013398 (IGFBP3, Insulin-like growth factor binding protein 3), Genebank Accession Number: AB209361 [FAS, Fas (TNF receptor superfamily, member 6)], Genebank Accession Number: NM_147780 (CTSB, Cathepsin B), Genebank Accession Number: NM_001165 (BIRC3, Baculoviral IAP repeat-containing 3), Genebank Accession Number: BM557864 (HSPB1, Heat shock 27 kDa protein 1), Genebank Accession Number: AB033060 (PDCD6, Aryl-hydrocarbon receptor repressor), Genebank Accession Number: AK125880 (TP53INP1, Tumor protein p53 inducible nuclear protein 1), Genebank Accession Number: NM_004574 (SEP4, Septin 4), Genebank Accession Number: NM_003820 [TNFRSF14, Tumor necrosis factor receptor superfamily, member 14 (herpesvirus entry mediator)], Genebank Accession Number: CN478604 [LGALS7, Lectin, galactoside-binding, soluble, 7 (galectin 7)], Genebank Accession Number: NM_004879 (EI24, Etoposide induced 2.4 mRNA), Genebank Accession Number: NM_003311 (PHLDA2, Pleckstrin homology-like domain, family A, member 2), Genebank Accession Number: NM_003897 (IER3, Immediate early response 3), Genebank Accession Number: AK097284 (TNFAIP8, Tumor necrosis factor, alpha-induced protein 8), Genebank Accession Number: NM_000582 [SPP1, Secreted phosphoprotein 1(osteopontin, bone sialoprotein I, early T-lymphocyte activation 1)], Genebank Accession Number: NM_013258 (PYCARD, PYD and CARD domain containing), Genebank Accession Number: NM_002305 [LGALS1, Lectin, galactoside-binding, soluble, 1(galectin 1)], Genebank Accession Number: AF055634 [UNC5C, Unc-5 homolog C (C. elegans)], Genebank Accession Number: CR614015 (CD14, CD14 antigen), Genebank Accession Number: AK129595 (GADD45B, Growth arrest and DNA-damage-inducible, beta), Genebank Accession Number: AF356193 (CARD6, Caspase recruitment domain family, member 6), Genebank Accession Number: BC063043 [PRF1, Perforin 1 (pore forming protein)], Genebank Accession Number: BX537586 [STK17A, Serine/threonine kinase 17a (apoptosis-inducing)], Genebank Accession Number: NM_003842 (TNFRSF10B, Tumor necrosis factor receptor superfamily, member 10b), Genebank Accession Number: AF208043 (IFI16, Interferon, gamma-inducible protein 16), Genebank Accession Number: BX641114 (ANXA4, Annexin A4), Genebank Accession Number: NM_001009552 (PPP2CB, Protein phosphatase 2 (formerly 2A), catalytic subunit, beta isoform), Genebank Accession Number: BX386171 (CGB5, Chorionic gonadotropin, beta polypeptide 8), Genebank Accession Number: AY358103 (HIP1, Huntingtin interacting protein 1), Genebank Accession Number: BC027949 (P2RX1, Purinergic receptor P2X, ligand-gated ion channel, 1), Genebank Accession Number: BC042844 (CASP10, Caspase 10, apoptosis-related cysteine peptidase), Genebank Accession Number: NM_000733 [CD3E, CD3E antigen, epsilon polypeptide (TiT3 complex)], Genebank Accession Number: NM_033245 (PML, Promyelocytic leukemia), Genebank Accession Number: BC047362 (PHLDA1, Pleckstrin homology-like domain, family A, member 1), Genebank Accession Number: NM_006763 (BTG2, BTG family, member 2), Genebank Accession Number: BC050455 (DDB2, LIM homeobox 3), Genebank Accession Number: BC068535 (TP53AP1, TP53 activated protein 1), Genebank Accession Number: AF033122 (SESN1, Sestrin 1), Genebank Accession Number: AB024313 (POLH, Polymerase (DNA directed), eta), Genebank Accession Number: NM_001012716 (TYMS, Thymidylate synthetase), Genebank Accession Number: BC095402 (ATXN3, Ataxin 3), Genebank Accession Number: BU675073 (PTTG1, Pituitary tumor-transforming 1), Genebank Accession Number: BC073161 (RAD51C, RAD51 homolog C (S. cerevisiae), Genebank Accession Number: NM_001983 [ERCC1, Excision repair cross-complementing rodent repair deficiency, complementation group 1 (includes overlapping antisense sequence)], Genebank Accession Number: NM_018965 (TREM2, Triggering receptor expressed on myeloid cells 2), Genebank Accession Number: BX649164 (PAI, serpin peptidase inhibitor, clade E (nexin, plasminogen activator inhibitor type 1), member 1), Genebank Accession Number: NM_006404 [PROCR, Protein C receptor, endothelial (EPCR)], Genebank Accession Number: C035582 (TRIM22, Tripartite motif-containing 22), Genebank Accession Number: NM_006691 (XLKD1, Extracellular link domain containing 1), Genebank Accession Number: NM_015831 [ACHE, Acetylcholinesterase (YT blood group)], Genebank Accession Number: BC045666 (TP53I11, Tumor protein p53 inducible protein 11), Genebank Accession Number: NM_005438 (FOSL1, FOS-like antigen 1), Genebank Accession Number: NM_005755 (EBI3, Epstein-Barr virus induced gene 3), Genebank Accession Number: BM918324 (LY96, Lymphocyte antigen 96), Genebank Accession Number: NM_000022 (ADA, Adenosine deaminase), Genebank Accession Number: NM_004167 (CCL14, Chemokine (C-C motif) ligand 15), Genebank Accession Number: NM_014278 (HSPA4L, Heat shock 70 kDa protein 4-like), Genebank Accession Number: BC006523 (SGK2, Serum/glucocorticoid regulated kinase 2), Genebank Accession Number: NM_000641 (IL11, Interleukin 11), Genebank Accession Number: H18681 [C20orf139, Sulfiredoxin 1 homolog (S. cerevisiae)], Genebank Accession Number: NM_001769 [CD9, CD9 antigen (p24)], Genebank Accession Number: BG564326 (SAA4, Serum amyloid A4, constitutive), Genebank Accession Number: NM_016816 (OAS1, 2',5'-oligoadenylate synthetase 1, 40/46 kDa), Genebank Accession Number: CB055213 (ICOSLG, Inducible T-cell co-stimulator ligand), Genebank Accession Number: CR591007 (CCL3, Chemokine (C-C motif) ligand 3), Genebank Accession Number: NM_145641 (APOL3, Apolipoprotein L, 3), Genebank Accession Number: AK127663 (PTGES, Prostaglandin E synthase), Genebank Accession Number: NM_001734 (C1S, Complement component 1, s subcomponent), Genebank Accession Number: NM_002260 (KLRC3, Killer cell lectin-like receptor subfamily C, member 2), Genebank Accession Number: NM_001733 (C1R, Complement component 1, r subcomponent), Genebank Accession Number: AB209922 (DNAJB4, DnaJ (Hsp40) homolog, subfamily B, member 4), Genebank Accession Number: NM_201397 (GPX1, Glutathione peroxidase 1), Genebank Accession Number: AK090482 [CXCL12, Chemokine (C-X-C motif) ligand 12 (stromal cell-derived factor 1)], Genebank Accession Number: BF662985 (CCL3L1, Chemokine (C-C motif) ligand 3-like 1), Genebank Accession Number: NM_001779 [CD58, CD58 antigen, (lymphocyte function-associated antigen 3)], Genebank Accession Number: NM_005064 (CCL23, Chemokine (C-C motif) ligand 23), Genebank Accession Number: NM_000242 [MBL2, Mannose-binding lectin (protein C) 2, soluble (opsonic defect)], Genebank Accession Number: NM_032036 (FAM14A, Family with sequence similarity 14, member A), Genebank Accession Number: AJ890082 (HSPCA, Heat shock 90 kDa protein 1, alpha), Genebank Accession Number: BC068487 (TLR3, Toll-like receptor 3), Genebank Accession Number: NM_000552 (VWF, Von Willebrand factor), Genebank Accession Number: NM_000132 [F8, Coagulation factor VIII, procoagulant component (hemophilia A)], Genebank Accession Number: AY154461 (NALP6, NACHT, leucine rich repeat and PYD containing 6), Genebank Accession Number: AK127679 (DUSP1, Dual specificity phosphatase 1), Genebank Accession Number: NM_014314 (DDX58, DEAD (Asp-Glu-Ala-Asp) box polypeptide 58), Genebank Accession Number: NM_000311 [PRNP, Prion protein (p27-30) (Creutzfeld-Jakob disease, Gerstmann-Strausler-Scheinker syndrome, fatal familial insomnia)], Genebank Accession Number: NM_006597 (HSPA8, Heat shock 70 kDa protein 8), Genebank Accession Number: AK092040 (ZCSL2, Zinc finger, CSL-type containing 2), Genebank Accession Number: NM_031483 [ITCH, Itchy homolog E3 ubiquitin protein ligase (mouse)], Genebank Accession Number: U25029 [NR3C1, Nuclear receptor subfamily 3, group C, member 1 (glucocorticoid receptor)], Genebank Accession Number: NM_005242 (F2RL1, Coagulation factor II (thrombin) receptor-like 1), Genebank Accession Number: AK172851 (ADORA2B, Adenosine A2b receptor), Genebank Accession Number: BQ053419 (BATF, Basic leucine zipper transcription factor, ATF-like), Genebank Accession Number: BC020698 (CCL20, Chemokine (C-C motif) ligand 20), Genebank Accession Number: NM_001124 (ADM, Adrenomedullin), Genebank Accession Number: NM_153609 (TMPRSS6, Transmembrane protease, serine 6), Genebank Accession Number: NM_004148 (NINJ1, Ninjurin 1), Genebank Accession Number: AF324224 (APOL2, Apolipoprotein L, 2), Genebank Accession Number: BC040494 (DNAJB2, DnaJ (Hsp40) homolog, subfamily B, member 2), Genebank Accession Number: BE512691 [GPX2, Glutathione peroxidase 2 (gastrointestinal)], Genebank Accession Number: NM_001002029 (C4A, Complement component 4B, telomeric), Genebank Accession Number: NM_000732 [CD3D, CD3D antigen, delta polypeptide (TiT3 complex)], Genebank Accession Number: AK223210 [CD79B, CD79B antigen (immunoglobulin-associated beta)], Genebank Accession Number: NM_002309 (LIF, Hypothetical protein MGC20647), Genebank Accession Number: AF031469 (MR1, Major histocompatibility complex, class I-related), Genebank Accession Number: NM_172208 [TAPBP, TAP binding protein (tapasin)], Genebank Accession Number: BC021117 [CSF1, Colony stimulating factor 1 (macrophage)], Genebank Accession Number: NM_001421 [ELF4, E74-like factor 4 (ets domain transcription factor)], Genebank Accession Number: NM_002119 (HLA-DOA, Major histocompatibility complex, class II, DO alpha), Genebank Accession Number: BX648013 [TAP1, Transporter 1, ATP-binding cassette, sub-family B (MDR/TAP)], Genebank Accession Number: AL832287 (ZAP70, Zeta-chain (TCR) associated protein kinase 70 kDa), Genebank Accession Number: BF569086 (NK4, Interleukin 32), Genebank Accession Number: AL832451 (DKFZp451C2311, guanylate binding protein 2, interferon-inducible), Genebank Accession Number: AF069493 (SEMA7A, Sema domain, immunoglobulin domain (Ig), and GPI membrane anchor, (semaphorin) 7A), Genebank Accession Number: NM_001008490 (KLF6, Kruppel-like factor 6), Genebank Accession Number: NM_000418 (IL4R, Interleukin 4 receptor), Genebank Accession Number: NM_004048 (B2M, Beta-2-microglobulin), Genebank Accession Number: AF116720 (DNAJA2, DnaJ (Hsp40) homolog, subfamily A, member 2), Genebank Accession Number: NM_001007271 (DUSP13, Dual specificity phosphatase 13), Genebank Accession Number: BM904612 [S100A6, S100 calcium binding protein A6 (calcyclin)], Genebank Accession Number: AK074652 (SERTAD1, SERTA domain containing 1), Genebank Accession Number: NM_203394 (E2F7, E2F transcription factor 7), Genebank Accession Number: NM_003620 (PPM1D, Protein phosphatase 1D magnesium-dependent, delta isoform), Genebank Accession Number: BC060797 [PARD6G, Par-6 partitioning defective 6 homolog gamma (C. elegans)], Genebank Accession Number: NM_021913 (AXL, AXL receptor tyrosine kinase), Genebank Accession Number: BC040303 (PTP4A1, Protein tyrosine phosphatase type IVA, member 1), Genebank Accession Number: BC008564 (PPP1R9B, Protein phosphatase 1, regulatory subunit 9B, spinophilin), Genebank Accession Number: AK097024 [RAE1, RAE1 RNA export 1 homolog (S. pombe)], Genebank Accession Number: BC011957 (BTG3, BTG family, member 3), Genebank Accession Number: NM_078487 [CDKN2B, Cyclin-dependent kinase inhibitor 2B (p15, inhibits CDK4)], Genebank Accession Number: BC023552 (SFN, Stratifin), Genebank Accession Number: BC060847 [PARD6B, Par-6 partitioning defective 6 homolog beta (C.

*elegans*)], Genebank Accession Number: NM_003236 (TGFA, Transforming growth factor, alpha), Genebank Accession Number: NM_002632 (PGF, Placental growth factor, vascular endothelial growth factor-related protein), Genebank Accession Number: NM_015278 (SASH1, SAM and SH3 domain containing 1), Genebank Accession Number: AL834276 (MGC3207, Hypothetical protein MGC3207), Genebank Accession Number: AK096276 (CCND3, Cyclin D3), Genebank Accession Number: AB209373 (CCNK, Chromosome 14 open reading frame 65), Genebank Accession Number: NM_021132 [PPP3CB, Protein phosphatase 3 (formerly 2B), catalytic subunit, beta isoform (calcineurin A beta)], Genebank Accession Number: NM_005072 (SLC12A4, Solute carrier family 12 (potassium/chloride transporters), member 4), Genebank Accession Number: BX647886 [PCNP, SPT2, Suppressor of Ty, domain containing 1 (*S. cerevisiae*)], Genebank Accession Number: NM_044472 [CDC42, Cell division cycle 42 (GTP binding protein, 25 kDa)], Genebank Accession Number: AL832973 [REC8L1, REC8-like 1 (yeast)], Genebank Accession Number: NM_002031 (FRK, Fyn-related kinase), Genebank Accession Number: BM913048 (TIMP1, TIMP metallopeptidase inhibitor 1), Genebank Accession Number: NM_003975 (SH2D2A, SH2 domain protein 2A), Genebank Accession Number: NM_198129 (LAMA3, Laminin, alpha 3), Genebank Accession Number: NM_006152 (LRMP, Lymphoid-restricted membrane protein), Genebank Accession Number: X96753 [CSPG4, Chondroitin sulfate proteoglycan 4 (melanoma-associated)], Genebank Accession Number: NM_000474 [TWIST1, Twist homolog 1(acrocephalosyndactyly 3; Saethre-Chotzen syndrome) (*Drosophila*)], Genebank Accession Number: AF052152 (DCAMKL1, Doublecortin and CaM kinase-like 1), Genebank Accession Number: AF333334 (CCIN, Calicin), Genebank Accession Number: NM_005979 (S100A13, S100 calcium binding protein A13), Genebank Accession Number: NM_004429 (EFNB1, Ephrin-B1), Genebank Accession Number: NM_003873 (NRP1, Neuropilin 1), Genebank Accession Number: AF026692 (SFRP4, Secreted frizzled-related protein 4), Genebank Accession Number: AK124583 (DAZAP1, DAZ associated protein 1), Genebank Accession Number: AF003837 [JAG1, Jagged 1 (Alagille syndrome)], Genebank Accession Number: AB209590 (BMP1, Bone morphogenetic protein 1), Genebank Accession Number: X54457 [CEL, Carboxyl ester lipase (bile salt-stimulated lipase)], Genebank Accession Number: Y11307 (CYR61, Cysteine-rich, angiogenic inducer, 61), Genebank Accession Number: NM_000596 (IGFBP1, Insulin-like growth factor binding protein 1), Genebank Accession Number: NM_020997 (LEFTY1, Left-right determination factor 1), Genebank Accession Number: NM_001553 (IGFBP7, Insulin-like growth factor binding protein 7), Genebank Accession Number: AB209509 (IGFBP2, Insulin-like growth factor binding protein 2, 36 kDa), Genebank Accession Number: NM_001552 (IGFBP4, Insulin-like growth factor binding protein 4), Genebank Accession Number: AB209321 (CSRP2, Cysteine and glycine-rich protein 2), Genebank Accession Number: BM556279 (EMP3, Epithelial membrane protein 3), Genebank Accession Number: NM_005727 (TSPAN1, Tetraspanin 1), Genebank Accession Number: BQ683841 [S100A11, S100 calcium binding protein A11 (calgizzarin)], Genebank Accession Number: BC042390 [VTI1B, Vesicle transport through interaction with t-SNAREs homolog 1B (yeast)], Genebank Accession Number: NM_000899 (KITLG, KIT ligand), Genebank Accession Number: BC032940 (LAMP3, Lysosomal-associated membrane protein 3), Genebank Accession Number: BQ939577 [AKR1C3, Aldo-keto reductase family 1, member C3 (3-alpha hydroxysteroid dehydrogenase, type II)], Genebank Accession Number: BC063468 (OSMR, Oncostatin M receptor), Genebank Accession Number: CR936719 [SSR1, Signal sequence receptor, alpha (translocon-associated protein alpha)], Genebank Accession Number: AB024057 [TBC1D8, TBC1 domain family, member 8 (with GRAM domain)], Genebank Accession Number: NM_003329 (TXN, Thioredoxin), Genebank Accession Number: NM_012125 (CHRM5, Cholinergic receptor, muscarinic 5), Genebank Accession Number: NM_007045 (FGFR1OP, FGFR1 oncogene partner), Genebank Accession Number: AK094474 (RHOC, Ras homolog gene family, member C), Genebank Accession Number: BC017706 (6PGL, 6-phosphogluconolactonase), Genebank Accession Number: AF153821 (ADH1B, Alcohol dehydrogenase IB (class I), beta polypeptide), Genebank Accession Number: AK124656 [ENO2, Enolase 2 (gamma, neuronal)], Genebank Accession Number: D42047 (GPD1L, Glycerol-3-phosphate dehydrogenase 1-like), Genebank Accession Number: AK130060 (TALDO1, Transaldolase 1), Genebank Accession Number: AL833069 (KIAA1434, Hypothetical protein KIAA1434), Genebank Accession Number: XM_496436 (UNQ6077, C219-reactive peptide), Genebank Accession Number: NM_199186 (BPGM, 2,3-bisphosphoglycerate mutase), Genebank Accession Number: U86136 (TEP1, Telomerase-associated protein 1), Genebank Accession Number: BU603483 (HIST1H1E, Histone 1, H1e), Genebank Accession Number: NM_005319 (HIST1H1C, Histone 1, H1c), Genebank Accession Number: NM_005320 (HIST1H1D, Histone 1, H1d), Genebank Accession Number: NM_003516 (HIST2H2AA, Histone 2, H2aa), Genebank Accession Number: F02250 (HDAC2, Histone deacetylase 2), Genebank Accession Number: NM_004739 (MTA2, Metastasis associated 1 family, member 2), Genebank Accession Number: BC042589 (HIST1H2BD, Histone 1, H2bd), Genebank Accession Number: CB529694 (HIST2H2BE, Histone 2, H2be), Genebank Accession Number: AK126154 (NP, Nucleoside phosphorylase), Genebank Accession Number: AB040899 (KIAA1466, KIAA1466 gene), Genebank Accession Number: CR608156 (HIST1H2AC, Histone 1, H2ac), Genebank Accession Number: BX436525 (HIST1H2BH, Histone 1, H2bh), Genebank Accession Number: AK057762 (TDH, L-threonine dehydrogenase), Genebank Accession Number: BC035124 (UNQ2541, MSFL2541), Genebank Accession Number: BC034763 (FDXR, Ferredoxin reductase), Genebank Accession Number: AK093461 (ISYNA1, Myo-inositol 1-phosphate synthase A1), Genebank Accession Number: AK097009 (PLTP, phospholipid transfer protein), Genebank Accession Number: AF524864 [AKR1B10, Aldo-keto reductase family 1, member B10 (aldose reductase)], Genebank Accession Number: NM_021727 (FADS3, Fatty acid desaturase 3), Genebank Accession Number: CR627415 (HSD3B2, Hydroxy-delta-5-steroid dehydrogenase, 3 beta- and steroid delta-isomerase 2), Genebank Accession Number: CD013987 (CYP21A2, Cytochrome P450, family 21, subfamily A, polypeptide 2), Genebank Accession Number: BC020744 (AKR1C4, Aldo-keto reductase family 1, member C4 (chlordecone reductase; 3-alpha hydroxysteroid dehydrogenase, type I; dihydrodiol), dehydrogenase 4), Genebank Accession Number: NM_004753 (DHRS3, Dehydrogenase/reductase (SDR family) member 3), Genebank Accession Number: BC030207 (NR0B2, Nuclear receptor subfamily 0, group B, member 2), Genebank Accession Number: AK091948 (LTB4DH, Leukotriene B4 12-hydroxydehydrogenase), Genebank Accession Number: NM_002900

(RBP3, Retinol binding protein 3, interstitial), Genebank Accession Number: BX647927 (PLCD1, Phospholipase C, delta 1), Genebank Accession Number: NM_145323 (OSBPL3, Oxysterol binding protein-like 3), Genebank Accession Number: NM_000169 (GLA, Galactosidase, alpha), Genebank Accession Number: BC094756 (CRA, Myotubularin related protein 11), Genebank Accession Number: AB043587 (ACBD3, Acyl-Coenzyme A binding domain containing 3), Genebank Accession Number: NM_001478 [GALGT, UDP-N-acetyl-alpha-D-galactosamine: (N-acetyl-neuraminyl)-galactosylglucosylceramide N-acetylgalac-tosaminyltransferase (GalNAc-T)], Genebank Accession Number: J05428 (UGT2B7, UDP glucuronosyltransferase 2 family, polypeptide B7), Genebank Accession Number: AB002454 (CYP4F3, Cytochrome P450, family 4, subfamily F, polypeptide 3), Genebank Accession Number: NM_000405 (GM2A, GM2 ganglioside activator), Genebank Accession Number: BC001823 (PRKAB1, Protein kinase, AMP-activated, beta 1 non-catalytic subunit), Genebank Accession Number: NM_145343 (APOL1, Apolipoprotein L, 1), Genebank Accession Number: NM_006571 (DCTN6, Dynactin 6), Genebank Accession Number: NM_020139 (DHRS6, Dehydrogenase/reductase (SDR family) member 6), Genebank Accession Number: NM_000499 (CYP1A1, Cytochrome P450, family 1, subfamily A, polypeptide 1), Genebank Accession Number: BC007003 [TGM4, Transglutaminase 4 (prostate)], Genebank Accession Number: NM_012189 [CABYR, Calcium binding tyrosine-(Y)-phosphorylation regulated (fibroushealthin 2)], Genebank Accession Number: CR615530 (CYGB, Cytoglobin), Genebank Accession Number: NM_004199 (P4HA2, Procollagen-proline, 2-oxoglutarate 4-dioxygenase (proline 4-hydroxylase), alpha polypeptide II), Genebank Accession Number: AK027560 (CYP26A1, Cytochrome P450, family 26, subfamily A, polypeptide 1), Genebank Accession Number: NM_145298 (APOBEC3F, Apolipoprotein B mRNA editing enzyme, catalytic polypeptide-like 3F), Genebank Accession Number: NM_005576 (LOXL1, Lysyl oxidase-like 1), Genebank Accession Number: AK024854 [APOBEC3B, Apolipoprotein B mRNA editing enzyme, catalytic polypeptide-like 3D (putative)], Genebank Accession Number: NM_014301 (NIFUN, NifU-like N-terminal domain containing), Genebank Accession Number: BF670653 (MB, Myoglobin), Genebank Accession Number: AK126982 (LHX6, LIM homeobox 6), Genebank Accession Number: Y13786 [ADAM19, ADAM metallopeptidase domain 19 (meltrin beta)], Genebank Accession Number: AB051455 (MICAL-L1, MICAL-like 1), Genebank Accession Number: AK074068 (MICAL-L2, MICAL-like 2), Genebank Accession Number: AK124421 [CPA1, Carboxypeptidase A1 (pancreatic)], Genebank Accession Number: NM_030622 (CYP2S1, Cytochrome P450, family 2, subfamily S, polypeptide 1), Genebank Accession Number: BC012027 (CYP2U1, Cytochrome P450, family 2, subfamily U, polypeptide 1), Genebank Accession Number: AY461717 (ZNF385, Zinc finger protein 385), Genebank Accession Number: AK092424 (ZSCAN4, Zinc finger and SCAN domain containing 4), Genebank Accession Number: AB208935 [RASAL1, RAS protein activator like 1 (GAP1 like)], Genebank Accession Number: NM_201444 (DGKA, Diacylglycerol kinase, alpha 80 kDa), Genebank Accession Number: BC035625 [EGR2, Early growth response 2 (Krox-20 homolog, *Drosophila*)], Genebank Accession Number: BF983391 (RPS27L, Ribosomal protein S27-like), Genebank Accession Number: BC036545 (PLAC2, Placenta-specific 2), Genebank Accession Number: BC034569 (ZNF337, Zinc finger protein 337), Genebank Accession Number: CR936707 (TRIM38, Tripartite motif-containing 38), Genebank Accession Number: AK091940 (MGC4734, Ring finger protein 183), Genebank Accession Number: NM_024101 (MLPH, Melanophilin), Genebank Accession Number: CR601823 (HIVEP3, Human immunodeficiency virus type I enhancer binding protein 3), Genebank Accession Number: BC041578 (MGC17986, zinc finger protein 114), Genebank Accession Number: BC038432 (RARA, Retinoic acid receptor, alpha), Genebank Accession Number: BX641053 (FXYD2, FXYD domain containing ion transport regulator 2), Genebank Accession Number: AK095363 (AQP3, Aquaporin 3), Genebank Accession Number: AK074100 (SLC37A2, Solute carrier family 37 (glycerol-3-phosphate transporter), member 2), Genebank Accession Number: AK024002 (TUBA4, Tubulin, alpha 4), Genebank Accession Number: AK092677 (TUBB6, Tubulin, beta 6), Genebank Accession Number: NM_001297 (CNGB1, Cyclic nucleotide gated channel beta 1), Genebank Accession Number: NM_032872 (SYTL1, Synaptotagmin-like 1), Genebank Accession Number: NM_014045 (LRP10, Low density lipoprotein receptor-related protein 10), Genebank Accession Number: NM_014585 (SLC40A1, Solute carrier family 40 (iron-regulated transporter), member 1), Genebank Accession Number: L02870 [COL7A1, Collagen, type VII, alpha 1 (epidermolysis bullosa, dystrophic, dominant and recessive)], Genebank Accession Number: AK054731 [TUBA1, Tubulin, alpha 1 (testis specific)], Genebank Accession Number: AF336127 (SLC4A11, Solute carrier family 4, sodium bicarbonate transporter-like, member 11), Genebank Accession Number: AB075951 (SLC22A2, Solute carrier family 22 (organic cation transporter), member 2), Genebank Accession Number: AK125026 (SLC6A12, Solute carrier family 6 (neurotransmitter transporter, betaine/GABA), member 12), Genebank Accession Number: BX537541 (MGC13186, Chromosome 1 open reading frame 57), Genebank Accession Number: CD013956 (SHBG, Sex hormone-binding globulin), Genebank Accession Number: BC029057 (DAO, D-amino-acid oxidase), Genebank Accession Number: BC041479 (COL9A2, Collagen, type IX, alpha 2), Genebank Accession Number: AL050210 (LOC283130, Hypothetical protein LOC283130), Genebank Accession Number: NM_004798 (KIF3B, Kinesin family member 3B), Genebank Accession Number: AK025742 [UCP2, Uncoupling protein 2 (mitochondrial, proton carrier)], Genebank Accession Number: NM_021990 (GABRE, Gamma-aminobutyric acid (GABA) A receptor, epsilon), Genebank Accession Number: NM_005819 (STX6, Syntaxin 6), Genebank Accession Number: BC092420 [CYP4F11, Similar to Cytochrome P450 4F12 (CYPIVF12) (UNQ568/PRO1129)], Genebank Accession Number: BC043423 (ABCB6, ATP-binding cassette, sub-family B (MDR/TAP), member 6), Genebank Accession Number: BC021025 (CTHRC1, Collagen triple helix repeat containing 1), Genebank Accession Number: NM_004999 (MYO6, Myosin VI), Genebank Accession Number: AF445025 (SLC35A4, Solute carrier family 35, member A4), Genebank Accession Number: NM_003330 (TXNRD1, Thioredoxin reductase 1), Genebank Accession Number: AK092512 (SLC16A5, Solute carrier family 16 (monocarboxylic acid transporters), member 5), Genebank Accession Number: AB075871 [FLJ42654, Golgi transport 1 homolog A (*S. cerevisiae*)], Genebank Accession Number: NM_004864 (GDF15, Growth differentiation factor 15), Genebank Accession Number: NM_022153 (PP2135, Chromosome 10 open reading frame 54), Genebank Accession Number: NM_001013632 (LOC343521, Similar to hypothetical protein 4833401D15), Genebank Accession Number:

AK124751 (CAPN2, Calpain 2, (m/II) large subunit), Genebank Accession Number: AK095079 (RGC32, Response gene to complement 32), Genebank Accession Number: NM_031286 (SH3BGRL3, SH3 domain binding glutamic acid-rich protein like 3), Genebank Accession Number: AK126182 (KIAA1949, KIAA1949), Genebank Accession Number: NM_080388 (S100A16, S100 calcium binding protein A16), Genebank Accession Number: NM_025106 (SSB1, SplA/ryanodine receptor domain and SOCS box containing 1), Genebank Accession Number: NM_203403 (C9orf150, Chromosome 9 open reading frame 150), Genebank Accession Number: AK096241 (SQSTM1, Sequestosome 1), Genebank Accession Number: BQ276852 (TMSB10, Thymosin, beta 10), Genebank Accession Number: BC101655 (HIST1H2BI, Histone 1, H2bi), Genebank Accession Number: W84524 (TM4SF5, Transmembrane 4 L six family member 5), Genebank Accession Number: BX647290 (HIST1H2BO, Histone 1, H2bo), Genebank Accession Number: NM_002467 [MYC, V-myc myelocytomatosis viral oncogene homolog (avian)], Genebank Accession Number: BC038295 (MAP2K7, Mitogen-activated protein kinase kinase 7), Genebank Accession Number: NM_004364 (CEBPA, CCAAT/enhancer binding protein (C/EBP), alpha), Genebank Accession Number: NM_145161 (MAP2K5, Mitogen-activated protein kinase kinase 5), Genebank Accession Number: XM_042066 (MAP3K1, Mitogen-activated protein kinase kinase kinase 1), Genebank Accession Number: Z25424 (MKNK2, MAP kinase interacting serine/threonine kinase 2), Genebank Accession Number: AB209047 (ELK1, ELK1, member of ETS oncogene family), Genebank Accession Number: NM_004755 (RPS6KA5, Ribosomal protein S6 kinase, 90 kDa, polypeptide 5), Genebank Accession Number: AB001872 (RPL4, Mitogen-activated protein kinase kinase kinase 13), Genebank Accession Number: NM_002758 (MAP2K6, Mitogen-activated protein kinase kinase 6), Genebank Accession Number: AK098095 (BRAF, V-raf murine sarcoma viral oncogene homolog B1), Genebank Accession Number: AB208919 [FGFR1, Fibroblast growth factor receptor 1 (fms-related tyrosine kinase 2, Pfeiffer syndrome)], Genebank Accession Number: BC060837 (DUSP9, Dual specificity phosphatase 9), Genebank Accession Number: NM_000142 [FGFR3, Fibroblast growth factor receptor 3 (achondroplasia, thanatophoric dwarfism)], Genebank Accession Number: AY247738 [TRIB3, Tribbles homolog 3 (*Drosophila*)], Genebank Accession Number: NM_030640 (DUSP16, Dual specificity phosphatase 16), Genebank Accession Number: NM_148957 (TNFRSF19, Tumor necrosis factor receptor superfamily, member 19), Genebank Accession Number: AB011123 (TNIK, TRAF2 and NCK interacting kinase), Genebank Accession Number: NM_006549 (CAMKK2, Calcium/calmodulin-dependent protein kinase kinase 2, beta), Genebank Accession Number: NM_022740 (HIPK2, Homeodomain interacting protein kinase 2), Genebank Accession Number: NM_005400 (PRKCE, Protein kinase C, epsilon), Genebank Accession Number: NM_000893 (KNG1, Kininogen 1), Genebank Accession Number: NM_000066 (C8B, Complement component 8, beta polypeptide), Genebank Accession Number: CR749293 (PLG, Plasminogen), Genebank Accession Number: BC013780 (ADORA2A, Adenosine A2a receptor), Genebank Accession Number: NM_001012271 (BIRC5, Effector cell peptidase receptor 1), Genebank Accession Number: NM_003811 (TNFSF9, Tumor necrosis factor (ligand) superfamily, member 9), Genebank Accession Number: BC050369 (E2F1, E2F transcription factor 1), Genebank Accession Number: NM_007313 (ABL1, V-abl Abelson murine leukemia viral oncogene homolog 1), Genebank Accession Number: BX647151 (MYBL2, V-myb myeloblastosis viral oncogene homolog (avian)-like 2), Genebank Accession Number: NM_004822 (NTN1, Netrin 1), Genebank Accession Number: BC033694 [BCL2L11, BCL2-like 11 (apoptosis facilitator)], Genebank Accession Number: AB208876 (AXIN1, Axin 1), Genebank Accession Number: BC051332 [F2, Coagulation factor II (thrombin)], Genebank Accession Number: AK122614 (PPARD, Peroxisome proliferative activated receptor, delta), Genebank Accession Number: L78790 [ITGB2, Integrin, beta 2 (antigen CD18 (p95), lymphocyte function-associated antigen 1; macrophage antigen 1 (mac-1) beta subunit)], Genebank Accession Number: AK223409 (BARD1, BRCA1 associated RING domain 1), Genebank Accession Number: NM_002737 (PRKCA, Protein kinase C, alpha), Genebank Accession Number: NM_012479 (YWHAG, Tyrosine 3-monooxygenase/tryptophan 5-monooxygenase activation protein, gamma polypeptide), Genebank Accession Number: CR596268 [ITGB3BP, Integrin beta 3 binding protein (beta 3-endonexin)], Genebank Accession Number: NM_003551 [NME5, Non-metastatic cells 5, protein expressed in (nucleoside-diphosphate kinase)], Genebank Accession Number: NM_013974 (DDAH2, Dimethylarginine dimethylaminohydrolase 2), Genebank Accession Number: D79987 [ESPL1, Extra spindle poles like 1 (*S. cerevisiae*)], Genebank Accession Number: NM_006427 (SIVA, CD27-binding (Siva) protein), Genebank Accession Number: NM_024900 (PHF17, PHD finger protein 17), Genebank Accession Number: AB046854 (MAGI-3, Membrane associated guanylate kinase, WW and PDZ domain containing 3), Genebank Accession Number: AK095578 (SPHK1, Sphingosine kinase 1), Genebank Accession Number: AK122762 (CIDEA, Cell death-inducing DFFA-like effector a), Genebank Accession Number: AK092872 [ERCC2, Excision repair cross-complementing rodent repair deficiency, complementation group 2 (xeroderma pigmentosum D)], Genebank Accession Number: NM_006290 (TNFAIP3, Tumor necrosis factor, alpha-induced protein 3), Genebank Accession Number: NM_000562 (C8A, Complement component 8, alpha polypeptide), Genebank Accession Number: AK122894 (AKT1, V-akt murine thymoma viral oncogene homolog 1), Genebank Accession Number: NM_005067 [SIAH2, Seven in absentia homolog 2 (*Drosophila*)], Genebank Accession Number: NM_203339 [CLU, Clusterin (complement lysis inhibitor, SP-40,40, sulfated glycoprotein 2, testosterone-repressed prostate message 2, apolipoprotein J)], Genebank Accession Number: NM_003376 (VEGF, Vascular endothelial growth factor), Genebank Accession Number: AK027590 (DAPK3, Death-associated protein kinase 3), Genebank Accession Number: AK122825 (HMGB1, High-mobility group box 1), Genebank Accession Number: NM_006904 (PRKDC, Protein kinase, DNA-activated, catalytic polypeptide), Genebank Accession Number: AK074377 (UHRF1, Chromosome 19 open reading frame 31), Genebank Accession Number: CR604810 (CCNA2, Cyclin A2), Genebank Accession Number: AK001720 [FLJ10858, Nei endonuclease VIII-like 3 (*E. coli*)], Genebank Accession Number: CR600021 (HMGB2, High-mobility group box 2), Genebank Accession Number: NM_006230 (POLD2, Polymerase (DNA directed), delta 2, regulatory subunit 50 kDa), Genebank Accession Number: NM_018151 [RIF1, RAP1 interacting factor homolog (yeast)], Genebank Accession Number: BX248766 [RAD51L1, RAD51-like 1 (*S. cerevisiae*)], Genebank Accession Number: NM_014502 [PRP19, PRP19/PSO4 pre-mRNA processing factor 19 homolog (*S. cerevisiae*)], Genebank Accession Number: NM_013975

(LIG3, Ligase III, DNA, ATP-dependent), Genebank Accession Number: NM_173627 (FLJ35220, Hypothetical protein FLJ35220), Genebank Accession Number: NM_003362 (UNG, Uracil-DNA glycosylase), Genebank Accession Number: AF076494 (IRF7, Interferon regulatory factor 7), Genebank Accession Number: CR625391 (RAD51AP1, RAD51 associated protein 1), Genebank Accession Number: NM_006231 (POLE, Polymerase (DNA directed), epsilon), Genebank Accession Number: NM_130398 (EXO1, Exonuclease 1), Genebank Accession Number: DQ140356 (KIAA1596, Fanconi anemia, complementation group M), Genebank Accession Number: NM_002105 (H2AFX, H2A histone family, member X), Genebank Accession Number: AB209560 (POLD1, Polymerase (DNA directed), delta 1, catalytic subunit 125 kDa), Genebank Accession Number: NM_000136 (FANCC, Fanconi anemia, complementation group C), Genebank Accession Number: NM_003368 (USP1, Ubiquitin specific peptidase 1), Genebank Accession Number: NM_022836 [DCLRE1B, DNA cross-link repair 1B (PSO2 homolog, S. cerevisiae)], Genebank Accession Number: NM_001067 (TOP2A, Topoisomerase (DNA) II alpha 170 kDa), Genebank Accession Number: NM_002913 (RFC1, Replication factor C (activator 1) 1, 145 kDa), Genebank Accession Number: NM_002412 (MGMT, O-6-methylguanine-DNA methyltransferase), Genebank Accession Number: NM_000251 [MSH2, MutS homolog 2, colon cancer, nonpolyposis type 1 (E. coli)], Genebank Accession Number: NM_015254 (KIF13B, Kinesin family member 13B), Genebank Accession Number: NM_006037 (HDAC4, Histone deacetylase 4), Genebank Accession Number: NM_020995 (HPR, Haptoglobin-related protein), Genebank Accession Number: NM_153443 (KIR3DL1, Killer cell immunoglobulin-like receptor, three domains, long cytoplasmic tail, 1), Genebank Accession Number: BC071718 (CCL4L1, Chemokine (C-C motif) ligand 4-like 1), Genebank Accession Number: NM_020979 (APS, Adaptor protein with pleckstrin homology and src homology 2 domains), Genebank Accession Number: NM_001629 (ALOX5AP, Arachidonate 5-lipoxygenase-activating protein), Genebank Accession Number: NM_130852 (PLUNC, Palate, lung and nasal epithelium carcinoma associated), Genebank Accession Number: AK024499 (SPON2, Spondin 2, extracellular matrix protein), Genebank Accession Number: BC048198 (AHSG, Alpha-2-HS-glycoprotein), Genebank Accession Number: AK095849 (RNU22, RNA, U22 small nucleolar), Genebank Accession Number: BC005395 (HPX, Hemopexin), Genebank Accession Number: NM_012276 (ILT7, Leukocyte immunoglobulin-like receptor, subfamily A (with TM domain), member 4), Genebank Accession Number: NM_003152 (STAT5A, Signal transducer and activator of transcription 5A), Genebank Accession Number: BC037171 (CCL27, Chemokine (C-C motif) ligand 27), Genebank Accession Number: NM_002468 [MYD88, Myeloid differentiation primary response gene (88)], Genebank Accession Number: NM_002215 (ITIH1, Inter-alpha (globulin) inhibitor H1), Genebank Accession Number: NM_004750 (CRLF1, Cytokine receptor-like factor 1), Genebank Accession Number: DR004094 (HAMP, Hepcidin antimicrobial peptide), Genebank Accession Number: BC063245 (GNLY, Granulysin), Genebank Accession Number: AJ290445 (SARM1, Sterile alpha and TIR motif containing 1), Genebank Accession Number: AK122686 [IF, I factor (complement)], Genebank Accession Number: AB008535 (GPR44, G protein-coupled receptor 44), Genebank Accession Number: AK122912 (ZGPAT, Zinc finger, CCCH-type with G patch domain), Genebank Accession Number: BC022312 (C4BPA, Complement component 4 binding protein, alpha), Genebank Accession Number: BG564683 (ORM1, Orosomucoid 1), Genebank Accession Number: NM_000625 [NOS2A, Nitric oxide synthase 2A (inducible, hepatocytes)], Genebank Accession Number: NM_005515 (HLXB9, Homeo box HB9), Genebank Accession Number: BX537504 (C2, Complement component 2), Genebank Accession Number: BC028153 (LILRB3, Leukocyte immunoglobulin-like receptor, subfamily B (with TM and ITIM domains), member 3), Genebank Accession Number: AF130100 (SERPINC1, Serpin peptidase inhibitor, clade C (antithrombin), member 1), Genebank Accession Number: BC015110 (HHEX, Hematopoietically expressed homeobox), Genebank Accession Number: AB209179 [PLK1, Polo-like kinase 1 (Drosophila)], Genebank Accession Number: AY367065 [ASPM, Asp (abnormal spindle)-like, microcephaly associated (Drosophila)], Genebank Accession Number: NM_006101 (KNTC2, Kinetochore associated 2), Genebank Accession Number: NM_003550 [MAD1L1, MAD1 mitotic arrest deficient-like 1 (yeast)], Genebank Accession Number: NM_020242 (KNSL7, Kinesin family member 15), Genebank Accession Number: AB033068 [FZR1, Fizzy/cell division cycle 20 related 1 (Drosophila)], Genebank Accession Number: NM_018492 (PBK, PDZ binding kinase), Genebank Accession Number: NM_003318 (TTK, TTK protein kinase), Genebank Accession Number: BC011000 (CDCA5, Cell division cycle associated 5), Genebank Accession Number: NM_003981 (PRC1, Protein regulator of cytokinesis 1), Genebank Accession Number: NM_015097 (CLASP2, Cytoplasmic linker associated protein 2), Genebank Accession Number: U65410 [MAD2L1, MAD2 mitotic arrest deficient-like 1 (yeast)], Genebank Accession Number: NM_016343 [CENPF, Centromere protein F, 350/400 ka (mitosin)], Genebank Accession Number: NM_005504 (BCAT1, Branched chain aminotransferase 1, cytosolic), Genebank Accession Number: NM_003718 [CDC2L5, Cell division cycle 2-like 5 (cholinesterase-related cell division controller)], Genebank Accession Number: NM_002768 (PCOLN3, Procollagen (type III) N-endopeptidase), Genebank Accession Number: BC004352 (KIF22, Kinesin family member 22), Genebank Accession Number: NM_005983 [SKP2, S-phase kinase-associated protein 2 (p45)], Genebank Accession Number: NM_004523 (KIF11, Kinesin family member 11), Genebank Accession Number: CR592757 [BRRN1, Barren homolog 1 (Drosophila)], Genebank Accession Number: NM_019063 (EML4, Echinoderm microtubule associated protein like 4), Genebank Accession Number: NM_006845 (KIF2C, Kinesin family member 2C), Genebank Accession Number: NM_004701 (CCNB2, Cyclin B2), Genebank Accession Number: NM_138555 (KIF23, Kinesin family member 23), Genebank Accession Number: NM_182687 (PKMYT1, Protein kinase, membrane associated tyrosine/threonine 1), Genebank Accession Number: NM_001790 (CDC25C, Cell division cycle 25C), Genebank Accession Number: BC032677 (UBE2C, Ubiquitin-conjugating enzyme E2C), Genebank Accession Number: NM_005886 (KATNB1, Katanin p80 (WD repeat containing) subunit B 1), Genebank Accession Number: BC073878 (KIFC1, Kinesin family member C1), Genebank Accession Number: AL833191 [SMC2L1, SMC2 structural maintenance of chromosomes 2-like 1 (yeast)], Genebank Accession Number: AF053305 [BUB1, BUB1 budding uninhibited by benzimidazoles 1 homolog (yeast)], Genebank Accession Number: Z25431 (NEK1, NIMA (never in mitosis gene a)-related kinase 1), Genebank Accession Number: BC043371 [GFI1B, Growth factor independent 1B (potential regulator of CDKN1A, translocated in CML)], Genebank Accession Number: CR933728 (CDC2, Cell division cycle 2, G1 to S and G2 to M), Genebank Accession Number: NM_014750 [DLG7, Discs, large homolog 7 (*Drosophila*)], Genebank Accession Number: NM_018560 (WWOX, WW domain containing oxidoreductase), Genebank Accession Number: BG203702 (FHIT, Nasopharyngeal carcinoma, down-regulated 1), Genebank Accession Number: BC050384 [SUPT3H, Suppressor of Ty 3 homolog (*S. cerevisiae*)], Genebank Accession Number: NM_000189 (HK2, Hexokinase 2), Genebank Accession Number: CD049340 (AURKB, Aurora kinase B), Genebank Accession Number: AB011153 [PLCB1, Phospholipase C, beta 1 (phosphoinositide-specific)], Genebank Accession Number: AB209271 (ERF, Ets2 repressor factor), Genebank Accession Number: NM_014264 [PLK4, Polo-like kinase 4 (*Drosophila*)], Genebank Accession Number: NM_002417 (MKI67, Antigen identified by monoclonal antibody Ki-67), Genebank Accession Number: XM_496557 (RGP1, Plasminogen-like B2), Genebank Accession Number: NM_170715 (RASSF1, Ras association (RalGDS/AF-6) domain family 1), Genebank Accession Number: NM_004526 [MCM2, MCM2 minichromosome maintenance deficient 2, mitotin (*S. cerevisiae*)], Genebank Accession Number: BC033086 [TCF19, Transcription factor 19 (SC1)], Genebank Accession Number: NM_001007071 (RPS6KB2, Ribosomal protein S6 kinase, 70 kDa, polypeptide 2), Genebank Accession Number: NM_016272 (TOB2, Transducer of ERBB2, 2), Genebank Accession Number: AK126688 (CDYL2, Chromodomain protein, Y-like 2), Genebank Accession Number: NM_001759 (CCND2, Cyclin D2), Genebank Accession Number: NM_002388 [MCM3, MCM3 minichromosome maintenance deficient 3 (*S. cerevisiae*)], Genebank Accession Number: NM_182776 [MCM7, MCM7 minichromosome maintenance deficient 7 (*S. cerevisiae*)], Genebank Accession Number: NM_012145 [DTYMK, Deoxythymidylate kinase (thymidylate kinase)], Genebank Accession Number: NM_014751 (MTSS1, Metastasis suppressor 1), Genebank Accession Number: NM_024342 (GRLF1, Glucocorticoid receptor DNA binding factor 1), Genebank Accession Number: AK025627 (CABLES1, Cdk5 and Abl enzyme substrate 1), Genebank Accession Number: NM_005915 [MCM6, MCM6 minichromosome maintenance deficient 6 (MIS5 homolog, *S. pombe*) (*S. cerevisiae*)], Genebank Accession Number: AF196185 [PARD3, Par-3 partitioning defective 3 homolog (*C. elegans*)], Genebank Accession Number: NM_019001 (XRN1, 5'-3' exoribonuclease 1), Genebank Accession Number: NM_006739 [MCM5, MCM5 minichromosome maintenance deficient 5, cell division cycle 46 (*S. cerevisiae*)], Genebank Accession Number: NM_012218 (ILF3, Interleukin enhancer binding factor 3, 90 kDa), Genebank Accession Number: AB053172 (CDT1, DNA replication factor), Genebank Accession Number: AK074112 (CCNL2, Cyclin L2), Genebank Accession Number: NM_001005414 (ZWINT, ZW10 interactor antisense), Genebank Accession Number: BC033391 (PP1665, Glycerophosphodiester phosphodiesterase domain containing 5), Genebank Accession Number: NM_000672 [ADH6, Alcohol dehydrogenase 6 (class V)], Genebank Accession Number: NM_004563 [PCK2, Phosphoenolpyruvate carboxykinase 2 (mitochondrial)], Genebank Accession Number: XM_113962 (KIAA0650, Structural maintenance of chromosomes flexible hinge domain containing 1), Genebank Accession Number: NM_001500 (GMDS, GDP-mannose 4,6-dehydratase), Genebank Accession Number: NM_002541 [OGDH, Oxoglutarate (alpha-ketoglutarate) dehydrogenase (lipoamide)], Genebank Accession Number: NM_000298 (PKLR, Pyruvate kinase, liver and RBC), Genebank Accession Number: NM_005276 [GPD1, Glycerol-3-phosphate dehydrogenase 1 (soluble)], Genebank Accession Number: AB209127 (PFKL, Phosphofructokinase, liver), Genebank Accession Number: M15943 (ADH4, Alcohol dehydrogenase 4 (class II), pi polypeptide), Genebank Accession Number: NM_000671 (ADH5, Alcohol dehydrogenase 5 (class III), chi polypeptide), Genebank Accession Number: BC026320 (OGDHL, Oxoglutarate dehydrogenase-like), Genebank Accession Number: NM_009590 [AOC2, Amine oxidase, copper containing 2 (retina-specific)], Genebank Accession Number: BC015797 (SLC25A10, Solute carrier family 25 (mitochondrial carrier; dicarboxylate transporter), member 10), Genebank Accession Number: NM_003748 (ALDH4A1, Aldehyde dehydrogenase 4 family, member A1), Genebank Accession Number: NM_002108 (HAL, Histidine ammonia-lyase), Genebank Accession Number: NM_003486 (SLC7A5, Solute carrier family 7 (cationic amino acid transporter, y+ system), member 5), Genebank Accession Number: NM_003045 (SLC7A1, Solute carrier family 7 (cationic amino acid transporter, y+ system), member 1), Genebank Accession Number: NM_000277 (PAH, Phenylalanine hydroxylase), Genebank Accession Number: NM_012331 (MSRA, Methionine sulfoxide reductase A), Genebank Accession Number: BC008366 [DDC, Dopa decarboxylase (aromatic L-amino acid decarboxylase)], Genebank Accession Number: NM_006567 [FARS2, Phenylalanine-tRNA synthetase 2 (mitochondrial)], Genebank Accession Number: AK055862 (FLJ31300, Urocanase domain containing 1), Genebank Accession Number: NM_001875 (CPS1, Carbamoyl-phosphate synthetase 1, mitochondrial), Genebank Accession Number: AK122685 (GLUD1, Glutamate dehydrogenase 1), Genebank Accession Number: NM_003046 (SLC7A2, Solute carrier family 7 (cationic amino acid transporter, y+ system), member 2), Genebank Accession Number: AK093306 (PHGDH, Phosphoglycerate dehydrogenase), Genebank Accession Number: NM_080820 (HARS2, Histidyl-tRNA synthetase 2), Genebank Accession Number: NM_006907 (PYCR1, Pyrroline-5-carboxylate reductase 1), Genebank Accession Number: NM_020117 (LARS, Leucyl-tRNA synthetase), Genebank Accession Number: BC051726 [GLUL, Glutamate-ammonia ligase (glutamine synthetase)], Genebank Accession Number: BC012616 (BHMT, Betaine-homocysteine methyltransferase), Genebank Accession Number: AK055053 [SHMT2, Serine hydroxymethyltransferase 2 (mitochondrial)], Genebank Accession Number: NM_007101 (SARDH, Sarcosine dehydrogenase), Genebank Accession Number: AL833251 (LOC283970, Hypothetical protein LOC283970), Genebank Accession Number: AK027126 (ASS, Argininosuccinate synthetase), Genebank Accession Number: L00972 (CBS, Cystathionine-beta-synthase), Genebank Accession Number: NM_206965 (FTCD, Formiminotransferase cyclodeaminase), Genebank Accession Number: NM_000429 (MAT1A, Methionine adenosyltransferase I, alpha), Genebank Accession Number: NM_001801 (CDO1, Cysteine dioxygenase, type I), Genebank Accession Number: NM_006843 (SDS, Serine dehydratase), Genebank Accession Number: NM_000170 [GLDC, Glycine dehydrogenase (decarboxylating; glycine decarboxylase, glycine cleavage system protein P)], Genebank Accession Number: BX102654 (HIST1H4B, Histone 1, H4b), Genebank Accession Number: DQ097177 (UREB1, HECT, UBA and WWE domain containing 1), Genebank Accession Number: NM_022743 (SMYD3, SET and MYND domain containing 3), Genebank Accession Number: NM_001809 (CENPA, Centromere protein A, 17 kDa), Genebank Accession Number: AB028450 (NCOR1, Nuclear receptor co-repressor 1), Genebank Accession Number: NM_002967 (SAFB, Scaffold attachment factor B), Genebank Accession Number: NM_003074 (SMARCC1, SWI/SNF related, matrix associated, actin dependent regulator of chromatin, subfamily c, member 1), Genebank Accession Number: NM_015409 (EP400, E1A binding protein p400), Genebank Accession Number: BC044659 (SMARCA3, SWI/SNF related, matrix associated, actin dependent regulator of chromatin, subfamily a, member 3), Genebank Accession Number: AB209433 (BAT8, Euchromatic histone-lysine N-methyltransferase 2), Genebank Accession Number: XM_370756 (KIAA1305, KIAA1305), Genebank Accession Number: NM_020201 (NT5M, 5',3'-nucleotidase, mitochondrial), Genebank Accession Number: NM_001025248 (DUT, DUTP pyrophosphatase), Genebank Accession Number: AK123010 (RRM2, Ribonucleotide reductase M2 polypeptide), Genebank Accession Number: BX537961 (DNMT2, DNA (cytosine-5-)-methyltransferase 2), Genebank Accession Number: BX648935 (TBL1XR1, Transducin (beta)-like 1X-linked receptor 1), Genebank Accession Number: NM_001001888 (VCX-C, Variably charged X-C), Genebank Accession Number: NM_002501 [NFIX, Nuclear factor I/X (CCAAT-binding transcription factor)], Genebank Accession Number: NM_003483 (HMGA2, High mobility group AT-hook 2), Genebank Accession Number: U80628 (TK2, Thymidine kinase 2, mitochondrial), Genebank Accession Number: NM_006807 [CBX1, Chromobox homolog 1 (HP1 beta homolog Drosophila)], Genebank Accession Number: AY024361 (MLL3, Myeloid/lymphoid or mixed-lineage leukemia 3), Genebank Accession Number: NM_017519 [ARID1B, AT rich interactive domain 1B (SWI1-like)], Genebank Accession Number: NM_003077 (SMARCD2, SWI/SNF related, matrix associated, actin dependent regulator of chromatin, subfamily d, member 2), Genebank Accession Number: NM_016937 (POLA, Polymerase (DNA directed), alpha), Genebank Accession Number: AJ007583 (LARGE, Like-glycosyltransferase), Genebank Accession Number: AK124635 (PCSK9, Proprotein convertase subtilisin/kexin type 9), Genebank Accession Number: NM_030758 (OSBP2, Oxysterol binding protein 2), Genebank Accession Number: NM_005063 [SCD, Stearoyl-CoA desaturase (delta-9-desaturase)], Genebank Accession Number: NM_000236 (LIPC, Lipase, hepatic), Genebank Accession Number: AF288389 (GLT25D2, Glycosyltransferase 25 domain containing 2), Genebank Accession Number: AF202889 (APOA5, Apolipoprotein A-V), Genebank Accession Number: BX640945 (FADS2, Fatty acid desaturase 2), Genebank Accession Number: BI521580 (APOC3, Apolipoprotein C-III), Genebank Accession Number: NM_001277 (CHKA, Choline kinase alpha), Genebank Accession Number: Z28339 [AKR1D1, Aldo-keto reductase family 1, member D1 (delta 4-3-ketosteroid-5-beta-reductase)], Genebank Accession Number: BC035654 (NR1H4, Nuclear receptor subfamily 1, group H, member 4), Genebank Accession Number: AB209229 (MVD, Mevalonate (diphospho) decarboxylase), Genebank Accession Number: BC026264 (UGT2B4, UDP glucuronosyltransferase 2 family, polypeptide B4), Genebank Accession Number: NM_004104 (FASN, Fatty acid synthase), Genebank Accession Number: NM_147161 (THEA, Acyl-CoA thioesterase 11), Genebank Accession Number: AF059203 (SOAT2, Sterol O-acyltransferase 2), Genebank Accession Number: NM_020918 (GPAM, Glycerol-3-phosphate acyltransferase, mitochondrial), Genebank Accession Number: NM_001443 (FABP1, Fatty acid binding protein 1, liver), Genebank Accession Number: NM_014762 (DHCR24, 24-dehydrocholesterol reductase), Genebank Accession Number: AK093328 (PCYT2, Phosphate cytidylyltransferase 2, ethanolamine), Genebank Accession Number: BX538214 (C6orf167, Chromosome 6 open reading frame 167), Genebank Accession Number: X75311 [MVK, Mevalonate kinase (mevalonic aciduria)], Genebank Accession Number: NM_000497 (CYP11B1, Cytochrome P450, family 11, subfamily B, polypeptide 1), Genebank Accession Number: BC036102 (SIAT7F, ST6 (alpha-N-acetyl-neuraminyl-2,3-beta-galactosyl-1,3)-N-acetylgalactosaminide alpha-2,6-sialyltransferase 6), Genebank Accession Number: BC012172 (ACAS2, Acyl-CoA synthetase short-chain family member 2), Genebank Accession Number: NM_007169 (PEMT, Phosphatidylethanolamine N-methyltransferase), Genebank Accession Number: X91148 (MTP, Microsomal triglyceride transfer protein), Genebank Accession Number: NM_198839 (ACACA, Acetyl-Coenzyme A carboxylase alpha), Genebank Accession Number: NM_004687 (MTMR4, Myotubularin related protein 4), Genebank Accession Number: NM_000384 [APOB, Apolipoprotein B (including Ag (x) antigen)], Genebank Accession Number: AK127051 [ACAA1, Acetyl-Coenzyme A acyltransferase 1 (peroxisomal 3-oxoacyl-Coenzyme A thiolase)], Genebank Accession Number: BC035638 [LSS, Lanosterol synthase (2,3-oxidosqualene-lanosterol cyclase)], Genebank Accession Number: NM_004204 (PIGQ, Phosphatidylinositol glycan, class Q), Genebank Accession Number: NM_004457 (ACSL3, Acyl-CoA synthetase long-chain family member 3), Genebank Accession Number: AL138578 (ADPN, Adiponutrin), Genebank Accession Number: NM_002332 [LRP1, Low density lipoprotein-related protein 1 (alpha-2-macroglobulin receptor)], Genebank Accession Number: NM_016372 (GPR175, G protein-coupled receptor 175), Genebank Accession Number: NM_080476 [CDC91L1, CDC91 cell division cycle 91-like 1 (S. cerevisiae)], Genebank Accession Number: AF303134 (ALDH8A1, Aldehyde dehydrogenase 8 family, member A1), Genebank Accession Number: NM_002130 [HMGCS1, 3-hydroxy-3-methylglutaryl-Coenzyme A synthase 1 (soluble)], Genebank Accession Number: AK055414 [LASS4, LAG1 longevity assurance homolog 4 (S. cerevisiae)], Genebank Accession Number: NM_022977 (ACSL4, Acyl-CoA synthetase long-chain family member 4), Genebank Accession Number: NM_004631 (LRP8, Low density lipoprotein receptor-related protein 8, apolipoprotein e receptor), Genebank Accession Number: NM_002573 (PAFAH1B3, Platelet-activating factor acetylhydrolase, isoform Ib, gamma subunit 29 kDa), Genebank Accession Number: NM_021005 (NR2F2, Nuclear receptor subfamily 2, group F, member 2), Genebank Accession Number: CR620135 [DPEP1, Dipeptidase 1 (renal)], Genebank Accession Number: NM_002317 (LOX, Lysyl oxidase), Genebank Accession Number: NM_005949 [MT1F, Metallothionein 1F (functional)], Genebank Accession Number: AF279145 (ANTXR1, Anthrax toxin receptor 1), Genebank Accession Number: NM_005588 [MEP1A, Meprin A, alpha (PABA peptide hydrolase)], Genebank Accession Number: NM_014214 (IMPA2, Inositol (myo)-1 (or 4)-monophosphatase 2), Genebank Accession Number: NM_005940 [MMP11, Matrix metallopeptidase 11 (stromelysin 3)], Genebank Accession Number: AB193259 (ACE2, Angiotensin I converting enzyme (peptidyl-dipeptidase A) 2), Genebank Accession Number: AF018081 (COL18A1, Collagen, type XVIII, alpha 1), Genebank Accession Number: M28016 (cytochrome b, Human mitochondrial cytochrome b gene, partial cds.), Genebank Accession Number:

NM_002428 [MMP15, Matrix metallopeptidase 15 (membrane-inserted)], Genebank Accession Number: NM_025074 (FRAS1, Fraser syndrome 1), Genebank Accession Number: M75106 [CPB2, Carboxypeptidase B2 (plasma, carboxypeptidase U)], Genebank Accession Number: NM_000937 (POLR2A, Polymerase (RNA) II (DNA directed) polypeptide A, 220 kDa), Genebank Accession Number: NM_005060 (RORC, RAR-related orphan receptor C), Genebank Accession Number: BC092512 (MYRIP, Myosin VIIA and Rab interacting protein), Genebank Accession Number: NM_000901 (NR3C2, Nuclear receptor subfamily 3, group C, member 2), Genebank Accession Number: NM_005392 (PHF2, PHD finger protein 2), Genebank Accession Number: AK091289 (ZNF367, Zinc finger protein 367), Genebank Accession Number: NM_014788 (TRIM14, Tripartite motif-containing 14), Genebank Accession Number: NM_018660 (ZNF395, Zinc finger protein 395), Genebank Accession Number: AB209755 (MLLT10, Myeloid/lymphoid or mixed-lineage leukemia (trithorax homolog, *Drosophila*); translocated to, 10), Genebank Accession Number: AK097472 [MAZ, MYC-associated zinc finger protein (purine-binding transcription factor)], Genebank Accession Number: NM_020062 (SLC2A4RG, SLC2A4 regulator), Genebank Accession Number: BX571750 (HNF4G, Hepatocyte nuclear factor 4, gamma), Genebank Accession Number: NM_021807 (SEC8L1, Exocyst complex component 4), Genebank Accession Number: NM_006651 (CPLX1, Complexin 1), Genebank Accession Number: NM_005845 (ABCC4, ATP-binding cassette, sub-family C (CFTR/MRP), member 4), Genebank Accession Number: NM_006650 (CPLX2, Complexin 2), Genebank Accession Number: NM_004164 (RBP2, Retinol binding protein 2, cellular), Genebank Accession Number: NM_021069 (ARGBP2, Sorbin and SH3 domain containing 2), Genebank Accession Number: NM_201649 (SLC6A9, Solute carrier family 6 (neurotransmitter transporter, glycine), member 9), Genebank Accession Number: NM_005835 (SLC17A2, Solute carrier family 17 (sodium phosphate), member 2), Genebank Accession Number: AJ315644 (SLC2A13, Solute carrier family 2 (facilitated glucose transporter), member 13), Genebank Accession Number: NM_000340 (SLC2A2, Solute carrier family 2 (facilitated glucose transporter), member 2), Genebank Accession Number: NM_003685 [KHSRP, KH-type splicing regulatory protein (FUSE binding protein 2)], Genebank Accession Number: BX537382 (SLC38A3, Solute carrier family 38, member 3), Genebank Accession Number: NM_182964 (NAV2, Neuron navigator 2), Genebank Accession Number: BX640965 (SLC22A3, Solute carrier family 22 (extraneuronal monoamine transporter), member 3), Genebank Accession Number: AK127255 (SNX26, Sorting nexin 26), Genebank Accession Number: AY043484 (SCN1A, Sodium channel, voltage-gated, type I, alpha), Genebank Accession Number: AK074107 (C20orf59, Chromosome 20 open reading frame 59), Genebank Accession Number: NM_003056 (SLC19A1, Solute carrier family 19 (folate transporter), member 1), Genebank Accession Number: NM_020897 (HCN3, Hyperpolarization activated cyclic nucleotide-gated potassium channel 3), Genebank Accession Number: AY124771 (SLC26A1, Solute carrier family 26 (sulfate transporter), member 1), Genebank Accession Number: NM_001011554 (SLC13A3, Solute carrier family 13 (sodium-dependent dicarboxylate transporter), member 3), Genebank Accession Number: AK027855 (SLC5A6, Solute carrier family 5 (sodium-dependent vitamin transporter), member 6), Genebank Accession Number: NM_001005747 (CACNB4, Calcium channel, voltage-dependent, beta 4 subunit), Genebank Accession Number: NM_013277 (RACGAP1, Rac GTPase activating protein 1), Genebank Accession Number: NM_012340 (NFATC2, Nuclear factor of activated T-cells, cytoplasmic, calcineurin-dependent 2), Genebank Accession Number: NM_018291 (FLJ10986, Hypothetical protein FLJ10986), Genebank Accession Number: BC052951 (LMNB1, Lamin B1), Genebank Accession Number: AK075271 [SPTLC2L, Serine palmitoyltransferase, long chain base subunit 2-like (aminotransferase 2)], Genebank Accession Number: BI762502 (GSTA2, Glutathione S-transferase A2), Genebank Accession Number: AK055221 (FBXO5, F-box protein 5), Genebank Accession Number: XM_372695 (LOC390859, PREDICTED: *Homo sapiens* similar to Chain A, Crystal Structure Of The R463a Mutant Of Human Glutamate Dehydrogenase (LOC390859), mRNA), Genebank Accession Number: AB037805 [KLHL14, Kelch-like 14 (*Drosophila*)], Genebank Accession Number: NM_145061 (C13orf3, Chromosome 13 open reading frame 3), Genebank Accession Number: AK000643 (ASB9, Ankyrin repeat and SOCS box-containing 9), Genebank Accession Number: AL133031 (MLR1, Transcription factor MLR1), Genebank Accession Number: AB091343 (C10orf3, Centrosomal protein 55 kDa), Genebank Accession Number: AY007723 (MAL2, Mal, T-cell differentiation protein 2), Genebank Accession Number: BC098313 (FLJ20641, Hypothetical protein FLJ20641), Genebank Accession Number: BC041882 (ATF7IP2, Activating transcription factor 7 interacting protein 2), Genebank Accession Number: AK127098 (FLJ10706, Chromosome 1 open reading frame 112), Genebank Accession Number: BC022255 [Spc25, Spindle pole body component 25 homolog (*S. cerevisiae*)], and Genebank Accession Number: BC026283 [APOH, Apolipoprotein H (beta-2-glycoprotein I)].

1) The gene whose expression is increased by chrysene exposure is characteristically selected from the group consisting of the following genes:

Genebank Accession Number: NM_003954 (MAP3K14, Mitogen-activated protein kinase kinase kinase 14), Genebank Accession Number: AB209586 (MAPK13, Mitogen-activated protein kinase 13), Genebank Accession Number: NM_005343 (HRAS, V-Ha-ras Harvey rat sarcoma viral oncogene homolog), Genebank Accession Number: BX647104 (FOS, V-fos FBJ murine osteosarcoma viral oncogene homolog), Genebank Accession Number: NM_007315 (STAT1, Signal transducer and activator of transcription 1, 91 kDa), Genebank Accession Number: BC027933 (MAPK11, Mitogen-activated protein kinase 11), Genebank Accession Number: NM_020529 (NFKBIA, Nuclear factor of kappa light polypeptide gene enhancer in B-cells inhibitor, alpha), Genebank Accession Number: BC014966 (RPS6KA1, Ribosomal protein S6 kinase, 90 kDa, polypeptide 1), Genebank Accession Number: NM_181861 (APAF1, Apoptotic peptidase activating factor), Genebank Accession Number: L41870 [RB1, Retinoblastoma 1 (including osteosarcoma)], Genebank Accession Number: CR612719 (GADD45A, Growth arrest and DNA-damage-inducible, alpha), Genebank Accession Number: BM462208 (PCNA, Proliferating cell nuclear antigen), Genebank Accession Number: M92424 [MDM2, Mdm2, transformed 3T3 cell double minute 2, p53 binding protein (mouse)], Genebank Accession Number: NM_078467 [CDKN1A, Cyclin-dependent kinase inhibitor 1A (p21, Cip1)], Genebank Accession Number: BC089389 (IHPK3, Inositol hexaphosphate kinase 3), Genebank Accession Number: NM_001024807 (APLP1, Amyloid beta (A4) precursor-like protein 1), Genebank Accession Number: NM_001013398 (IGFBP3, Insulin-like growth factor binding protein 3), Genebank Accession Number: AB209361 [FAS, Fas (TNF receptor superfamily, member 6)], Genebank Accession Number: NM_147780 (CTSB, Cathepsin B), Genebank Accession Number: NM_001165 (BIRC3, Baculoviral IAP repeat-containing 3), Genebank Accession Number: BM557864 (HSPB1, Heat shock 27 kDa protein 1), Genebank Accession Number: AB033060 (PDCD6, Aryl-hydrocarbon receptor repressor), Genebank Accession Number: AK125880 (TP53INP1, Tumor protein p53 inducible nuclear protein 1), Genebank Accession Number: NM_004574 (SEP4, Septin 4), Genebank Accession Number: NM_003820 [TNFRSF14, Tumor necrosis factor receptor superfamily, member 14 (herpesvirus entry mediator)], Genebank Accession Number: CN478604 [LGALS7, Lectin, galactoside-binding, soluble, 7 (galectin 7)], Genebank Accession Number: NM_004879 (EI24, Etoposide induced 2.4 mRNA), Genebank Accession Number: NM_003311 (PHLDA2, Pleckstrin homology-like domain, family A, member 2), Genebank Accession Number: NM_003897 (IER3, Immediate early response 3), Genebank Accession Number: AK097284 (TNFAIP8, Tumor necrosis factor, alpha-induced protein 8), Genebank Accession Number: NM_000582 [SPP1, Secreted phosphoprotein 1 (osteopontin, bone sialoprotein I, early T-lymphocyte activation 1)], Genebank Accession Number: NM_013258 (PYCARD, PYD and CARD domain containing), Genebank Accession Number: NM_002305 [LGALS1, Lectin, galactoside-binding, soluble, 1 (galectin 1)], Genebank Accession Number: AF055634 [UNC5C, Unc-5 homolog C (C. elegans)], Genebank Accession Number: CR614015 (CD14, CD14 antigen), Genebank Accession Number: AK129595 (GADD45B, Growth arrest and DNA-damage-inducible, beta), Genebank Accession Number: AF356193 (CARD6, Caspase recruitment domain family, member 6), Genebank Accession Number: BC063043 [PRF1, Perforin 1 (pore forming protein)], Genebank Accession Number: BX537586 [STK17A, Serine/threonine kinase 17a (apoptosis-inducing)], Genebank Accession Number: NM_003842 (TNFRSF10B, Tumor necrosis factor receptor superfamily, member 10b), Genebank Accession Number: AF208043 (IFI16, Interferon, gamma-inducible protein 16), Genebank Accession Number: BX641114 (ANXA4, Annexin A4), Genebank Accession Number: NM_001009552 (PPP2CB, Protein phosphatase 2 (formerly 2A), catalytic subunit, beta isoform), Genebank Accession Number: BX386171 (CGB5, Chorionic gonadotropin, beta polypeptide 8), Genebank Accession Number: AY358103 (HIP1, Huntingtin interacting protein 1), Genebank Accession Number: BC027949 (P2RX1, Purinergic receptor P2X, ligand-gated ion channel, 1), Genebank Accession Number: BC042844 (CASP10, Caspase 10, apoptosis-related cysteine peptidase), Genebank Accession Number: NM_000733 [CD3E, CD3E antigen, epsilon polypeptide (TiT3 complex)], Genebank Accession Number: NM_033245 (PML, Promyelocytic leukemia), Genebank Accession Number: BC047362 (PHLDA1, Pleckstrin homology-like domain, family A, member 1), Genebank Accession Number: NM_006763 (BTG2, BTG family, member 2), Genebank Accession Number: BC050455 (DDB2, LIM homeobox 3), Genebank Accession Number: BC068535 (TP53AP1, TP53 activated protein 1), Genebank Accession Number: AF033122 (SESN1, Sestrin 1), Genebank Accession Number: AB024313 (POLH, Polymerase (DNA directed), eta), Genebank Accession Number: NM_001012716 (TYMS, Thymidylate synthetase), Genebank Accession Number: BC095402 (ATXN3, Ataxin 3), Genebank Accession Number: BU675073 (PTTG1, Pituitary tumor-transforming 1), Genebank Accession Number: BC073161 (RAD51C, RAD51 homolog C (S. cerevisiae), Genebank Accession Number: NM_001983 [ERCC1, Excision repair cross-complementing rodent repair deficiency, complementation group 1 (includes overlapping antisense sequence)], Genebank Accession Number: NM_018965 (TREM2, Triggering receptor expressed on myeloid cells 2), Genebank Accession Number: BX649164 (PAI, serpin peptidase inhibitor, clade E (nexin, plasminogen activator inhibitor type 1), member 1), Genebank Accession Number: NM_006404 [PROCR, Protein C receptor, endothelial (EPCR)], Genebank Accession Number: C035582 (TRIM22, Tripartite motif-containing 22), Genebank Accession Number: NM_006691 (XLKD1, Extracellular link domain containing 1), Genebank Accession Number: NM_015831 [ACHE, Acetylcholinesterase (YT blood group)], Genebank Accession Number: BC045666 (TP53I11, Tumor protein p53 inducible protein 11), Genebank Accession Number: NM_005438 (FOSL1, FOS-like antigen 1), Genebank Accession Number: NM_005755 (EBI3, Epstein-Barr virus induced gene 3), Genebank Accession Number: BM918324 (LY96, Lymphocyte antigen 96), Genebank Accession Number: NM_000022 (ADA, Adenosine deaminase), Genebank Accession Number: NM_004167 (CCL14, Chemokine (C-C motif) ligand 15), Genebank Accession Number: NM_014278 (HSPA4L, Heat shock 70 kDa protein 4-like), Genebank Accession Number: BC006523 (SGK2, Serum/glucocorticoid regulated kinase 2), Genebank Accession Number: NM_000641 (IL11, Interleukin 11), Genebank Accession Number: H18681 [C20orf139, Sulfiredoxin 1 homolog (S. cerevisiae)], Genebank Accession Number: NM_001769 [CD9, CD9 antigen (p24)], Genebank Accession Number: BG564326 (SAA4, Serum amyloid A4, constitutive), Genebank Accession Number: NM_016816 (OAS1, 2',5'-oligoadenylate synthetase 1, 40/46 kDa), Genebank Accession Number: CB055213 (ICOSLG, Inducible T-cell co-stimulator ligand), Genebank Accession Number: CR591007 (CCL3, Chemokine (C-C motif) ligand 3), Genebank Accession Number: NM_145641 (APOL3, Apolipoprotein L, 3), Genebank Accession Number: AK127663 (PTGES, Prostaglandin E synthase), Genebank Accession Number: NM_001734 (C1S, Complement component 1, s subcomponent), Genebank Accession Number: NM_002260 (KLRC3, Killer cell lectin-like receptor subfamily C, member 2), Genebank Accession Number: NM_001733 (C1R, Complement component 1, r subcomponent), Genebank Accession Number: AB209922 (DNAJB4, DnaJ (Hsp40) homolog, subfamily B, member 4), Genebank Accession Number: NM_201397 (GPX1, Glutathione peroxidase 1), Genebank Accession Number: AK090482 [CXCL12, Chemokine (C-X-C motif) ligand 12 (stromal cell-derived factor 1)], Genebank Accession Number: BF662985 (CCL3L1, Chemokine (C-C motif) ligand 3-like 1), Genebank Accession Number: NM_001779 [CD58, CD58 antigen, (lymphocyte function-associated antigen 3)], Genebank Accession Number: NM_005064 (CCL23, Chemokine (C-C motif) ligand 23), Genebank Accession Number: NM_000242 [MBL2, Mannose-binding lectin (protein C) 2, soluble (opsonic defect)], Genebank Accession Number: NM_032036 (FAM14A, Family with sequence similarity 14, member A), Genebank Accession Number: AJ890082 (HSPCA, Heat shock 90 kDa protein 1, alpha), Genebank Accession Number: BC068487 (TLR3, Toll-like receptor 3), Genebank Accession Number: NM_000552 (VWF, Von Willebrand factor), Genebank Accession Number: NM_000132 [F8, Coagulation factor VIII, procoagulant component (hemophilia A)], Genebank Accession Number: AY154461 (NALP6, NACHT, leucine rich repeat and PYD containing 6), Genebank Accession Number: AK127679 (DUSP1, Dual specificity phosphatase 1), Genebank Accession Number: NM_014314 (DDX58, DEAD (Asp-Glu-Ala-Asp) box polypeptide 58), Genebank Accession Number: NM_000311 [PRNP, Prion protein (p27-30) (Creutzfeld-Jakob disease, Gerstmann-Strausler-Scheinker syndrome, fatal familial insomnia)], Genebank Accession Number: NM_006597 (HSPA8, Heat shock 70 kDa protein 8), Genebank Accession Number: AK092040 (ZCSL2, Zinc finger, CSL-type containing 2), Genebank Accession Number: NM_031483 [ITCH, Itchy homolog E3 ubiquitin protein ligase (mouse)], Genebank Accession Number: U25029 [NR3C1, Nuclear receptor subfamily 3, group C, member 1 (glucocorticoid receptor)], Genebank Accession Number: NM_005242 (F2RL1, Coagulation factor II (thrombin) receptor-like 1), Genebank Accession Number: AK172851 (ADORA2B, Adenosine A2b receptor), Genebank Accession Number: BQ053419 (BATF, Basic leucine zipper transcription factor, ATF-like), Genebank Accession Number: BC020698 (CCL20, Chemokine (C-C motif) ligand 20), Genebank Accession Number: NM_001124 (ADM, Adrenomedullin), Genebank Accession Number: NM_153609 (TMPRSS6, Transmembrane protease, serine 6), Genebank Accession Number: NM_004148 (NINJ1, Ninjurin 1), Genebank Accession Number: AF324224 (APOL2, Apolipoprotein L, 2), Genebank Accession Number: BC040494 (DNAJB2, DnaJ (Hsp40) homolog, subfamily B, member 2), Genebank Accession Number: BE512691 [GPX2, Glutathione peroxidase 2 (gastrointestinal)], Genebank Accession Number: NM_001002029 (C4A, Complement component 4B, telomeric), Genebank Accession Number: NM_000732 [CD3D, CD3D antigen, delta polypeptide (TiT3 complex)], Genebank Accession Number: AK223210 [CD79B, CD79B antigen (immunoglobulin-associated beta)], Genebank Accession Number: NM_002309 (LIF, Hypothetical protein MGC20647), Genebank Accession Number: AF031469 (MR1, Major histocompatibility complex, class I-related), Genebank Accession Number: NM_172208 [TAPBP, TAP binding protein (tapasin)], Genebank Accession Number: BC021117 [CSF1, Colony stimulating factor 1 (macrophage)], Genebank Accession Number: NM_001421 [ELF4, E74-like factor 4 (ets domain transcription factor)], Genebank Accession Number: NM_002119 (HLA-DOA, Major histocompatibility complex, class II, DO alpha), Genebank Accession Number: BX648013 [TAP1, Transporter 1, ATP-binding cassette, sub-family B (MDR/TAP)], Genebank Accession Number: AL832287 (ZAP70, Zeta-chain (TCR) associated protein kinase 70 kDa), Genebank Accession Number: BF569086 (NK4, Interleukin 32), Genebank Accession Number: AL832451 (DKFZp451C2311, guanylate binding protein 2, interferon-inducible), Genebank Accession Number: AF069493 (SEMA7A, Sema domain, immunoglobulin domain (Ig), and GPI membrane anchor, (semaphorin) 7A), Genebank Accession Number: NM_001008490 (KLF6, Kruppel-like factor 6), Genebank Accession Number: NM_000418 (IL4R, Interleukin 4 receptor), Genebank Accession Number: NM_004048 (B2M, Beta-2-microglobulin), Genebank Accession Number: AF116720 (DNAJA2, DnaJ (Hsp40) homolog, subfamily A, member 2), Genebank Accession Number: NM_001007271 (DUSP13, Dual specificity phosphatase 13), Genebank Accession Number: BM904612 [S100A6, S100 calcium binding protein A6 (calcyclin)], Genebank Accession Number: AK074652 (SERTAD1, SERTA domain containing 1), Genebank Accession Number: NM_203394 (E2F7, E2F transcription factor 7), Genebank Accession Number: NM_003620 (PPM1D, Protein phosphatase 1D magnesium-dependent, delta isoform), Genebank Accession Number: BC060797 [PARD6G, Par-6 partitioning defective 6 homolog gamma (C. elegans)], Genebank Accession Number: NM_021913 (AXL, AXL receptor tyrosine kinase), Genebank Accession Number: BC040303 (PTP4A1, Protein tyrosine phosphatase type IVA, member 1), Genebank Accession Number: BC008564 (PPP1R9B, Protein phosphatase 1, regulatory subunit 9B, spinophilin), Genebank Accession Number: AK097024 [RAE1, RAE1 RNA export 1 homolog (S. pombe)], Genebank Accession Number: BC011957 (BTG3, BTG family, member 3), Genebank Accession Number: NM_078487 [CDKN2B, Cyclin-dependent kinase inhibitor 2B (p15, inhibits CDK4)], Genebank Accession Number: BC023552 (SFN, Stratifin), Genebank Accession Number: BC060847 [PARD6B, Par-6 partitioning defective 6 homolog beta (C. elegans)], Genebank Accession Number: NM_003236 (TGFA, Transforming growth factor, alpha), Genebank Accession Number: NM_002632 (PGF, Placental growth factor, vascular endothelial growth factor-related protein), Genebank Accession Number: NM_015278 (SASH1, SAM and SH3 domain containing 1), Genebank Accession Number: AL834276 (MGC3207, Hypothetical protein MGC3207), Genebank Accession Number: AK096276 (CCND3, Cyclin D3), Genebank Accession Number: AB209373 (CCNK, Chromosome 14 open reading frame 65), Genebank Accession Number: NM_021132 [PPP3CB, Protein phosphatase 3 (formerly 2B), catalytic subunit, beta isoform (calcineurin A beta)], Genebank Accession Number: NM_005072 (SLC12A4, Solute carrier family 12 (potassium/chloride transporters), member 4), Genebank Accession Number: BX647886 [PCNP, SPT2, Suppressor of Ty, domain containing 1 (S. cerevisiae)], Genebank Accession Number: NM_044472 [CDC42, Cell division cycle 42 (GTP binding protein, 25 kDa)], Genebank Accession Number: AL832973 [REC8L1, REC8-like 1 (yeast)], Genebank Accession Number: NM_002031 (FRK, Fyn-related kinase), Genebank Accession Number: BM913048 (TIMP1, TIMP metallopeptidase inhibitor 1), Genebank Accession Number: NM_003975 (SH2D2A, SH2 domain protein 2A), Genebank Accession Number: NM_198129 (LAMA3, Laminin, alpha 3), Genebank Accession Number: NM_006152 (LRMP, Lymphoid-restricted membrane protein), Genebank Accession Number: X96753 [CSPG4, Chondroitin sulfate proteoglycan 4 (melanoma-associated)], Genebank Accession Number: NM_000474 [TWIST1, Twist homolog 1 (acrocephalosyndactyly 3; Saethre-Chotzen syndrome) (Drosophila)], Genebank Accession Number: AF052152 (DCAMKL1, Doublecortin and CaM kinase-like 1), Genebank Accession Number: AF333334 (CCIN, Calicin), Genebank Accession Number: NM_005979 (S100A13, S100 calcium binding protein A13), Genebank Accession Number: NM_004429 (EFNB1, Ephrin-B1), Genebank Accession Number: NM_003873 (NRP1, Neuropilin 1), Genebank Accession Number: AF026692 (SFRP4, Secreted frizzled-related protein 4), Genebank Accession Number: AK124583 (DAZAP1, DAZ associated protein 1), Genebank Accession Number: AF003837 [JAG1, Jagged 1 (Alagille syndrome)], Genebank Accession Number: AB209590 (BMP1, Bone morphogenetic protein 1), Genebank Accession Number: X54457 [CEL, Carboxyl ester lipase (bile salt-stimulated lipase)], Genebank Accession Number: Y11307 (CYR61, Cysteine-rich, angiogenic inducer, 61), Genebank Accession Number: NM_000596 (IGFBP1, Insulin-like growth factor binding protein 1), Genebank Accession Number: NM_020997 (LEFTY1, Left-right determination factor 1), Genebank Accession Number: NM_001553 (IGFBP7, Insulin-like growth factor binding protein 7), Genebank Accession Number: AB209509 (IGFBP2, Insulin-like growth factor binding protein 2, 36 kDa), Genebank Accession Number: NM_001552 (IGFBP4, Insulin-like growth factor binding protein 4), Genebank Accession Number: AB209321 (CSRP2, Cysteine and glycine-rich protein 2), Genebank Accession Number: BM556279 (EMP3, Epithelial membrane protein 3), Genebank Accession Number: NM_005727 (TSPAN1, Tetraspanin 1), Genebank Accession Number: BQ683841 [S100A11, S100 calcium binding protein A11 (calgizzarin)], Genebank Accession Number: BC042390 [VTI1B, Vesicle transport through interaction with t-SNAREs homolog 1B (yeast)], Genebank Accession Number: NM_000899 (KITLG, KIT ligand), Genebank Accession Number: BC032940 (LAMP3, Lysosomal-associated membrane protein 3), Genebank Accession Number: BQ939577 [AKR1C3, Aldo-keto reductase family 1, member C3 (3-alpha hydroxysteroid dehydrogenase, type II)], Genebank Accession Number: BC063468 (OSMR, Oncostatin M receptor), Genebank Accession Number: CR936719 [SSR1, Signal sequence receptor, alpha (translocon-associated protein alpha)], Genebank Accession Number: AB024057 [TBC1D8, TBC1 domain family, member 8 (with GRAM domain)], Genebank Accession Number: NM_003329 (TXN, Thioredoxin), Genebank Accession Number: NM_012125 (CHRM5, Cholinergic receptor, muscarinic 5), Genebank Accession Number: NM_007045 (FGFR1OP, FGFR1 oncogene partner), Genebank Accession Number: AK094474 (RHOC, Ras homolog gene family, member C), Genebank Accession Number: BC017706 (6PGL, 6-phosphogluconolactonase), Genebank Accession Number: AF153821 (ADH1B, Alcohol dehydrogenase IB (class I), beta polypeptide), Genebank Accession Number: AK124656 [ENO2, Enolase 2 (gamma, neuronal)], Genebank Accession Number: D42047 (GPD1L, Glycerol-3-phosphate dehydrogenase 1-like), Genebank Accession Number: AK130060 (TALDO1, Transaldolase 1), Genebank Accession Number: AL833069 (KIAA1434, Hypothetical protein KIAA1434), Genebank Accession Number: XM-496436 (UNQ6077, C219-reactive peptide), Genebank Accession Number: NM_199186 (BPGM, 2,3-bisphosphoglycerate mutase), Genebank Accession Number: U86136 (TEP1, Telomerase-associated protein 1), Genebank Accession Number: BU603483 (HIST1H1E, Histone 1, H1e), Genebank Accession Number: NM_005319 (HIST1H1C, Histone 1, H1c), Genebank Accession Number: NM_005320 (HIST1H1D, Histone 1, H1d), Genebank Accession Number: NM_003516 (HIST2H2AA, Histone 2, H2aa), Genebank Accession Number: F02250 (HDAC2, Histone deacetylase 2), Genebank Accession Number: NM_004739 (MTA2, Metastasis associated 1 family, member 2), Genebank Accession Number: BC042589 (HIST1H2BD, Histone 1, H2bd), Genebank Accession Number: CB529694 (HIST2H2BE, Histone 2, H2be), Genebank Accession Number: AK126154 (NP, Nucleoside phosphorylase), Genebank Accession Number: AB040899 (KIAA1466, KIAA1466 gene), Genebank Accession Number: CR608156 (HIST1H2AC, Histone 1, H2ac), Genebank Accession Number: BX436525 (HIST1H2BH, Histone 1, H2bh), Genebank Accession Number: AK057762 (TDH, L-threonine dehydrogenase), Genebank Accession Number: BC035124 (UNQ2541, MSFL2541), Genebank Accession Number: BC034763 (FDXR, Ferredoxin reductase), Genebank Accession Number: AK093461 (ISYNA1, Myo-inositol 1-phosphate synthase A1), Genebank Accession Number: AK097009 (PLTP, phospholipid transfer protein), Genebank Accession Number: AF524864 [AKR1B10, Aldo-keto reductase family 1, member B10 (aldose reductase)], Genebank Accession Number: NM_021727 (FADS3, Fatty acid desaturase 3), Genebank Accession Number: CR627415 (HSD3B2, Hydroxy-delta-5-steroid dehydrogenase, 3 beta- and steroid delta-isomerase 2), Genebank Accession Number: CD013987 (CYP21A2, Cytochrome P450, family 21, subfamily A, polypeptide 2), Genebank Accession Number: BC020744 (AKR1C4, Aldo-keto reductase family 1, member C4 (chlordecone reductase; 3-alpha hydroxysteroid dehydrogenase, type I; dihydrodiol), dehydrogenase 4), Genebank Accession Number: NM_004753 (DHRS3, Dehydrogenase/reductase (SDR family) member 3), Genebank Accession Number: BC030207 (NR0B2, Nuclear receptor subfamily 0, group B, member 2), Genebank Accession Number: AK091948 (LTB4DH, Leukotriene B4 12-hydroxydehydrogenase), Genebank Accession Number: NM_002900 (RBP3, Retinol binding protein 3, interstitial), Genebank Accession Number: BX647927 (PLCD1, Phospholipase C, delta 1), Genebank Accession Number: NM_145323 (OSBPL3, Oxysterol binding protein-like 3), Genebank Accession Number: NM_000169 (GLA, Galactosidase, alpha), Genebank Accession Number: BC094756 (CRA, Myotubularin related protein 11), Genebank Accession Number: AB043587 (ACBD3, Acyl-Coenzyme A binding domain containing 3), Genebank Accession Number: NM_001478 [GALGT, UDP-N-acetyl-alpha-D-galactosamine: (N-acetylneuraminyl)-galactosylglucosylceramide N-acetylgalactosaminyltransferase (GalNAc-T)], Genebank Accession Number: J05428 (UGT2B7, UDP glucuronosyltransferase 2 family, polypeptide B7), Genebank Accession Number: AB002454 (CYP4F3, Cytochrome P450, family 4, subfamily F, polypeptide 3), Genebank Accession Number: NM_000405 (GM2A, GM2 ganglioside activator), Genebank Accession Number: BC001823 (PRKAB1, Protein kinase, AMP-activated, beta 1 non-catalytic subunit), Genebank Accession Number: NM_145343 (APOL1, Apolipoprotein L, 1), Genebank Accession Number: NM_006571 (DCTN6, Dynactin 6), Genebank Accession Number: NM_020139 (DHRS6, Dehydrogenase/reductase (SDR family) member 6), Genebank Accession Number: NM_000499 (CYP1A1, Cytochrome P450, family 1, subfamily A, polypeptide 1), Genebank Accession Number: BC007003 [TGM4, Transglutaminase 4 (prostate)], Genebank Accession Number: NM_012189 [CABYR, Calcium binding tyrosine-(Y)-phosphorylation regulated (fibrousheathin 2)], Genebank Accession Number: CR615530 (CYGB, Cytoglobin), Genebank Accession Number: NM_004199 (P4HA2, Procollagen-proline, 2-oxoglutarate 4-dioxygenase (proline 4-hydroxylase), alpha polypeptide II), Genebank Accession Number: AK027560 (CYP26A1, Cytochrome P450, family 26, subfamily A, polypeptide 1), Genebank Accession Number: NM_145298 (APOBEC3F, Apolipoprotein B mRNA editing enzyme, catalytic polypeptide-like 3F), Genebank Accession Number: NM_005576 (LOXL1, Lysyl oxidase-like 1), Genebank Accession Number: AK024854 [APOBEC3B, Apolipoprotein B mRNA editing enzyme, catalytic polypeptide-like 3D (putative)], Genebank Accession Number: NM_014301 (NIFUN, NifU-like N-terminal domain containing), Genebank Accession Number: BF670653 (MB, Myoglobin), Genebank Accession Number: AK126982 (LHX6, LIM homeobox 6), Genebank Accession Number: Y13786 [ADAM19, ADAM metallopeptidase domain 19 (meltrin beta)], Genebank Accession Number: AB051455 (MICAL-L1, MICAL-like 1), Genebank Accession Number: AK074068 (MICAL-L2, MICAL-like 2), Genebank Accession Number: AK124421 [CPA1, Carboxypeptidase A1 (pancreatic)], Genebank Accession Number: NM_030622 (CYP2S1, Cytochrome P450, family 2, subfamily S, polypeptide 1), Genebank Accession Number: BC012027 (CYP2U1, Cytochrome P450, family 2, subfamily U, polypeptide 1), Genebank Accession Number: AY461717 (ZNF385, Zinc finger protein 385), Genebank Accession Number: AK092424 (ZSCAN4, Zinc finger and SCAN domain containing 4), Genebank Accession Number: AB208935 [RASAL1, RAS protein activator like 1 (GAP1 like)], Genebank Accession Number: NM_201444 (DGKA, Diacylglycerol kinase, alpha 80 kDa), Genebank Accession Number: BC035625 [EGR2, Early growth response 2 (Krox-20 homolog, *Drosophila*)], Genebank Accession Number: BF983391 (RPS27L, Ribosomal protein S27-like), Genebank Accession Number: BC036545 (PLAC2, Placenta-specific 2), Genebank Accession Number: BC034569 (ZNF337, Zinc finger protein 337), Genebank Accession Number: CR936707 (TRIM38, Tripartite motif-containing 38), Genebank Accession Number: AK091940 (MGC4734, Ring finger protein 183), Genebank Accession Number: NM_024101 (MLPH, Melanophilin), Genebank Accession Number: CR601823 (HIVEP3, Human immunodeficiency virus type I enhancer binding protein 3), Genebank Accession Number: BC041578 (MGC17986, zinc finger protein 114), Genebank Accession Number: BC038432 (RARA, Retinoic acid receptor, alpha), Genebank Accession Number: BX641053 (FXYD2, FXYD domain containing ion transport regulator 2), Genebank Accession Number: AK095363 (AQP3, Aquaporin 3), Genebank Accession Number: AK074100 (SLC37A2, Solute carrier family 37 (glycerol-3-phosphate transporter), member 2), Genebank Accession Number: AK024002 (TUBA4, Tubulin, alpha 4), Genebank Accession Number: AK092677 (TUBB6, Tubulin, beta 6), Genebank Accession Number: NM_001297 (CNGB1, Cyclic nucleotide gated channel beta 1), Genebank Accession Number: NM_032872 (SYTL1, Synaptotagmin-like 1), Genebank Accession Number: NM_014045 (LRP10, Low density lipoprotein receptor-related protein 10), Genebank Accession Number: NM_014585 (SLC40A1, Solute carrier family 40 (iron-regulated transporter), member 1), Genebank Accession Number: L02870 [COL7A1, Collagen, type VII, alpha 1 (epidermolysis bullosa, dystrophic, dominant and recessive)], Genebank Accession Number: AK054731 [TUBA1, Tubulin, alpha 1 (testis specific)], Genebank Accession Number: AF336127 (SLC4A11, Solute carrier family 4, sodium bicarbonate transporter-like, member 11), Genebank Accession Number: AB075951 (SLC22A2, Solute carrier family 22 (organic cation transporter), member 2), Genebank Accession Number: AK125026 (SLC6A12, Solute carrier family 6 (neurotransmitter transporter, betaine/GABA), member 12), Genebank Accession Number: BX537541 (MGC13186, Chromosome 1 open reading frame 57), Genebank Accession Number: CD013956 (SHBG, Sex hormone-binding globulin), Genebank Accession Number: BC029057 (DAO, D-amino-acid oxidase), Genebank Accession Number: BC041479 (COL9A2, Collagen, type IX, alpha 2), Genebank Accession Number: AL050210 (LOC283130, Hypothetical protein LOC283130), Genebank Accession Number: NM_004798 (KIF3B, Kinesin family member 3B), Genebank Accession Number: AK025742 [UCP2, Uncoupling protein 2 (mitochondrial, proton carrier)], Genebank Accession Number: NM_021990 (GABRE, Gamma-aminobutyric acid (GABA) A receptor, epsilon), Genebank Accession Number: NM_005819 (STX6, Syntaxin 6), Genebank Accession Number: BC092420 [CYP4F11, Similar to Cytochrome P450 4F12 (CYPIVF12) (UNQ568/PRO1129)], Genebank Accession Number: BC043423 (ABCB6, ATP-binding cassette, sub-family B (MDR/TAP), member 6), Genebank Accession Number: BC021025 (CTHRC1, Collagen triple helix repeat containing 1), Genebank Accession Number: NM_004999 (MYO6, Myosin VI), Genebank Accession Number: AF445025 (SLC35A4, Solute carrier family 35, member A4), Genebank Accession Number: NM_003330 (TXNRD1, Thioredoxin reductase 1), Genebank Accession Number: AK092512 (SLC16A5, Solute carrier family 16 (monocarboxylic acid transporters), member 5), Genebank Accession Number: AB075871 [FLJ42654, Golgi transport 1 homolog A (*S. cerevisiae*)], Genebank Accession Number: NM_004864 (GDF15, Growth differentiation factor 15), Genebank Accession Number: NM_022153 (PP2135, Chromosome 10 open reading frame 54), Genebank Accession Number: NM_001013632 (LOC343521, Similar to hypothetical protein 4833401D15), Genebank Accession Number: AK124751 (CAPN2, Calpain 2, (m/II) large subunit), Genebank Accession Number: AK095079 (RGC32, Response gene to complement 32), Genebank Accession Number: NM_031286 (SH3BGRL3, SH3 domain binding glutamic acid-rich protein like 3), Genebank Accession Number: AK126182 (KIAA1949, KIAA1949), Genebank Accession Number: NM_080388 (S100A16, S100 calcium binding protein A16), Genebank Accession Number: NM_025106 (SSB1, SplA/ryanodine receptor domain and SOCS box containing 1), Genebank Accession Number: NM_203403 (C9orf150, Chromosome 9 open reading frame 150), Genebank Accession Number: AK096241 (SQSTM1, Sequestosome 1), Genebank Accession Number: BQ276852 (TMSB10, Thymosin, beta 10), Genebank Accession Number: BC101655 (HIST1H2BI, Histone 1, H2bi), Genebank Accession Number: W84524 (TM4SF5, Transmembrane 4 L six family member 5), and Genebank Accession Number: BX647290 (HIST1H2BO, Histone 1, H2bo).

2) The gene whose expression is decreased by chrysene exposure is characteristically selected from the group consisting of the following genes:

Genebank Accession Number: NM_002467 [MYC, V-myc myelocytomatosis viral oncogene homolog (avian)], Genebank Accession Number: BC038295 (MAP2K7, Mitogen-activated protein kinase kinase 7), Genebank Accession Number: NM_004364 (CEBPA, CCAAT/enhancer binding protein (C/EBP), alpha), Genebank Accession Number: NM_145161 (MAP2K5, Mitogen-activated protein kinase kinase 5), Genebank Accession Number: XM_042066 (MAP3K1, Mitogen-activated protein kinase kinase kinase 1), Genebank Accession Number: Z25424 (MKNK2, MAP kinase interacting serine/threonine kinase 2), Genebank Accession Number: AB209047 (ELK1, ELK1, member of ETS oncogene family), Genebank Accession Number: NM_004755 (RPS6KA5, Ribosomal protein S6 kinase, 90 kDa, polypeptide 5), Genebank Accession Number: AB001872 (RPL4, Mitogen-activated protein kinase kinase kinase 13), Genebank Accession Number: NM_002758 (MAP2K6, Mitogen-activated protein kinase kinase 6), Genebank Accession Number: AK098095 (BRAF, V-raf murine sarcoma viral oncogene homolog B1), Genebank Accession Number: AB208919 [FGFR1, Fibroblast growth factor receptor 1 (fms-related tyrosine kinase 2, Pfeiffer syndrome)], Genebank Accession Number: BC060837 (DUSP9, Dual specificity phosphatase 9), Genebank Accession Number: NM_000142 [FGFR3, Fibroblast growth factor receptor 3 (achondroplasia, thanatophoric dwarfism)], Genebank Accession Number: AY247738 [TRIB3, Tribbles homolog 3 (*Drosophila*)], Genebank Accession Number: NM_030640 (DUSP16, Dual specificity phosphatase 16), Genebank Accession Number: NM_148957 (TNFRSF19, Tumor necrosis factor receptor superfamily, member 19), Genebank Accession Number: AB011123 (TNIK, TRAF2 and NCK interacting kinase), Genebank Accession Number: NM_006549 (CAMKK2, Calcium/calmodulin-dependent protein kinase kinase 2, beta), Genebank Accession Number: NM_022740 (HIPK2, Homeodomain interacting protein kinase 2), Genebank Accession Number: NM_005400 (PRKCE, Protein kinase C, epsilon), Genebank Accession Number: NM_000893 (KNG1, Kininogen 1), Genebank Accession Number: NM_000066 (C8B, Complement component 8, beta polypeptide), Genebank Accession Number: CR749293 (PLG, Plasminogen), Genebank Accession Number: BC013780 (ADORA2A, Adenosine A2a receptor), Genebank Accession Number: NM_001012271 (BIRC5, Effector cell peptidase receptor 1), Genebank Accession Number: NM_003811 (TNFSF9, Tumor necrosis factor (ligand) superfamily, member 9), Genebank Accession Number: BC050369 (E2F1, E2F transcription factor 1), Genebank Accession Number: NM_007313 (ABL1, V-abl Abelson murine leukemia viral oncogene homolog 1), Genebank Accession Number: BX647151 (MYBL2, V-myb myeloblastosis viral oncogene homolog (avian)-like 2), Genebank Accession Number: NM_004822 (NTN1, Netrin 1), Genebank Accession Number: BC033694 [BCL2L11, BCL2-like 11 (apoptosis facilitator)], Genebank Accession Number: AB208876 (AXIN1, Axin 1), Genebank Accession Number: BC051332 [F2, Coagulation factor II (thrombin)], Genebank Accession Number: AK122614 (PPARD, Peroxisome proliferative activated receptor, delta), Genebank Accession Number: L78790 [ITGB2, Integrin, beta 2 (antigen CD18 (p95), lymphocyte function-associated antigen 1; macrophage antigen 1 (mac-1) beta subunit)], Genebank Accession Number: AK223409 (BARD1, BRCA1 associated RING domain 1), Genebank Accession Number: NM_002737 (PRKCA, Protein kinase C, alpha), Genebank Accession Number: NM_012479 (YWHAG, Tyrosine 3-monooxygenase/tryptophan 5-monooxygenase activation protein, gamma polypeptide), Genebank Accession Number: CR596268 [ITGB3BP, Integrin beta 3 binding protein (beta 3-endonexin)], Genebank Accession Number: NM_003551 [NME5, Non-metastatic cells 5, protein expressed in (nucleoside-diphosphate kinase)], Genebank Accession Number: NM_013974 (DDAH2, Dimethylarginine dimethylaminohydrolase 2), Genebank Accession Number: D79987 [ESPL1, Extra spindle poles like 1 (S. cerevisiae)], Genebank Accession Number: NM_006427 (SIVA, CD27-binding (Siva) protein), Genebank Accession Number: NM_024900 (PHF17, PHD finger protein 17), Genebank Accession Number: AB046854 (MAGI-3, Membrane associated guanylate kinase, WW and PDZ domain containing 3), Genebank Accession Number: AK095578 (SPHK1, Sphingosine kinase 1), Genebank Accession Number: AK122762 (CIDEA, Cell death-inducing DFFA-like effector a), Genebank Accession Number: AK092872 [ERCC2, Excision repair cross-complementing rodent repair deficiency, complementation group 2 (xeroderma pigmentosum D)], Genebank Accession Number: NM_006290 (TNFAIP3, Tumor necrosis factor, alpha-induced protein 3), Genebank Accession Number: NM_000562 (C8A, Complement component 8, alpha polypeptide), Genebank Accession Number: AK122894 (AKT1, V-akt murine thymoma viral oncogene homolog 1), Genebank Accession Number: NM_005067 [SIAH2, Seven in absentia homolog 2 (Drosophila)], Genebank Accession Number: NM_203339 [CLU, Clusterin (complement lysis inhibitor, SP-40,40, sulfated glycoprotein 2, testosterone-repressed prostate message 2, apolipoprotein J)], Genebank Accession Number: NM_003376 (VEGF, Vascular endothelial growth factor), Genebank Accession Number: AK027590 (DAPK3, Death-associated protein kinase 3), Genebank Accession Number: AK122825 (HMGB1, High-mobility group box 1), Genebank Accession Number: NM_006904 (PRKDC, Protein kinase, DNA-activated, catalytic polypeptide), Genebank Accession Number: AK074377 (UHRF1, Chromosome 19 open reading frame 31), Genebank Accession Number: CR604810 (CCNA2, Cyclin A2), Genebank Accession Number: AK001720 [FLJ10858, Nei endonuclease VIII-like 3 (E. coli)], Genebank Accession Number: CR600021 (HMGB2, High-mobility group box 2), Genebank Accession Number: NM_006230 (POLD2, Polymerase (DNA directed), delta 2, regulatory subunit 50 kDa), Genebank Accession Number: NM_018151 [RIF1, RAP1 interacting factor homolog (yeast)], Genebank Accession Number: BX248766 [RAD51L1, RAD51-like 1 (S. cerevisiae)], Genebank Accession Number: NM_014502 [PRP19, PRP19/PSO4 pre-mRNA processing factor 19 homolog (S. cerevisiae)], Genebank Accession Number: NM_013975 (LIG3, Ligase III, DNA, ATP-dependent), Genebank Accession Number: NM_173627 (FLJ35220, Hypothetical protein FLJ35220), Genebank Accession Number: NM_003362 (UNG, Uracil-DNA glycosylase), Genebank Accession Number: AF076494 (IRF7, Interferon regulatory factor 7), Genebank Accession Number: CR625391 (RAD51AP1, RAD51 associated protein 1), Genebank Accession Number: NM_006231 (POLE, Polymerase (DNA directed), epsilon), Genebank Accession Number: NM_130398 (EXO1, Exonuclease 1), Genebank Accession Number: DQ140356 (KIAA1596, Fanconi anemia, complementation group M), Genebank Accession Number: NM_002105 (H2AFX, H2A histone family, member X), Genebank Accession Number: AB209560 (POLD1, Polymerase (DNA directed), delta 1, catalytic subunit 125 kDa), Genebank Accession Number: NM_000136 (FANCC, Fanconi anemia, complementation group C), Genebank Accession Number: NM_003368 (USP1, Ubiquitin specific peptidase 1), Genebank Accession Number: NM_022836 [DCLRE1B, DNA cross-link repair 1B (PSO2 homolog, S. cerevisiae)], Genebank Accession Number: NM_001067 (TOP2A, Topoisomerase (DNA) II alpha 170 kDa), Genebank Accession Number: NM_002913 (RFC1, Replication factor C (activator 1) 1, 145 kDa), Genebank Accession Number: NM_002412 (MGMT, O-6-methylguanine-DNA methyltransferase), Genebank Accession Number: NM_000251 [MSH2, MutS homolog 2, colon cancer, nonpolyposis type 1 (E. coli)], Genebank Accession Number: NM_015254 (KIF13B, Kinesin family member 13B), Genebank Accession Number: NM_006037 (HDAC4, Histone deacetylase 4), Genebank Accession Number: NM_020995 (HPR, Haptoglobin-related protein), Genebank Accession Number: NM_153443 (KIR3DL1, Killer cell immunoglobulin-like receptor, three domains, long cytoplasmic tail, 1), Genebank Accession Number: BC071718 (CCL4L1, Chemokine (C-C motif) ligand 4-like 1), Genebank Accession Number: NM_020979 (APS, Adaptor protein with pleckstrin homology and src homology 2 domains), Genebank Accession Number: NM_001629 (ALOX5AP, Arachidonate 5-lipoxygenase-activating protein), Genebank Accession Number: NM_130852 (PLUNC, Palate, lung and nasal epithelium carcinoma associated), Genebank Accession Number: AK024499 (SPON2, Spondin 2, extracellular matrix protein), Genebank Accession Number: BC048198 (AHSG, Alpha-2-HS-glycoprotein), Genebank Accession Number: AK095849 (RNU22, RNA, U22 small nucleolar), Genebank Accession Number: BC005395 (HPX, Hemopexin), Genebank Accession Number: NM_012276 (ILT7, Leukocyte immunoglobulin-like receptor, subfamily A (with TM domain), member 4), Genebank Accession Number: NM_003152 (STAT5A, Signal transducer and activator of transcription 5A), Genebank Accession Number: BC037171 (CCL27, Chemokine (C-C motif) ligand 27), Genebank Accession Number: NM_002468 [MYD88, Myeloid differentiation primary response gene (88)], Genebank Accession Number: NM_002215 (ITIH1, Inter-alpha (globulin) inhibitor H1), Genebank Accession Number: NM_004750 (CRLF1, Cytokine receptor-like factor 1), Genebank Accession Number: DR004094 (HAMP, Hepcidin antimicrobial peptide), Genebank Accession Number: BC063245 (GNLY, Granulysin), Genebank Accession Number: AJ290445 (SARM1, Sterile alpha and TIR motif containing 1), Genebank Accession Number: AK122686 [IF, I factor (complement)], Genebank Accession Number: AB008535 (GPR44, G protein-coupled receptor 44), Genebank Accession Number: AK122912 (ZGPAT, Zinc finger, CCCH-type with G patch domain), Genebank Accession Number: BC022312 (C4BPA, Complement component 4 binding protein, alpha), Genebank Accession Number: BG564683 (ORM1, Orosomucoid 1), Genebank Accession Number: NM_000625 [NOS2A, Nitric oxide synthase 2A (inducible, hepatocytes)], Genebank Accession Number: NM_005515 (HLXB9, Homeo box HB9), Genebank Accession Number: BX537504 (C2, Complement component 2), Genebank Accession Number: BC028153 (LILRB3, Leukocyte immunoglobulin-like receptor, subfamily B (with TM and ITIM domains), member 3), Genebank Accession Number: AF130100 (SERPINC1, Serpin peptidase inhibitor, clade C (antithrombin), member 1), Genebank Accession Number: BC015110 (HHEX, Hematopoietically expressed homeobox), Genebank Accession Number: AB209179 [PLK1, Polo-like kinase 1 (*Drosophila*)], Genebank Accession Number: AY367065 [ASPM, Asp (abnormal spindle)-like, microcephaly associated (*Drosophila*)], Genebank Accession Number: NM_006101 (KNTC2, Kinetochore associated 2), Genebank Accession Number: NM_003550 [MAD1L1, MAD1 mitotic arrest deficient-like 1 (yeast)], Genebank Accession Number: NM_020242 (KNSL7, Kinesin family member 15), Genebank Accession Number: AB033068 [FZR1, Fizzy/cell division cycle 20 related 1 (*Drosophila*)], Genebank Accession Number: NM_018492 (PBK, PDZ binding kinase), Genebank Accession Number: NM_003318 (TTK, TTK protein kinase), Genebank Accession Number: BC011000 (CDCA5, Cell division cycle associated 5), Genebank Accession Number: NM_003981 (PRC1, Protein regulator of cytokinesis 1), Genebank Accession Number: NM_015097 (CLASP2, Cytoplasmic linker associated protein 2), Genebank Accession Number: U65410 [MAD2L1, MAD2 mitotic arrest deficient-like 1 (yeast)], Genebank Accession Number: NM_016343 [CENPF, Centromere protein F, 350/400 ka (mitosin)], Genebank Accession Number: NM_005504 (BCAT1, Branched chain aminotransferase 1, cytosolic), Genebank Accession Number: NM_003718 [CDC2L5, Cell division cycle 2-like 5 (cholinesterase-related cell division controller)], Genebank Accession Number: NM_002768 (PCOLN3, Procollagen (type III) N-endopeptidase), Genebank Accession Number: BC004352 (KIF22, Kinesin family member 22), Genebank Accession Number: NM_005983 (SKP2, S-phase kinase-associated protein 2 (p45)), Genebank Accession Number: NM_004523 (KIF11, Kinesin family member 11), Genebank Accession Number: CR592757 [BRRN1, Barren homolog 1 (*Drosophila*)], Genebank Accession Number: NM_019063 (EML4, Echinoderm microtubule associated protein like 4), Genebank Accession Number: NM_006845 (KIF2C, Kinesin family member 2C), Genebank Accession Number: NM_004701 (CCNB2, Cyclin B2), Genebank Accession Number: NM_138555 (KIF23, Kinesin family member 23), Genebank Accession Number: NM_182687 (PKMYT1, Protein kinase, membrane associated tyrosine/threonine 1), Genebank Accession Number: NM_001790 (CDC25C, Cell division cycle 25C), Genebank Accession Number: BC032677 (UBE2C, Ubiquitin-conjugating enzyme E2C), Genebank Accession Number: NM_005886 (KATNB1, Katanin p80 (WD repeat containing) subunit B 1), Genebank Accession Number: BC073878 (KIFC1, Kinesin family member C1), Genebank Accession Number: AL833191 [SMC2L1, SMC2 structural maintenance of chromosomes 2-like 1 (yeast)], Genebank Accession Number: AF053305 [BUB1, BUB1 budding uninhibited by benzimidazoles 1 homolog (yeast)], Genebank Accession Number: Z25431 (NEK1, NIMA (never in mitosis gene a)-related kinase 1), Genebank Accession Number: BC043371 [GFI1B, Growth factor independent 1B (potential regulator of CDKN1A, translocated in CML)], Genebank Accession Number: CR933728 (CDC2, Cell division cycle 2, G1 to S and G2 to M), Genebank Accession Number: NM_014750 [DLG7, Discs, large homolog 7 (*Drosophila*)], Genebank Accession Number: NM_018560 (WWOX, WW domain containing oxidoreductase), Genebank Accession Number: BG203702 (FHIT, Nasopharyngeal carcinoma, down-regulated 1), Genebank Accession Number: BC050384 [SUPT3H, Suppressor of Ty 3 homolog (*S. cerevisiae*)], Genebank Accession Number: NM_000189 (HK2, Hexokinase 2), Genebank Accession Number: CD049340 (AURKB, Aurora kinase B), Genebank Accession Number: AB011153 [PLCB1, Phospholipase C, beta 1 (phosphoinositide-specific)], Genebank Accession Number: AB209271 (ERF, Ets2 repressor factor), Genebank Accession Number: NM_014264 [PLK4, Polo-like kinase 4 (*Drosophila*)], Genebank Accession Number: NM_002417 (MKI67, Antigen identified by monoclonal antibody Ki-67), Genebank Accession Number: XM_496557 (RGP1, Plasminogen-like B2), Genebank Accession Number: NM_170715 (RASSF1, Ras association (RalGDS/AF-6) domain family 1), Genebank Accession Number: NM_004526 [MCM2, MCM2 minichromosome maintenance deficient 2, mitotin (*S. cerevisiae*)], Genebank Accession Number: BC033086 [TCF19, Transcription factor 19 (SC1)], Genebank Accession Number: NM_001007071 (RPS6KB2, Ribosomal protein S6 kinase, 70 kDa, polypeptide 2), Genebank Accession Number: NM_016272 (TOB2, Transducer of ERBB2, 2), Genebank Accession Number: AK126688 (CDYL2, Chromodomain protein, Y-like 2), Genebank Accession Number: NM_001759 (CCND2, Cyclin D2), Genebank Accession Number: NM_002388 [MCM3, MCM3 minichromosome maintenance deficient 3 (*S. cerevisiae*)], Genebank Accession Number: NM_182776 [MCM7, MCM7 minichromosome maintenance deficient 7 (*S. cerevisiae*)], Genebank Accession Number: NM_012145 [DTYMK, Deoxythymidylate kinase (thymidylate kinase)], Genebank Accession Number: NM_014751 (MTSS1, Metastasis suppressor 1), Genebank Accession Number: NM_024342 (GRLF1, Glucocorticoid receptor DNA binding factor 1), Genebank Accession Number: AK025627 (CABLES1, Cdk5 and Abl enzyme substrate 1), Genebank Accession Number: NM_005915 [MCM6, MCM6 minichromosome maintenance deficient 6 (MIS5 homolog, *S. pombe*) (*S. cerevisiae*)], Genebank Accession Number: AF196185 [PARD3, Par-3 partitioning defective 3 homolog (*C. elegans*)], Genebank Accession Number: NM_019001 (XRN1, 5'-3' exoribonuclease 1), Genebank Accession Number: NM_006739 [MCM5, MCM5 minichromosome maintenance deficient 5, cell division cycle 46 (*S. cerevisiae*)], Genebank Accession Number: NM_012218 (ILF3, Interleukin enhancer binding factor 3, 90 kDa), Genebank Accession Number: AB053172 (CDT1, DNA replication factor), Genebank Accession Number: AK074112 (CCNL2, Cyclin L2), Genebank Accession Number: NM_001005414 (ZWINT, ZW10 interactor antisense), Genebank Accession Number: BC033391 (PP1665, Glycerophosphodiester phosphodiesterase domain containing 5), Genebank Accession Number: NM_000672 [ADH6, Alcohol dehydrogenase 6 (class V)], Genebank Accession Number: NM_004563 [PCK2, Phosphoenolpyruvate carboxykinase 2 (mitochondrial)], Genebank Accession Number: XM_113962 (KIAA0650, Structural maintenance of chromosomes flexible hinge domain containing 1), Genebank Accession Number: NM_001500 (GMDS, GDP-mannose 4,6-dehydratase), Genebank Accession Number: NM_002541 [OGDH, Oxoglutarate (alpha-ketoglutarate) dehydrogenase (lipoamide)], Genebank Accession Number: NM_000298 (PKLR, Pyruvate kinase, liver and RBC), Genebank Accession Number: NM_005276 [GPD1, Glycerol-3-phosphate dehydrogenase 1 (soluble)], Genebank Accession Number: AB209127 (PFKL, Phosphofructokinase, liver), Genebank Accession Number: M15943 (ADH4, Alcohol dehydrogenase 4 (class II), pi polypeptide), Genebank Accession Number: NM_000671 (ADH5, Alcohol dehydrogenase 5 (class III), chi polypeptide), Genebank Accession Number: BC026320 (OGDHL, Oxoglutarate dehydrogenase-like), Genebank Accession Number: NM_009590 [AOC2, Amine oxidase, copper containing 2 (retina-specific)], Genebank Accession Number: BC015797 (SLC25A10, Solute carrier family 25 (mitochondrial carrier; dicarboxylate transporter), member 10), Genebank Accession Number: NM_003748 (ALDH4A1, Aldehyde dehydrogenase 4 family, member A1), Genebank Accession Number: NM_002108 (HAL, Histidine ammonia-lyase), Genebank Accession Number: NM_003486 (SLC7A5, Solute carrier family 7 (cationic amino acid transporter, y+ system), member 5), Genebank Accession Number: NM_003045 (SLC7A1, Solute carrier family 7 (cationic amino acid transporter, y+ system), member 1), Genebank Accession Number: NM_000277 (PAH, Phenylalanine hydroxylase), Genebank Accession Number: NM_012331 (MSRA, Methionine sulfoxide reductase A), Genebank Accession Number: BC008366 [DDC, Dopa decarboxylase (aromatic L-amino acid decarboxylase)], Genebank Accession Number: NM_006567 [FARS2, Phenylalanine-tRNA synthetase 2 (mitochondrial)], Genebank Accession Number: AK055862 (FLJ31300, Urocanase domain containing 1), Genebank Accession Number: NM_001875 (CPS1, Carbamoyl-phosphate synthetase 1, mitochondrial), Genebank Accession Number: AK122685 (GLUD1, Glutamate dehydrogenase 1), Genebank Accession Number: NM_003046 (SLC7A2, Solute carrier family 7 (cationic amino acid transporter, y+ system), member 2), Genebank Accession Number: AK093306 (PHGDH, Phosphoglycerate dehydrogenase), Genebank Accession Number: NM_080820 (HARS2, Histidyl-tRNA synthetase 2), Genebank Accession Number: NM_006907 (PYCR1, Pyrroline-5-carboxylate reductase 1), Genebank Accession Number: NM_020117 (LARS, Leucyl-tRNA synthetase), Genebank Accession Number: BC051726 [GLUL, Glutamate-ammonia ligase (glutamine synthetase)], Genebank Accession Number: BC012616 (BHMT, Betaine-homocysteine methyltransferase), Genebank Accession Number: AK055053 [SHMT2, Serine hydroxymethyltransferase 2 (mitochondrial)], Genebank Accession Number: NM_007101 (SARDH, Sarcosine dehydrogenase), Genebank Accession Number: AL833251 (LOC283970, Hypothetical protein LOC283970), Genebank Accession Number: AK027126 (ASS, Argininosuccinate synthetase), Genebank Accession Number: L00972 (CBS, Cystathionine-beta-synthase), Genebank Accession Number: NM_206965 (FTCD, Formiminotransferase cyclodeaminase), Genebank Accession Number: NM_000429 (MAT1A, Methionine adenosyltransferase I, alpha), Genebank Accession Number: NM_001801 (CDO1, Cysteine dioxygenase, type I), Genebank Accession Number: NM_006843 (SDS, Serine dehydratase), Genebank Accession Number: NM_000170 [GLDC, Glycine dehydrogenase (decarboxylating; glycine decarboxylase, glycine cleavage system protein P)], Genebank Accession Number: BX102654 (HIST1H4B, Histone 1, H4b), Genebank Accession Number: DQ097177 (UREB1, HECT, UBA and WWE domain containing 1), Genebank Accession Number: NM_022743 (SMYD3, SET and MYND domain containing 3), Genebank Accession Number: NM_001809 (CENPA, Centromere protein A, 17 kDa), Genebank Accession Number: AB028450 (NCOR1, Nuclear receptor co-repressor 1), Genebank Accession Number: NM_002967 (SAFB, Scaffold attachment factor B), Genebank Accession Number: NM_003074 (SMARCC1, SWI/SNF related, matrix associated, actin dependent regulator of chromatin, subfamily c, member 1), Genebank Accession Number: NM_015409 (EP400, E1A binding protein p400), Genebank Accession Number: BC044659 (SMARCA3, SWI/SNF related, matrix associated, actin dependent regulator of chromatin, subfamily a, member 3), Genebank Accession Number: AB209433 (BAT8, Euchromatic histone-lysine N-methyltransferase 2), Genebank Accession Number: XM_370756 (KIAA1305, KIAA1305), Genebank Accession Number: NM_020201 (NT5M, 5',3'-nucleotidase, mitochondrial), Genebank Accession Number: NM_001025248 (DUT, DUTP pyrophosphatase), Genebank Accession Number: AK123010 (RRM2, Ribonucleotide reductase M2 polypeptide), Genebank Accession Number: BX537961 (DNMT2, DNA (cytosine-5-)-methyltransferase 2), Genebank Accession Number: BX648935 (TBL1XR1, Transducin (beta)-like 1X-linked receptor 1), Genebank Accession Number: NM_001001888 (VCX-C, Variably charged X-C), Genebank Accession Number: NM_002501 [NFIX, Nuclear factor I/X (CCAAT-binding transcription factor)], Genebank Accession Number: NM_003483 (HMGA2, High mobility group AT-hook 2), Genebank Accession Number: U80628 (TK2, Thymidine kinase 2, mitochondrial), Genebank Accession Number: NM_006807 [CBX1, Chromobox homolog 1 (HP1 beta homolog *Drosophila*)], Genebank Accession Number: AY024361 (MLL3, Myeloid/lymphoid or mixed-lineage leukemia 3), Genebank Accession Number: NM_017519 [ARID1B, AT rich interactive domain 1B (SWI1-like)], Genebank Accession Number: NM_003077 (SMARCD2, SWI/SNF related, matrix associated, actin dependent regulator of chromatin, subfamily d, member 2), Genebank Accession Number: NM_016937 (POLA, Polymerase (DNA directed), alpha), Genebank Accession Number: AJ007583 (LARGE, Like-glycosyltransferase), Genebank Accession Number: AK124635 (PCSK9, Proprotein convertase subtilisin/kexin type 9), Genebank Accession Number: NM_030758 (OSBP2, Oxysterol binding protein 2), Genebank Accession Number: NM_005063 [SCD, Stearoyl-CoA desaturase (delta-9-desaturase)], Genebank Accession Number: NM_000236 (LIPC, Lipase, hepatic), Genebank Accession Number: AF288389 (GLT25D2, Glycosyltransferase 25 domain containing 2), Genebank Accession Number: AF202889 (APOA5, Apolipoprotein A-V), Genebank Accession Number: BX640945 (FADS2, Fatty acid desaturase 2), Genebank Accession Number: BI521580 (APOC3, Apolipoprotein C-III), Genebank Accession Number: NM_001277 (CHKA, Choline kinase alpha), Genebank Accession Number: Z28339 [AKR1D1, Aldo-keto reductase family 1, member D1 (delta 4-3-ketosteroid-5-beta-reductase)], Genebank Accession Number: BC035654 (NR1H4, Nuclear receptor subfamily 1, group H, member 4), Genebank Accession Number: AB209229 (MVD, Mevalonate (diphospho) decarboxylase), Genebank Accession Number: BC026264 (UGT2B4, UDP glucuronosyltransferase 2 family, polypeptide B4), Genebank Accession Number: NM_004104 (FASN, Fatty acid synthase), Genebank Accession Number: NM_147161 (THEA, Acyl-CoA thioesterase 11), Genebank Accession Number: AF059203 (SOAT2, Sterol O-acyltransferase 2), Genebank Accession Number: NM_020918 (GPAM, Glycerol-3-phosphate acyltransferase, mitochondrial), Genebank Accession Number: NM_001443 (FABP1, Fatty acid binding protein 1, liver), Genebank Accession Number: NM_014762 (DHCR24, 24-dehydrocholesterol reductase), Genebank Accession Number: AK093328 (PCYT2, Phosphate cytidylyltransferase 2, ethanolamine), Genebank Accession Number: BX538214 (C6orf167, Chromosome 6 open reading frame 167), Genebank Accession Number: X75311 [MVK, Mevalonate kinase (mevalonic aciduria)], Genebank Accession Number: NM_000497 (CYP11B1, Cytochrome P450, family 11, subfamily B, polypeptide 1), Genebank Accession Number: BC036102 (SIAT7F, ST6 (alpha-N-acetyl-neuraminyl-2,3-beta-galactosyl-1,3)-N-acetylgalactosaminide alpha-2,6-sialyltransferase 6), Genebank Accession Number: BC012172 (ACAS2, Acyl-CoA synthetase short-chain family member 2), Genebank Accession Number: NM_007169 (PEMT, Phosphatidylethanolamine N-methyltransferase), Genebank Accession Number: X91148 (MTP, Microsomal triglyceride transfer protein), Genebank Accession Number: NM_198839 (ACACA, Acetyl-Coenzyme A carboxylase alpha), Genebank Accession Number: NM_004687 (MTMR4, Myotubularin related protein 4), Genebank Accession Number: NM_000384 [APOB, Apolipoprotein B (including Ag(x) antigen)], Genebank Accession Number: AK127051 [ACAA1, Acetyl-Coenzyme A acyltransferase 1 (peroxisomal 3-oxoacyl-Coenzyme A thiolase)], Genebank Accession Number: BC035638 [LSS, Lanosterol synthase (2,3-oxidosqualene-lanosterol cyclase)], Genebank Accession Number: NM_004204 (PIGQ, Phosphatidylinositol glycan, class Q), Genebank Accession Number: NM_004457 (ACSL3, Acyl-CoA synthetase long-chain family member 3), Genebank Accession Number: AL138578 (ADPN, Adiponutrin), Genebank Accession Number: NM_002332 [LRP1, Low density lipoprotein-related protein 1 (alpha-2-macroglobulin receptor)], Genebank Accession Number: NM_016372 (GPR175, G protein-coupled receptor 175), Genebank Accession Number: NM_080476 [CDC91L1, CDC91 cell division cycle 91-like 1 (S. cerevisiae)], Genebank Accession Number: AF303134 (ALDH8A1, Aldehyde dehydrogenase 8 family, member A1), Genebank Accession Number: NM_002130 [HMGCS1, 3-hydroxy-3-methylglutaryl-Coenzyme A synthase 1 (soluble)], Genebank Accession Number: AK055414 [LASS4, LAG1 longevity assurance homolog 4 (S. cerevisiae)], Genebank Accession Number: NM_022977 (ACSL4, Acyl-CoA synthetase long-chain family member 4), Genebank Accession Number: NM_004631 (LRP8, Low density lipoprotein receptor-related protein 8, apolipoprotein e receptor), Genebank Accession Number: NM_002573 (PAFAH1B3, Platelet-activating factor acetylhydrolase, isoform Ib, gamma subunit 29 kDa), Genebank Accession Number: NM_021005 (NR2F2, Nuclear receptor subfamily 2, group F, member 2), Genebank Accession Number: CR620135 [DPEP1, Dipeptidase 1 (renal)], Genebank Accession Number: NM_002317 (LOX, Lysyl oxidase), Genebank Accession Number: NM_005949 [MT1F, Metallothionein 1F (functional)], Genebank Accession Number: AF279145 (ANTXR1, Anthrax toxin receptor 1), Genebank Accession Number: NM_005588 [MEP1A, Meprin A, alpha (PABA peptide hydrolase)], Genebank Accession Number: NM_014214 (IMPA2, Inositol (myo)-1 (or 4)-monophosphatase 2), Genebank Accession Number: NM_005940 [MMP11, Matrix metallopeptidase 11 (stromelysin 3)], Genebank Accession Number: AB193259 (ACE2, Angiotensin I converting enzyme (peptidyl-dipeptidase A) 2), Genebank Accession Number: AF018081 (COL18A1, Collagen, type XVIII, alpha 1), Genebank Accession Number: M28016 (cytochrome b, Human mitochondrial cytochrome b gene, partial cds.), Genebank Accession Number: NM_002428 [MMP15, Matrix metallopeptidase 15 (membrane-inserted)], Genebank Accession Number: NM_025074 (FRAS1, Fraser syndrome 1), Genebank Accession Number: M75106 [CPB2, Carboxypeptidase B2 (plasma, carboxypeptidase U)], Genebank Accession Number: NM_000937 (POLR2A, Polymerase (RNA) II (DNA directed) polypeptide A, 220 kDa), Genebank Accession Number: NM_005060 (RORC, RAR-related orphan receptor C), Genebank Accession Number: BC092512 (MYRIP, Myosin VIIA and Rab interacting protein), Genebank Accession Number: NM_000901 (NR3C2, Nuclear receptor subfamily 3, group C, member 2), Genebank Accession Number: NM_005392 (PHF2, PHD finger protein 2), Genebank Accession Number: AK091289 (ZNF367, Zinc finger protein 367), Genebank Accession Number: NM_014788 (TRIM14, Tripartite motif-containing 14), Genebank Accession Number: NM_018660 (ZNF395, Zinc finger protein 395), Genebank Accession Number: AB209755 (MLLT10, Myeloid/lymphoid or mixed-lineage leukemia (trithorax homolog, *Drosophila*); translocated to, 10), Genebank Accession Number: AK097472 [MAZ, MYC-associated zinc finger protein (purine-binding transcription factor)], Genebank Accession Number: NM_020062 (SLC2A4RG, SLC2A4 regulator), Genebank Accession Number: BX571750 (HNF4G, Hepatocyte nuclear factor 4, gamma), Genebank Accession Number: NM_021807 (SEC8L1, Exocyst complex component 4), Genebank Accession Number: NM_006651 (CPLX1, Complexin 1), Genebank Accession Number: NM_005845 (ABCC4, ATP-binding cassette, sub-family C (CFTR/MRP), member 4), Genebank Accession Number: NM_006650 (CPLX2, Complexin 2), Genebank Accession Number: NM_004164 (RBP2, Retinol binding protein 2, cellular), Genebank Accession Number: NM_021069 (ARGBP2, Sorbin and SH3 domain containing 2), Genebank Accession Number: NM_201649 (SLC6A9, Solute carrier family 6 (neurotransmitter transporter, glycine), member 9), Genebank Accession Number: NM_005835 (SLC17A2, Solute carrier family 17 (sodium phosphate), member 2), Genebank Accession Number: AJ315644 (SLC2A13, Solute carrier family 2 (facilitated glucose transporter), member 13), Genebank Accession Number: NM_000340 (SLC2A2, Solute carrier family 2 (facilitated glucose transporter), member 2), Genebank Accession Number: NM_003685 [KHSRP, KH-type splicing regulatory protein (FUSE binding protein 2)], Genebank Accession Number: BX537382 (SLC38A3, Solute carrier family 38, member 3), Genebank Accession Number: NM_182964 (NAV2, Neuron navigator 2), Genebank Accession Number: BX640965 (SLC22A3, Solute carrier family 22 (extraneuronal monoamine transporter), member 3), Genebank Accession Number: AK127255 (SNX26, Sorting nexin 26), Genebank Accession Number: AY043484 (SCN1A, Sodium channel, voltage-gated, type I, alpha), Genebank Accession Number: AK074107 (C20orf59, Chromosome 20 open reading frame 59), Genebank Accession Number: NM_003056 (SLC19A1, Solute carrier family 19 (folate transporter), member 1), Genebank Accession Number: NM_020897 (HCN3, Hyperpolarization activated cyclic nucleotide-gated potassium channel 3), Genebank Accession Number: AY124771 (SLC26A1, Solute carrier family 26 (sulfate transporter), member 1), Genebank Accession Number: NM_001011554 (SLC13A3, Solute carrier family 13 (sodium-dependent dicarboxylate transporter), member 3), Genebank Accession Number: AK027855 (SLC5A6, Solute carrier family 5 (sodium-dependent vitamin transporter), member 6), Genebank Accession Number: NM_001005747 (CACNB4, Calcium channel, voltage-dependent, beta 4 subunit), Genebank Accession Number: NM_013277 (RACGAP1, Rac GTPase activating protein 1), Genebank Accession Number: NM_012340 (NFATC2, Nuclear factor of activated T-cells, cytoplasmic, calcineurin-dependent 2), Genebank Accession Number: NM_018291 (FLJ10986, Hypothetical protein FLJ10986), Genebank Accession Number: BC052951 (LMNB1, Lamin B1), Genebank Accession Number: AK075271 [SPTLC2L, Serine palmitoyltransferase, long chain base subunit 2-like (aminotransferase 2)], Genebank Accession Number: BI762502 (GSTA2, Glutathione S-transferase A2), Genebank Accession Number: AK055221 (FBXO5, F-box protein 5), Genebank Accession Number: XM_372695 (LOC390859, PREDICTED: *Homo sapiens* similar to Chain A, Crystal Structure Of The R463a Mutant Of Human Glutamate Dehydrogenase (LOC390859), mRNA), Genebank Accession Number: AB037805 [KLHL14, Kelch-like 14 (*Drosophila*)], Genebank Accession Number: NM_145061 (C13orf3, Chromosome 13 open reading frame 3), Genebank Accession Number: AK000643 (ASB9, Ankyrin repeat and SOCS box-containing 9), Genebank Accession Number: AL133031 (MLR1, Transcription factor MLR1), Genebank Accession Number: AB091343 (C10orf3, Centrosomal protein 55 kDa), Genebank Accession Number: AY007723 (MAL2, Mal, T-cell differentiation protein 2), Genebank Accession Number: BC098313 (FLJ20641, Hypothetical protein FLJ20641), Genebank Accession Number: BC041882 (ATF7IP2, Activating transcription factor 7 interacting protein 2), Genebank Accession Number: AK127098 (FLJ10706, Chromosome 1 open reading frame 112), Genebank Accession Number: BC022255 [Spc25, Spindle pole body component 25 homolog (*S. cerevisiae*)], and Genebank Accession Number: BC026283 [APOH, Apolipoprotein H (beta-2-glycoprotein I)].

To find out the gene whose expression is changed by chrysene exposure, the human hepatoma cell line HepG2 was treated with chrysene and cytotoxicity was confirmed. As a result, chrysene demonstrated cytotoxicity in the human hepatoma cell line (see FIG. 1). Based on the experiment, chrysene concentration exhibiting 80% cell survival rate ($IC_{20}$) was determined.

Figure 2:
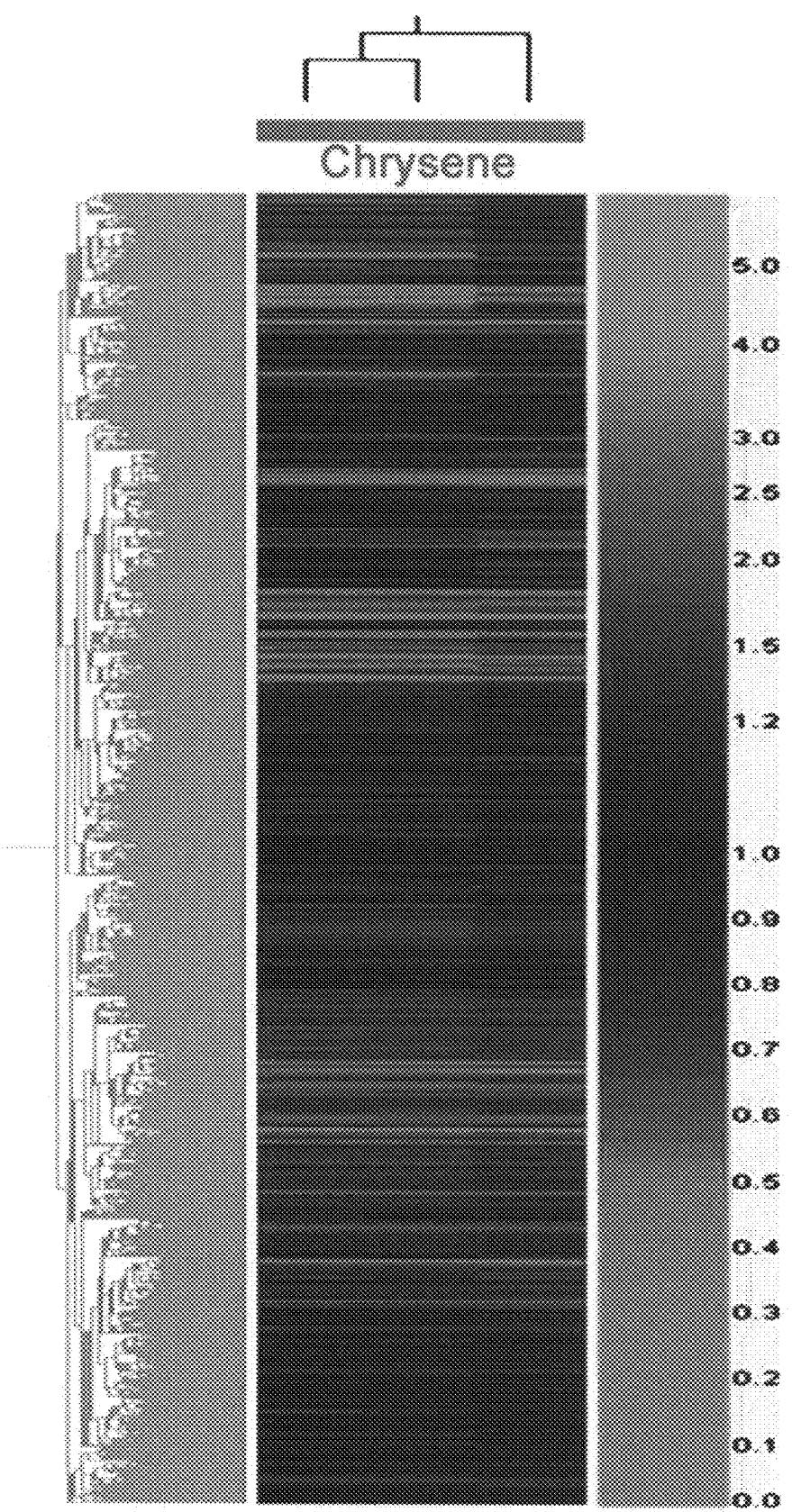
FIG. 2 is a diagram illustrating the gene expression pattern in the human Hepatoma cell line treated with chrysene, investigated by using the microarray chip.

The human Hepatoma cell line was treated with chrysene by the determined concentration and mRNA was extracted therefrom. During cDNA synthesis, it was labeled with Cy5. The control group not treated with the chrysene was labeled with Cy3. The fluorescence-labeled cDNA was hybridized with the 44 k human whole genome oligo-microarray chip (Agilent, USA), followed by scanning of fluorescent images to analyze the gene expression patterns (see FIG. 2). When the margin of the ratio of Cy5 to Cy3 was more than 2.0 fold, the gene expression was considered to be increased so that the gene was classified into the up-regulated gene group. When the margin of the ratio of Cy5 to Cy3 was less than 0.5 fold, the gene expression was considered to be decreased so that the gene was classified into the down-regulated gene group. As a result, the gene identified to be up-regulated was 0.73% (323 genes out of 44,000 genes) and the gene identified to be down-regulated was 0.82% (361 genes out of 44,000 genes). At this time, the genes exhibiting 2.0 fold higher or less expression by chrysene exposure were classified according to the functions. The genes are composed of those genes involved in MAPKinase Signaling Pathway, MAPKKK cascade, p53 Signaling Pathway, apoptosis, response to DNA damage stimulus, Response to stress, immune response, cell cycle, Mitotic cell cycle, Cell differentiation, Cell growth, cell proliferation, Alcohol metabolism, DNA metabolism, lipid metabolism, Amino acid metabolism, metal binding, and Transport (see Table 2 and Table 3). There have been no reports that those selected genes are involved in cytotoxicity in human Hepatoma cells according to the chrysene treatment.

The present inventors separated 25 over-expressed genes and 10 under-expressed genes. Then, primers were designed to amplify those genes, followed by real time RT-PCR (real-time reverse transcript polymerase chain reaction) to examine their expression patterns.

As a result, 25 up-regulated genes and 10 down-regulated genes were detected, consistent with the result of the experiment using the oligo-microarray chip (see Table 5). The genes are Genebank Accession Number: NM_000499 (Cytochrome P450, family 1, subfamily A, polypeptide 1), Genebank Accession Number: BX649164 (serpin peptidase inhibitor, clade E (nexin, plasminogen activator inhibitor type 1), member 1), Genebank Accession Number: NM_004881 (Tumor protein p53 inducible protein 3), Genebank Accession Number: BM913048 (TIMP metallopeptidase inhibitor 1), Genebank Accession Number: NM_006426 (Dihydropyrimidinase-like 4), Genebank Accession Number: NM_133493 [CD109 antigen (Gov platelet alloantigens)], Genebank Accession Number: AB033073 (Sulfatase 2), Genebank Accession Number: NM_021603 (FXYD domain containing ion transport regulator 2), Genebank Accession Number: BC035124 (MSFL2541), Genebank Accession Number: Y11307 (Cysteine-rich, angiogenic inducer, 61), Genebank Accession Number: AK095363 (Aquaporin 3), Genebank Accession Number: AK097009 (phospholipid transfer protein), Genebank Accession Number: NM_004864 (Growth differentiation factor 15), Genebank Accession Number: BU587578 (Regulator of G-protein signaling 10), Genebank Accession Number: BQ683841 [S100 calcium binding protein A11 (calgizzarin)], Genebank Accession Number: NM_001013632 [polo-like kinase 3 (*Drosophila*)], Genebank Accession Number: NM_032872 (Synaptotagmin-like 1), Genebank Accession Number: BC042390 [Vesicle transport through interaction with t-SNAREs homolog 1B (yeast)], Genebank Accession Number: NM_000596 (Insulin-like growth factor binding protein 1), Genebank Accession Number: NM_005319 (Histone 1, H1c), Genebank Accession Number: AK094474 (Ras homolog gene family, member C), Genebank Accession Number: NM_001769 [CD9 antigen (p24)], Genebank Accession Number: NM_001553 (Insulin-like growth factor binding protein 7), Genebank Accession Number: NM_003897 (Immediate early response 3), Genebank Accession Number: NM_003516 (Histone 2, H2aa), Genebank Accession Number: AK074377 (Chromosome 19 open reading frame 31), Genebank Accession Number: BX640965 (Solute carrier family 22 (extraneuronal monoamine transporter), member 3), Genebank Accession Number: NM_018492 (PDZ binding kinase), Genebank Accession Number: CR600021 (High-mobility group box 2), Genebank Accession Number: NM_006101 (Kinetochore associated 2), Genebank Accession Number: NM_003318 (TTK protein kinase), Genebank Accession Number: U65410 [MAD2 mitotic arrest deficient-like 1 (yeast)], Genebank Accession Number: NM_001067 (Topoisomerase (DNA) II alpha 170 kDa), Genebank Accession Number: AB091343 (Centrosomal protein 55 kDa), and Genebank Accession Number: BC022255 [Spindle pole body component 25 homolog (*S. cerevisiae*)].

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Cell Culture and Chemical Treatment

<1-1> Cell Culture

The human hepatoma cell line HepG2 (Korean Cell Line Bank) was cultured in DMEM (Gibco-BRL, USA) supplemented with 10% FBS in 100 mm dish until it grew 80%. The present inventors selected chrysene (Sigma-Aldrich, USA) among polycyclic aromatic hydrocarbons known to have carcinogenicity, based on the previous studies and reports. Chrysene was dissolved in DMSO. The concentration of vehicle was up to 0.1% in every experiment.

<1-2> Cytotoxicity Assay (MTT Assay) and Chemical Treatment

MTT assay with the HepG2 cell line was performed according to the method of Mossman et al. (*J. Immunol. Methods*, 65: 55-63, 1983). The cells were inoculated in a 24-well plate containing DMEM at the concentration of $4 \times 10^5$ cells/well, to which chrysene dissolved in DMSO was treated. 48 hours later, MTT (3-[4,5-dimethylthiazol-2-yl]-2, 5-diphenyltetra zolium bromide) was added at the concentration of 5 mg/ml, followed by culture at 37° C. for 3 hours. Then, medium was eliminated and generated formazan crystal was dissolved in 500 μl of DMSO. The solution was aliquoted in a 96 well-plate and $OD_{540}$ was measured. Cytotoxicity in the HepG2 cell line caused by chrysene was investigated. As a result, $IC_{20}$ was 34.97 μM (see FIG. 1) and thus the concentration of chrysene for the further experiment was determined as the above.

Example 2

Microarray Experiment

<2-1> Separation of a Target RNA and Labeling with a Fluorescent Material

HepG2 cells were distributed on a 100 mm dish at the concentration of $6 \times 10^6$ cell/ml, to which chrysene was treated for 48 hours at the concentration that was determined in Example <1-2>. Total RNA was extracted from the cells using trizol reagent (Invitrogen life technologies, USA) according to the manufacturer's instruction and the extracted RNA was purified by using RNeasy mini kit (Qiagen, USA). The genomic DNA was eliminated during the purification of RNA using RNase-free DNase set (Qiagen, USA). The total RNA was quantified by spectrophotometer and purity was measured by Agilent 2100 Bioanalyzer (Agilent Technologies, USA) and agarose gel-electrophoration.

<2-2> Preparation of Labeled cDNA

For oligo-microarray analysis, cDNA was synthesized using the total RNA extracted from the experimental group treated with chrysene obtained in Example <2-1>. 30 μg of the total RNA and 2 μg (1 μg/μl) of oligo (dT) primer were mixed, followed by reaction for 10 minutes at 65° C. Then, the reaction mixture was put in ice, followed by annealing. Reagents were mixed as shown in Table 1 for reverse transcription of the RNA.

TABLE 1

| Composition | volume (μl) |
|---|---|
| 5X first strand buffer | 6 |
| dNTPs | 0.6 |
| 0.1 M DDT | 3 |
| SuperScript II enzyme | 3 |
| Cy-3 or Cy-5 dUTP | 2 |

The total RNA extracted from the control HepG2 cell line was labeled with Cy3-dUTP (green), while the RNA extracted from the experimental HepG2 cell line treated with chrysene was labeled with Cy5-dUTP (red). At this time, the two samples were mixed and purified by Microcon YM-30 column (Millipore, USA).

<2-3> Hybridization

Hybridization and washing were performed according to the instruction of GeneoCheck Co., Ltd. Hybridization was performed in a 62° C. oven for 12 hours. At this time, 44 k whole human genome oligo microarray (Agilent, USA) was used as a DNA microarray chip. After washing (with 2×SSC/ 0.1% SDS for 2 minutes, with 1×SSC for 3 minutes, with 0.2×SSC for 2 minutes), the slide was centrifuged at 800 rpm for 3 minutes and dried.

<2-4> Fluorescence Image Obtaining

Scanning of the hybridized images on the slide was performed by using Genepix 4000B (Axon Instruments, USA). Fluorescence images of the chip washed to eliminate non-binding genes were obtained by laser fluorescence scanner. At this time, green fluorescent images indicated the activity of the gene expressed in the control, whereas red fluorescent images indicated the activity of the gene expressed specifically in the experimental group. In the meantime, yellow fluorescent images (complementary color of red and green) indicated that there was not much difference in the expression between the two groups. The scanned images were analyzed by GenePix 4.1 software (Axon Instruments, USA) to calculate the gene expression rate. Based on the obtained data, marker genes for chrysene were selected (see FIG. 2).

As a result, the gene identified to be 2.0 fold higher up-regulated was 0.73% (323 genes out of 44,000 genes) and the gene identified to be 2.0 fold less down-regulated was 0.82% (361 genes out of 44,000 genes) among approximately 44,000 genes loaded on the oligo chip.

At this time, genes exhibiting 2.0 fold higher or less expressions by exposure to chrysene were classified according to the functions. The genes are composed of those genes involved in MAPKinase Signaling Pathway, MAPKKK cascade, p53 Signaling Pathway, apoptosis, response to DNA damage stimulus, Response to stress, immune response, cell cycle, Mitotic cell cycle, Cell differentiation, Cell growth, cell proliferation, Alcohol metabolism, DNA metabolism, lipid metabolism, Amino acid metabolism, metal binding, and Transport (see Table 2 and Table 3). There have been no reports so far that those selected genes are involved in cytotoxicity in human Hepatoma cells according to the chrysene treatment.

TABLE 2

Genes up-regulated by chrysene

| Accession number | Gene abbreviation | Gene name | Ratio of intermediate value |
|---|---|---|---|
| (a) MAPKinase Signaling Pathway ||||
| NM_003954 | MAP3K14 | Mitogen-activated protein kinase kinase kinase 14 | 2.642090915 |
| AB209586 | MAPK13 | Mitogen-activated protein kinase 13 | 2.32604791 |
| NM_005343 | HRAS | V-Ha-ras Harvey rat sarcoma viral oncogene homolog | 2.300183763 |
| BX647104 | FOS | V-fos FBJ murine osteosarcoma viral oncogene homolog | 2.286644731 |
| NM_007315 | STAT1 | Signal transducer and activator of transcription 1, 91 kDa | 2.268249473 |
| BC027933 | MAPK11 | Mitogen-activated protein kinase 11 | 2.256117014 |
| NM_020529 | NFKBIA | Nuclear factor of kappa light polypeptide gene enhancer in B-cells inhibitor, alpha | 2.242341043 |
| BC014966 | RPS6KA1 | Ribosomal protein S6 kinase, 90 kDa, polypeptide 1 | 2.109933874 |
| (b) p53 Signaling Pathway ||||
| NM_181861 | APAF1 | Apoptotic peptidase activating factor | 2.323610287 |
| L41870 | RB1 | Retinoblastoma 1 (including osteosarcoma) | 2.431277919 |
| CR612719 | GADD45A | Growth arrest and DNA-damage-inducible, alpha | 2.785095956 |
| BM462208 | PCNA | Proliferating cell nuclear antigen | 5.94704061 |
| M92424 | MDM2 | Mdm2, transformed 3T3 cell double minute 2, p53 binding protein(mouse) | 4.056640879 |
| NM_078467 | CDKN1A | Cyclin-dependent kinase inhibitor1A(p21, Cip1) | 21.05152341 |
| (c) Apoptosis ||||
| BC089389 | IHPK3 | Inositol hexaphosphate kinase 3 | 17.86623375 |
| NM_001024807 | APLP1 | Amyloid beta(A4) precursor-like protein 1 | 14.60038469 |
| NM_001013398 | IGFBP3 | Insulin-like growth factor binding protein 3 | 11.51469533 |
| AB209361 | FAS | Fas(TNF receptor superfamily, member 6) | 9.282797498 |
| NM_147780 | CTSB | Cathepsin B | 6.625352723 |
| NM_001165 | BIRC3 | Baculoviral IAP repeat-containing 3 | 6.105445052 |
| BM557864 | HSPB1 | Heat shock 27 kDa protein 1 | 5.988972006 |
| AB033060 | PDCD6 | Aryl-hydrocarbon receptor repressor | 5.709323333 |
| AK125880 | TP53INP1 | Tumor protein p53 inducible nuclear protein 1 | 4.730741529 |
| NM_004574 | 04-Sep | Septin 4 | 4.420718644 |
| NM_003820 | TNFRSF14 | Tumor necrosis factor receptor superfamily, member 14(herpesvirus entry mediator) | 4.241834154 |
| CN478604 | LGALS7 | Lectin, galactoside-binding, soluble, 7(galectin 7) | 4.215529017 |
| NM_004879 | EI24 | Etoposide induced 2.4 mRNA | 3.840012717 |
| NM_003311 | PHLDA2 | Pleckstrin homology-like domain, family A, member 2 | 3.66045378 |
| NM_003897 | IER3 | Immediate early response 3 | 3.323689948 |
| AK097284 | TNFAIP8 | Tumor necrosis factor, alpha-induced protein 8 | 3.301416171 |
| NM_000582 | SPP1 | Secreted phosphoprotein 1(osteopontin, bone sialoprotein I, early T-lymphocyte activation 1) | 3.007301243 |
| NM_013258 | PYCARD | PYD and CARD domain containing | 2.704730239 |
| NM_002305 | LGALS1 | Lectin, galactoside-binding, soluble, 1(galectin 1) | 2.685571797 |
| AF055634 | UNC5C | Unc-5 homolog C(C. elegans) | 2.64453651 |
| CR614015 | CD14 | CD14 antigen | 2.620138457 |
| AK129595 | GADD45B | Growth arrest and DNA-damage-inducible, beta | 2.431892144 |
| AF356193 | CARD6 | Caspase recruitment domain family, member 6 | 2.315498432 |
| BC063043 | PRF1 | Perforin 1(pore forming protein) | 2.300936607 |
| BX537586 | STK17A | Serine/threonine kinase 17a(apoptosis-inducing) | 2.173582084 |
| NM_003842 | TNFRSF10B | Tumor necrosis factor receptor superfamily, member 10b | 2.164540104 |

TABLE 2-continued

Genes up-regulated by chrysene

| Accession number | Gene abbreviation | Gene name | Ratio of intermediate value |
|---|---|---|---|
| AF208043 | IFI16 | Interferon, gamma-inducible protein 16 | 2.147368247 |
| BX641114 | ANXA4 | Annexin A4 | 2.143018533 |
| NM_001009552 | PPP2CB | Protein phosphatase 2 (formerly 2A), catalytic subunit, beta isoform | 2.132316431 |
| BX386171 | CGB5 | Chorionic gonadotropin, beta polypeptide 8 | 2.11678504 |
| AY358103 | HIP1 | Huntingtin interacting protein 1 | 2.101135287 |
| BC027949 | P2RX1 | Purinergic receptor P2X, ligand-gated ion channel, 1 | 2.093924251 |
| BC042844 | CASP10 | Caspase 10, apoptosis-related cysteine peptidase | 2.071460864 |
| NM_000733 | CD3E | CD3E antigen, epsilon polypeptide(TiT3 complex) | 2.069295152 |
| NM_033245 | PML | Promyelocytic leukemia | 2.031289487 |
| BC047362 | PHLDA1 | Pleckstrin homology-like domain, family A, member 1 | 2.030766246 |
| (d) Response to DNA damage stimulus | | | |
| NM_006763 | BTG2 | BTG family, member 2 | 8.033431013 |
| BC050455 | DDB2 | LIM homeobox 3 | 5.130890941 |
| BC068535 | TP53AP1 | TP53 activated protein 1 | 3.847202974 |
| AF033122 | SESN1 | Sestrin 1 | 3.728462177 |
| AB024313 | POLH | Polymerase(DNA directed), eta | 3.515123881 |
| NM_001012716 | TYMS | Thymidylate synthetase | 3.123891212 |
| BC095402 | ATXN3 | Ataxin 3 | 2.201860506 |
| BU675073 | PTTG1 | Pituitary tumor-transforming 1 | 2.178628404 |
| BC073161 | RAD51C | RAD51 homolog C(S. cerevisiae) | 2.092699518 |
| NM_001983 | ERCC1 | Excision repair cross-complementing rodent repair deficiency, complementation group 1 (includes overlapping antisense sequence) | 1.811298942 |
| (e) Response to stress | | | |
| NM_018965 | TREM2 | Triggering receptor expressed on myeloid cells 2 | 43.66510076 |
| BX649164 | PAI; PAI1; PAI-1; PLANH1 | serpin peptidase inhibitor, clade E(nexin, plasminogen activator inhibitor type 1), member 1 | 29.04597327 |
| NM_006404 | PROCR | Protein C receptor, endothelial(EPCR) | 24.52788989 |
| BC035582 | TRIM22 | Tripartite motif-containing 22 | 13.78919459 |
| NM_006691 | XLKD1 | Extracellular link domain containing 1 | 10.05591814 |
| NM_015831 | ACHE | Acetylcholinesterase (YT blood group) | 6.223349052 |
| BC045666 | TP53I11 | Tumor protein p53 inducible protein 11 | 6.007745545 |
| NM_005438 | FOSL1 | FOS-like antigen 1 | 5.642502876 |
| NM_005755 | EBI3 | Epstein-Barr virus induced gene 3 | 5.606891978 |
| BM918324 | LY96 | Lymphocyte antigen 96 | 5.438550593 |
| NM_000022 | ADA | Adenosine deaminase | 5.212717207 |
| NM_004167 | CCL14 | Chemokine(C-C motif) ligand 15 | 5.102559642 |
| NM_014278 | HSPA4L | Heat shock 70 kDa protein 4-like | 4.710398517 |
| BC006523 | SGK2 | Serum/glucocorticoid regulated kinase 2 | 4.64953324 |
| NM_000641 | IL11 | Interleukin 11 | 4.520629217 |
| H18681 | C20orf139 | Sulfiredoxin 1 homolog(S. cerevisiae) | 4.383369833 |
| NM_001769 | CD9 | CD9 antigen(p24) | 4.153073307 |
| BG564326 | SAA4 | Serum amyloid A4, constitutive | 4.075835655 |
| NM_016816 | OAS1 | 2',5'-oligoadenylate synthetase 1, 40/46 kDa | 3.710610826 |
| CB055213 | ICOSLG | Inducible T-cell co-stimulator ligand | 3.643779829 |
| CR591007 | CCL3 | Chemokine(C-C motif) ligand 3 | 3.346884519 |
| NM_145641 | APOL3 | Apolipoprotein L, 3 | 3.195513004 |
| AK127663 | PTGES | Prostaglandin E synthase | 3.183821649 |
| NM_001734 | C1S | Complement component 1, s subcomponent | 3.018342133 |
| NM_002260 | KLRC3 | Killer cell lectin-like receptor subfamily C, member 2 | 2.941895363 |
| NM_001733 | C1R | Complement component 1, r subcomponent | 2.893399755 |
| AB209922 | DNAJB4 | DnaJ(Hsp40) homolog, subfamily B, member 4 | 2.872000914 |
| NM_201397 | GPX1 | Glutathione peroxidase 1 | 2.850015447 |
| AK090482 | CXCL12 | Chemokine(C-X-C motif) ligand 12(stromal cell-derived factor 1) | 2.842225911 |
| BF662985 | CCL3L1 | Chemokine(C-C motif) ligand 3-like 1 | 2.838582233 |
| NM_001779 | CD58 | CD58 antigen, (lymphocyte function-associated antigen 3) | 2.794341637 |
| NM_005064 | CCL23 | Chemokine(C-C motif) ligand 23 | 2.761400386 |
| NM_000242 | MBL2 | Mannose-binding lectin(protein C) 2, soluble(opsonic defect) | 2.755428358 |

TABLE 2-continued

Genes up-regulated by chrysene

| Accession number | Gene abbreviation | Gene name | Ratio of intermediate value |
|---|---|---|---|
| NM_032036 | FAM14A | Family with sequence similarity 14, member A | 2.706203775 |
| AJ890082 | HSPCA | Heat shock 90 kDa protein 1, alpha | 2.54395008 |
| BC068487 | TLR3 | Toll-like receptor 3 | 2.540522037 |
| NM_000552 | VWF | Von Willebrand factor | 2.476094941 |
| NM_000132 | F8 | Coagulation factor VIII, procoagulant component(hemophilia A) | 2.414521007 |
| AY154461 | NALP6 | NACHT, leucine rich repeat and PYD containing 6 | 2.392028958 |
| AK127679 | DUSP1 | Dual specificity phosphatase 1 | 2.382519952 |
| NM_014314 | DDX58 | DEAD (Asp-Glu-Ala-Asp) box polypeptide 58 | 2.333495418 |
| NM_000311 | PRNP | Prion protein (p27-30)(Creutzfeld-Jakob disease, Gerstmann-Strausler-Scheinker syndrome, fatal familial insomnia) | 2.313144503 |
| NM_006597 | HSPA8 | Heat shock 70 kDa protein 8 | 2.313144445 |
| AK092040 | ZCSL2 | Zinc finger, CSL-type containing 2 | 2.303019345 |
| NM_031483 | ITCH | Itchy homolog E3 ubiquitin protein ligase(mouse) | 2.300924118 |
| U25029 | NR3C1 | Nuclear receptor subfamily 3, group C, member 1(glucocorticoid receptor) | 2.273770608 |
| NM_005242 | F2RL1 | Coagulation factor II (thrombin) receptor-like 1 | 2.25765938 |
| AK172851 | ADORA2B | Adenosine A2b receptor | 2.248876245 |
| BQ053419 | BATF | Basic leucine zipper transcription factor, ATF-like | 2.220924757 |
| BC020698 | CCL20 | Chemokine(C-C motif) ligand 20 | 2.199037915 |
| NM_001124 | ADM | Adrenomedullin | 2.186497254 |
| NM_153609 | TMPRSS6 | Transmembrane protease, serine 6 | 2.118468174 |
| NM_004148 | NINJ1 | Ninjurin 1 | 2.106988819 |
| AF324224 | APOL2 | Apolipoprotein L, 2 | 2.105247356 |
| BC040494 | DNAJB2 | DnaJ(Hsp40) homolog, subfamily B, member 2 | 2.053186934 |
| BE512691 | GPX2 | Glutathione peroxidase 2(gastrointestinal) | 2.014366573 |
| NM_001002029 | C4A | Complement component 4B, telomeric | 2.002292152 |
| | | (f) Immune response | |
| NM_000732 | CD3D | CD3D antigen, delta polypeptide(TiT3 complex) | 54.93792815 |
| AK223210 | CD79B | CD79B antigen (immunoglobulin-associated beta) | 15.33023863 |
| NM_002309 | LIF | Hypothetical protein MGC20647 | 8.088491848 |
| AF031469 | MR1 | Major histocompatibility complex, class I-related | 7.058743082 |
| NM_172208 | TAPBP | TAP binding protein (tapasin) | 7.020261414 |
| BC021117 | CSF1 | Colony stimulating factor 1(macrophage) | 4.788017417 |
| NM_001421 | ELF4 | E74-like factor 4 (ets domain transcription factor) | 4.315617246 |
| NM_002119 | HLA-DOA | Major histocompatibility complex, class II, DO alpha | 4.208814419 |
| BX648013 | TAP1 | Transporter 1, ATP-binding cassette, sub-family B(MDR/TAP) | 4.079915559 |
| AL832287 | ZAP70 | Zeta-chain(TCR) associated protein kinase 70 kDa | 3.830282261 |
| BF569086 | NK4 | Interleukin 32 | 3.137700229 |
| AL832451 | DKFZp451C2311 | guanylate binding protein 2, interferon-inducible | 2.638811674 |
| AF069493 | SEMA7A | Sema domain, immunoglobulin domain(Ig), and GPI membrane anchor, (semaphorin) 7A | 2.530855422 |
| NM_001008490 | KLF6 | Kruppel-like factor 6 | 2.300245668 |
| NM_000418 | IL4R | Interleukin 4 receptor | 2.254471504 |
| NM_004048 | B2M | Beta-2-microglobulin | 2.006239064 |
| | | (g) Cell cycle | |
| AF116720 | DNAJA2 | DnaJ(Hsp40) homolog, subfamily A, member 2 | 10.94418029 |
| NM_001007271 | DUSP13 | Dual specificity phosphatase 13 | 7.030871577 |
| BM904612 | S100A6 | S100 calcium binding protein A6(calcyclin) | 5.937525522 |
| AK074652 | SERTAD1 | SERTA domain containing 1 | 4.83549333 |
| NM_203394 | E2F7 | E2F transcription factor 7 | 3.647469222 |
| NM_003620 | PPM1D | Protein phosphatase 1D magnesium-dependent, delta isoform | 3.646783838 |
| BC060797 | PARD6G | Par-6 partitioning defective 6 homolog gamma(C. elegans) | 3.501662527 |

TABLE 2-continued

Genes up-regulated by chrysene

| Accession number | Gene abbreviation | Gene name | Ratio of intermediate value |
|---|---|---|---|
| NM_021913 | AXL | AXL receptor tyrosine kinase | 3.268484061 |
| BC040303 | PTP4A1 | Protein tyrosine phosphatase type IVA, member 1 | 3.182840665 |
| BC008564 | PPP1R9B | Protein phosphatase 1, regulatory subunit 9B, spinophilin | 3.169099614 |
| AK097024 | RAE1 | RAE1 RNA export 1 homolog(*S. pombe*) | 2.920923726 |
| BC011957 | BTG3 | BTG family, member 3 | 2.73961999 |
| NM_078487 | CDKN2B | Cyclin-dependent kinase inhibitor 2B(p15, inhibits CDK4) | 2.55897751 |
| BC023552 | SFN | Stratifin | 2.524571283 |
| BC060847 | PARD6B | Par-6 partitioning defective 6 homolog beta(*C. elegans*) | 2.507221799 |
| NM_003236 | TGFA | Transforming growth factor, alpha | 2.487048846 |
| NM_002632 | PGF | Placental growth factor, vascular endothelial growth factor-related protein | 2.435909331 |
| NM_015278 | SASH1 | SAM and SH3 domain containing 1 | 2.368157793 |
| AL834276 | MGC3207 | Hypothetical protein MGC3207 | 2.364392455 |
| AK096276 | CCND3 | Cyclin D3 | 2.291774022 |
| AB209373 | CCNK | Chromosome 14 open reading frame 65 | 2.27376643 |
| NM_021132 | PPP3CB | Protein phosphatase 3 (formerly 2B), catalytic subunit, beta isoform(calcineurin A beta) | 2.19575961 |
| NM_005072 | SLC12A4 | Solute carrier family 12(potassium/chloride transporters), member 4 | 2.184117922 |
| BX647886 | PCNP | SPT2, Suppressor of Ty, domain containing 1(*S. cerevisiae*) | 2.132837165 |
| NM_044472 | CDC42 | Cell division cycle 42(GTP binding protein, 25 kDa) | 2.08723035 |
| AL832973 | REC8L1 | REC8-like 1(yeast) | 2.050105112 |
| NM_002031 | FRK | Fyn-related kinase | 2.008244265 |
| (h) Cell differentiation | | | |
| BM913048 | TIMP1 | TIMP metallopeptidase inhibitor 1 | 14.51811118 |
| NM_003975 | SH2D2A | SH2 domain protein 2A | 6.609387012 |
| NM_198129 | LAMA3 | Laminin, alpha 3 | 6.313840426 |
| NM_006152 | LRMP | Lymphoid-restricted membrane protein | 3.452878243 |
| X96753 | CSPG4 | Chondroitin sulfate proteoglycan 4(melanoma-associated) | 3.342871665 |
| NM_000474 | TWIST1 | Twist homolog 1 (acrocephalosyndactyly 3; Saethre-Chotzen syndrome)(*Drosophila*) | 2.962045566 |
| AF052152 | DCAMKL1 | Doublecortin and CaM kinase-like 1 | 2.946594775 |
| AF333334 | CCIN | Calicin | 2.907611782 |
| NM_005979 | S100A13 | S100 calcium binding protein A13 | 2.38786608 |
| NM_004429 | EFNB1 | Ephrin-B1 | 2.290394007 |
| NM_003873 | NRP1 | Neuropilin 1 | 2.102000337 |
| AF026692 | SFRP4 | Secreted frizzled-related protein 4 | 2.097767188 |
| AK124583 | DAZAP1 | DAZ associated protein 1 | 2.09304534 |
| AF003837 | JAG1 | Jagged 1(Alagille syndrome) | 2.052565745 |
| AB209590 | BMP1 | Bone morphogenetic protein 1 | 2.018231591 |
| (i) Cell growth | | | |
| X54457 | CEL | Carboxyl ester lipase (bile salt-stimulated lipase) | 11.0110822 |
| Y11307 | CYR61 | Cysteine-rich, angiogenic inducer, 61 | 8.870510533 |
| NM_000596 | IGFBP1 | Insulin-like growth factor binding protein 1 | 4.426373693 |
| NM_020997 | LEFTY1 | Left-right determination factor 1 | 4.011782013 |
| NM_001553 | IGFBP7 | Insulin-like growth factor binding protein 7 | 3.467233091 |
| AB209509 | IGFBP2 | Insulin-like growth factor binding protein 2, 36 kDa | 2.280688594 |
| NM_001552 | IGFBP4 | Insulin-like growth factor binding protein 4 | 2.170002081 |
| AB209321 | CSRP2 | Cysteine and glycine-rich protein 2 | 2.079139635 |
| BM556279 | EMP3 | Epithelial membrane protein 3 | 2.029076597 |
| (j) Cell proliferation | | | |
| NM_005727 | TSPAN1 | Tetraspanin 1 | 8.454659213 |
| BQ683841 | S100A11 | S100 calcium binding protein A11(calgizzarin) | 6.064178076 |
| BC042390 | VTI1B | Vesicle transport through interaction with t-SNAREs homolog 1B(yeast) | 4.485613104 |

TABLE 2-continued

Genes up-regulated by chrysene

| Accession number | Gene abbreviation | Gene name | Ratio of intermediate value |
|---|---|---|---|
| NM_000899 | KITLG | KIT ligand | 3.751569954 |
| BC032940 | LAMP3 | Lysosomal-associated membrane protein 3 | 2.728811271 |
| BQ939577 | AKR1C3 | Aldo-keto reductase family 1, member C3(3-alpha hydroxysteroid dehydrogenase, type II) | 2.683290824 |
| BC063468 | OSMR | Oncostatin M receptor | 2.652841837 |
| CR936719 | SSR1 | Signal sequence receptor, alpha(translocon-associated protein alpha) | 2.559482267 |
| AB024057 | TBC1D8 | TBC1 domain family, member 8(with GRAM domain) | 2.53463919 |
| NM_003329 | TXN | Thioredoxin | 2.324939817 |
| NM_012125 | CHRM5 | Cholinergic receptor, muscarinic 5 | 2.112618735 |
| NM_007045 | FGFR1OP | FGFR1 oncogene partner | 2.09430482 |
| (k) Alcohol metabolism | | | |
| AK094474 | RHOC | Ras homolog gene family, member C | 4.227972245 |
| BC017706 | 6PGL | 6-phosphogluconolactonase | 2.621428387 |
| AF153821 | ADH1B | Alcohol dehydrogenase IB(class I), beta polypeptide | 2.420867965 |
| AK124656 | ENO2 | Enolase 2(gamma, neuronal) | 2.273190922 |
| D42047 | GPD1L | Glycerol-3-phosphate dehydrogenase 1-like | 2.170305169 |
| AK130060 | TALDO1 | Transaldolase 1 | 2.107113338 |
| AL833069 | KIAA1434 | Hypothetical protein KIAA1434 | 2.042123428 |
| XM_496436 | UNQ6077 | C219-reactive peptide | 2.011483091 |
| NM_199186 | BPGM | 2,3-bisphosphoglycerate mutase | 2.001621684 |
| (l) DNA metabolism | | | |
| U86136 | TEP1 | Telomerase-associated protein 1 | 5.354849784 |
| BU603483 | HIST1H1E | Histone 1, H1e | 4.639090453 |
| NM_005319 | HIST1H1C | Histone 1, H1c | 4.25715277 |
| NM_005320 | HIST1H1D | Histone 1, H1d | 3.30127345 |
| NM_003516 | HIST2H2AA | Histone 2, H2aa | 3.052311773 |
| F02250 | HDAC2 | Histone deacetylase 2 | 2.559211106 |
| NM_004739 | MTA2 | Metastasis associated 1 family, member 2 | 2.439100864 |
| BC042589 | HIST1H2BD | Histone 1, H2bd | 2.361377538 |
| CB529694 | HIST2H2BE | Histone 2, H2be | 2.358417445 |
| AK126154 | NP | Nucleoside phosphorylase | 2.252382538 |
| AB040899 | KIAA1466 | KIAA1466 gene | 2.150614231 |
| CR608156 | HIST1H2AC | Histone 1, H2ac | 1.894716468 |
| BX436525 | HIST1H2BH | Histone 1, H2bh | 1.564280897 |
| (m) Lipid metabolism | | | |
| AK057762 | TDH | L-threonine dehydrogenase | 12.35436994 |
| BC035124 | UNQ2541 | MSFL2541 | 11.28144368 |
| BC034763 | FDXR | Ferredoxin reductase | 9.626878353 |
| AK093461 | ISYNA1 | Myo-inositol 1-phosphate synthase A1 | 8.506076027 |
| AK097009 | PLTP | phospholipid transfer protein | 6.838113748 |
| AF524864 | AKR1B10 | Aldo-keto reductase family 1, member B10(aldose reductase) | 5.170205623 |
| NM_021727 | FADS3 | Fatty acid desaturase 3 | 4.914325733 |
| CR627415 | HSD3B2 | Hydroxy-delta-5-steroid dehydrogenase, 3 beta- and steroid delta-isomerase 2 | 3.576157214 |
| CD013987 | CYP21A2 | Cytochrome P450, family 21, subfamily A, polypeptide 2 | 3.499529399 |
| BC020744 | AKR1C4 | Aldo-keto reductase family 1, member C4(chlordecone reductase; 3-alpha hydroxysteroid dehydrogenase, type I; dihydrodiol dehydrogenase 4) | 3.073709856 |
| NM_004753 | DHRS3 | Dehydrogenase/reductase (SDR family) member 3 | 2.952592956 |
| BC030207 | NR0B2 | Nuclear receptor subfamily 0, group B, member 2 | 2.923794075 |
| AK091948 | LTB4DH | Leukotriene B4 12-hydroxydehydrogenase | 2.915047859 |
| NM_002900 | RBP3 | Retinol binding protein 3, interstitial | 2.882318017 |
| BX647927 | PLCD1 | Phospholipase C, delta 1 | 2.79125248 |
| NM_145323 | OSBPL3 | Oxysterol binding protein-like 3 | 2.683653218 |
| NM_000169 | GLA | Galactosidase, alpha | 2.640805113 |
| BC094756 | CRA | Myotubularin related protein 11 | 2.621196547 |
| AB043587 | ACBD3 | Acyl-Coenzyme A binding domain containing 3 | 2.387297906 |

TABLE 2-continued

Genes up-regulated by chrysene

| Accession number | Gene abbreviation | Gene name | Ratio of intermediate value |
|---|---|---|---|
| NM_001478 | GALGT | UDP-N-acetyl-alpha-D-galactosamine:(N-acetylneuraminyl)-galactosylglucosylceramide N-acetylgalactosaminyltransferase(GalNAc-T) | 2.371502969 |
| J05428 | UGT2B7 | UDP glucuronosyltransferase 2 family, polypeptide B7 | 2.29241428 |
| AB002454 | CYP4F3 | Cytochrome P450, family 4, subfamily F, polypeptide 3 | 2.282463636 |
| NM_000405 | GM2A | GM2 ganglioside activator | 2.078054404 |
| BC001823 | PRKAB1 | Protein kinase, AMP-activated, beta 1 non-catalytic subunit | 2.069992917 |
| NM_145343 | APOL1 | Apolipoprotein L, 1 | 2.065071129 |
| NM_006571 | DCTN6 | Dynactin 6 | 2.032649122 |
| NM_020139 | DHRS6 | Dehydrogenase/reductase (SDR family) member 6 | 2.017235349 |
| (n) Metal-binding | | | |
| NM_000499 | CYP1A1 | Cytochrome P450, family 1, subfamily A, polypeptide 1 | 88.34463354 |
| BC007003 | TGM4 | Transglutaminase 4 (prostate) | 24.06656282 |
| NM_012189 | CABYR | Calcium binding tyrosine-(Y)-phosphorylation regulated(fibroussheathin 2) | 15.7546354 |
| CR615530 | CYGB | Cytoglobin | 5.509895512 |
| NM_004199 | P4HA2 | Procollagen-proline, 2-oxoglutarate 4-dioxygenase(proline 4-hydroxylase), alpha polypeptide II | 4.763879118 |
| AK027560 | CYP26A1 | Cytochrome P450, family 26, subfamily A, polypeptide 1 | 4.292062656 |
| NM_145298 | APOBEC3F | Apolipoprotein B mRNA editing enzyme, catalytic polypeptide-like 3F | 4.282991592 |
| NM_005576 | LOXL1 | Lysyl oxidase-like 1 | 3.991893457 |
| AK024854 | APOBEC3B | Apolipoprotein B mRNA editing enzyme, catalytic polypeptide-like 3D(putative) | 3.958267305 |
| NM_014301 | NIFUN | NifU-like N-terminal domain containing | 3.922562485 |
| BF670653 | MB | Myoglobin | 3.907590399 |
| AK126982 | LHX6 | LIM homeobox 6 | 3.753938819 |
| Y13786 | ADAM19 | ADAM metallopeptidase domain 19(meltrin beta) | 3.418775374 |
| AB051455 | MICAL-L1 | MICAL-like 1 | 3.221168592 |
| AK074068 | MICAL-L2 | MICAL-like 2 | 3.121829223 |
| AK124421 | CPA1 | Carboxypeptidase A1 (pancreatic) | 3.111462293 |
| NM_030622 | CYP2S1 | Cytochrome P450, family 2, subfamily S, polypeptide 1 | 2.768815748 |
| BC012027 | CYP2U1 | Cytochrome P450, family 2, subfamily U, polypeptide 1 | 2.36896757 |
| AY461717 | ZNF385 | Zinc finger protein 385 | 20.23244477 |
| AK092424 | ZSCAN4 | Zinc finger and SCAN domain containing 4 | 17.62610589 |
| AB208935 | RASAL1 | RAS protein activator like 1(GAP1 like) | 13.22811232 |
| NM_201444 | DGKA | Diacylglycerol kinase, alpha 80 kDa | 6.831831283 |
| BC035625 | EGR2 | Early growth response 2(Krox-20 homolog, *Drosophila*) | 5.012409534 |
| BF983391 | RPS27L | Ribosomal protein S27-like | 4.896252688 |
| BC036545 | PLAC2 | Placenta-specific 2 | 4.739700637 |
| BC034569 | ZNF337 | Zinc finger protein 337 | 4.082511332 |
| CR936707 | TRIM38 | Tripartite motif-containing 38 | 3.756338118 |
| AK091940 | MGC4734 | Ring finger protein 183 | 3.644058609 |
| NM_024101 | MLPH | Melanophilin | 3.369249376 |
| CR601823 | HIVEP3 | Human immunodeficiency virus type I enhancer binding protein 3 | 3.290777497 |
| BC041578 | MGC17986 | zinc finger protein 114 | 3.166948191 |
| BC038432 | RARA | Retinoic acid receptor, alpha | 2.87080107 |
| (o) Transport | | | |
| BX641053 | FXYD2 | FXYD domain containing ion transport regulator 2 | 14.84364998 |
| AK095363 | AQP3 | Aquaporin 3 | 8.623096731 |
| AK074100 | SLC37A2 | Solute carrier family 37(glycerol-3-phosphate transporter), member 2 | 8.471999196 |
| AK024002 | TUBA4 | Tubulin, alpha 4 | 7.427767363 |
| AK092677 | TUBB6 | Tubulin, beta 6 | 6.458458484 |
| NM_001297 | CNGB1 | Cyclic nucleotide gated channel beta 1 | 5.653120818 |
| NM_032872 | SYTL1 | Synaptotagmin-like 1 | 4.930987441 |

TABLE 2-continued

Genes up-regulated by chrysene

| Accession number | Gene abbreviation | Gene name | Ratio of intermediate value |
|---|---|---|---|
| NM_014045 | LRP10 | Low density lipoprotein receptor-related protein 10 | 4.616793009 |
| NM_014585 | SLC40A1 | Solute carrier family 40(iron-regulated transporter), member 1 | 4.60980312 |
| L02870 | COL7A1 | Collagen, type VII, alpha 1(epidermolysis bullosa, dystrophic, dominant and recessive) | 4.294284493 |
| AK054731 | TUBA1 | Tubulin, alpha 1 (testis specific) | 4.193322321 |
| AF336127 | SLC4A11 | Solute carrier family 4, sodium bicarbonate transporter-like, member 11 | 4.116663762 |
| AB075951 | SLC22A2 | Solute carrier family 22(organic cation transporter), member 2 | 3.98434766 |
| AK125026 | SLC6A12 | Solute carrier family 6(neurotransmitter transporter, betaine/GABA), member 12 | 3.756467829 |
| BX537541 | MGC13186 | Chromosome 1 open reading frame 57 | 3.712498811 |
| CD013956 | SHBG | Sex hormone-binding globulin | 3.685973664 |
| BC029057 | DAO | D-amino-acid oxidase | 3.657991139 |
| BC041479 | COL9A2 | Collagen, type IX, alpha 2 | 3.573628765 |
| AL050210 | LOC283130 | Hypothetical protein LOC283130 | 3.265255922 |
| NM_004798 | KIF3B | Kinesin family member 3B | 3.214670618 |
| AK025742 | UCP2 | Uncoupling protein 2 (mitochondrial, proton carrier) | 3.187327318 |
| NM_021990 | GABRE | Gamma-aminobutyric acid(GABA) A receptor, epsilon | 3.110885736 |
| NM_005819 | STX6 | Syntaxin 6 | 3.089406302 |
| BC092420 | CYP4F11 | Similar to Cytochrome P450 4F12(CYPIVF12)(UNQ568/PRO1129) | 3.048152378 |
| BC043423 | ABCB6 | ATP-binding cassette, sub-family B(MDR/TAP), member 6 | 3.039132233 |
| BC021025 | CTHRC1 | Collagen triple helix repeat containing 1 | 3.022775957 |
| NM_004999 | MYO6 | Myosin VI | 3.020625421 |
| AF445025 | SLC35A4 | Solute carrier family 35, member A4 | 3.018853063 |
| NM_003330 | TXNRD1 | Thioredoxin reductase 1 | 2.810879753 |
| AK092512 | SLC16A5 | Solute carrier family 16(monocarboxylic acid transporters), member 5 | 2.5780312 |
| AB075871 | FLJ42654 | Golgi transport 1 homolog A(*S. cerevisiae*) | 2.278893633 |
| (p) The others | | | |
| NM_004864 | GDF15 | Growth differentiation factor 15 | 6.654247181 |
| NM_022153 | PP2135 | Chromosome 10 open reading frame 54 | 6.333855415 |
| NM_001013632 | LOC343521 | Similar to hypothetical protein 4833401D15 | 5.344247617 |
| AK124751 | CAPN2 | Calpain 2, (m/II) large subunit | 4.877328363 |
| AK095079 | RGC32 | Response gene to complement 32 | 3.2942944 |
| NM_031286 | SH3BGRL3 | SH3 domain binding glutamic acid-rich protein like 3 | 2.915143493 |
| AK126182 | KIAA1949 | KIAA1949 | 2.807348634 |
| NM_080388 | S100A16 | S100 calcium binding protein A16 | 2.607982075 |
| NM_025106 | SSB1 | SplA/ryanodine receptor domain and SOCS box containing 1 | 2.522542864 |
| NM_203403 | C9orf150 | Chromosome 9 open reading frame 150 | 2.200130419 |
| AK096241 | SQSTM1 | Sequestosome 1 | 2.015574807 |
| BQ276852 | TMSB10 | Thymosin, beta 10 | 1.863965907 |
| BC101655 | HIST1H2BI | Histone 1, H2bi | 1.863164701 |
| W84524 | TM4SF5 | Transmembrane 4 L six family member 5 | 1.768210846 |
| BX647290 | HIST1H2BO | Histone 1, H2bo | 1.511861325 |

TABLE 3

Genes down-regulated by chrysene

| Accession number | Gene abbreviation | Gene name | Ratio of intermediate value |
|---|---|---|---|
| (a) MAPKinase Signaling Pathway | | | |
| NM_002467 | MYC | V-myc myelocytomatosis viral oncogene homolog(avian) | 0.153957027 |
| BC038295 | MAP2K7 | Mitogen-activated protein kinase kinase 7 | 0.250015644 |

TABLE 3-continued

| | Genes down-regulated by chrysene | | |
|---|---|---|---|
| Accession number | Gene abbreviation | Gene name | Ratio of intermediate value |
| NM_004364 | CEBPA | CCAAT/enhancer binding protein(C/EBP), alpha | 0.291022284 |
| NM_145161 | MAP2K5 | Mitogen-activated protein kinase kinase 5 | 0.396692291 |
| XM_042066 | MAP3K1 | Mitogen-activated protein kinase kinase kinase 1 | 0.424190161 |
| Z25424 | MKNK2 | MAP kinase interacting serine/threonine kinase 2 | 0.440953544 |
| AB209047 | ELK1 | ELK1, member of ETS oncogene family | 0.46931591 |
| NM_004755 | RPS6KA5 | Ribosomal protein S6 kinase, 90 kDa, polypeptide 5 | 0.486533941 |
| AB001872 | RPL4 | Mitogen-activated protein kinase kinase 13 | 0.488828813 |
| NM_002758 | MAP2K6 | Mitogen-activated protein kinase kinase 6 | 0.489648933 |
| AK098095 | BRAF | V-raf murine sarcoma viral oncogene homolog B1 | 0.490796917 |
| | | (b) MAPKKK cascade | |
| AB208919 | FGFR1 | Fibroblast growth factor receptor 1(fms-related tyrosine kinase 2, Pfeiffer syndrome) | 0.306072231 |
| BC060837 | DUSP9 | Dual specificity phosphatase 9 | 0.309017123 |
| NM_000142 | FGFR3 | Fibroblast growth factor receptor 3(achondroplasia, thanatophoric dwarfism) | 0.316732251 |
| AY247738 | TRIB3 | Tribbles homolog 3 (*Drosophila*) | 0.319013779 |
| NM_030640 | DUSP16 | Dual specificity phosphatase 16 | 0.346335506 |
| NM_148957 | TNFRSF19 | Tumor necrosis factor receptor superfamily, member 19 | 0.373948519 |
| AB011123 | TNIK | TRAF2 and NCK interacting kinase | 0.375429687 |
| NM_006549 | CAMKK2 | Calcium/calmodulin-dependent protein kinase kinase 2, beta | 0.375436076 |
| NM_022740 | HIPK2 | Homeodomain interacting protein kinase 2 | 0.491170791 |
| | | (c) Apoptosis | |
| NM_005400 | PRKCE | Protein kinase C, epsilon | 0.110495908 |
| NM_000893 | KNG1 | Kininogen 1 | 0.123179781 |
| NM_000066 | C8B | Complement component 8, beta polypeptide | 0.168259363 |
| CR749293 | PLG | Plasminogen | 0.214468702 |
| BC013780 | ADORA2A | Adenosine A2a receptor | 0.25462881 |
| NM_001012271 | BIRC5 | Effector cell peptidase receptor 1 | 0.261340346 |
| NM_003811 | TNFSF9 | Tumor necrosis factor (ligand) superfamily, member 9 | 0.278995394 |
| BC050369 | E2F1 | E2F transcription factor 1 | 0.284336508 |
| NM_007313 | ABL1 | V-abl Abelson murine leukemia viral oncogene homolog 1 | 0.286557271 |
| BX647151 | MYBL2 | V-myb myeloblastosis viral oncogene homolog(avian)-like 2 | 0.292335923 |
| NM_004822 | NTN1 | Netrin 1 | 0.298168066 |
| BC033694 | BCL2L11 | BCL2-like 11 (apoptosis facilitator) | 0.334908167 |
| AB208876 | AXIN1 | Axin 1 | 0.346768268 |
| BC051332 | F2 | Coagulation factor II (thrombin) | 0.347828025 |
| AK122614 | PPARD | Peroxisome proliferative activated receptor, delta | 0.348064401 |
| L78790 | ITGB2 | Integrin, beta 2 (antigen CD18(p95), lymphocyte function-associated antigen 1; macrophage antigen 1(mac-1) beta subunit) | 0.377717722 |
| AK223409 | BARD1 | BRCA1 associated RING domain 1 | 0.385577392 |
| NM_002737 | PRKCA | Protein kinase C, alpha | 0.38570547 |
| NM_012479 | YWHAG | Tyrosine 3-monooxygenase/tryptophan 5-monooxygenase activation protein, gamma polypeptide | 0.38743105 |
| CR596268 | ITGB3BP | Integrin beta 3 binding protein(beta3-endonexin) | 0.392340911 |
| NM_003551 | NME5 | Non-metastatic cells 5, protein expressed in(nucleoside-diphosphate kinase) | 0.397002326 |
| NM_013974 | DDAH2 | Dimethylarginine dimethylaminohydrolase 2 | 0.397010628 |
| D79987 | ESPL1 | Extra spindle poles like 1(*S. cerevisiae*) | 0.397660686 |
| NM_006427 | SIVA | CD27-binding(Siva) protein | 0.399556277 |
| NM_024900 | PHF17 | PHD finger protein 17 | 0.400845508 |
| AB046854 | MAGI-3 | Membrane associated guanylate kinase, WW and PDZ domain containing 3 | 0.423418754 |
| AK095578 | SPHK1 | Sphingosine kinase 1 | 0.442516388 |
| AK122762 | CIDEA | Cell death-inducing DFFA-like effector a | 0.448550433 |

TABLE 3-continued

Genes down-regulated by chrysene

| Accession number | Gene abbreviation | Gene name | Ratio of intermediate value |
|---|---|---|---|
| AK092872 | ERCC2 | Excision repair cross-complementing rodent repair deficiency, complementation group 2 (xeroderma pigmentosum D) | 0.448557114 |
| NM_006290 | TNFAIP3 | Tumor necrosis factor, alpha-induced protein 3 | 0.452157996 |
| NM_000562 | C8A | Complement component 8, alpha polypeptide | 0.463461593 |
| AK122894 | AKT1 | V-akt murine thymoma viral oncogene homolog 1 | 0.467334939 |
| NM_005067 | SIAH2 | Seven in absentia homolog 2(*Drosophila*) | 0.467840694 |
| NM_203339 | CLU | Clusterin(complement lysis inhibitor, SP-40,40, sulfated glycoprotein 2, testosterone-repressed prostate message 2, apolipoprotein J) | 0.469884724 |
| NM_003376 | VEGF | Vascular endothelial growth factor | 0.481416264 |
| AK027590 | DAPK3 | Death-associated protein kinase 3 | 0.48390449 |
| AK122825 | HMGB1 | High-mobility group box 1 | 0.505043422 |
| (d) Response to DNA damage stimulus | | | |
| NM_006904 | PRKDC | Protein kinase, DNA-activated, catalytic polypeptide | 0.136872821 |
| AK074377 | UHRF1 | Chromosome 19 open reading frame 31 | 0.162554272 |
| CR604810 | CCNA2 | Cyclin A2 | 0.271739971 |
| AK001720 | FLJ10858 | Nei endonuclease VIII-like 3(*E. coli*) | 0.272320034 |
| CR600021 | HMGB2 | High-mobility group box 2 | 0.292500615 |
| NM_006230 | POLD2 | Polymerase(DNA directed), delta 2, regulatory subunit 50 kDa | 0.296598073 |
| NM_018151 | RIF1 | RAP1 interacting factor homolog(yeast) | 0.337901829 |
| BX248766 | RAD51L1 | RAD51-like 1(*S. cerevisiae*) | 0.35239904 |
| NM_014502 | PRP19 | PRP19/PSO4 pre-mRNA processing factor 19 homolog(*S. cerevisiae*) | 0.352412499 |
| NM_013975 | LIG3 | Ligase III, DNA, ATP-dependent | 0.366235708 |
| NM_173627 | FLJ35220 | Hypothetical protein FLJ35220 | 0.370187726 |
| NM_003362 | UNG | Uracil-DNA glycosylase | 0.378408018 |
| AF076494 | IRF7 | Interferon regulatory factor 7 | 0.385612995 |
| CR625391 | RAD51AP1 | RAD51 associated protein 1 | 0.391222632 |
| NM_006231 | POLE | Polymerase(DNA directed), epsilon | 0.394826988 |
| NM_130398 | EXO1 | Exonuclease 1 | 0.407524268 |
| DQ140356 | KIAA1596 | Fanconi anemia, complementation group M | 0.412353616 |
| NM_002105 | H2AFX | H2A histone family, member X | 0.41455303 |
| AB209560 | POLD1 | Polymerase(DNA directed), delta 1, catalytic subunit 125 kDa | 0.443656469 |
| NM_000136 | FANCC | Fanconi anemia, complementation group C | 0.444998791 |
| NM_003368 | USP1 | Ubiquitin specific peptidase 1 | 0.445903079 |
| NM_022836 | DCLRE1B | DNA cross-link repair 1B(PSO2 homolog, *S. cerevisiae*) | 0.446832858 |
| NM_001067 | TOP2A | Topoisomerase(DNA) II alpha 170 kDa | 0.450120675 |
| NM_002913 | RFC1 | Replication factor C(activator1) 1, 145 kDa | 0.471937101 |
| NM_002412 | MGMT | O-6-methylguanine-DNA methyltransferase | 0.492152777 |
| NM_000251 | MSH2 | MutS homolog2, colon cancer, nonpolyposis type 1(*E. coli*) | 0.582053356 |
| (e) Immune response | | | |
| NM_015254 | KIF13B | Kinesin family member 13B | 0.20677975 |
| NM_006037 | HDAC4 | Histone deacetylase 4 | 0.233288586 |
| NM_020995 | HPR | Haptoglobin-related protein | 0.242867738 |
| NM_153443 | KIR3DL1 | Killer cell immunoglobulin-like receptor, three domains, long cytoplasmic tail, 1 | 0.281426014 |
| BC071718 | CCL4L1 | Chemokine(C-C motif) ligand 4-like 1 | 0.294604522 |
| NM_020979 | APS | Adaptor protein with pleckstrin homology and src homology 2 domains | 0.29487541 |
| NM_001629 | ALOX5AP | Arachidonate 5-lipoxygenase-activating protein | 0.300419669 |
| NM_130852 | PLUNC | Palate, lung and nasal epithelium carcinoma associated | 0.320441751 |
| AK024499 | SPON2 | Spondin 2, extracellular matrix protein | 0.328221638 |
| BC048198 | AHSG | Alpha-2-HS-glycoprotein | 0.344058212 |
| AK095849 | RNU22 | RNA, U22 small nucleolar | 0.353888139 |
| BC005395 | HPX | Hemopexin | 0.367891973 |
| NM_012276 | ILT7 | Leukocyte immunoglobulin-like receptor, subfamily A(with TM domain), member 4 | 0.392427034 |
| NM_003152 | STAT5A | Signal transducer and activator of transcription 5A | 0.400291045 |

TABLE 3-continued

| Accession number | Gene abbreviation | Gene name | Ratio of intermediate value |
|---|---|---|---|
| BC037171 | CCL27 | Chemokine(C-C motif) ligand 27 | 0.40075022 |
| NM_002468 | MYD88 | Myeloid differentiation primary response gene(88) | 0.403137375 |
| NM_002215 | ITIH1 | Inter-alpha (globulin) inhibitor H1 | 0.405944172 |
| NM_004750 | CRLF1 | Cytokine receptor-like factor 1 | 0.413787497 |
| DR004094 | HAMP | Hepcidin antimicrobial peptide | 0.413938464 |
| BC063245 | GNLY | Granulysin | 0.422712087 |
| AJ290445 | SARM1 | Sterile alpha and TIR motif containing 1 | 0.430080233 |
| AK122686 | IF | I factor(complement) | 0.436309666 |
| AB008535 | GPR44 | G protein-coupled receptor 44 | 0.440552612 |
| AK122912 | ZGPAT | Zinc finger, CCCH-type with G patch domain | 0.44067651 |
| BC022312 | C4BPA | Complement component 4 binding protein, alpha | 0.442950052 |
| BG564683 | ORM1 | Orosomucoid 1 | 0.445506981 |
| NM_000625 | NOS2A | Nitric oxide synthase 2A(inducible, hepatocytes) | 0.460550527 |
| NM_005515 | HLXB9 | Homeo box HB9 | 0.467040193 |
| BX537504 | C2 | Complement component 2 | 0.484853058 |
| BC028153 | LILRB3 | Leukocyte immunoglobulin-like receptor, subfamily B(with TM and ITIM domains), member 3 | 0.490534341 |
| AF130100 | SERPINC1 | Serpin peptidase inhibitor, clade C(antithrombin), member 1 | 0.491818077 |
| BC015110 | HHEX | Hematopoietically expressed homeobox | 0.602852309 |
| (f) Mitotic cell cycle | | | |
| AB209179 | PLK1 | Polo-like kinase 1 (*Drosophila*) | 0.120946155 |
| AY367065 | ASPM | Asp(abnormal spindle)-like, microcephaly associated(*Drosophila*) | 0.186885667 |
| NM_006101 | KNTC2 | Kinetochore associated 2 | 0.257114298 |
| NM_003550 | MAD1L1 | MAD1 mitotic arrest deficient-like 1(yeast) | 0.268688634 |
| NM_020242 | KNSL7 | Kinesin family member 15 | 0.280736071 |
| AB033068 | FZR1 | Fizzy/cell division cycle 20 related 1(*Drosophila*) | 0.281781782 |
| NM_018492 | PBK | PDZ binding kinase | 0.284074566 |
| NM_003318 | TTK | TTK protein kinase | 0.3026269 |
| BC011000 | CDCA5 | Cell division cycle associated 5 | 0.31212201 |
| NM_003981 | PRC1 | Protein regulator of cytokinesis 1 | 0.313872555 |
| NM_015097 | CLASP2 | Cytoplasmic linker associated protein 2 | 0.336054596 |
| U65410 | MAD2L1 | MAD2 mitotic arrest deficient-like 1(yeast) | 0.34214776 |
| NM_016343 | CENPF | Centromere protein F, 350/400 ka(mitosin) | 0.344911485 |
| NM_005504 | BCAT1 | Branched chain aminotransferase 1, cytosolic | 0.345858236 |
| NM_003718 | CDC2L5 | Cell division cycle 2-like 5(cholinesterase-related cell division controller) | 0.354681271 |
| NM_002768 | PCOLN3 | Procollagen(type III) N-endopeptidase | 0.389132906 |
| BC004352 | KIF22 | Kinesin family member 22 | 0.391492074 |
| NM_005983 | SKP2 | S-phase kinase-associated protein 2(p45) | 0.39153455 |
| NM_004523 | KIF11 | Kinesin family member 11 | 0.421587881 |
| CR592757 | BRRN1 | Barren homolog 1 (*Drosophila*) | 0.430159766 |
| NM_019063 | EML4 | Echinoderm microtubule associated protein like 4 | 0.434736842 |
| NM_006845 | KIF2C | Kinesin family member 2C | 0.43971662 |
| NM_004701 | CCNB2 | Cyclin B2 | 0.442694391 |
| NM_138555 | KIF23 | Kinesin family member 23 | 0.449014129 |
| NM_182687 | PKMYT1 | Protein kinase, membrane associated tyrosine/threonine 1 | 0.452437142 |
| NM_001790 | CDC25C | Cell division cycle 25C | 0.460379159 |
| BC032677 | UBE2C | Ubiquitin-conjugating enzyme E2C | 0.462505602 |
| NM_005886 | KATNB1 | Katanin p80(WD repeat containing) subunit B1 | 0.464765241 |
| BC073878 | KIFC1 | Kinesin family member C1 | 0.481322258 |
| AL833191 | SMC2L1 | SMC2 structural maintenance of chromosomes 2-like 1(yeast) | 0.486060683 |
| AF053305 | BUB1 | BUB1 budding uninhibited by benzimidazoles 1 homolog(yeast) | 0.491236752 |
| Z25431 | NEK1 | NIMA(never in mitosis gene a)-related kinase 1 | 0.49168642 |
| BC043371 | GFI1B | Growth factor independent 1B(potential regulator of CDKN1A, translocated in CML) | 0.494495314 |

TABLE 3-continued

Genes down-regulated by chrysene

| Accession number | Gene abbreviation | Gene name | Ratio of intermediate value |
|---|---|---|---|
| CR933728 | CDC2 | Cell division cycle 2, G1 to S and G2 to M | 0.496459108 |
| NM_014750 | DLG7 | Discs, large homolog 7(*Drosophila*) | 0.580070458 |
| (g) Cell cycle | | | |
| NM_018560 | WWOX | WW domain containing oxidoreductase | 0.079825512 |
| BG203702 | FHIT | Nasopharyngeal carcinoma, down-regulated 1 | 0.093083555 |
| BC050384 | SUPT3H | Suppressor of Ty 3 homolog(*S. cerevisiae*) | 0.126706068 |
| NM_000189 | HK2 | Hexokinase 2 | 0.173385257 |
| CD049340 | AURKB | Aurora kinase B | 0.19031938 |
| AB011153 | PLCB1 | Phospholipase C, beta 1(phosphoinositide-specific) | 0.215552494 |
| AB209271 | ERF | Ets2 repressor factor | 0.232018189 |
| NM_014264 | PLK4 | Polo-like kinase 4 (*Drosophila*) | 0.247388103 |
| NM_002417 | MKI67 | Antigen identified by monoclonal antibody Ki-67 | 0.258796008 |
| XM_496557 | RGP1 | Plasminogen-like B2 | 0.294326139 |
| NM_170715 | RASSF1 | Ras association (RalGDS/AF-6) domain family 1 | 0.298232376 |
| NM_004526 | MCM2 | MCM2 minichromosome maintenance deficient 2, mitotin(*S. cerevisiae*) | 0.302992712 |
| BC033086 | TCF19 | Transcription factor 19(SC1) | 0.32373718 |
| NM_001007071 | RPS6KB2 | Ribosomal protein S6 kinase, 70 kDa, polypeptide 2 | 0.324307585 |
| NM_016272 | TOB2 | Transducer of ERBB2, 2 | 0.330193495 |
| AK126688 | CDYL2 | Chromodomain protein, Y-like 2 | 0.387113875 |
| NM_001759 | CCND2 | Cyclin D2 | 0.389524403 |
| NM_002388 | MCM3 | MCM3 minichromosome maintenance deficient 3(*S. cerevisiae*) | 0.398257469 |
| NM_182776 | MCM7 | MCM7 minichromosome maintenance deficient 7(*S. cerevisiae*) | 0.404714589 |
| NM_012145 | DTYMK | Deoxythymidylate kinase(thymidylate kinase) | 0.423208336 |
| NM_014751 | MTSS1 | Metastasis suppressor 1 | 0.43748772 |
| NM_024342 | GRLF1 | Glucocorticoid receptor DNA binding factor 1 | 0.442555888 |
| AK025627 | CABLES1 | Cdk5 and Abl enzyme substrate 1 | 0.471323938 |
| NM_005915 | MCM6 | MCM6 minichromosome maintenance deficient 6(MIS5 homolog, *S. pombe*) (*S. cerevisiae*) | 0.472089288 |
| AF196185 | PARD3 | Par-3 partitioning defective 3 homolog(*C. elegans*) | 0.484933312 |
| NM_019001 | XRN1 | 5'-3' exoribonuclease 1 | 0.488883063 |
| NM_006739 | MCM5 | MCM5 minichromosome maintenance deficient 5, cell division cycle 46(*S. cerevisiae*) | 0.491549947 |
| NM_012218 | ILF3 | Interleukin enhancer binding factor 3, 90 kDa | 0.492503876 |
| AB053172 | CDT1 | DNA replication factor | 0.493969454 |
| AK074112 | CCNL2 | Cyclin L2 | 0.498469976 |
| NM_001005414 | ZWINT | ZW10 interactor antisense | 0.584517014 |
| (h) Alcohol metabolism | | | |
| BC033391 | PP1665 | Glycerophosphodiester phosphodiesterase domain containing 5 | 0.215800503 |
| NM_000672 | ADH6 | Alcohol dehydrogenase 6(class V) | 0.271123842 |
| NM_004563 | PCK2 | Phosphoenolpyruvate carboxykinase 2(mitochondrial) | 0.337047159 |
| XM_113962 | KIAA0650 | Structural maintenance of chromosomes flexible hinge domain containing 1 | 0.348581608 |
| NM_001500 | GMDS | GDP-mannose 4,6-dehydratase | 0.354747755 |
| NM_002541 | OGDH | Oxoglutarate (alpha-ketoglutarate) dehydrogenase(lipoamide) | 0.357289949 |
| NM_000298 | PKLR | Pyruvate kinase, liver and RBC | 0.39231759 |
| NM_005276 | GPD1 | Glycerol-3-phosphate dehydrogenase 1(soluble) | 0.394511398 |
| AB209127 | PFKL | Phosphofructokinase, liver | 0.396666891 |
| M15943 | ADH4 | Alcohol dehydrogenase 4(class II), pi polypeptide | 0.441308466 |
| NM_000671 | ADH5 | Alcohol dehydrogenase 5(class III), chi polypeptide | 0.448054959 |
| BC026320 | OGDHL | Oxoglutarate dehydrogenase-like | 0.464556343 |
| NM_009590 | AOC2 | Amine oxidase, copper containing 2(retina-specific) | 0.479506902 |
| BC015797 | SLC25A10 | Solute carrier family 25(mitochondrial carrier; dicarboxylate transporter), member 10 | 0.489192347 |

TABLE 3-continued

Genes down-regulated by chrysene

| Accession number | Gene abbreviation | Gene name | Ratio of intermediate value |
|---|---|---|---|
| (i) Amino acid metabolism | | | |
| NM_003748 | ALDH4A1 | Aldehyde dehydrogenase 4 family, member A1 | 0.179005599 |
| NM_002108 | HAL | Histidine ammonia-lyase | 0.19694868 |
| NM_003486 | SLC7A5 | Solute carrier family 7(cationic amino acid transporter, y+ system), member 5 | 0.201120723 |
| NM_003045 | SLC7A1 | Solute carrier family 7(cationic amino acid transporter, y+ system), member 1 | 0.204215808 |
| NM_000277 | PAH | Phenylalanine hydroxylase | 0.207720611 |
| NM_012331 | MSRA | Methionine sulfoxide reductase A | 0.21152792 |
| BC008366 | DDC | Dopa decarboxylase (aromatic L-amino acid decarboxylase) | 0.219970928 |
| NM_006567 | FARS2 | Phenylalanine-tRNA synthetase 2(mitochondrial) | 0.242735735 |
| AK055862 | FLJ31300 | Urocanase domain containing 1 | 0.265306391 |
| NM_001875 | CPS1 | Carbamoyl-phosphate synthetase 1, mitochondrial | 0.284603831 |
| AK122685 | GLUD1 | Glutamate dehydrogenase 1 | 0.290594908 |
| NM_003046 | SLC7A2 | Solute carrier family 7(cationic amino acid transporter, y+ system), member 2 | 0.303490377 |
| AK093306 | PHGDH | Phosphoglycerate dehydrogenase | 0.315789771 |
| NM_080820 | HARS2 | Histidyl-tRNA synthetase 2 | 0.337699715 |
| NM_006907 | PYCR1 | Pyrroline-5-carboxylate reductase 1 | 0.343360051 |
| NM_020117 | LARS | Leucyl-tRNA synthetase | 0.359457546 |
| BC051726 | GLUL | Glutamate-ammonia ligase(glutamine synthetase) | 0.363765571 |
| BC012616 | BHMT | Betaine-homocysteine methyltransferase | 0.369989797 |
| AK055053 | SHMT2 | Serine hydroxymethyltransferase 2(mitochondrial) | 0.401235464 |
| NM_007101 | SARDH | Sarcosine dehydrogenase | 0.402864636 |
| AL833251 | LOC283970 | Hypothetical protein LOC283970 | 0.40730291 |
| AK027126 | ASS | Argininosuccinate synthetase | 0.418690738 |
| L00972 | CBS | Cystathionine-beta-synthase | 0.440354778 |
| NM_206965 | FTCD | Formiminotransferase cyclodeaminase | 0.47079397 |
| NM_000429 | MAT1A | Methionine adenosyltransferase I, alpha | 0.472559543 |
| NM_001801 | CDO1 | Cysteine dioxygenase, type I | 0.480848737 |
| NM_006843 | SDS | Serine dehydratase | 0.488304529 |
| NM_000170 | GLDC | Glycine dehydrogenase (decarboxylating; glycine decarboxylase, glycine cleavage system protein P) | 0.491686799 |
| (j) DNA metabolism | | | |
| BX102654 | HIST1H4B | Histone 1, H4b | 0.172360533 |
| DQ097177 | UREB1 | HECT, UBA and WWE domain containing 1 | 0.213344474 |
| NM_022743 | SMYD3 | SET and MYND domain containing 3 | 0.265102932 |
| NM_001809 | CENPA | Centromere protein A, 17 kDa | 0.272224677 |
| AB028450 | NCOR1 | Nuclear receptor co-repressor 1 | 0.31777205 |
| NM_002967 | SAFB | Scaffold attachment factor B | 0.3219512 |
| NM_003074 | SMARCC1 | SWI/SNF related, matrix associated, actin dependent regulator of chromatin, subfamily c, member 1 | 0.353538227 |
| NM_015409 | EP400 | E1A binding protein p400 | 0.371543731 |
| BC044659 | SMARCA3 | SWI/SNF related, matrix associated, actin dependent regulator of chromatin, subfamily a, member 3 | 0.393689415 |
| AB209433 | BAT8 | Euchromatic histone-lysine N-methyltransferase 2 | 0.398851055 |
| XM_370756 | KIAA1305 | KIAA1305 | 0.41059832 |
| NM_020201 | NT5M | 5',3'-nucleotidase, mitochondrial | 0.425450039 |
| NM_001025248 | DUT | DUTP pyrophosphatase | 0.4301363 |
| AK123010 | RRM2 | Ribonucleotide reductase M2 polypeptide | 0.443733966 |
| BX537961 | DNMT2 | DNA (cytosine-5-)-methyltransferase 2 | 0.449895729 |
| BX648935 | TBL1XR1 | Transducin (beta)-like 1X-linked receptor 1 | 0.45144224 |
| NM_001001888 | VCX-C | Variably charged X-C | 0.451813598 |
| NM_002501 | NFIX | Nuclear factor I/X (CCAAT-binding transcription factor) | 0.455473267 |
| NM_003483 | HMGA2 | High mobility group AT-hook 2 | 0.45812854 |
| U80628 | TK2 | Thymidine kinase 2, mitochondrial | 0.460005269 |
| NM_006807 | CBX1 | Chromobox homolog 1 (HP1 beta homolog Drosophila) | 0.46081477 |
| AY024361 | MLL3 | Myeloid/lymphoid or mixed-lineage leukemia 3 | 0.461050924 |

TABLE 3-continued

Genes down-regulated by chrysene

| Accession number | Gene abbreviation | Gene name | Ratio of intermediate value |
|---|---|---|---|
| NM_017519 | ARID1B | AT rich interactive domain 1B(SWI1-like) | 0.46115551 |
| NM_003077 | SMARCD2 | SWI/SNF related, matrix associated, actin dependent regulator of chromatin, subfamily d, member 2 | 0.461333882 |
| NM_016937 | POLA | Polymerase(DNA directed), alpha | 0.463508595 |
| (k) Lipid metabolism | | | |
| AJ007583 | LARGE | Like-glycosyltransferase | 0.142759166 |
| AK124635 | PCSK9 | Proprotein convertase subtilisin/kexin type 9 | 0.146781198 |
| NM_030758 | OSBP2 | Oxysterol binding protein 2 | 0.148618668 |
| NM_005063 | SCD | Stearoyl-CoA desaturase(delta-9-desaturase) | 0.16572839 |
| NM_000236 | LIPC | Lipase, hepatic | 0.198492731 |
| AF288389 | GLT25D2 | Glycosyltransferase 25 domain containing 2 | 0.198600514 |
| AF202889 | APOA5 | Apolipoprotein A-V | 0.209911653 |
| BX640945 | FADS2 | Fatty acid desaturase 2 | 0.213145374 |
| BI521580 | APOC3 | Apolipoprotein C-III | 0.23320201 |
| NM_001277 | CHKA | Choline kinase alpha | 0.244381018 |
| Z28339 | AKR1D1 | Aldo-keto reductase family 1, member D1(delta 4-3-ketosteroid-5-beta-reductase) | 0.254902416 |
| BC035654 | NR1H4 | Nuclear receptor subfamily 1, group H, member 4 | 0.262741172 |
| AB209229 | MVD | Mevalonate (diphospho) decarboxylase | 0.269846903 |
| BC026264 | UGT2B4 | UDP glucuronosyltransferase 2 family, polypeptide B4 | 0.271647964 |
| NM_004104 | FASN | Fatty acid synthase | 0.280448461 |
| NM_147161 | THEA | Acyl-CoA thioesterase 11 | 0.285998121 |
| AF059203 | SOAT2 | Sterol O-acyltransferase 2 | 0.288070163 |
| NM_020918 | GPAM | Glycerol-3-phosphate acyltransferase, mitochondrial | 0.292909604 |
| NM_001443 | FABP1 | Fatty acid binding protein 1, liver | 0.296451689 |
| NM_014762 | DHCR24 | 24-dehydrocholesterol reductase | 0.297972079 |
| AK093328 | PCYT2 | Phosphate cytidylyltransferase 2, ethanolamine | 0.311874518 |
| BX538214 | C6orf167 | Chromosome 6 open reading frame 167 | 0.323543551 |
| X75311 | MVK | Mevalonate kinase (mevalonic aciduria) | 0.333966231 |
| NM_000497 | CYP11B1 | Cytochrome P450, family 11, subfamily B, polypeptide 1 | 0.338436304 |
| BC036102 | SIAT7F | ST6(alpha-N-acetyl-neuraminyl-2,3-beta-galactosyl-1,3)-N-acetylgalactosaminide alpha-2,6-sialyltransferase 6 | 0.34576685 |
| BC012172 | ACAS2 | Acyl-CoA synthetase short-chain family member 2 | 0.350569281 |
| NM_007169 | PEMT | Phosphatidylethanolamine N-methyltransferase | 0.356048412 |
| X91148 | MTP | Microsomal triglyceride transfer protein | 0.362753622 |
| NM_198839 | ACACA | Acetyl-Coenzyme A carboxylase alpha | 0.380784496 |
| NM_004687 | MTMR4 | Myotubularin related protein 4 | 0.401837935 |
| NM_000384 | APOB | Apolipoprotein B (including Ag(x) antigen) | 0.416233282 |
| AK127051 | ACAA1 | Acetyl-Coenzyme A acyltransferase 1(peroxisomal 3-oxoacyl-Coenzyme A thiolase) | 0.423299321 |
| BC035638 | LSS | Lanosterol synthase (2,3-oxidosqualene-lanosterol cyclase) | 0.430665775 |
| NM_004204 | PIGQ | Phosphatidylinositol glycan, class Q | 0.45218399 |
| NM_004457 | ACSL3 | Acyl-CoA synthetase long-chain family member 3 | 0.454938664 |
| AL138578 | ADPN | Adiponutrin | 0.461837251 |
| NM_002332 | LRP1 | Low density lipoprotein-related protein 1(alpha-2-macroglobulin receptor) | 0.468691544 |
| NM_016372 | GPR175 | G protein-coupled receptor 175 | 0.479022743 |
| NM_080476 | CDC91L1 | CDC91 cell division cycle 91-like 1(S. cerevisiae) | 0.479354103 |
| AF303134 | ALDH8A1 | Aldehyde dehydrogenase 8 family, member A1 | 0.481811965 |
| NM_002130 | HMGCS1 | 3-hydroxy-3-methylglutaryl-Coenzyme A synthase 1(soluble) | 0.483678121 |
| AK055414 | LASS4 | LAG1 longevity assurance homolog 4(S. cerevisiae) | 0.485211697 |
| NM_022977 | ACSL4 | Acyl-CoA synthetase long-chain family member 4 | 0.485591269 |
| NM_004631 | LRP8 | Low density lipoprotein receptor-related protein 8, apolipoprotein e receptor | 0.490795611 |

TABLE 3-continued

Genes down-regulated by chrysene

| Accession number | Gene abbreviation | Gene name | Ratio of intermediate value |
|---|---|---|---|
| NM_002573 | PAFAH1B3 | Platelet-activating factor acetylhydrolase, isoform Ib, gamma subunit 29 kDa | 0.495601801 |
| NM_021005 | NR2F2 | Nuclear receptor subfamily 2, group F, member 2 | 0.497299707 |
| (l) Metal-binding | | | |
| CR620135 | DPEP1 | Dipeptidase 1(renal) | 0.190430174 |
| NM_002317 | LOX | Lysyl oxidase | 0.198239785 |
| NM_005949 | MT1F | Metallothionein 1F (functional) | 0.22405551 |
| AF279145 | ANTXR1 | Anthrax toxin receptor 1 | 0.230840625 |
| NM_005588 | MEP1A | Meprin A, alpha(PABA peptide hydrolase) | 0.259485084 |
| NM_014214 | IMPA2 | Inositol(myo)-1(or 4)-monophosphatase 2 | 0.263186701 |
| NM_005940 | MMP11 | Matrix metallopeptidase 11(stromelysin 3) | 0.264566247 |
| AB193259 | ACE2 | Angiotensin I converting enzyme(peptidyl-dipeptidase A) 2 | 0.273758292 |
| AF018081 | COL18A1 | Collagen, type XVIII, alpha 1 | 0.291828069 |
| M28016 | cytochrome b | Human mitochondrial cytochrome b gene, partial cds. | 0.297761706 |
| NM_002428 | MMP15 | Matrix metallopeptidase 15(membrane-inserted) | 0.31207988 |
| NM_025074 | FRAS1 | Fraser syndrome 1 | 0.33237663 |
| M75106 | CPB2 | Carboxypeptidase B2 (plasma, carboxypeptidase U) | 0.614512721 |
| NM_000937 | POLR2A | Polymerase(RNA) II (DNA directed) polypeptide A, 220 kDa | 0.204681289 |
| NM_005060 | RORC | RAR-related orphan receptor C | 0.221567885 |
| BC092512 | MYRIP | Myosin VIIA and Rab interacting protein | 0.248675106 |
| NM_000901 | NR3C2 | Nuclear receptor subfamily 3, group C, member 2 | 0.266066448 |
| NM_005392 | PHF2 | PHD finger protein 2 | 0.268831722 |
| AK091289 | ZNF367 | Zinc finger protein 367 | 0.275012045 |
| NM_014788 | TRIM14 | Tripartite motif-containing 14 | 0.276556442 |
| NM_018660 | ZNF395 | Zinc finger protein 395 | 0.296616246 |
| AB209755 | MLLT10 | Myeloid/lymphoid or mixed-lineage leukemia(trithorax homolog, Drosophila); translocated to, 10 | 0.300538557 |
| AK097472 | MAZ | MYC-associated zinc finger protein(purine-binding transcription factor) | 0.313722345 |
| NM_020062 | SLC2A4RG | SLC2A4 regulator | 0.33059257 |
| BX571750 | HNF4G | Hepatocyte nuclear factor 4, gamma | 0.332470234 |
| (m) Transport | | | |
| NM_021807 | SEC8L1 | Exocyst complex component 4 | 0.089545841 |
| NM_006651 | CPLX1 | Complexin 1 | 0.131109907 |
| NM_005845 | ABCC4 | ATP-binding cassette, sub-family C(CFTR/MRP), member 4 | 0.133334881 |
| NM_006650 | CPLX2 | Complexin 2 | 0.134012051 |
| NM_004164 | RBP2 | Retinol binding protein 2, cellular | 0.156673775 |
| NM_021069 | ARGBP2 | Sorbin and SH3 domain containing 2 | 0.166678886 |
| NM_201649 | SLC6A9 | Solute carrier family 6(neurotransmitter transporter, glycine), member 9 | 0.214191554 |
| NM_005835 | SLC17A2 | Solute carrier family 17(sodium phosphate), member 2 | 0.221982855 |
| AJ315644 | SLC2A13 | Solute carrier family 2(facilitated glucose transporter), member 13 | 0.222684082 |
| NM_000340 | SLC2A2 | Solute carrier family 2(facilitated glucose transporter), member 2 | 0.227123291 |
| NM_003685 | KHSRP | KH-type splicing regulatory protein(FUSE binding protein 2) | 0.22945097 |
| BX537382 | SLC38A3 | Solute carrier family 38, member 3 | 0.242568721 |
| NM_182964 | NAV2 | Neuron navigator 2 | 0.247250994 |
| BX640965 | SLC22A3 | Solute carrier family 22(extraneuronal monoamine transporter), member 3 | 0.255608537 |
| AK127255 | SNX26 | Sorting nexin 26 | 0.260176313 |
| AY043484 | SCN1A | Sodium channel, voltage-gated, type I, alpha | 0.260866507 |
| AK074107 | C20orf59 | Chromosome 20 open reading frame 59 | 0.271346073 |
| NM_003056 | SLC19A1 | Solute carrier family 19(folate transporter), member 1 | 0.29688016 |
| NM_020897 | HCN3 | Hyperpolarization activated cyclic nucleotide-gated potassium channel 3 | 0.313835834 |

TABLE 3-continued

Genes down-regulated by chrysene

| Accession number | Gene abbreviation | Gene name | Ratio of intermediate value |
|---|---|---|---|
| AY124771 | SLC26A1 | Solute carrier family 26(sulfate transporter), member 1 | 0.317100952 |
| NM_001011554 | SLC13A3 | Solute carrier family 13(sodium-dependent dicarboxylate transporter), member 3 | 0.321469735 |
| AK027855 | SLC5A6 | Solute carrier family 5(sodium-dependent vitamin transporter), member 6 | 0.327464039 |
| NM_001005747 | CACNB4 | Calcium channel, voltage-dependent, beta 4 subunit | 0.332952777 |
| NM_013277 | RACGAP1 | Rac GTPase activating protein 1 | 0.378143166 |
| (n) The others ||||
| NM_012340 | NFATC2 | Nuclear factor of activated T-cells, cytoplasmic, calcineurin-dependent 2 | 0.417449456 |
| NM_018291 | FLJ10986 | Hypothetical protein FLJ10986 | 0.181870965 |
| BC052951 | LMNB1 | Lamin B1 | 0.197126008 |
| AK075271 | SPTLC2L | Serine palmitoyltransferase, long chain base subunit 2-like(aminotransferase 2) | 0.230098147 |
| BI762502 | GSTA2 | Glutathione S-transferase A2 | 0.31916011 |
| AK055221 | FBXO5 | F-box protein 5 | 0.342113931 |
| XM_372695 | LOC390859 | PREDICTED: *Homo sapiens* similar to Chain A, Crystal Structure Of The R463a Mutant Of Human Glutamate Dehydrogenase(LOC390859), mRNA | 0.356013687 |
| AB037805 | KLHL14 | Kelch-like 14 (*Drosophila*) | 0.376251676 |
| NM_145061 | C13orf3 | Chromosome 13 open reading frame 3 | 0.377419925 |
| AK000643 | ASB9 | Ankyrin repeat and SOCS box-containing 9 | 0.419775956 |
| AL133031 | MLR1 | Transcription factor MLR1 | 0.438551394 |
| AB091343 | C10orf3 | Centrosomal protein 55 kDa | 0.451690933 |
| AY007723 | MAL2 | Mal, T-cell differentiation protein 2 | 0.456188931 |
| BC098313 | FLJ20641 | Hypothetical protein FLJ20641 | 0.508085568 |
| BC041882 | ATF7IP2 | Activating transcription factor 7 interacting protein 2 | 0.521200373 |
| AK127098 | FLJ10706 | Chromosome 1 open reading frame 112 | 0.527226934 |
| BC022255 | Spc25 | Spindle pole body component 25 homolog(*S. cerevisiae*) | 0.537391579 |
| BC026283 | APOH | Apolipoprotein H (beta-2-glycoprotein I) | 0.650367241 |

Example 3

Quantification by Real Time RT-PCR (Reverse Transcriptase Polymerase Chain Reaction)

Among genes apt to be more than 2 fold up-regulated or down-regulated by chrysene, confirmed in Example 2, 25 genes up-regulated and 10 genes down-regulated were selected. The genes are Genebank Accession Number: NM_000499 (Cytochrome P450, family 1, subfamily A, polypeptide 1), Genebank Accession Number: BX649164 (serpin peptidase inhibitor, clade E (nexin, plasminogen activator inhibitor type 1), member 1), Genebank Accession Number: NM_004881 (Tumor protein p53 inducible protein 3), Genebank Accession Number: BM913048 (TIMP metallopeptidase inhibitor 1), Genebank Accession Number: NM_006426 (Dihydropyrimidinase-like 4), Genebank Accession Number: NM_133493 [CD109 antigen (Gov platelet alloantigens)], Genebank Accession Number: AB033073 (Sulfatase 2), Genebank Accession Number: NM_021603 (FXYD domain containing ion transport regulator 2), Genebank Accession Number: BC035124 (MSFL2541), Genebank Accession Number: Y11307 (Cysteine-rich, angiogenic inducer, 61), Genebank Accession Number: AK095363 (Aquaporin 3), Genebank Accession Number: AK097009 (phospholipid transfer protein), Genebank Accession Number: NM_004864 (Growth differentiation factor 15), Genebank Accession Number: BU587578 (Regulator of G-protein signaling 10), Genebank Accession Number: BQ683841 [S100 calcium binding protein A11 (calgizzarin)], Genebank Accession Number: NM_001013632 [polo-like kinase 3 (*Drosophila*)], Genebank Accession Number: NM_032872 (Synaptotagmin-like 1), Genebank Accession Number: BC042390 [Vesicle transport through interaction with t-SNAREs homolog 1B (yeast)], Genebank Accession Number: NM_000596 (Insulin-like growth factor binding protein 1), Genebank Accession Number: NM_005319 (Histone 1, H1c), Genebank Accession Number: AK094474 (Ras homolog gene family, member C), Genebank Accession Number: NM_001769 [CD9 antigen (p24)], Genebank Accession Number: NM_001553 (Insulin-like growth factor binding protein 7), Genebank Accession Number: NM_003897 (Immediate early response 3), Genebank Accession Number: NM_003516 (Histone 2, H2aa), Genebank Accession Number: AK074377 (Chromosome 19 open reading frame 31), Genebank Accession Number: BX640965 (Solute carrier family 22 (extraneuronal monoamine transporter), member 3), Genebank Accession Number: NM_018492 (PDZ binding kinase), Genebank Accession Number: CR600021 (High-mobility group box 2), Genebank Accession Number: NM_006101 (Kinetochore associated 2), Genebank Accession Number: NM_003318 (TTK protein kinase), Genebank Accession Number: U65410 [MAD2 mitotic arrest deficient-like 1 (yeast)], Genebank Accession Number: NM_001067 (Topoisomerase (DNA) II alpha 170 kDa), Genebank Accession Number: AB091343 (Centrosomal protein 55 kDa) and Genebank Accession Number: BC022255 [Spindle pole body component 25 homolog (*S. cerevisiae*)].

To investigate and quantify the expressions of those genes, primers which can specifically proliferate of those genes' mRNA (see Table 4) were prepared, and quantitative real time RT-PCR was performed using My IQ Real-time PCR (Bio-rad, USA). Particularly, reverse transcription was performed using oligo dT primer and Superscript kit (Omniscript™ kit, Qiagen, Colo., USA) to synthesize cDNA. 0.2 μl of the cDNA, 3.8 μl of water, 0.5 μl of sense primer, 0.5 μl of antisense primer, and 5 μl of SYBR Green I staining supermix (Bio-rad, USA) were mixed, and the mixture was placed in PCR tube, followed by RT-PCR in My IQ real time PCR machine as follows: step 1, at 95° C. for 3 minutes; step 2 (repeated 45 times), step 2-1, at 95° C. for 10 seconds, step 2-2, at 55-65° C. for 45 seconds; step 3, at 95° C. for 1 minute; step 4 at 55° C. for 1 minute; and step 5 (repeated 80 times) at 55° C. for 10 seconds. To quantify PCR product, SYBR Green I (Bio-rad, USA) staining was performed. SYBR Green I staining is based on binding to double stranded DNA, so that as double stranded DNA increases during PCR, fluorescence intensity increases. The target gene used for PCR and primers for endogenous GAPDH were added to SYBR Green master mix, followed by PCR. Then, primer optimization was performed to select optimum concentration. The synthesized cDNA was mixed with each primer (Table 4), to which the SYBR Green master mix was added, followed by PCR. Quantification was performed using quantitative software (see Table 5).

TABLE 4

Primer sequences

| Accession number | Gene name | PCR primer sequence (5'→3') | |
|---|---|---|---|
| NM_000499 | Cytochrome P450, family 1, subfamily A, polypeptide 1 | sense (SEQ. ID. NO: 1) | CACCATCCCCACAGCAC |
| | | antisense (SEQ. ID. NO: 2) | ACAAAGACACAACGCCCCTT |
| BX649164 | Serpin peptidase inhibitor, clade E (nexin, plasminogen activator inhibitor type 1), member 1 | sense (SEQ. ID. NO: 3) | CAGACCAAGAGCCTCTCCAC |
| | | antisense (SEQ. ID. NO: 4) | ATCACTTGGCCCATGAAAAG |
| NM_004881 | Tumor protein p53 inducible protein 3 | sense (SEQ. ID. NO: 5) | AGGGTGAAGTCCTCCTGAAGGT |
| | | antisense (SEQ. ID. NO: 6) | GTGGGTCATACTGGCCTTGTCT |
| BM913048 | TIMPmetallopeptidase inhibitor1 | sense (SEQ. ID. NO: 7) | GATACTTCCACAGGTCCCACAAC |
| | | antisense (SEQ. ID. NO: 8) | GCAAGAGTCCATCCTGCAGTT |
| NM_006426 | Dihydropyrimidinase-like4 | sense (SEQ. ID. NO: 9) | TGGGAAGATGGACGAGAATGAGTTCG |
| | | antisense (SEQ. ID. NO: 10) | ACTCCACTCCCTCGAAGATGTTGT |
| NM_133493 | CD109 antigen (Gov platelet alloantigens) | sense (SEQ. ID. NO: 11) | GCCAAGATTTACCACGTTTGCCCA |
| | | antisense (SEQ. ID. NO: 12) | TGAAGGACCAGAACTGAGCCACAT |
| AB033073 | Sulfatase 2 | sense (SEQ. ID. NO: 13) | TGCGGATATGGACGGGAAATCCAT |
| | | antisense (SEQ. ID. NO: 14) | TCTCTTGTGTAGCAGCTTGCCTCT |
| NM_021603 | FXYDdomain containing ion transport regulator 2 | sense (SEQ. ID. NO: 15) | GGCAATAAGAAGCGCAGGCAAATC |
| | | antisense (SEQ. ID. NO: 16) | AAGGTCTAAAGCCCAGGGAAGAAG |

TABLE 4-continued

Primer sequences

| Accession number | Gene name | PCR primer sequence (5'→3') | |
|---|---|---|---|
| BC035124 | MSFL2541 | sense (SEQ. ID. NO: 17) | TTCGCCGTCCTTTACATCTAC |
| | | antisense (SEQ. ID. NO: 18) | AGAGCCTGGGGACTCACAT |
| Y11307 | Cysteine-rich, angiogenic inducer, 61 | sense (SEQ. ID. NO: 19) | ATTGTAGAAAGGAAGCCTTGCTCAT |
| | | antisense (SEQ. ID. NO: 20) | TCCAATCGTGGCTGCATTAG |
| AK095363 | Aquaporin 3 | sense (SEQ. ID. NO: 21) | TTCACGATCCACCCTTTCAGGCTA |
| | | antisense (SEQ. ID. NO: 22) | ACACATACCTGCTGCCCATTCTCT |
| AK097009 | Phospholipid transfer protein | sense (SEQ. ID. NO: 23) | TGCCACAGAGAAGACGGGATTTGA |
| | | antisense (SEQ. ID. NO: 24) | AGGTGGTGGACGGACTGTAATTGA |
| NM_004864 | Growth differentiation factor 15 | sense (SEQ. ID. NO: 25) | CCTGAGACACCCGATTCCT |
| | | antisense (SEQ. ID. NO: 26) | ACAGTTCCATCAGACCAGCC |
| BU587578 | Regulator of G-protein signalling 10 | sense (SEQ. ID. NO: 27) | CCGTGCCGGGTTTATCATTGCTTT |
| | | antisense (SEQ. ID. NO: 28) | TCGACGTGTCCAGTGTTGAAGGAA |
| BQ683841 | S100 calcium binding protein A11 (calgizzarin) | sense (SEQ. ID. NO: 29) | AGTCCCTGATTGCTGTCTTCCAGA |
| | | antisense (SEQ. ID. NO: 30) | ACCAGGGTCCTTCTGGTTCTTTGT |
| NM_0010136 32 | polo-like kinase 3 (Drosophila) | sense (SEQ. ID. NO: 31) | GACTACTCCAATAAGTTCGGCTTTG |
| | | antisense (SEQ. ID. NO: 32) | CATATGTGTGCCATCGTTGAAGA |
| NM_032872 | Synaptotagmin-like 1 | sense (SEQ. ID. NO: 33) | GGCGGTGAAGAAACGGAATCTGAA |
| | | antisense (SEQ. ID. NO: 34) | GAAAGATGTTGCGACCCAGGCTTT |
| BC042390 | Vesicle transport through interaction with t-SNAREs homolog 1B (yeast) | sense (SEQ. ID. NO: 35) | GGGGGACTAACCTATCGAGAA |
| | | antisense (SEQ. ID. NO: 36) | GATCCAGTGCTGATAGCAACC |
| NM_000596 | Insulin-like growth factor binding protein 1 | sense (SEQ. ID. NO: 37) | ATCATTCCATCCTTTGGGACGCCA |
| | | antisense 9SEQ. ID. NO: 38) | TGTCTCCTGTGCCTTGGCTAAACT |

TABLE 4-continued

Primer sequences

| Accession number | Gene name | PCR primer sequence (5'→3') | |
|---|---|---|---|
| NM_005319 | Histone 1, H1c | sense (SEQ. ID. NO: 39) | ACCAAACCTAAGAAGCCAGTTG |
| | | antisense (SEQ. ID. NO: 40) | TAGCGCTCTTCTTCGGAGTT |
| AK094474 | Ras homolog gene family, member C | sense (SEQ. ID. NO: 41) | ACCTGCCTCCTCATCGTCTTC |
| | | antisense (SEQ. ID. NO: 42) | CACCTGCTTGCCGTCCAC |
| NM_001769 | CD9 antigen (p24) | sense (SEQ. ID. NO: 43) | GCACCAAGTGCATCAAATACCTGC |
| | | antisense (SEQ. ID. NO: 44) | AGCCATAGTCCAATGGCAAGGACA |
| NM_001553 | Insulin-like growth factor binding protein 7 | sense (SEQ. ID. NO: 45) | ACTTGAGCTGTGAGGTCATCGGAA |
| | | antisense (SEQ. ID. NO: 46) | ATACCAGCACCCAGCCAGTTACTT |
| NM_003897 | Immediate early response 3 | sense (SEQ. ID. NO: 47) | AGCCCTTTAATCTGACTTCGGAGC |
| | | antisense (SEQ. ID. NO: 48) | CAGGTACGCCTGGTGTTTCTTTGT |
| NM_003516 | Histone 2, H2aa | sense (SEQ. ID. NO: 49) | GAACTGAACAAGCTGCTGGGCAAA |
| | | antisense (SEQ ID. NO: 50) | TCTCCGTCTTCTTAGGGAGCAGTA |
| AK074377 | Chromosome 19 open reading frame 31 | sense (SEQ. ID. NO: 51) | CTGGTACGACGCGGAGAT |
| | | antisense (SEQ. ID. NO: 52) | CGACAGTCGTTCAGAGAATCA |
| BX640965 | Solute carrier family 22 (extraneuronal monoamine transporter), member 3 | sense (SEQ. ID. NO: 53) | GCCCTGTTCCAGCAATAAGA |
| | | antisense (SEQ. ID. NO: 54) | GAGAGCCAAAAATGTCCCAA |
| NM_018492 | PDZ binding kinase | sense (SEQ. ID. NO: 55) | TCTGGACTGAGAGTGGCTTTCACA |
| | | antisense (SEQ. ID. NO: 56) | AGCCAAGCTTCTGCATAAACGGAG |
| CR600021 | High-mobility group box 2 | sense (SEQ. ID. NO: 57) | CTTGGCACGATATGCAGCAA |
| | | antisense (SEQ. ID. NO: 58) | CAGCCAAAGATAAACAACCATATGA |
| NM_006101 | Kinetochore associated 2 | sense (SEQ. ID. NO: 59) | TGCTACACATGTTGGGTCTGTA |
| | | antisense (SEQ. ID. NO: 60) | CCGAGAGATCTTCTGACATGC |
| NM_003318 | TTK protein kinase | sense (SEQ. ID. NO: 61) | TCATGCCCATTTGGAAGAGTCCCA |
| | | antisense (SEQ. ID. NO: 62) | AGGCACAACCAAATCTCGGCATTC |

TABLE 4-continued

Primer sequences

| Accession number | Gene name | PCR primer sequence (5'→3') | |
|---|---|---|---|
| U65410 | MAD2 mitotic arrest deficient-like 1 (yeast) | sense (SEQ. ID. NO: 63) | ACTTAAATATCTCCCTACCTATA CTGAGTCAA |
| | | antisense (SEQ. ID. NO: 64) | TAGTAACTGTAGATGGAAAAACT TGTGCTA |
| NM_001067 | Topoisomerase (DNA) II alpha 170 kDa | sense (SEQ. ID. NO: 65) | CTAGTTAATGCTGCGGACAACA |
| | | antisense (SEQ. ID. NO: 66) | CATTTCGACCACCTGTCACTT |
| AB091343 | Centrosomal protein 55 kDa | sense (SEQ. ID. NO: 67) | GCTGTGCATTTCTCTTGGCAGTGA |
| | | antisense (SEQ. ID. NO: 68) | TAGACGCTGCTCACCACATTCTGT |
| BC022255 | Spindle pole body component 25 homolog (*S. cerevisiae*) | sense (SEQ. ID. NO: 69) | GAATGGTTGAGATGTTTCTGGA |
| | | antisense (SEQ. ID. NO: 70) | GCAATCAATTTTAACAAGTTATC CTTT |

TABLE 5

Quantitative real time RT-PCR results

| Accession number | Gene name | Gene abbreviation | Microarray (Cy3/Cy5 ratio) | Real time PCR (relative ratio) |
|---|---|---|---|---|
| Up-regulated | | | | |
| NM_000499.3 | Cytochrome P450, family1, subfamily A, polypeptide 1 | CYP1A1 (SEQ ID NO: 71) | 88.34 | 863.07 |
| BX649164 | serpin peptidase inhibitor, clade E(nexin, plasminogen activator inhibitor type 1), member 1 | SERPINE1 (SEQ ID NO: 72) | 29.05 | 38.54 |
| NM_004881.2 | Tumor protein p53 inducible protein 3 | TP53I3 (SEQ ID NO: 73) | 16.67 | 26.57 |
| BM913048 | TIMP metallopeptidase inhibitor 1 | TIMP1 (SEQ ID NO: 74) | 14.52 | 26.48 |
| NM_006426.2 | Dihydropyrimidinase-like 4 | DPYSL4 (SEQ ID NO: 75) | 13.51 | 101.13 |
| NM_133493.2 | CD109 antigen(Gov platelet alloantigens) | CD109 (SEQ ID NO: 76) | 12.97 | 45.46 |
| AB033073.2 | Sulfatase 2 | SULF2 (SEQ ID NO: 77) | 12.78 | 13.78 |
| NM_021603.3 | FXYD domain containing ion transport regulator 2 | FXYD2 (SEQ ID NO: 78) | 12.63 | 29.86 |
| BC035124 | MSFL2541 | UNQ2541 (SEQ ID NO: 79) | 11.28 | 13.61 |
| Y11307 | Cysteine-rich, angiogenic inducer, 61 | CYR61 (SEQ ID NO: 80) | 8.79 | 12.85 |
| AK095363 | Aquaporin 3 | AQP3 (SEQ ID NO: 81) | 8.26 | 46.53 |
| AK097009 | phospholipid transfer protein | PLTP (SEQ ID NO: 82) | 6.84 | 46.74 |
| NM_004864.2 | Growth differentiation factor 15 | GDF15 (SEQ ID NO: 83) | 6.65 | 38.76 |
| BU587578 | Regulator of G-protein signalling 10 | RGS10 (SEQ ID NO: 84) | 6.15 | 13.03 |
| BQ683841 | S100 calcium binding protein A11(calgizzarin) | S100A11 (SEQ ID NO: 85) | 6.06 | 8.38 |
| NM_001013632.2 | polo-like kinase 3 (*Drosophila*) | PLK3 (SEQ ID NO: 86) | 5.34 | 9.23 |
| NM_032872.1 | Synaptotagmin-like 1 | SYTL1 (SEQ ID NO: 87) | 4.93 | 10.43 |

TABLE 5-continued

Quantitative real time RT-PCR results

| Accession number | Gene name | Gene abbreviation | Microarray (Cy3/Cy5 ratio) | Real time PCR (relative ratio) |
|---|---|---|---|---|
| BC042390 | Vesicle transport through interaction with t-SNAREs homolog 1B(yeast) | VTI1B (SEQ ID NO: 88) | 4.49 | 8.21 |
| NM_000596.2 | Insulin-like growth factor binding protein 1 | IGFBP1 (SEQ ID NO: 89) | 4.43 | 5.07 |
| NM_005319.3 | Histone 1, H1c | HIST1H1C (SEQ ID NO: 90) | 4.26 | 3.38 |
| AK094474 | Ras homolog gene family, member C | RHOC (SEQ ID NO: 91) | 4.23 | 3.41 |
| NM_001769.2 | CD9 antigen(p24) | CD9 (SEQ ID NO: 92) | 4.15 | 1.71 |
| NM_001553.1 | Insulin-like growth factor binding protein 7 | IGFBP7 (SEQ ID NO: 93) | 3.47 | 11.02 |
| NM_003897.3 | Immediate early response 3 | IER3 (SEQ ID NO: 94) | 3.32 | 6.84 |
| NM_003516.2 | Histone 2, H2aa | HIST2H2AA (SEQ ID NO: 95) | 3.05 | 3.47 |
| Down-regulated | | | | |
| AK074377 | Chromosome 19 open reading frame 31 | UHRF1 (SEQ ID NO: 96) | 0.16 | 0.19 |
| BX640965 | Solute carrier family 22(extraneuronal monoamine transporter), member 3 | SLC22A3 (SEQ ID NO: 97) | 0.26 | 0.23 |
| NM_018492.2 | PDZ binding kinase | PBK (SEQ ID NO: 98) | 0.28 | 0.21 |
| CR600021 | High-mobility group box 2 | HMGB2 (SEQ ID NO: 99) | 0.29 | 0.23 |
| NM_006101.1 | Kinetochore associated 2 | KNTC2 (SEQ ID NO: 100) | 0.30 | 0.26 |
| NM_003318.3 | TTK protein kinase | TTK (SEQ ID NO: 101) | 0.30 | 0.47 |
| U65410 | MAD2 mitotic arrest deficient-like 1(yeast) | MAD2L1 (SEQ ID NO: 102) | 0.34 | 0.34 |
| NM_001067.2 | Topoisomerase(DNA) II alpha 170 kDa | TOP2A (SEQ ID NO: 103) | 0.45 | 0.14 |
| AB091343 | Centrosomal protein 55 kDa | C10orf3 (SEQ ID NO: 104) | 0.45 | 0.63 |
| BC022255 | Spindle pole body component 25 homolog(S. cerevisiae) | Spc25 (SEQ ID NO: 105) | 0.54 | 0.25 |

As a result, the expression profiles of 25 up-regulated genes and 10 down-regulated genes were consistent with the result of oligo-microarray examining the gene expressions by the chrysene.

The invention claimed is:

1. A method for confirming the exposure to chrysene comprising the following steps:
  1) separating RNAs from human somatic cells of a sample of an experimental group, and from somatic cells of a control group, wherein the human somatic cells originate from human liver or liver cancer cells;
  2) comparing the expression level of all selected genes of the sample with that of the control, wherein the selected genes are:
    CYP1A1 (Cytochrome P450, family 1, subfamily A, polypeptide 1) (SEQ. ID. NO: 71), PAI [serpin peptidase inhibitor, Glade E (nexin, plasminogen activator inhibitor type 1), member 1] (SEQ. ID. NO: 72), Tumor protein p53 inducible protein 3 (SEQ. ID. NO: 73), TIMP metallopeptidase inhibitor 1 (SEQ. ID. NO: 74), Dihydropyrimidinase-like 4 (SEQ. ID. NO: 75), CD109 antigen (Gov platelet alloantigens) (SEQ. ID. NO: 76), Sulfatase 2 (SEQ. ID. NO: 77), FXYD domain containing ion transport regulator 2 (SEQ. ID. NO: 78), MSFL2541 (SEQ. ID. NO: 79), Cysteine-rich, angiogenic inducer, 61 (SEQ. ID. NO: 80), Aquaporin 3 (SEQ. ID. NO: 81), phospholipid transfer protein (SEQ. ID. NO: 82), Growth differentiation factor 15 (SEQ. ID. NO: 83), Regulator of G-protein signalling 10 (SEQ. ID. NO: 84), S100 calcium binding protein All (calgizzarin) (SEQ. ID. NO: 85), polo-like kinase 3 (Drosophila) (SEQ. ID. NO: 86), Synaptotagmin-like 1 (SEQ. ID. NO: 87), Vesicle transport through interaction with t-SNAREs homolog 1B (yeast) (SEQ. ID. NO: 88), Insulin-like growth factor binding protein 1 (SEQ. ID. NO: 89), Histone 1, H1c (SEQ. ID. NO: 90), Ras homolog gene family, member C (SEQ. ID. NO: 91), CD9 antigen (p24) (SEQ. ID. NO: 92), Insulin-like growth factor binding protein 7 (SEQ. ID. NO: 93), Immediate early response 3 (SEQ. ID. NO: 94), H1stone 2, H2aa (SEQ. ID. NO: 95), Chromosome 19 open reading frame 31 (SEQ. ID. NO: 96), Solute carrier family 22 (extraneuronal monoamine transporter), member 3 (SEQ. ID. NO: 97), PDZ binding kinase (SEQ. ID. NO: 98), High-mobility group box 2 (SEQ. ID. NO: 99), Kinetochore associated 2 (SEQ. ID. NO: 100), TTK protein kinase (SEQ. ID. NO: 101), MAD2 mitotic arrest deficient-like 1 (yeast) (SEQ. ID. NO: 102), Topoisomerase (DNA) II alpha 170 kDa (SEQ. ID. NO: 103), Centrosomal protein 55 kDa (SEQ. ID. NO: 104), and Spindle pole body component 25 homolog (S. cerevisiae) (SEQ. ID. NO: 105); and
  3) determining that the sample is exposed to the chrysene, when the expression level of the genes of CYP1A1 (Cytochrome P450, family 1, subfamily A, polypeptide 1) (SEQ. ID. NO: 71), PAI [serpin peptidase inhibitor, clade E (nexin, plasminogen activator inhibitor type 1), member 1] (SEQ. ID. NO: 72), Tumor protein p53 inducible protein 3 (SEQ. ID. NO: 73), TIMP metallopeptidase inhibitor 1 (SEQ. ID. NO: 74), Dihydropyrimidinase-like 4 (SEQ. ID. NO: 75), CD109 antigen (Gov platelet alloantigens) (SEQ. ID. NO: 76), Sulfatase 2 (SEQ. ID. NO: 77), FXYD domain containing ion transport regulator 2 (SEQ. ID. NO: 78), MSFL2541 (SEQ. ID. NO: 79), Cysteine-rich, angiogenic inducer, 61 (SEQ. ID. NO: 80), Aquaporin 3 (SEQ. ID. NO: 81), phospholipid transfer protein (SEQ. ID. NO: 82), Growth differentiation factor 15 (SEQ. ID. NO: 83), Regulator of G-protein signalling 10 (SEQ. ID. NO: 84), S100 calcium binding protein A11 (calgizzarin) (SEQ. ID. NO: 85), polo-like kinase 3 (Drosophila) (SEQ. ID.

NO: 86), Synaptotagmin-like 1 (SEQ. ID. NO: 87), Vesicle transport through interaction with t-SNAREs homolog 1B (yeast) (SEQ. ID. NO: 88), Insulin-like growth factor binding protein 1 (SEQ. ID. NO: 89), Histone 1, H1c (SEQ. ID. NO: 90), Ras homolog gene family, member C (SEQ. ID. NO: 91), CD9 antigen (p24) (SEQ. ID. NO: 92), Insulin-like growth factor binding protein 7 (SEQ. ID. NO: 93), Immediate early response 3 (SEQ. ID. NO: 94), and H1stone 2, H2aa (SEQ. ID. NO: 95), is significantly up-regulated, compared with that of the control, and when the expression level of the genes Chromosome 19 open reading frame 31 (SEQ. ID. NO: 96), Solute carrier family 22 (extraneuronal monoamine transporter), member 3 (SEQ. ID. NO: 97), PDZ binding kinase (SEQ. ID. NO: 98), High-mobility group box 2 (SEQ. ID. NO: 99), Kinetochore associated 2 (SEQ. ID. NO: 100), TTK protein kinase (SEQ. ID. NO: 101), MAD2 mitotic arrest deficient-like 1 (yeast) (SEQ. ID. NO: 102), Topoisomerase (DNA) II alpha 170 kDa (SEQ. ID. NO: 103), Centrosomal protein 55 kDa (SEQ. ID. NO: 104), and Spindle pole body component 25 homolog (S. cerevisiae) (SEQ. ID. NO: 105) is significantly down-regulated, compared with that of the control.

2. The method according to claim 1, wherein the human liver cancer cells are HepG2.

3. The method according to claim 1, wherein the comparing of the expression of step 2) is performed as mRNA expression level.

4. The method according to claim 3, wherein the mRNA expression level comparison is performed by oligonucleotide or polynucleotide microarray, or RT-PCR.

5. A method for confirming the exposure to chrysene comprising the following steps:

1) separating RNAs from human somatic cells of a sample of an experimental group, and from somatic cells of a control group, wherein the human somatic cells originate from human liver or liver cancer cells;

2) synthesizing cDNAs with the RNAs separated from the experimental group and the control of step 1) and labeling them with different fluorescent materials;

3) hybridizing the cDNAs of step 2) each labeled with different fluorescent materials with DNA microarray chip comprising oligonucleotide containing the full length or complement oligonucleotides of all selected genes, wherein the selected genes are:

CYP1A1 (Cytochrome P450, family 1, subfamily A, polypeptide 1) (SEQ. ID. NO: 71), PAI [serpin peptidase inhibitor, Glade E (nexin, plasminogen activator inhibitor type 1), member 1] (SEQ. ID. NO: 72), Tumor protein p53 inducible protein 3 (SEQ. ID. NO: 73), TIMP metallopeptidase inhibitor 1 (SEQ. ID. NO: 74), Dihydropyrimidinase-like 4 (SEQ. ID. NO: 75), CD109 antigen (Gov platelet alloantigens) (SEQ. ID. NO: 76), Sulfatase 2 (SEQ. ID. NO: 77), FXYD domain containing ion transport regulator 2 (SEQ. ID. NO: 78), MSFL2541 (SEQ. ID. NO: 79), Cysteine-rich, angiogenic inducer, 61 (SEQ. ID. NO: 80), Aquaporin 3 (SEQ. ID. NO: 81), phospholipid transfer protein (SEQ. ID. NO: 82), Growth differentiation factor 15 (SEQ. ID. NO: 83), Regulator of G-protein signalling 10 (SEQ. ID. NO: 84), S100 calcium binding protein A11 (calgizzarin) (SEQ. ID. NO: 85), polo-like kinase 3 (Drosophila) (SEQ. ID. NO: 86), Synaptotagmin-like 1 (SEQ. ID. NO: 87), Vesicle transport through interaction with t-SNARES homolog 1B (yeast) (SEQ. ID. NO: 88), Insulin-like growth factor binding protein 1 (SEQ. ID. NO: 89), Histone 1, H1c (SEQ. ID. NO: 90), Ras homolog gene family, member C (SEQ. ID. NO: 91), CD9 antigen (p24) (SEQ. ID. NO: 92), Insulin-like growth factor binding protein 7 (SEQ. ID. NO: 93), Immediate early response 3 (SEQ. ID. NO: 94), H1stone 2, H2aa (SEQ. ID. NO: 95), Chromosome 19 open reading frame 31 (SEQ. ID. NO: 96), Solute carrier family 22 (extraneuronal monoamine transporter), member 3 (SEQ. ID. NO: 97), PDZ binding kinase (SEQ. ID. NO: 98), High-mobility group box 2 (SEQ. ID. NO: 99), Kinetochore associated 2 (SEQ. ID. NO: 100), TTK protein kinase (SEQ. ID. NO: 101), MAD2 mitotic arrest deficient-like 1 (yeast) (SEQ. ID. NO: 102), Topoisomerase (DNA) II alpha 170 kDa (SEQ. ID. NO: 103), Centrosomal protein 55 kDa (SEQ. ID. NO: 104), and Spindle pole body component 25 homolog (S. cerevisiae) (SEQ. ID. NO: 105);

4) analyzing the DNA microarray chip reacted in step 3);

5) comparing the expression of all of the selected genes of the sample with that of the control, wherein the genes are regarded as being exposed to a chrysene; and 6) determining that the sample is exposed to the chrysene, when the expression level of the genes of CYP1A1 (Cytochrome P450, family 1, subfamily A, polypeptide 1) (SEQ. ID. NO: 71), PAI [serpin peptidase inhibitor, Glade E (nexin, plasminogen activator inhibitor type 1), member 1] (SEQ. ID. NO: 72), Tumor protein p53 inducible protein 3 (SEQ. ID. NO: 73), TIMP metallopeptidase inhibitor 1 (SEQ. ID. NO: 74), Dihydropyrimidinase-like 4 (SEQ. ID. NO: 75), CD109 antigen (Gov platelet alloantigens) (SEQ. ID. NO: 76), Sulfatase 2 (SEQ. ID. NO: 77), FXYD domain containing ion transport regulator 2 (SEQ. ID. NO: 78), MSFL2541 (SEQ. ID. NO: 79), Cysteine-rich, angiogenic inducer, 61 (SEQ. ID. NO: 80), Aquaporin 3 (SEQ. ID. NO: 81), phospholipid transfer protein (SEQ. ID. NO: 82), Growth differentiation factor 15 (SEQ. ID. NO: 83), Regulator of G-protein signalling 10 (SEQ. ID. NO: 84), S100 calcium binding protein A11 (calgizzarin) (SEQ. ID. NO: 85), polo-like kinase 3 (Drosophila) (SEQ. ID. NO: 86), Synaptotagmin-like 1 (SEQ. ID. NO: 87), Vesicle transport through interaction with t-SNAREs homolog 1B (yeast) (SEQ. ID. NO: 88), Insulin-like growth factor binding protein 1 (SEQ. ID. NO: 89), Histone 1, H1c (SEQ. ID. NO: 90), Ras homolog gene family, member C (SEQ. ID. NO: 91), CD9 antigen (p24) (SEQ. ID. NO: 92), Insulin-like growth factor binding protein 7 (SEQ. ID. NO: 93), Immediate early response 3 (SEQ. ID. NO: 94), and H1stone 2, H2aa (SEQ. ID. NO: 95), is significantly up-regulated, compared with that of the control, and when the expression level of the genes Chromosome 19 open reading frame 31 (SEQ. ID. NO: 96), Solute carrier family 22 (extraneuronal monoamine transporter), member 3 (SEQ. ID. NO: 97), PDZ binding kinase (SEQ. ID. NO: 98), High-mobility group box 2 (SEQ. ID. NO: 99), Kinetochore associated 2 (SEQ. ID. NO: 100), TTK protein kinase (SEQ. ID. NO: 101), MAD2 mitotic arrest deficient-like 1 (yeast) (SEQ. ID. NO: 102), Topoisomerase (DNA) II alpha 170 kDa (SEQ. ID. NO: 103), Centrosomal protein 55 kDa (SEQ. ID. NO: 104), and Spindle pole body component 25 homolog (S. cerevisiae) (SEQ. ID. NO: 105) is significantly down-regulated, compared with that of the control.

6. The method according to claim 5, wherein the human liver cancer cells are HepG2.

7. The method according to claim 5, wherein the fluorescent material of step 2) is selected from the group consisting of Cy3, Cy5, poly L-lysine-fluorescein isothiocyanate (FITC), rhodamine-B-isothiocyanate (RITC) and rhodamine.

8. The method according to claim 5, wherein the oligonucleotide or its complement oligonucleotide of step 3) contains 18-30 nucleotides of the gene whose expression is changed by chrysene.

9. The method according to claim 8, wherein the oligonucleotide or its complement oligonucleotide of step 3) contains 20-25 nucleotides of the gene whose expression is changed by chrysene.

* * * * *